US010561714B2

(12) United States Patent
Pierce et al.

(10) Patent No.: US 10,561,714 B2
(45) Date of Patent: *Feb. 18, 2020

(54) FACTOR IX POLYPEPTIDES AND METHODS OF USE THEREOF

(71) Applicant: Bioverativ Therapeutics Inc., Waltham, MA (US)

(72) Inventors: Glenn Pierce, Cambridge, MA (US); Samantha Truex, Sudbury, MA (US); Robert T. Peters, Needham, MA (US); Haiyan Jiang, Belmont, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/890,284

(22) Filed: Feb. 6, 2018

(65) Prior Publication Data

US 2018/0228878 A1 Aug. 16, 2018

Related U.S. Application Data

(60) Continuation of application No. 15/820,080, filed on Nov. 21, 2017, which is a continuation of application No. 14/982,934, filed on Dec. 29, 2015, now Pat. No. 9,867,873, which is a division of application No. 13/793,796, filed on Mar. 11, 2013, now Pat. No. 9,233,145, which is a continuation of application No. 13/809,276, filed as application No. PCT/US2011/043569 on Jul. 11, 2011, now Pat. No. 9,670,475.

(60) Provisional application No. 61/363,064, filed on Jul. 9, 2010, provisional application No. 61/424,555, filed on Dec. 17, 2010, provisional application No. 61/430,819, filed on Jan. 7, 2011, provisional application No. 61/438,572, filed on Feb. 1, 2011, provisional application No. 61/442,079, filed on Feb. 11, 2011, provisional application No. 61/470,951, filed on Apr. 1, 2011.

(51) Int. Cl.
| | | |
|---|---|---|
| *A61K 38/36* | (2006.01) |
| *A61K 38/48* | (2006.01) |
| *A61K 47/64* | (2017.01) |
| *A61K 39/395* | (2006.01) |
| *C12N 9/96* | (2006.01) |
| *A61K 38/38* | (2006.01) |
| *C07K 16/18* | (2006.01) |
| *C12N 9/64* | (2006.01) |
| *C07K 14/76* | (2006.01) |
| *A61K 9/00* | (2006.01) |
| *A61P 7/04* | (2006.01) |

(52) U.S. Cl.
CPC ........ *A61K 38/4846* (2013.01); *A61K 9/0019* (2013.01); *A61K 38/38* (2013.01); *A61K 39/395* (2013.01); *A61K 39/3955* (2013.01); *A61K 39/39533* (2013.01); *A61K 47/643* (2017.08); *A61P 7/04* (2018.01); *C07K 14/76* (2013.01); *C07K 16/18* (2013.01); *C12N 9/644* (2013.01); *C12N 9/96* (2013.01); *C12Y 304/21022* (2013.01); *C07K 2317/21* (2013.01); *C07K 2317/90* (2013.01); *C07K 2317/94* (2013.01); *C07K 2319/30* (2013.01); *C07K 2319/31* (2013.01); *C07K 2319/33* (2013.01)

(58) Field of Classification Search
None
See application file for complete search history.

(56) References Cited

U.S. PATENT DOCUMENTS

| | | |
|---|---|---|
| 4,786,726 A | 11/1988 | Smith |
| 4,994,371 A | 2/1991 | Davie et al. |
| 5,112,946 A | 5/1992 | Maione et al. |
| 5,336,603 A | 8/1994 | Capon et al. |
| 5,349,053 A | 9/1994 | Landolfi et al. |
| 5,359,046 A | 10/1994 | Capon et al. |
| 5,447,851 A | 9/1995 | Beutler et al. |
| 5,480,981 A | 1/1996 | Goodwin et al. |
| 5,622,929 A | 4/1997 | Willner et al. |
| 5,723,125 A | 3/1998 | Chang et al. |
| 5,766,883 A | 6/1998 | Ballance et al. |
| 5,783,181 A | 7/1998 | Browne et al. |
| 5,808,029 A | 9/1998 | Brockhaus et al. |
| 5,844,095 A | 12/1998 | Linsley et al. |
| 5,908,626 A | 6/1999 | Chang et al. |
| 5,969,040 A | 10/1999 | Hallahan et al. |
| 5,981,285 A | 11/1999 | Carroll et al. |
| 6,030,613 A | 2/2000 | Blumberg et al. |

(Continued)

FOREIGN PATENT DOCUMENTS

| | | |
|---|---|---|
| EP | 0 367 166 A1 | 5/1990 |
| EP | 0 394 827 A1 | 10/1990 |

(Continued)

OTHER PUBLICATIONS

White et al., Thromb Haemost. Mar. 2001;85(3):560.*
Collins et al., J Thromb Haemost. Feb. 2010;8(2):269-75. doi: 10.1111/j.1538-7836.2009.03703.x. Epub Nov. 23, 2009.*
Ahnstrom, J., et al., "A 6-year Follow-Up of Dosing, Coagulation Factor Levels and Bleedings in Relation to Joint Status in the Prophylactic Treatment of Haemophilia," Haemophilia 10(6):689-697, Blackwell Publishing Ltd., England (2004).

(Continued)

*Primary Examiner* — Michael Szperka
(74) *Attorney, Agent, or Firm* — Lathrop GPM LLP; James H. Velema, Esq.

(57) ABSTRACT

The present invention provides methods of administering Factor IX; methods of administering chimeric and hybrid polypeptides comprising Factor IX; polynucleotides encoding such chimeric and hybrid polypeptides; cells comprising such polynucleotides; and methods of producing such chimeric and hybrid polypeptides using such cells.

20 Claims, 24 Drawing Sheets

Figure 1:
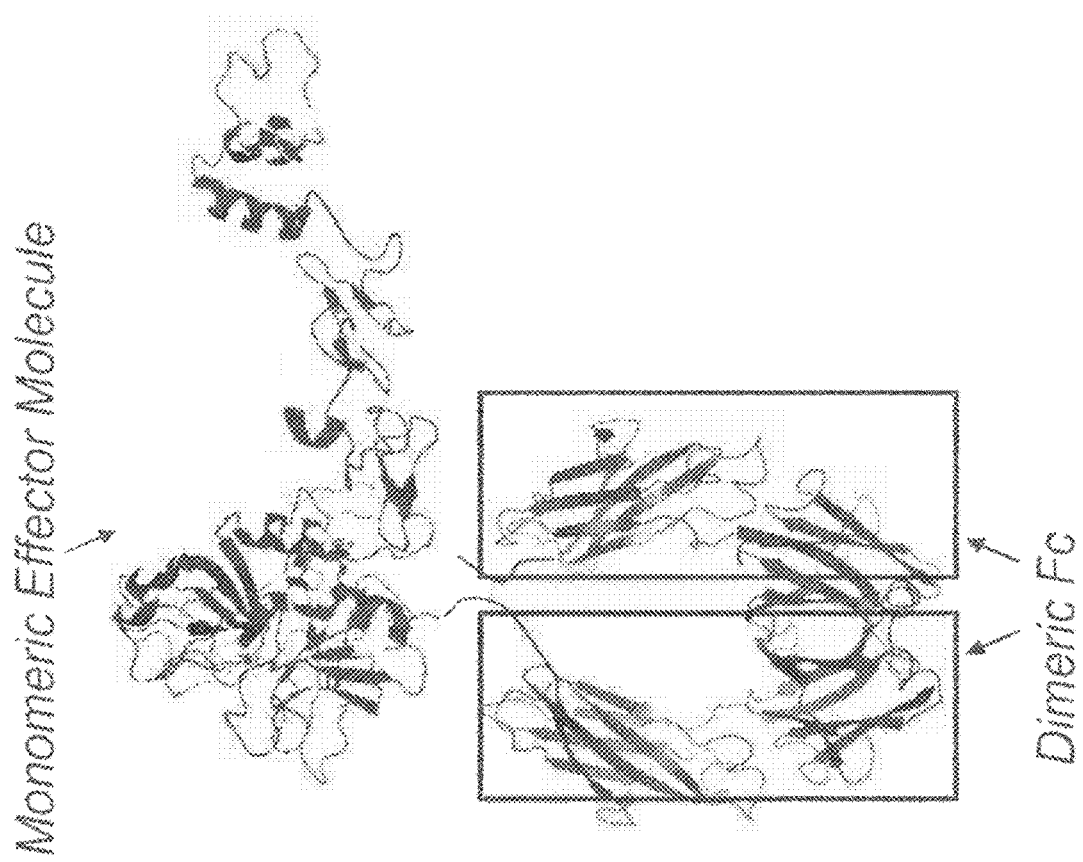

Specification includes a Sequence Listing.

(56) References Cited

U.S. PATENT DOCUMENTS

| | | | |
|---|---|---|---|
| 6,037,452 A | 3/2000 | Minamino et al. | |
| 6,277,975 B1 | 8/2001 | Larsen et al. | |
| 6,403,769 B1 | 6/2002 | Larochelle et al. | |
| 6,406,697 B1 | 6/2002 | Capon et al. | |
| 6,686,179 B2 | 2/2004 | Fleer et al. | |
| 7,112,580 B2 | 9/2006 | Raymond et al. | |
| 7,212,798 B1 | 5/2007 | Adams et al. | |
| 7,217,798 B2 | 5/2007 | Hinton et al. | |
| 7,348,004 B2 | 3/2008 | Peters et al. | |
| 7,381,408 B2 | 6/2008 | Mezo et al. | |
| 7,404,956 B2 | 7/2008 | Peters et al. | |
| 7,482,013 B2 | 1/2009 | Balance et al. | |
| 7,566,565 B2 * | 7/2009 | Peters | C12Y 304/2102 435/325 |
| 7,592,010 B2 | 9/2009 | Rosen et al. | |
| 7,790,415 B2 | 9/2010 | Gillies et al. | |
| 7,939,632 B2 | 5/2011 | Metzner et al. | |
| 8,329,182 B2 | 12/2012 | Peters et al. | |
| 8,367,805 B2 | 2/2013 | Chamberlain et al. | |
| 8,748,380 B2 | 6/2014 | Plumridge et al. | |
| 8,822,417 B2 | 9/2014 | Andersen et al. | |
| 9,233,145 B2 * | 1/2016 | Pierce | A61K 38/4846 |
| 9,493,545 B2 | 11/2016 | Finnis et al. | |
| 9,623,091 B2 * | 4/2017 | Pierce | A61K 38/4846 |
| 9,629,903 B2 * | 4/2017 | Pierce | A61K 38/4846 |
| 9,670,475 B2 * | 6/2017 | Pierce | A61K 38/4846 |
| 9,675,676 B2 * | 6/2017 | Pierce | A61K 38/4846 |
| 9,775,888 B2 | 10/2017 | Ballance et al. | |
| 9,867,873 B2 * | 1/2018 | Pierce | A61K 38/4846 |
| 2001/0031721 A1 | 10/2001 | Webb et al. | |
| 2003/0199043 A1 | 10/2003 | Balance et al. | |
| 2003/0203845 A1 | 10/2003 | Knudsen et al. | |
| 2005/0008580 A1 | 1/2005 | Gong et al. | |
| 2005/0032174 A1 | 2/2005 | Peters et al. | |
| 2006/0162552 A1 | 7/2006 | Yost et al. | |
| 2007/0135343 A1 | 6/2007 | Webb et al. | |
| 2008/0260755 A1 | 10/2008 | Metzner et al. | |
| 2009/0092582 A1 | 4/2009 | Bogin et al. | |
| 2009/0163699 A1 | 6/2009 | Chamberlain et al. | |
| 2009/0252720 A1 | 10/2009 | Ostergaard et al. | |
| 2009/0264627 A1 | 10/2009 | Gillies et al. | |
| 2010/0189682 A1 | 7/2010 | Schellenberger et al. | |
| 2010/0222554 A1 | 9/2010 | Weimer et al. | |
| 2010/0239554 A1 | 9/2010 | Schellenberger et al. | |
| 2011/0236412 A1 | 9/2011 | Drew | |
| 2012/0208759 A1 | 8/2012 | Fima et al. | |
| 2013/0171175 A1 | 7/2013 | Pierce et al. | |
| 2013/0202595 A1 | 8/2013 | Pierce et al. | |
| 2014/0315817 A1 | 10/2014 | Schmidt et al. | |
| 2015/0252345 A1 | 9/2015 | Pierce et al. | |
| 2016/0000888 A1 | 1/2016 | Brader | |
| 2016/0033523 A1 | 2/2016 | Cameron et al. | |
| 2016/0166657 A1 | 6/2016 | Pierce et al. | |
| 2016/0243206 A1 | 8/2016 | Pierce et al. | |
| 2016/0257943 A1 | 9/2016 | Pierce et al. | |
| 2016/0346365 A1 | 12/2016 | Pierce et al. | |
| 2018/0002684 A1 | 1/2018 | Pierce et al. | |

FOREIGN PATENT DOCUMENTS

| | | |
|---|---|---|
| EP | 0399666 A1 | 10/1990 |
| EP | 0 307 434 B2 | 7/1998 |
| EP | 2353588 A1 | 8/2011 |
| JP | 2009525724 A | 7/2009 |
| JP | 2009539391 A | 11/2009 |
| JP | 201063462 A | 3/2010 |
| WO | WO 91/06570 A1 | 5/1991 |
| WO | WO-1993015199 A1 | 8/1993 |
| WO | WO 96/04388 A1 | 2/1996 |
| WO | WO 96/22024 A1 | 7/1996 |
| WO | WO 97/34631 A1 | 9/1997 |
| WO | WO-1998035689 A1 | 8/1998 |
| WO | WO 99/04813 A1 | 2/1999 |
| WO | WO-2001079271 A1 | 10/2001 |
| WO | WO-0240544 A2 | 5/2002 |
| WO | WO-03020764 A2 | 3/2003 |
| WO | WO-2003031464 A2 | 4/2003 |
| WO | WO-2003059934 A2 | 7/2003 |
| WO | WO-2004101739 A2 | 11/2004 |
| WO | WO-2004101740 A2 | 11/2004 |
| WO | WO-2005001025 A2 | 1/2005 |
| WO | WO-2005014035 A2 | 2/2005 |
| WO | WO-2005014049 A2 | 2/2005 |
| WO | WO-2005055950 A2 | 6/2005 |
| WO | WO-2006018204 A1 | 2/2006 |
| WO | WO-2006067116 A1 | 6/2006 |
| WO | WO-2006074199 A1 | 7/2006 |
| WO | WO-2006127896 A2 | 11/2006 |
| WO | WO-2007090584 A1 | 8/2007 |
| WO | WO-2007103515 A2 | 9/2007 |
| WO | WO-2007112005 A2 | 10/2007 |
| WO | WO-2007115724 A2 | 10/2007 |
| WO | WO-2007135182 A2 | 11/2007 |
| WO | WO-2007144173 A1 * 12/2007 ........... C07K 14/745 | |
| WO | WO-2007149406 A2 | 12/2007 |
| WO | WO-2008009634 A3 | 1/2008 |
| WO | WO-2008009635 A2 | 1/2008 |
| WO | WO-2008022151 A1 | 2/2008 |
| WO | WO-2008118507 A2 | 10/2008 |
| WO | WO-2008119815 A1 | 10/2008 |
| WO | WO-2009023270 A2 | 2/2009 |
| WO | WO-2009051717 A2 | 4/2009 |
| WO | WO-2009130198 A2 | 10/2009 |
| WO | WO-2009130602 A2 | 10/2009 |
| WO | WO-2009137254 A2 | 11/2009 |
| WO | WO-2009140014 A1 | 11/2009 |
| WO | WO-2009140015 A2 | 11/2009 |
| WO | WO 2010/020690 A1 | 2/2010 |
| WO | WO-2010091122 A1 | 8/2010 |
| WO | WO-2011030641 A1 | 3/2011 |
| WO | WO-2011051489 A2 | 5/2011 |
| WO | WO-2011124718 A1 | 10/2011 |
| WO | WO-2012006624 A2 | 1/2012 |
| WO | WO-2014052490 A1 | 4/2014 |
| WO | WO-2014144549 A1 | 9/2014 |
| WO | WO-2015095925 A1 | 7/2015 |

OTHER PUBLICATIONS

Andersson, L.O., et al., "Purification and characterization of human factor IX," Thrombosis Research 7(3):451-459, Pergamon Press, United States (1975).

Armour, K,L. et al., "Recombinant human IgG molecules lacking Fcgamma receptor I binding and monocyte triggering activities," European Journal of Immunology 29(8):2613-2624, Wiley-VCH Verlag GmbH, Germany (1999).

Bjorkman, S. and Berntorp, E., "Pharmacokinetics of Coagulation Factors: Clinical Relevance for Patients with Haemophilia," Clinical Pharmacokinetics 40(11):815-832, Adis International Ltd., New Zealand (2001).

Bjorkman, S., "Prophylactic Dosing of Factor VIII and factor IX from a Clinical Pharmacokinetic Perspective," Haemophilia 9(1):101-110, Blackwell Publishing Ltd., England (2003).

Brinkhous, K.M., et al., "Recombinant Human Factor IX: Replacement Therapy, Prophylaxis, and Pharmacokinetics in Canine Hemophilia B," Blood 88(7):2603-2610, The American Society of Hematology, United States (1996).

Brutlag, D.L. et al., "Improved sensitivity of biological sequence database searches," Computer Applications in the Biosciences 6(3):237-245, Oxford University Press, England (1990).

Burmeister, W.P., et al., "Crystal structure of the complex of rat neonatal Fc receptor with Fc," Nature 372(6504):379-383, Nature Publishing Group/Macmillan Journals Ltd., England (1994).

Collins, P., et al., "Break-Through Bleeding in Relation to Predicted Factor VIII Levels in Patients Receiving Prophylactic Treatment for Severe Hemophilia A," Thrombosis and Haemostasis 7(3):413-420, Blackwell Pub., England, (2009).

Dobeli, H., et al., "Role of the carboxy-terminal sequence on the biological activity of human interferon (IFN-y)," Journal of Biotechnology 7:199-216, Elsevier, the Netherlands (1988).

(56) References Cited

OTHER PUBLICATIONS

Dumont, J.A., et al., "Monomeric Fc Fusion Molecules," in Therapeutic Monoclonal Antibodies from Bench to Clinic, Chapter 33, pp. 779-795, John Wiley & Sons., Inc., United States (2009).

Friend, P.J., et al., "Phase I study of an engineered aglycosylated humanized CD3 antibody in renal transplant rejection," Transplantation 68(11):1632-1637, Lippincott Wilkins, Inc., United States (1999).

Gayle, R.B. III., et al., "Identification of Regions in Interleukin-1alpha Important for Activity," The Journal of Biological Chemistry 268(29):22105-22111, The American Society for Biochemistry and Molecular Biology, Inc., United States (1993).

Gillis, S., et al., "Gamma-Carboxyglutamic Acids 36 and 40 do not Contribute to Human Factor IX Function," Protein Science 6(1):185-196, Cambridge University Press, United States (1997).

Hansson, K. and Stenflo, J., "Post-Translational Modifications in Proteins Involved in Blood Coagulation," Journal Thrombosis and Haemostasis 3(12):2633-2648, Blackwell Pub., England (2005).

Huang, C., "Receptor-Fc Fusion Therapeutics, Traps, and MIMETIBODY Technology," Current Opinion in Biotechnology 20(6):692-699, Elsevier, England (2009).

International Search Report and Written Opinion for Application No. PCT/US2011/043569, ISA/US, Alexandria, Virginia, United States, dated Feb. 14, 2012, 11 pages.

Kisker, C.T., et al., "Prophylaxis in Factor IX Deficiency Product and Patient Variation," Haemophilia 9(3):279-284, Blackwell Publishing Ltd., England (2003).

"MASAC Recommendations Concerning Products Licensed for the Treatment of Hemophilia and Other Bleeding Disorders," Hemophilia. org, accessed at http://www.hemophilia.org/Researchers-Healthcare-Providers/Medical-and-Scientific-Advisory-Council-MASAC/All-MASAC-Recommendations/Recommendations-Concerning-Products-Licensed-for-the-Treatment-of-Hemophilia-and-Other-Bleeding-Disorders, accessed on Sep. 8, 2014, 37 pages.

McCarthy, K., et al., "Pharmacokinetics of Recombinant Factor IX After Intravenous and Subcutaneous Administration in Dogs and Cynomolgus Monkeys," Thrombosis and Haemostasis 87(5):824-830, Schattauer GmbH, Stuttgart, Germany (2002).

Negrier, C., et al., "Enhanced Pharmacokinetic Properties of a Glycopegylated Recombinant Factor IX: A First Human Dose Trial in Patients with Hemophilia B," Blood 118(10):2695-2701, The American Society of Hematology, United States (2011).

Nilsson, I.M., et al., "Twenty-Five Years' Experience of Prophylactic Treatment in Severe Haemophilia A and B," Journal of Internal Medicine 232(1):25-32, Blackwell Scientific Publications, England (1992).

Oganesyan, V., et al., "Structural characterization of a human Fc fragment engineered for extended serum half-life," Molecular Immunology 46(8-9):1750-1755, Elsevier, United States (2009).

Reagan-Shaw, S., et al., "Dose Translation from Animal to Human Studies Revisited," Federation of American Societies for Experimental Biology Journal 22(3):659-661, The Federation, United States (2008).

Ron, D., et al., "Expression of biologically active recombinant keratinocyte growth factor: Structure/function analysis of aminoterminal truncation mutants," The Journal of Biological Chemistry 268(4):2984-2988, American Society for Biochemistry and Molecular Biology, United States (1993).

Roth, D.A., et al., "Human Recombinant Factor IX: Safety and Efficacy Studies in Hemophilia B Patients Previously Treated with Plasma-Derived Factor IX Concentrates," Blood 98(13):3600-3606, The American Society of Hematology, United States (2001).

Routledge, E.G., et al., "The effect of aglycosylation on the immunogenicity of a humanized therapeutic CD3 monoclonal antibody," Transplantation 60(8):847-853, Williams & Wilkins, United States (1995).

Schellenberger, V., et al., "A recombinant polypeptide extends the in vivo half-life of peptides and proteins in a tunable manner," Nature Biotechnology 27(12):1186-1190, Nature America, Inc., United States (2009).

Schulte, S., "Half-life extension through albumin fusion technologies," Thrombosis Research 124(2):56-58, Elsevier, United States (2009).

Shapiro, A.D., et al., "Use of Pharmacokinetics in the Coagulation Factor Treatment of Patients with Haemophilia," Haemophilia 11(6):571-582, Blackwell Publishing Ltd., England (2005).

Shields, R.L., et al., "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R," Journal of Biological Chemistry 276(9):6591-6604, The American Society for Biochemistry and Molecular Biology, Inc, United States (2001).

Story, C.M., et al., "A major histocompatibility complex class I-like Fc receptor cloned from human placenta: possible role in transfer of immunoglobulin G from mother to fetus," The Journal of Experimental Medicine 180(6):2377-2381, The Rockefeller University Press, United States (1994).

Summary of Product Characteristics for BENEFIXTM, Electronic Medicines Compendium, medicines.org.uk, accessed at http://www.medicines.org.uk/emc/medicine/20376/SPC/BENEFIXTtm/#PHARMACODYNAMIC_PROPS, accessed on Sep. 16, 2014, 11 pages.

Supplementary European Search Report for Application No. EP11804476, Munich, Germany, dated Mar. 5, 2014, 6 pages.

Vaccaro, C., et al., "Engineering the Fc region of immunoglobulin G to modulate in vivo antibody levels," Nature Biotechnology 23(10):1283-1288, Nature Publishing Group, United States (2005).

Wang, D.D., et al., "Fixed Dosing Versus Body Size-Based Dosing of Monoclonal Antibodies in Adult Clinical Trials," The Journal of Clinical Pharmacology 49(9):1012-1024, American College of Clinical Pharmacology, United States (2009).

Ward, E,S., et al., "The effector functions of immunoglobulins: implications for therapy," Therapeutic Immunology 2(2):77-94, Blackwell Science Ltd., England (1995).

White, G.C. II., et al., "Recombinant Factor IX," Thrombosis and Haemostasis 78(1):261-265, Stuttgart, Schattauer, Germany (1997).

White, G.C. II., et al., "Variability of in Vivo Recovery of Factor Ix after Infusion of Monoclonal Antibody Purified Factor IX Concentrates in Patients with Hemophilia B. The Mononine Study Group," Thrombosis and Haemostasis 73(5):779-784, Stuttgart, Schattauer, Germany (1995).

Chang, L.C., et al., "Sustained Release of transgenic Human Factor IX: Preparation, Characterization, and in Vivo Efficacy," Molecular Pharmaceutics 8(5):1767-1774, American Chemical Society, United States (2011).

Non-Final Office Action dated Sep. 28, 2015 in U.S. Appl. No. 13/809,276, filed Apr. 24, 2013.

Ragni, M.V., et al., "Use of recombinant factor IX in subjects with haemophilia B undergoing surgery," Haemophilia 8(2):91-97, Blackwell Science, England (2002).

Shapiro, A.D., et al., "Safety and prolonged biological activity following a single administration of a recombinant molecular fusion of native human coagulation factor IX and the Fc region of immunoglobulin G (IgG) (rFIXFc) to subjects with hemophilia B," Haemophilia 16(Suppl. 4):30, Blackwell Publishing Ltd., United Kingdom, Abstract 07FP07 (Jul. 2010).

Screenshot of "Special Issue: Abstracts of the XXIXth International Congress of the World Federation of Hemophilia, Buenos Aires, Argentina, Jul. 10-14, 2010," Haemophilia 16(Suppl. 4):1-170.

U.S. Food and Drug Administration, "Highlights of Prescribing Information, ALPROLIX®," revised Mar. 2014.

Ezban, M., et al., "Pharmacokinetic (PK) and pharmacodynamic (PD) properties of a new recombinant long acting factor IX (40KPEG-RFIX) product after intravenous (IV) administration to hemophilia b dogs," PP-TH-579, Poster Presentation, Journal of Thrombosis and Haemostasis 7(Suppl. 2):1-1204:134, International Society on Thrombosis and Haemostasis, United States (Jun. 2009).

Ezban, M., et al., "Pharmacokinetic (PK) and pharmacodynamic (PD) properties of a new recombinant long acting Factor IX (40K PEG-rFIX) product after intravenous (iv) administration to hemophilia B (HB) dogs," PP-TH-579, Poster Presentation, presented at

(56) References Cited

OTHER PUBLICATIONS

XXII Congress of the International Society of Thrombosis and Haemostasis, Boston, MA, USA, Jul. 11-16, 2009. (Best Available Copy).
Third Party Pre-Issuance Submission I Under 37 C.F.R. §1.290, submitted Nov. 3, 2015 in U.S. Appl. No. 14/430,848, filed Mar. 24, 2015 (371(c) date).
Third Party Pre-Issuance Submission II Under 37 C.F.R. §1.290, submitted Nov. 3, 2015 in U.S. Appl. No. 14/430,848, filed Mar. 24, 2015 (371(c) date).
Non-Final Office Action dated Feb. 19, 2015 in U.S. Appl. No. 13/793,796, filed Mar. 11, 2013.
Final Office Action dated Jun. 1, 2015 in U.S. Appl. No. 13/793,796, filed Mar. 11, 2013.
Notification of Material Filed Under Section 27 mailed Jan. 12, 2016 in Australian Patent Application No. 2011274414, filed Jul. 11, 2011, 13 pages.
Shapiro, A.D., et al., "Abstracts of the XXIXth International Congress of the World Federation of Hemophilia," Haemophilia 16(Suppl. 4):1-158, Abstract 07FP07 at 30, Buenos Aires, Argentina, Jul. 10-14, 2010.
Biogen Idec and Swedish Orphan Biovitrum, "Biogen Idec and Swedish Orphan Biovitrum Present Data on Long-Lasting Hemophilia B Therapy at the World Federation of Hemophilia Congress," Jul. 12, 2010, Weston, Mass. and Stockholm, Sweden, accessed at http://www.sobi.com/PageFiles/352/FIXFc_20100712.pdf, 3 pages.
Page, D., "The Blood Factor: Breakthrough in factor IX products, Canadian study results point to importance of early prophylaxis," *Hemophilia Today* 45(3):29, Canadian Hemophilia Society, Canada (Nov. 2010).
Communication pursuant to Article 94(3) EPC, dated Mar. 4, 2016, for EP Application No. EP11804476.7, European Patent Office, Germany, 6 pages.
Beal, S.L., "Ways to Fit a PK Model with Some Data Below the Quantification Limit," Journal of Pharmacokinetics and Pharmacodynamics 28(5):481-504, Plenum Publishing Corporation, United States (2001).
Bergstrand, M. and Karlsson, M.O., "Handling Data Below the Limit of Quantification in Mixed Effect Models," The AAPS Journal 11(2):371-380, American Association of Pharmaceutical Scientists, United States (2009).
Björkman, S., and Åhlén, V., et al., "Population Pharmacokinetics of Plasma-Derived Factor IX in Adult Patients with Haemophilia B: Implications for Dosing in Prophylaxis," European Journal of Clinical Pharmacology 68(6):969-977, Springer-Verlag, Germany (2012).
Björkman, S., et al., "Pharmacokinetics of Factor IX in Patients With Haemophilia B, Methodological Aspects and Physiological Interpretation," European Journal of Clinical Pharmacology 46(4):325-332, Springer-Verlag, Germany (1994).
Björkman, S., et al., "Pharmacokinetics of Recombinant Factor IX in Relation to Age of the Patient: Implications for Dosing in Prophylaxis," Haemophilia 7(2):133-139, Blackwell Science Ltd., England (2001).
Björkman, S., "Population Pharmacokinetics of Recombinant Factor IX: Implications for Dose Tailoring," Haemophilia 19(5):753-757, John Wiley & Sons Ltd., England (2013).
Brendel, K., et al., "Are Population Pharmacokinetic and/or Pharmacodynamic Models Adequately Evaluated? A Survey of the Literature from 2002 to 2004," Clinical Pharmacokinetics 46(3):221-234, Adis Data Information BV, New Zealand (2007).
Byon, W., et al., "Establishing Best Practices and Guidance in Population Modeling: An Experience with an Internal Population Pharmacokinetic Analysis Guidance," CPT: Pharmacometrics & Systems Pharmacology 2:e51:1-8, ASCPT, United States (2013).
Chang, C.W., et al., "Non-Ionic Amphiphilic Biodegradable PEG-PLGA-PEG Copolymer Enhances Gene Delivery Efficiency in Rat Skeletal Muscle," Journal of Controlled Release 118(2):245-253, Elsevier B.V., Netherlands (2007).

Chitlur, M., et al, "Inhibitors in factor IX deficiency a report of the ISTH-SSC international FIX inhibitor registry (1997-2006)," Haemophilia 15(5):1027-1031, Blackwell Publishing Ltd., England (2009).
Dimichele, D., "Inhibitor Development in Haemophilia B: an Orphan Disease in Need of Attention," British Journal of Haematology 138(3):305-315, Blackwell Publishing Ltd., England (2007).
Dimichele, D., "Inhibitors: Resolving Diagnostic and Therapeutic Dilemmas," Haemophilia 8(3):280-287, Blackwell Science Ltd., England (2002).
Ette, E.I. and Ludden, T.M., "Population Pharmacokinetic Modeling: the Importance of Informative Graphics," Pharmaceutical Research 12(12):1845-1855, Plenum Publishing Corporation, United States (1995).
Extended European Search Report for Application No. EP 13842864.4, Munich, Germany, dated Apr. 11, 2016, 8 pages.
Order No. 18., "Suspending Procedural Schedule, Inv. No. 337-TA-1066.," United States International Trade Commission, Washington D.C., Feb. 7, 2018.
Food and Drug Administration, "Guidance for Industry on Population Pharmacokinetics; Availability," Federal Register 64(27):6663-6664, Food and Drug Administration, HHS, United States (1999).
Giangrande, P., "Haemophilia B: Christmas Disease," Expert Opinion on Pharmacotherapy 6(9):1517-1524, Ashley Publications Ltd., England (2005).
Gui, T., et al., "Circulating and Binding Characteristics of Wild-type Factor IX and Certain Gla Domain Mutants in Vivo," Blood 100(1):153-158, American Society of Hematology, United States (2002).
Jonsson, E.N. and Karlsson, M.O., "Xpose—an S-PLUS Based Population Pharmacokinetic/pharmacodynamic Model Building Aid for NONMEM," Computer Methods and Programs in Biomedicine 58(1):51-64, Elsevier Science Ireland Ltd., Ireland (1999).
Karlsson, M.O. and Sheiner, L.B., "The Importance of Modeling Interoccasion Variability in Population Pharmacokinetic Analyses," Journal of Pharmacokinetics and Biopharmaceutics 21(6):735-750, Plenum Publishing Corporation, United States (1993).
Kiang, T.K.L., et al., "Fundamentals of Population Pharmacokinetic Modelling, Modelling and Software," Clinical Pharmacokinetics 51(8):515-525, Springer International Publishing AG, New Zealand (2012).
Kuo, T.T. and Aveson, V.G., "Neonatal Fc Receptor and IgG-based Therapeutics," mAbs 3(5):422-430, Landes Bioscience, United States (2011).
Lambert, C. and Prange, R., "Posttranslational N-glycosylation of the hepatitis B Virus Large Envelope Protein," Virology Journal 4:45, BioMed Central Ltd., England, 9 pages (2007).
Lindbom, L., et al., "Perl-speaks-NONMEM (PsN)—a Perl Module for NONMEM Related Programming," Computer Methods and Programs in Biomedicine 75(2):85-94, Elsevier Ireland Ltd., Ireland (2004).
Mahmood, I., "Theoretical Versus Empirical Allometry: Facts Behind Theories and Application to Pharmacokinetics," Journal of Pharmaceutical Sciences 99(7):2927-2933, Wiley-Liss, Inc. and the American Pharmacists Association, United States (2010).
Mannucci, P.M. and Tuddenham, E.G.D., "The Hemophilias—from Royal Genes to Gene Therapy," The New England Journal of Medicine 344(23):1773-1779, Massachusetts Medical Society, United States (2001).
Martinowitz, U., et al., "Pharmacokinetic Properties of IB1001, an Investigational Recombinant Factor IX, in Patients With Haemophilia B: Repeat Pharmacokinetic Evaluation and Sialylation Analysis," Haemophilia 18(6):881-887, Blackwell Publishing Ltd., England (2012).
Mei, B., et al., "Expression of Human Coagulation Factor VIII in a Human Hybrid Cell Line, HKB11," Molecular Biotechnology 34(2):165-178, Humana Press Inc., United States (2006).
Neumann, E., et al., "Gene Transfer into Mouse Lyoma Cells by Electroporation in High• Electric Fields," The EMBO Journal 1(7):841-845, IRL Press Limited, England (1982).
Roopenian, D.C. and Akilesh, S., "FcRn: the Neonatal Fc Receptor Comes of Age," Nature Reviews Immunology 7(9):715-725, Nature Publishing Group, England (2007).

(56) References Cited

OTHER PUBLICATIONS

Savic, R.M. and Karlsson, M.O., "Importance of Shrinkage in Empirical Bayes Estimates for Diagnostics: Problems and Solutions," The AAPS Journal 11(3):558-569, American Association of Pharmaceutical Scientists, United States (2009).
Shapiro, A.D., "Recombinant factor IX-Fc fusion protein (rFIXFc) demonstrates safety and prolonged activity in a phase 1/2a study in hemophilia B patients," Blood 119(3):666-672, The American Society of Hematology, United States (2012).
Sherwin, C.M.T., et al., "Fundamentals of Population Pharmacokinetic Modelling, Validation Methods," Clinical Pharmacokinetics 51(9):573-590, Springer International Publishing AG, New Zealand (2012).
Srivastava, A., et al., "Guidelines for the Management of Hemophilia," Haemophilia 19(1):e1-e47, Blackwell Publishing Ltd., England (2013).
Wade, J.R., et al., "A Guide for Reporting the Results of Population Pharmacokinetic Analyses: a Swedish Perspective," The AAPS Journal 7(2):45:E456-E460, American Association of Pharmaceutical Scientists, United States (2005).
Wigler, M., et al., "Biochemical Transfer of Single-Copy Eucaryotic Genes Using Total Cellular DNA as Donor," Cell 14(3):725-731, Cell Press, United States (1978).
Xu, X.S., et al., "Shrinkage in Nonlinear Mixed-effects Population Models: Quantification, Influencing Factors, and Impact," The AAPS Journal 14(4):927-936, American Association of Pharmaceutical Scientists, United States (2012).
Response to Complaint's Motion for Termination of Investigation and Motion for Suspension of Procedural Schedule Pending Ruling on Motion for Termination., Inv. No. 337-TA-1066, United States International Trade Commission, Washington D.C., Feb. 8, 2018.
Docket Navigator, "Filings for Recombinant Factor IX Products ITC-337-TA-1066," Feb. 6, 2018. 6 pages.
Peters, R., Slides entitled *"Improved Pharmacokinetics of Factor IX as a Monomeric Fc Fusion Protein,"* presented at National Hemophilia Foundation Workshop Mar. 30, 2006, 11 pages.
International Search Report and Written Opinion for Application No. PCT/US2013/061747, ISA/US, Alexandria, Virginia, United States, dated Dec. 16, 2013, 9 pages.
Non-Final Office Action dated Aug. 11, 2016, in U.S. Appl. No. 14/430,848, inventors Pierce, G., et al., filed Sep. 25, 2013.
Non-Final Office Action dated Sep. 15, 2016, in U.S. Appl. No. 13/809,276, inventors Pierce, G., et al., 371(c) date Apr. 24, 2013.
Non-Final Office Action dated Jun. 2, 2016, in U.S. Appl. No. 15/043,457, inventors Pierce, G., et al., filed Feb. 12, 2016.
Final Office Action dated Dec. 12, 2016, in U.S. Appl. No. 14/430,848, inventors Pierce, G., et al., filed Sep. 25, 2013.
Final Office Action dated Nov. 30, 2016, in U.S. Appl. No. 15/043,457, inventors Pierce, G., et al., filed Feb. 12, 2016.
National Hemophilia Foundation, "Hemophilia B," hemophilia.org, accessed at https://www.hemophilia.org/Bleeding-Disorders/Types-of-Bleeding-Disorders/Hemophilia-B, accessed on Mar. 4, 2014, 2 pages.
Complaint and Statement of Public Interest, "Certain Recombinant Factor IX Products, Inv. No. 337-TA-," International Trade Commission, Washington D.C., Jul. 7, 2017. 41 pages.
Respondent, "Verified Response to the Complaint of Bioverativ Inc., Bioverativ Therapeutics, Inc., and Biovemtiv U.S. LLC under Section 337 of the Tariff Act of 1930 and Notice of Investigation," Inv. No. 337-TA-1066, International Trade Commission, Washington D.C., Sep. 5, 2017. 58 pages.
Respondent, "Respondent Recombinant Facility AG's Notice of Prior Art," Inv. No. 337-TA-1066, International Trade Commission, Washington D.C., Dec. 1, 2017. 78 pages.
Initial Markman Brief, "Bioverativ's Initial Markman Brief, Inv. No. 337-TA-1066," International Trade Commission, Washington D.C., Nov. 20, 2017, 422 Pages.
Respondent's Opening Markman Brief, "Respondent's Opening Markman Brief Inv. No. 337-TA-1066," International Trade Commission, Washington D.C., Nov. 20, 2017, 49 Pages.
Corrected Rebuttal, "Bioverativ's Corrected Rebuttal Markman Brief Inv. No. 337-TA-1066," International Trade Commission, Washington D.C., Dec. 18, 2017, 22 Pages.
Rebuttal, "Bioverativ's Rebuttal Markman Brief Inv. No. 337-TA-1066," International Trade Commission, Washington D.C., Dec. 11, 2017, 35 Pages.
Co-pending Application, U.S. Appl. No. 15/890,284, inventors Pierece, G., et al., filed Feb. 6, 2018 (Not Published).
WIR Staff, "Biogen Idec, Syntonix Deal," BioCentury, Jan. 8, 2007, 1 page.
Abrahamson et al., "Intestinal Absorption of Immune Complexes by Neonatal Rats: A Route of Antigen Transfer from Mother to Young," Science 206(2): 567-569, (Nov. 1979).
Abstracts, Haemophilia 16 (Suppl. 4): 1-158 (2010).
ACTEMRA® (Tocilizumab) Highlights of Prescribing Information, United States Food and Drug Administration, (2013), 43 pages.
Adcock et al., "The Value of the Chromogenic Activity Assay in Diagnosis and Therapeutic Monitoring of Hemophilia," (Jan. 23, 2017), 12 pages.
Szymkowski, "Advancing Protein Therapeutics: Engineering the Next Generation of Proteins for Therapeutics and Current Challenges in Protein Therapeutics (Part I)," IDdb Meeting Report. Xencor Inc., Monrovia CA, USA, (2006), 7 pages.
Ahouse et al., "Mouse MHC class I like Fc receptor encoded outside the MHC," The Journal of Immunology 151:6076-6088, (Dec. 1, 1993), 14 pages.
Alphanine® SD Product Label, Mar. 2014, 31 pages.
Andersen et al., "The Versatile MHC Class I—Related FcRn Protects IgG and Albumin from Degradation: Implications for Development of New Diagnostics and Therapeutics," Drug Metab. Pharmacokinet. 24(4):318-322, (2009).
Andersen et al., "The conserved histidine 166 residue of the human neonatal Fc receptor heavy chain is critical for the pH-dependent binding to albumin," Eur. J. Immunology 36:3044-3051, Wiley, United States, (2006).
Andersen et al., "Cross-species Binding Analyses of Mouse and Human Neonatal Fc Receptor Show Dramatic Differences in Immunoglobulin G and Albumin Binding," The Journal of Biological Chemistry 285: 4826-4836, American Society for Biochemistry and Molecular Biology, (Feb. 12, 2010).
Andersen et al., "Single-chain Variable Fragment Albumin Fusion Bind the Neonatal Fc Receptor (FcRn) in a Species-dependent Manner," The Journal of Biological Chemistry 288: 24277-24285, American Society for Biochemistry and Molecular Biology, United States, (Aug. 16, 2013).
Final Office Action dated Feb. 17, 2017, in U.S. Appl. No. 15/043,445, inventors Pierce, G., et al., filed Feb. 12, 2016.
Anderson et al., "Perspective—FcRn Transports Albumin: Relevance to Immunology and Medicine," Trends in Immunolgy 27: 343-348, Elsevier, (Jul. 2006).
Non-Final Office Action dated Sep. 7, 2016, in U.S. Appl. No. 15/043,445, inventors Pierce, G., et al., filed Feb. 12, 2016.
Final Office Action dated Nov. 29, 2016, in U.S. Appl. No. 15/043,455, inventors Pierce, G., et al., filed Feb. 12, 2016.
Arnold et al., "The impact of glycosylation on the biological function and structure of human immunoglobulins," Annual Review of Immunology 25: 21-50, (Feb. 2007).
Aruffo et al., "CD44 is the Principal Cell Surface Receptor for Hyaluronate," Cell 61:1303-13, Cell Press, United States (Jun. 29, 1990).
ARZERRA® (Ofatumumab) Highlights of Prescribing Information, United States Food and Drug Administration, 2016.
Ashkenazi et al., "Protection Against Endotoxic Shock by a Tumor Necrosis Factor Receptor Immunoadhesin," Medical Sciences 88:10535-10539, Proc. Natl Acad Science University, United States (Dec. 1991).
Avisar et al., "First-in-Human, Phase I/IIa Dose-Escalation and Safety Study of Balugrastim in Breast Cancer Patients Receiving Myelosuppressive Chemotherapy," Cancer Chemotherapy Pharmacology, 75:929-939, Springer, Germany (May 2015).
Bain et al., "A Phase 2 Study to Evaluate the Antiviral Activity, Safety, and Pharmacokinetics of Recombinant Human Albumin-

(56) References Cited

OTHER PUBLICATIONS

Interferon Alfa Fusion Protein in Genotype 1 Chronic Hepatitis C Patients," Journal of Hepatology 44:671-678, Elservier, Netherlands (2006).

Autmizguine et al., "Rilonacept Pharmacokinetics in Children with Systemic Juvenile Idiopathic Arthritis," Journal of Clinical Pharmacology 55:39-44, Wiley, United States (Jan. 2015).

AVASTIN® (Panitumumab) Highlights of Prescribing Information, United States Food and Drug Administration, 2016.

Baker et al, "Cross-presentation of IgG containing immune complexes," Cell Mol Life Science 70:1319-1334, Springer, United States (2012).

Baker et al., "Immune and non-immune functions of the (not so) neonatal Fc receptor, FcRn.," Semin Immunopathology, 31:223-236, Springer, United States, (Jul. 2009).

Baker et al., "Neonatal Fc receptor for IgG (FcRn) regulates cross-presentation of IgG immune complexes by CD8-CD11b dendritic cells,", Immunology, 108:9927-9932, Proceedings of the National Academy of Sciences of the United States of America, United States, (Jun. 14, 2011).

Barrowcliffe, "Insights from Factor IX Activation Studies with Chromogenic Assays: Implications of Disparate Product Results," Haemophilia 16:9-12, Blackwell Publishing Ltd., United States (2010).

Barrowcliffe, "Laboratory Testing and Standardization," Haemophilia 19:799-804, Wiley, United States, (2013).

Barrowcliffe et al., "Standards and Monitoring Treatment," Haemophilia 18:61-65, Blackwell Publishing Ltd., United States (2012).

Bebulin® VH Product Label, Mar. 2011.

Beck et al., "Strategies and challenges for the next generation of therapeutic antibodies," Immunology 10: 345-352, Macmillan Publishers, United Kingdom, (2010).

Beck et al., "Therapeutic antibodies and derivatives: from the bench to the clinic," Current Pharmaceutical Biotechnology, 9: 421-422, (2008), 2 pages.

Beck, "Biosimilar, biobetter and next generation therapeutic antibodies," mAbs, 3(2):107-110, 2011.

Behr et al., "Reducing the Renal Uptake of Radiolabeled Antibody Fragments and Peptides for Diagnosis and Therapy: Present Status, Future Prospects and Limitations," European Journal of Nuclear Medicine 25:201-212, Springer-Verlag, Germany, (Feb. 1998).

BeneFix FDA label, BenefFix Circular-Wyeth Biopharma for United States, Sep. 13, 2006, 2 pages.

BeneFix, Summary of Product Characteristics 2010, 34 pages.

BENEFIX® Pfizer Wyeth Summary of Product Characteristics, EMEA 1997, 80 pages.

BENLYSTA® (Belimumab) Highlights of Prescribing Information, United States Food and Drug Administration, 22 pages, 2012.

Bennett et al., "Extracellular Domain-IgG Fusion Proteins for Three Human Natriuretic Peptide Receptors," The Journal of Biological Chemistry 266:23060-23067, The American Society for Biochemistry and Molecular Biology, Inc., United States (Dec. 1991).

Bergman, "Progress in the Treatment of Bleeding Disorders," Thrombosis Research 127: S3-S5, Elservier, Netherlands (2011).

Berntorp et al., "Modern Haemophilia Care," Lancet 379:1447-1456, Elsevier, Netherlands, (Apr. 14, 2012).

Berntorp et al., "Pharmacokinetic Dosing in Prophylactic Treatment of Hemophilia A," European Journal of Haematology, 51:247-252, Wiley, United States (1993).

Bezemer et al., "F9 Malmo, Factor IX and Deep Vein Thrombosis," Haematologica, 94:693-699, Ferrata Storti Foundation, Italy (2009).

Bienvenu et al., "Recombinant Soluble P-Selectin Glycoprotein Ligand-1-Ig Reduces Restenosis Through Inhibition of Platelet-Neutrophil Adhesion After Double Angioplasty in Swine," Circulation, 103:1128-1234, American Heart Association, United States (2000).

BIIB—Biogen Idec Inc. Hemophilia R&D Roundtable—Final Transcript, 29 pages, Sep. 28, 2010.

BIIB—Biogen Idec Research & Development Day—Breakout Session Final Transcript, 19 pages, Mar. 25, 2009.

Pierce et al., "Muscial parents," BioCentury, 4 pages, Mar. 22, 1999.

WIR Staff, "Long Acting rFactorIX: Interim Phase III data," Biocentury, 5 page, Sep. 7, 2015.

Trista, M., "Biogen Idec Acquires Syntonix, Moves into Hemophilia Arena," BIOWORLD Today 18(4), 2 pages, Jan. 5, 2007.

Biogen Idec agrees to acquire Syntonix, ESPICOM Pharmaceutical and Medical Device News, Jan. 5, 2007.

Biogen Idec and Biovitrum Announce Decision to Advance Long-Acting Hemophilia B Therapy into Registrational Trial, Business Wire, 2 pages, Oct. 19, 2009.

Biogen Idec and Swedish Orphan Biovitrum Present Data on Long-Lasting Hemophilia B Therapy at the World Federation of Hemophilia Congress, 3 pages, Jul. 12, 2010.

Non-Final Office Action dated May 19, 2016, in U.S. Appl. No. 15/043,455, inventors Pierce, G., et al., filed Feb. 12, 2016.

Biogen Idec Australia Pty Ltd, Extract from the Clinical Evaluation Report for Eftrenonacog Alfa, Austrlian Government, Department of Health Therapeutic Goods Administration, 46 pages, Sep. 29, 2013.

"Biogen Idec buys Syntonix in $120M deal," Pharma Marketletter, Jan. 15, 2007, 2 pages.

"Biogen Idec to acquire Syntonix," Business Wire, Jan. 4, 2007, 3 pages.

Biogen Idec, 2007 Research & Development Day, May 17, 2007, 189 pages.

Biogen Idec, American Thrombosis and Hemostasis Network (ATHN), National Hemophilia Foundation, Puget Sound Blood Center hematology news, BioCentury, Nov. 12, 2012, 1 page.

WIR Staff, "Long Acting rFactor IX regulatory update," BioCentury, Jul. 28, 2014, 1 page.

BC Staff, "Biogen Idec, Swedish Orphan Biovitrum amend deal," BioCentury, Feb. 18, 2010, 1 page.

Biogen Idec, Swedish Orphan Biovitrum Clinical Data (Phase I/II) (Hemophilia), R&D Focus Drug News, 2 pages, Jul. 12, 2010.

Biogen Idec, Swedish Orphan Biovitrum Licensing Agreement Modified, R&D Focus Drug News, 2 pages, Feb. 24, 2010.

Biogen Idec, Swedish Orphan Biovitrum Phase Change II/III, USA (Hemophilia), R&D Focus Drug News, 2 pages, Jan. 28, 2010.

Biogen Quarterly Report, form 10-Q, United States Securities and Exchange Commission, 80 pages, Oct. 2009.

Letter from Department of Health & Human Services, RE:BL 103677/5261, Biogen Summary of Product Characteristics—Annex I, II, III, 1 page, dated Jul. 11, 2016.

Clarke, "Biogen to build blood disorder drug franchise," Reuters Health, 4 pages, Mar. 4, 2011.

Heat Stress Stability of GPG-290, Excel, Undated.

Biogen, Alprolix-Product-Monograph, Coagulation Factor IX (Recombinant),Fc Fusion Protein, 28 pages, Nov. 19, 2015.

BC Staff, "Doubling up for half-life," Biocentury, 2 pages, Feb. 12, 2007.

Bouchie, "Global Reinvention," BioCentury, 3 pages, Sep. 22, 2008.

Exhibit E to Bioverativ's Response to Initial Invalidity Disclosures, ITC Inv. No. 337-TA-1066, dated Dec. 8, 2017, 70 pages.

Biogen, Projects in pre-clinical development: FIXFc for treatment of hemophilia B, 5 pages, Feb. 23, 2008.

Zheng et al., "Influence of Glycosylation Pattern on the Molecular Properties of Monoclonal Antibodies," mAbs 6(3):649-658, Landes Bioscience, United States (2014).

BC Staff, "Specialty Plays," BioCenutry, Jan. 15, 2007, 1 page.

"Biotechnology company deals with other biotechnology companies: Jan. 19-Apr. 19, 2006," Bioworld Financial Watch 14(17), Apr. 24, 2006, 20 pages.

"Biovitrum and Syntonix Dose First Hemophilia B Patient in Clinical Trial of a Novel Factor IXFc Treatment," Biovitrum AB, May 27, 2008, 2 pages.

"Biovitrum and Syntonix Dose First Hemophilia B Patient in Novel Factor IXFc Trial," ProusScienceDailyEssentials, May 28, 2008, 1 page.

"Biovitrum and Syntonix Sign Agreement for Long-Acting Recombinant Factor IX," ProusScienceDailyEssentials, Jan. 25, 2006, 1 page.

(56) References Cited

OTHER PUBLICATIONS

"Biovitrum and Syntonix sign Factor IX accord," Pharma Marketletter, Jan. 30, 2006, 1 page.
BC Staff, "Biovitrum pipeline," BioCentury, Sep. 22, 2008, 1 page.
BC Staff, "Biovitrum, Syntonix hemophilia deal," BioCentury, Jan. 23, 2006, 1 page.
"Biovitrum's and Syntonix's Novel Factor IXFc for Hemophilia B Has Received Orphan Drug Designation From the FDA," FierceBiotech, Nov. 25, 2008, accessed at http://www.fiercebiotech.com/biotech/biovitrum-s-and-syntonix-s-novel-factor-ixfc-for-hemophilia-b-has-received-orphan-drug, 3 pages.
"Syntonix, Biovitrum in Clotting Product Deal," BioWorld Week 14(5), Jan. 30, 2006, 2 pages.
Bjorkman et al., "Pharmacokinetics of Recombinant Factor IX in Relation to Age of the Patent: Implications for Dosing in Prophylaxis," Haemophilia 7:133-139, 2001.
Bjorkman et al., "Population pharmacokinetics of plasma-derived factor IX in adult patients with haemophilia B: implications for dosing in prophylaxis," Eur J Clin Pharmacol 68:969-977 (2012).
"Biovitrum Enters FIX:Fc Agreement with Syntonix," ESPICOM Pharmaceutical and Medical Device News, Jan. 24, 2006, 1 page.
Bowyer et al., "Measuring Factor IX Activity of Nonacog Beta Pegol with Commercially Available One-Stage Clotting and Chromogenic Assay Kits: A Two-Center Study," J Thromb Haemos 14:1428-1435, 2016.
Brambell et al., "A theoretical model of gamma-globulin catabolism," Nature 203:1352-1355, 1964.
Brambell, F.W., "Resemblances between passive anaphylactic sensitization and transmission of passive immunity," Nature 199:1164-1166, 1963.
Brekkan et al., "Population Pharmacokinetics of Plasma-Derived Factor IX: Procedures for Dose Individualization," J Thromb Haemos 14:724-732, 2016.
Brønden et al., "Clinical Pharmacokinetics and Pharmacodynamics of Albiglutide," Clin Pharmacokinet 56:719-731, 2017.
Bruno et al., "Population Pharmacokinetics of Trastuzumab in Patients with HER2+ Metastatic Breast Cancer," Cancer Chemother Pharmacol 56:361-369, 2005.
Burmeister et al., "Crystal structure at 2.2 a resolution of the MHC-related neonatal Fc receptor," Nature 372:336-343, 1994.
Burmeister et al., "Crystal structure of the complex of rat neonatal Fc receptor with Fc," Nature 372:379-383, 1994.
Bush et al., "Safety, tolerability, Pharmacodynamics and Pharmacokinetics of Albiglutide, a Long-Acting Glucagon-Like Peptide-1 Mimetic, in Healthy Subjects," Diabetes, Obesity and Metabolism 11:498-505, 2009.
Buyue et al., FVIII28, Product-Specific Calibration Standards Do Not Correct One-Stage Clotting Assay Discrepancies for Modified Recombinant FIX Molecules with Reagents that Significantly Over- or Under-Recover Labeled Potency, Thrombosis and Haemostasis 14:1-168 at p. 52, 2016.
Byrn et al., "Biological Properties of a CD4 Immunoadhesin," Nature 344:667-670, Apr. 1990.
CAMPATH® (Alemtuzumab) Highlights of Prescribing Information, United States Food and Drug Administration, 2009.
Capon et al., "Designing CD4 Immunoadhesins for AIDS Therapy," Nature 337:525-531, Feb. 1989.
Carcao, M. et al., "Prophylactic factor replacement in hemophilia," Blood Reviews 18:101-113, 2004.
Chalupny et al., "T-cell activation molecule 4-1BB binds to Extracellular Matrix Proteins," PNAS 89:10360-10364, Nov. 1992.
Chan, A., "Pharmacokinetics, Safety and Efficacy Results of a Phase III Study of rIX-FP in 27 Children with Hemophilia B," 2015, 52 pages.
Chang, "Biodistribution and Pharmacokinetics of Transgenic Pig-produced Recombinant Human Factor IX (rhFIX) in Rats," In Vivo 22:693-698, 2008.
Chang, "Glycosylation of the Activation Peptide of Factor IX Determines Plasma Half-Life," J Thromb Haemost 5:(suppl2) [O-M-088], 2007.
Chapter 5: Pharmacokinetics of tg-FIX in the Factor IX-Knockout Mouse Hemophilia B Animal Model, 2004, 38 pages.
Chaudhury et al, "The Major Histocompatibility Complex-related Fc Receptor for IgG (FcRn) Binds Albumin and Prolongs Its Lifespan," J Exp Med 3:315-322, Feb. 3, 2003.
Chaudhury et al., "Albumin Binding to FcRn: Distinct from the FcRn-IgG Interaction," Biochemistry 45:4983-4990, 2006.
Christiansen, "Comparable in-Vitro Potency and Efficacy of 40K PEG-rFIX and BeneFIX® in TEG® in Haemophilia B Patient," Blood, Haemophlia 16(Suppl4) 1-158, at 08P05, 2010.
Christiansen, et al., "Effect of 40K PEG-rFIX in blood from haemophilia B patients using thromboelastography, ( TEG®)," 2009.
Christiansen, et al., "Effect of 40K PEG-Rfix in blood from hemophilia B patients using thromboelastography (TEG®)," Thrombosis and Haemostasis 7(Suppl. 2): 1-1204 at PP-WE-590, 2009.
Clinical Pharmacology BLA Review p. 1- 25, Jan. 8, 2013.
ClinicalTrials.gov archive, NCT01233440, Safety and Pharmacokinetic Study of a Recombinant Coagulation Factor IX Albumin Fusion Protein in Subjects with Hemophilia B, first posted Nov. 3, 2010, last updated Jan. 31, 2012.
ClinicalTrials.gov archive, NCT01361126, A Safety and Efficacy Study of a Recombinant Factor IX in Patients with Severe Hemophilia B, first posted May 26, 2011, last updated May 9, 2016.
ClinicalTrials.gov archive, NCT00956345, Safety of 40K Pegylated Recombinant Factor IX in Non-Bleeding Patients with Haemophilia B, first posted Aug. 11, 2009, last posted Jan. 20, 2017.
ClinicalTrials.gov archive, NCT01027364, Study of Recombinant Factor IX Fc Fusion Protein (rFIXFc) in Subjects with Hemophilia B, first posted Dec. 7, 2009, last posted Mar. 28, 2017.
"CNS Deal with Elbion, Too," BIOWORLD Today 18(25), Feb. 6, 2007, 3 pages.
Cohen-Barak et al., "Assessment of the Pharmacokinetics, Pharmacodynamics, and Safety of Single Doses of TV-1106, a Long-Acting Growth Hormone, in Healthy Japanese and Caucasian Subjects," Clin Pharm in Drug Dev 6(4):331-342, 2017.
Cohen-Barak et al., "Safety, Pharmacokinetic and Pharmacodynamic Properties of TV-1106, a Long-Acting GH Treatment for GH Deficiency," Eur J Endocrinology 173:541-551, 2015.
Collins et al, "Factor VIII Requirement to Maintain a Target Plasma Level in Prophylactic Treatment of Severe Hemophilia A: Influences Variance in Pharmacokinetics and Treatment Regimens," J Thromb Haemos 8:269-275, 2010.
Collins et al., "Diagnosis and Treatment of Factor VII and IX Inhibitors in Congenital Haemophilia. (4th edition)," Brit J Haematology 160:153-170, 2013.
Collins et al., "The Use of Enhanced Half-Life Coagulation Factor Concentrates in Routine Clinical Practice: Guidance from UKHCDO," Haemophilia 22:487-498, 2016.
Choy, M. "Pharmaceutical Approval Update," P&T® 41(11): 677, 682, and 712, 2016.
Collins et al., "Implications of Coagulation Factor VIII and IX Pharmacokinetics in the Prophylactic Treatment of Haemophilia," Haemophilia 17:2-10, 2011.
Collins, "Recombinant Long-Acting GlycoPEGylated Factor IX in Hemophilia B: A Multinational Randomized Phase 3 Trial," Blood 124(26):3880-3886, Dec. 18, 2014.
Coppola et. al. "Treatment of Hemophilia: a Review of Current Advances and Ongoing Issues," J Blood Medicine 1:183-195, 2010.
COSENTYX® (Secukinumab) Highlights of Prescribing Information, United States Food and Drug Administration, 2016.
CSL Behring Gerinnungsforum 2016, Klinische Studiendaten rIX-FP, Oct. 21, 2016, 52 pages.
Dickneite et al., "CSL Behring, Preclinical Research & Development, Recombinant Factor IX Albumin Fusion Protein—Preclinical Investigations to Evaluate and Define a Development Candidate," Jun. 25, 2011, 84 pages.
Cunningham et al., "Quality Assurance in Hemostasis: The Perspective from the College of American Pathologists Proficiency Testing Program," Semin Thromb Hemost 33:250-258, 2007.
CYRAMZA® (Ramucirumab) Highlights of Prescribing Information, United States Food and Drug Administration, 2017.

(56) References Cited

OTHER PUBLICATIONS

Dall'Acqua et al., "Properties of human IgG1s engineered for enhanced binding to the neonatal Fc receptor (FcRn)," J Biol Chem 281(33):23514-23524, 2006.
Dall'Acqua et al., "Increasing the affinity of a human IgG1 for the neonatal Fc receptor: biological consequences," J Immunol 169:5171-5180, 2002.
Dargaud & Negrier, "Haemophilia therapies, Peptides, Proteins & Antisense," Expert Opin Biol Ther 7(5):651-663, 2007.
Datta-Mannan et al., "Monoclonal antibody clearance. Impact of modulating the interaction of IgG with the neonatal Fc receptor," J Biol Chem 282(3):1709-1717, 2007.
Den Uijl et al., "Analysis of Low Frequency Bleeding Data: The Association of Joint Bleeds According to Baseline FVIII Activity Levels," Haemophilia 17:41-44, 2011.
Den Uijl et al., "Clinical Outcome of Moderate Haemophilia Compared with severe and Mild Haemophilia," Haemophilia 15:83-90, 2009.
Deng et al., "Pharmacokinetics of Humanized Monoclonal Anti-Tumor Necrosis Factor-{alpha} Antibody and its Neonatal Fc Receptor Variants in Mice and Cynomolgus Monkeys," Drug Metabolism and Disposition 38(4):600-605, 2010.
Deng et al., "Projecting Human :Pharmacokinetics of Therapeutic Antibodies from Nonclinical Data," mABS 3(1):61-66, Jan. 2011.
Denson et al., "An Investigation of Three Patients with Christmas Disease Due to an Abnormal Type of Factor IX," J Clin Path 21:160-165, 1968.
Diao et al., "Population Pharmacokinetic Modelling of Recombinant Factor IX Fc Fusion Protein (rFIXFc) in Patients with Haemophilia B," Clin Pharmokinet 53:467-477, 2014.
Dingermann, T., "Recombinant Therapeutic Proteins: Production Platforms and Challenges," Biotechnol J 3:90-97, 2008.
Dodt et al., "Potency Determination of Factor VIII and Factor IX for New Product Labelling and Post Infusion Testing: Challenges for Caregivers and Regulators," Haemophilia 21:543-549, 2015.
Doronina et al., "Enhanced Activity of Monomethylauristatin F Through Monoclonal Antibody Delivery: Effects of Linker Technology on Efficacy and Toxicity," Bioconjugate Chemistry 17(1):114-124, 2006.
Ducongé, "Interspecies Scaling of the Monoclonal Anti-EGF Receptor or EGF/r3 Antibody Disposition Using Allometric Paradigm: is it Really Suitable?," Biopharmaceutics & Drug Disposition 25:177-186, 2004.
Ducore et al., "Alprolix (recombinant Factor IX Fc fusion protein): extended half-life product for the prophylaxis and treatment of hemophilia B," Expert Rev. Hematol. 7(5):559-571, 2014.
Dumont et al., "Monomeric Fc Fusion Technology: An Approach to Create Long-Lasting Clotting Factors," Therapeutic Proteins: Strategies to Modulate Their Plasma Half-lives, First Edition, Chapter 10:189-206, Wiley-VCH Verlag GmbH & Co. KgaA, 2012.
ELOCTATE® (Efmoroctocog alpha) Highlights of Prescribing Information, United States Food and Drug Administration, 2017.
ENBREL® (Etanercept) Highlights of Prescribing Information, United States Food and Drug Administration, 2017.
Enbrel® Package Insert, Jun. 5, 2003, 23 pages.
EPAR Summary for the Public—Alprolix, European Medicines Agency, 2016, 3 pages.
European Medicines Agency, Assessment Report, Alprolix, International Non- Proprietary Name: eftrenonacog alfa, Feb. 25, 2016, 98 pages.
European Medicines Agency, Assessment Report, Idelvion, International Non-Proprietary Name: albutrepenonacog alfa, Feb. 25, 2016, 117 pages.
European Medicines Agency Decision, P/123/2011, Jun. 7, 2011, 8 pages.
European Medicines Agency, Recommendation for maintenance of orphan Designation at the time of marketing authorization—Alprolix (eftrenonacog alfa) for the treatment of haemophilia B, May 24, 2016, 2 pages.
Ewensiein et al., "Pharmacokinetic analysis of plasma-derived and recombinant FIX concentrates in previously treated patients with moderate or severe hemophilia B," Transfusion 42:190-197, 2002.
Ezban et al., "Functional characterization of N9-GP (rFIX GlycoPegylated) after intravenous administration to haemophilia B dogs," [08P10], Haemophilia 16(Suppl. 4):1-158 (2010) at p. 35.
Favaloro et al., "Problems and Solutions in Laboratory Testing for Hemophilia," Semin Thromb Hemost 39:816-833, Sep. 2013.
Feldman et al., "Tailored Prophylaxis in Severe Hemophilia A: Interim Results From the First 5 Years of the Canadian Hemophilia Primary Prophylaxis Study," J Thromb Haemost 4:1228-1236, 2006.
"First MS, Now Infertility Fusion Bid," BIOWORLD Today:17(180), 3 pages, Sep. 19, 2006.
Fischer et al., "Prophylactic Treatment for Severe Haemophilia: Comparison of an Intermediate-Dose to a High-Dose Regimen," Haemophilia 8:753-760, 2002.
Fischer et al., "Prophylactic Versus on-Demand Treatment Strategies for Severe Haemophilia: A Comparison of Costs and Long-Tenn Outcome," Haemophilia 8:745-752, 2002.
Fischer et al., "Prophylaxis for Severe Haemophilia: Clinical and Economical Issues," Haemophilia 9:376-381, 2003.
Fischer, et al., "The effects of postponing prophylactic treatment on long-term outcome in patients with severe hemophilia," Blood 99(7):2337-2341, 2002.
"FIX:Fc Syntonix, Biovitrum Licensing Agreement," R & D Focus Drug News, Jan. 30, 2006, 2 pages.
"FIXFc Biovitrum, Syntonix Orphan Drug, USA (Hemophilia)," R & D Focus Drug News, Dec. 1, 2008.
"FIXFc Biovitrum, Syntonix phase change II USA(hemophilia)," R & D Focus Drug News, Jun. 9, 2008.
Franchini et al., "Haemophilia B: current pharmacotherapy and future directions," Expert Opin. Pharmacother 13(14):2053-2063, 2012.
Gahart et al., Antihemophilic Factor, Intravenous Medications, Twenty-Sixth Edition, Mosby Elsevier Inc., 2010, at pp. 116-127 and 567-572.
Ganesan et al., "FcγRIIb on Liver Sinusoidal Endothelium Clears Small Immune Complexes," J Immunol. 189(10):4981-4988, 2012.
Gascoigne et al., "Secretion of a Chimeric T-cell Receptor-Immunoglobulin Protein," PNAS 84:2936-2940, May 1987.
GAZYVA® (Obinutuzumab) Highlights of Prescribing Information, United States Food and Drug Administration, 2016, 25 pages.
GeneTest Website, https://www.genetest.org/, last accessed on Nov. 28, 2017.
Geraghty et al., "Practice Patterns in Haemophilia A Therapy—Global Progress Towards Optimal Care," Haemophilia 12:75-81, 2006.
Geske et al., "Recombinant Factor IX Fc Fusion Protein (rFIXFc) Clotting Activity Assessment in International Hemophilia Treatment Centers," Poster presented at THSNA 2016, Apr. 14-16, 2016, Chicago.
Ghaderi et al., "Implications of the presence of N-glycolylneuraminic acid in recombinant therapeutic glycoproteins," Nat Biotechnol. 28(8):863-867, 2010.
Ghaderi et al., "Production platforms for biotherapeutic glycoproteins. Occurrence, impact, and challenges of non-human sialylation," Biotechnology and Genetic Engineering Reviews 28:147-176, 2012.
Gorman, C. et al., "Expression and Activity of IgF Receptor Alpha Chain-IgG Chimeric Molecules," Abstract 1448, The American Society for Cell Biology, Thirty-first Annual Meeting, Boston, Massachusetts, Dec. 8-12, 1991, J Cell Biology 115(3): 1a-570(a), 991, at p. 250a.
Gray et al., "Collaborative Study for the Establishment of Replacement Batches for Human Coagulation Factor IX Concentrate Reference Standards," Pharmeuropa Bio 1:19-30, Dec. 2008.
Grene-Lerouge et al., "Interspecies Scaling of Clearance and Volume of Distribution for Digoxin-Specific Fab," Toxicology and Applied Pharmacology 138:84-89, 1996.
Guidance for Industry: Estimating the Maximum Safe Starting Dose in Initial Clinical Trials for Therapeutics in Adult Healthy Volunteers, Food and Drug Administration, US Dept. Health and Human Services, FDA, CDER, Jul. 2005, 30 pages.

(56) References Cited

OTHER PUBLICATIONS

Guidelines for the Management of Hemophilia: Knowledge and Expertise in Coagulation Laboratory Testing, 2nd Edition, World Federation of Hemophilia, 2012, 80 pages.
Haemost, "Supporting Information to Sommer et al., Comparative Field Study: Impact of Laboratory Assay Variability on the Assessment of Recombinant Factor IX Fc Fusion Protein (rFIXFc) activity," Thromb Haemo 112(5), 2014.
Hanabusa et al., "Effect of once-weekly prophylaxis treatment with a recombinant fusion protein linking coagulation factor IX with albumin (rIX-FP) on target joints in patients with hemophilia B during the PROLONG-9FP clinical trial program," Poster PO-W-138, CSL Behring, 2016.
Hansen et al., "Recombinant glycopegylated FIX (40K PEG-rFIX) demonstrates prolonged half-life in several animal species," Haemophilia 16(Suppl. 4): 1-158, 2010.
Hansen et al., "Recombinant glycoPEGylated FIX (N9-GP) demonstrates prolonged half-life in several animal species," Poster, 2010 World Federation of Hemophilia XXIX Congress, Jul. 10-14, 2010.
Haraldsson et al., "Why Do We Not All Have Proteinuria? An Update of Our Current Understanding of the Glomerular Barrier," News Physiol Sci 19:7-10, 2004.
Hennan et al., "Pharmacologic Inhibition of Platelet vWF-GBIba Interaction Prevents Coronary Artery Thrombosis," Thromb Haemost 95: 1-7, 2006.
Herzog et al., "Biodistribution of the recombinant fusion protein linking coagulation factor IX with albumin (rIX-FP) in rats," Thromb Res 133:900-907, 2014.
Higel et al., "N-glycosylation Heterogeneity and the Influence on Structure, Function and Pharmacokinetics of Monoclonal Antibodies and Fc Fusion Proteins," Eur J Pharmaceutics and Biopharmaceutics 100:94-100, 2016.
Hinton et al., "Engineered human IgG antibodies with longer serum half-lives in primates," J Biol Chem 279(8):6213-6216, 2004.
Hinton et al., "An engineered human IgG1 antibody with longer serum half-life," J Immunol. 176:346-356, 2006.
Holm et al., "Prolonged In Vivo half-life and retained activity of factor IX glycopegylated in the activation peptide," PP-MO-575, International Society on Thrombosis and Haemostasis 7(Suppl.2):1-1204, 2009.
Metzner et al., "Prolonged serum half-life of a recombinant, albumin-fused, human coagulation factor IX (rIX-FP) in different animal species," 08P41, Hemophilia 16(Suppl. 4):1-158 (2010).
Horn et al., "Concept and Structure Model of Factor IX Albumin Fusion Proteins," CSL Behring, Undated, Poster.
Horn et al., "Functional characterization of recombinant factor IX albumin fusion protein," Poster P2-45, 56 Annual Meeting of Gesellschaft fur Thorsibose und Haemosteseforschung (GTH), Feb. 1-4, 2012, St. Gallen, Switzerland.
Houde et al., "Conformational Comparability of Factor IX-Fc Fusion Protein, Factor IX, and Purified Fc Fragment in the Absence and Presence of Calcium," J Pharm Sci 101(5):1688-1700, May 2012.
Exhibit D to Bioverativ's Response to Initial Invalidity Disclosures, ITC Inv. No. 337-TA-1066, dated Dec. 8, 2017, 54 pages.
Hubbard, A. R., "Potency Labeling of Novel Factor VIII and Factor IX Concentrates: Past Experience and Current Strategy," Semin Thromb Hemost 41:849-854, 2015.
Huber et al., "Crystallization and stoichiometry of binding of a complex between a rat intestinal Fc receptor and Fc," J. Mol. Biol. 230:1077-1083, 1993.
Huber et al., "Crystallographic structure studies of an IgG molecule and an Fc fragment," Nature 264:415-420, 1976.
HUMIRA® (Adalimumab) Highlights of Prescribing Information, United States Food and Drug Administration, 2016.
IDELVION® [Coagulation Factor IX (Recombinant), Albumin Fusion Protein] Highlights of Prescribing Information, Feb. 2018.
Santagostino, E., "Idelvion®: Revolutionizing the Treatment of Hemophilia B," CSL Behring Symposium, Jul. 7, 2007, 38 pages.

Igawa et al., "Reduced Elimination of IgG Antibodies by Engineering the Variable Region," Protein Engineering, Design & Selection 23(5):385-392, 2010.
Igawa et al., "Antibody recycling by engineered pH-dependent antigen binding improves the duration of antigen neutralization," Nature Biotechnology 28(11):1203-1208, 2010.
ILARIS® (Canakinumab) Highlights of Prescribing Information, United States Food and Drug Administration, Revised: Dec. 2016, 24 pages.
"FVIIIFc, FIXFc, Licensing Agreement," IMS R & D Focus Drug News, Jan. 30, 2006, 2 pages.
International Blood/Plasma News, 26(12):165-180, Jul. 2009.
Itinerary & Abstracts of the XXII Congress, International Society on Thrombosis and Haemostasis, Boston USA, Jul. 11-16, 2009, 55 pages.
IXINITY® Highlights of Prescribing Information, United States Food and Drug Administration, 2015.
Iyer et al., "Antibody drug conjugates—Trojan horses in the war on cancer," Journal of Pharmacological and Toxicological Methods 64:207-212, 2011.
Jaffray et al., "Recent trial results in recombinant coagulation factors for the treatment of hemophilia B," Clin Invest (Lond. ):5(2):205-216, 2015.
Jaggi et al., "Improved Tumor Imaging and Therapy via i.v. IgG-Mediated Time-Sequential Modulation of Neonatal Fc Receptor," J Clin Inves. 117(9):2422-2430, 2007.
Jazayeri et al., "Fc-based cytokines: prospects for engineering superior therapeutics," Biodrugs 22(1):11-26, 2008.
Jenkins et al., Manual of Emergency Medicine, chapter 3, Fifth Edition, Lippincott Williams & Wilkins, 2005, pp. 29-40.
Jenkins et al., "Post-Translational Modifications of Recombinant Proteins: Significance for Biopharmaceuticals," Mol Biotechnol. 39:113-118, 2008.
Kandil et al., "The human gene encoding the heavy chain of the major histocompatibility complex class 1-like Fc receptor (FCGRT) maps to 19q13.3," Cytogenet Cell Genet 73(1-2): 97-98, 1996.
Keeling et al., "Guideline on the Selection and Use of Therapeutic Products to Treat Haemophilia and Other Hereditary Bleeding Disorders," Haemophilia 14:671-684, 2008.
Kemshead et al., "Uses and limitations of monoclonal antibodies (MoAbs) in the treatment of malignant disease: a review," J Royal Society of Medicine 86:219-224, 1993.
Kenet et al., "Long-acting recombinant fusion protein linking coagulation factor IX with albumin (rIX-FP) in children—Results of a phase 3 trial," Thromb Haemost 116(4):659-668, 2016.
KEYTRUDA® (Pembrolizumab) Highlights of Prescribing Information, United States Food and Drug Administration, 2017, 45 pages.
Khor et al., "Phannacokinetics, Pharmacodynamics, Allometry, and Dose Selection of rPSGL-Ig for Phase 1 Trial," J Phatmacol Exp Ther 293(2):618-624, 2000.
Kim et al, "Albumin turnover: FcRn-mediated recycling saves as much albumin from degradation as the liver produces," Am. J. Physiol Gastrointest Liver Physiol, 290:G352-360, 2006.
Kim et al., "Kinetics of FcRn-mediated recycling of IgG and albumin in human: Pathophysiology and therapeutic implications using a simplified mechanism-based model," Clin Immunol. 122(2):146-155, 2007.
Kitchen et al., "Current Laboratory Practices in the Diagnosis and Management of Haemophilia: A Global Assessment," Haemophilia 21:550-557, 2015.
Kitchen et al., "Monitoring of Modified Factor VIII and IX Products," Haemophilia 20(Suppl. 4): 36-42, 2014.
Kitchen et al., "Recombinant to Modified Factor VIII and Factor IX-Chromogenic and One-Stage Assays Issues," Haemophilia 22(Suppl. 5.):72-77, 2016.
Kitchen et al., "Factor Activity Assays for Monitoring Extended Half-Life FVIII and Factor IX Replacement Therapies," Semin Thromb Hemost 43:331-337, 2017.
Sand et al., "Unraveling the Interaction Between FcRn and Albumin: Opportunities for Design of Albumin-Based Therapeutics," Front Immunol, 5:682, Jan. 2015, pp. 1-2.

(56) References Cited

OTHER PUBLICATIONS

Korth-Bradley et al., "Pharmacokinetic (PK) and clinical data support for effectiveness of once-weekly recombinant coagulation factor IX (RFIX) dosing for prophylaxis in patients with moderately severe or severe hemophilia B," Abstract PO167-MON, Thromb Haemost 13(Suppl. 2):1-997, 2015.

Kumar et al., "Changing Paradigm of Hemophilia Management: Extended Half-Life Factor Concentrates and Gene Therapy," Semin Thromb Hemost 42:18-29, 2016.

Kurschner et al., "Construction, Purification, and Characterization of New Interferon (IFNr) Inhibitor Proteins," J. Biol. Chem. 267(13):9354-9360, 1992.

Kwon et al., "Individual Differences in Oscillatory Brain Activity in Response to Varying Attentional Demands During a Word Recall and Oculomotor Dual Task," Front Hum Neurosci 9:381, Jun. 2015, pp. 1-11.

Lambert et al., "Reformulated BeneFIX®: Efficacy and Safety in Previously Treated Patients with Moderately Severe to Severe Haemophilia B," Haemophilia 13:233-243, 2007.

Larsen et al, "Albumin-based drug delivery: harnessing nature to cure disease," Molecular and Cellular Therapies 4:3, 2016, pp. 1-12.

Lee et al., Textbook of Hemophilia, Blackwell Publishing, 2006.

Lesslauer et al., "Recombinant Soluble Tumor Necrosis Factor Receptor Proteins Protect Mice from Lipopolysaccharide-Induced Lethality," Eur J Immunol 21:2883-2886, 1991.

Li et al., "Calcium Binding to a Factor IX Fc Fusion Protein and Effects on High-Order Structure," J Pharm Sci 100:4597-4606, Nov. 2011.

Exhibit B "Table of Exemplary Support" to Bioverativ's Response to Initial Invalidity Disclosures, ITC Inv. No. 337-TA-1066, dated Dec. 8, 2017.

Lillicrap, D., "Improvements in Factor Concentrates," Current Opinion in Haemotology 17:393-397, 2010.

Lin et al., "Generation of a Novel Factor IX with Augmented Clotting Activities In Vitro and In Vivo," J Thomb Haemost 8:1773-1783, Aug. 2010.

Ling et al., "Interspecies Scaling of Therapeutic Monoclonal Antibodies: Initial Look," J Clin Pharmacology 49:1382-1402, Dec. 2009.

Linsley et al., "Binding of the B Cell Activation Antigen B7 to CD28 Costimulates T Cell Proliferation and Interleukin 2 mRNA Accumulation," J. Exp Med. 173:721-730, 1991.

Linsley et al.,"CTLA-4 is a Second Receptor for the B Cell Activation Antigen B7," J. Exp Med. 174:561-569, 1991.

Lissitchkov et al., "Head-to-head comparison of the pharmacokinetic profiles of a high-purity factor IX concentrate (AlphaNine®) and a recombinant factor IX (BeneFIX®) in patients with severe haemophilia B," Haemophilia 19:674-678, 2013.

Liu et al., "NF-kB Signaling Regulates Functional Expression of the MHC Class I-Related Neonatal Fc Receptor for IgG via Intronic Binding Sequences," J Immunol 179(5):2999-3011, 2007.

"Long-acting factor IX phase 1 results (NN7999-3639)," Oct. 27, 2010.

Leubetsky et al., "Long-term safety and efficacy of recombinant fusion protein linking coagulation factor IX with albumin (rIX-FP) in previously treated patients with hemophilia B", PO-T-122, 2016, Poster.

Low et al., "Inhibitors of the FcRn: IgG Protein-Protein Interaction," AAPS Journal 11(3):432-434, Sep. 2009.

Lubetsky et al., "Efficacy, PK and Safety Results of Clinical Study of Recombinant Fusion Protein Linking Coagulation Factor IX with Albumin (rIX-FP) in Previously Treated Patients with Hemophilia B," Abstract, American Society of Hematology, 2013.

Ludwig et al., "Prophylaktische Behandlung bei Schwerer Hamophilie B mit einem Faktor-IX-Konzentrat," Dtsch. Med. Wschr. 99: 1355-1361, Jun. 1974.

Deutsch et al., "Prophylaktische Behandlung bei Schwerer Hamophilie B mit einem Faktor-IX-Konzentrat," Apr. 7, 2009.

Lyseng-Williamson, K.A., "Coagulation Factor IX (Recombinant), Albumin Fusion Protein (Albutrepenonacog Alfa; Idelvion®): A Review of Its Use in Haemophilia B," Drugs 77:97-106, Springer Publishing, Switzerland (2017).

Maack et al., "Renal Filtration, Transport, and Metabolism of Low-Molecular-Weight Proteins: a Review," Kidney Int. 16:251-270, International Society of Nephrology (1979).

Mackie et al., "Guidelines on the Laboratory Aspects of Assays Used in Haemostasis and Thrombosis," Int. J. Lab. Hematol. 35:1-13, Blackwell Publishing (2013).

Mahmood et al., "A bodyweight-dependent allometric exponent model for scaling clearance of clotting factor VIII and IX from infants to adults," Haemophilia 22:545-575, John Wiley & Sons (2016).

Mahmood, I., "Allometric extrapolation of factors VII, VIII and IX clearance in children from adults," J Thromb Haemost 10: 1609-1613, John Wiley & Sons, United States (2012).

Mahmood, I., "Interspecies Scaling of Protein Drugs: Prediction of Clearance from Animals to Humans," J Pharm Sci 93(1):177-185, Wiley-Liss, United States (2004).

Mahmood, I.., "Pharmacokinetic Allometric Scaling of Antibodies: Application to the First-In-Human Dose Estimation", J Pharm Sci 98(10):3850-3861, Wiley-Liss, United States (2009).

Manco-Johnson et al., "Prophylaxis Versus Episodic Treatment to Prevent Joint Disease in Boys with Severe Hemophilia," N Engl J Med 357(6):535-544, Massachusetts Medical Society, United States (2007).

Manco-Johnson et al., "Results of Secondary Prophylaxis in Children with Severe Hemophilia," Am J Hematol 47:113-117, Wiley-Liss, United States (1994).

Mancuso et al., "Fc-Fusion Technology and Recombinant FVIII and FIX in the Management of the Hemophilias," Drug Design, Development and Therapy 8:365-371, Dove Medical Press Limited, England (2014).

Mannucci, P. M., "Back to the Future: A Recent History of Haemophilia Treatment," Haemophilia 14 (Suppl. 3):10-18, 2008.

Mannucci et al., "Emerging drugs for Hemophilia B," Expert Opinion on Emerging Drugs 19(3):407-414, Informa, England (2014).

Martin et al., "Crystal structure at 2.8 Å of an FcRn/heterodimeric Fc complex: mechanism of pH dependent binding," Molecular Cell 7:867-877, Cell Press, United States (2001).

Martinowitz et al., "Phase I/II, Open-Label, Multicenter, Safety, Efficacy and PK Study of a Recombinant Coagulation Factor IX Albumin Fusion Protein (rIX-FP) in Subjects with Hemophilia B," Thromb Res 131 (Suppl. 2): S11-S14, Elsevier Ltd., Netherlands (2013).

Martinowitz et al., "Results of a phase I/II open-label, safety and efficacy trial of coagulation factor IX (recombinant), albumin fusion protein in haemophilia B patients," Haemophilia 21(6):784-790, John Wiley & Sons Ltd., United States (2015).

Matsumoto et al., "The Measurement of Low Levels of Factor VIII or Factor IX in Hemophilia A and Hemophilia B Plasma by Clot Waveform Analysis and Thrombin Generation Assay," J Thromb Haemost 4(2):377-384, 2006.

McCarthy et al., "Effect of Point Mutations in Recombinant Factor IX on Recovery and Pharmacokinetics in the Sprague Dawley Rat," Journal of Thrombosis and Haemostasis, Abstract p. 2106, Jul. 2001.

McCue et al., "Validation of the manufacturing process used to produce long-acting recombinant factor IX Fc fusion protein," Haemophilia 20(4):e327-e335, John Wiley & Sons Ltd., United States (2014).

Merlot et al., "Unraveling the mysteries of serum albumin—more than just a serum protein," Front Physiol.5:299, 2014.

Metzner et al., "Improved concept of factor IX albumin fusion proteins," CSL Behring, Marburg, Germany, Abstract OC-WE-120, 2009.

Miguelino et al., "Clinical Utility and Patient Perspectives on the Use of Extended Half-Life rFIXFc in the Management of Hemophilia B," Patient Prefer Adherence 8:1073-1083, Dove Medical Press Limited, England (2014).

(56) References Cited

OTHER PUBLICATIONS

Minghetti et al., "Molecular Structure of the Human Albumin Gene is Revealed by Nucleotide Sequence within q11-22 of Chromosome 4," *J Biol Chem* 15:6747-6757, The American Society of Biological Chemists, Inc., United States (1986).
Moeller et al., "Prolonged haemostatic effect of 40K PEG-RFIX compared to RFIX in a FeC13 Induced Injury model in hemophilia B mice," Journal of Thrombosis and Haemostasis 7(Suppl. 2):1-1204, International Society on Thrombosis and Haemostasis, England, Abstract PP-MO-573 (2009).
CSL Behring, "Coagulation factor IX (Human)Mononine®" Product Label, Apr. 2016, 2 pages.
Mordenti, J ., et al., "Pharmacokinetics and Interspecies Scaling of Recombinant Human Factor VIII" Toxicology and Applied Pharmacology 136:75-78, Elsevier, Netherlands (1996).
Morfini, M., et al., "Emerging Drugs for the Treatment of Hemophilia A and B," Review: Expert Opinion on Emerging Drugs 21 (3):301-313, Taylor and Francis, England (2016).
Morfini, M., "Pharmacokinetic drug evaluation of albutrepenonacog alfa (CSL654) for the treatment of hemophilia," Expert Opinion on Drug Metabolism & Toxicology 12(11): 1359-1365, Taylor & Francis Group, England (2016).
Morfini, M., et al., "Evaluation of Prophylactic Replacement Therapy in Haemophilia B," Scand. J. Haematol, 16(1):41-47, Wiley Online Library, United States (1976).
Respondent CSL Behring's Invalidity Contentions, Exhibit A-3, ITC Inv. No. 337-TA-1066, dated Nov. 15, 2017.
Respondent CSL Behring's Invalidity Contentions, Exhibit A-2, ITC Inv. No. 337-TA-1066, dated Nov. 15, 2017.
Respondent CSL Behring's Invalidity Contentions, Exhibit A-1, ITC Inv. No. 337-TA-1066, dated Nov. 15, 2017.
Morfini, M, "Pharmacokinetics of Factor VIII and Factor IX," Haemophilia 9(Suppl. 1):94-100, Blackwell Publishing Limited, United States (2003).
Myers, D., et al., "New and Effective Treatment of Experimentally Induced Venous Thrombosis with Anti-Inflammatory rPSGL-Ig," Thromb Haemost 87:374-382, Schattauer GmbH, Germany (2002).
Nazeef et al., "New developments in the management of moderate-to-severe hemophilia B," Journal of Blood Medicine 7:27-38, Dove Online Press, England, 2016.
Negier, C., et al., "Efficacy and safety of long-acting recombinant fusion protein linking factor IX with albumin in haemophilia B patients undergoing surgery," Haemophilia 22:e259-e266, John Wiley & Sons Ltd., United States (2016).
BENEFIX®: Highlights of Prescribing Information was published on Sep. 13, 2006 (original approval 1997), 2 pages.
Negier C., "Achieving new standards: Linking Factor IX with Albumin (rIX-FP) in Hemophilia B Patients Undergoing Surgery," Centre Regional de Traitement de l'Hemophile, 2016, 16 pages.
Nichols, T.C., "Lessons Learned from Animal Models of Inherited Bleeding Disorders," Hematol Educ., 8(1):39-46, 2014.
Nolte, M.W., et al., "Improved kinetics of rIX-FP, a recombinant fusion protein linking factor IX with albumin, in cynomolgus monkeys and hemophilia B dogs," Journal of Thrombosis and Haemostasis 10(8): 1591-1599, 2012.
Amgen, "Nplate® (Romiplostim) Highlights of Prescribing Information," Product label, United States Food and Drug Administration, 2008, 11 pages.
Nucala® (Mepolizumab) Highlights of Prescribing Information, United States Food and Drug Administration, 2015, 28 pages.
Nulojix® (Belatacept) Highlights of Prescribing Information, United States Food and Drug Administration, 2017, 14 pages.
Nussinov, R., et al., "Allosteric Post-Translational Modification Codes," Trends in Biochemical Sciences 37(10):447-455, Cell Press, Netherlands (2012).
Ober, R. J., et al., "Differences in promiscuity for antibody-FcRN interactions across species: implications for therapeutic antibodies," International Immunology 13(12):1551-1559, Japanese Society for Immunology, Japan (2001).
Ober, R.J., et al., "Visualizing the site and dynamics of IgG salvage by the MHC class I-related receptor, FcRn," The Journal of Immunology 172:2021-2029, American Association of Immunologist, United States (2004).
Ober, R.J., et al., "Exocytosis of IgG as mediated by the receptor, FcRn: an analysis at the single-molecule level," PNAS 101(30): 11076-11081, The National Academy of Sciences, United States (2004).
Offenberg, "GlycoPEGylated human recombinant Factor IX showed prolonged haemostatic activity in cynomolgus monkeys," Poster presentation, 1 page, 2009.
Offenberg, H., et al., "Glycopegylated human recombinant factor IX showed prolonged haemostatic activity in cynomolgus monkeys," Journal of Thrombosis and Haemostasis 7(Suppl. 2):1-1204, International Society on Thrombosis and Haemostasis, England, Abstract PP-MO-578 (2009).
Oldenburg, J., et al., "Genetic risk factors for inhibitors to factors VIII and IX," Haemophilia 12(Suppl. 6):15-22, (2006).
OPDIVO® (Nivolumab) Highlights of Prescribing Information, United States Food and Drug Administration, 2016, 60 pages.
ORENCIA® (Abatacept) Highlights of Prescribing Information, United States Food and Drug Administration, 2013, 55 pages.
ORENCIA® (Abatcept) of Prescribing Information, United States Food and Highlights Drug Administration, 2017, 29 pages.
Ostergaard, H., et al., "A long acting rFIX for prophylaxis with once-weekly or less frequent dosing," P05-22, 2010, 1 page.
Ostergaard, H., et al., "Prolonged half-life and preserved enzymatic properties of factor IX selectively PEGylated on native N-glycans in the activation peptide," Blood 118(8): 2333-2341, American Society of Hematology, United States (2011).
P-Selection Interactions in Perfusion Injury, Undated.
Peppel, K., et al., "A Tumor Necrosis Factor (TNF) Receptor-IgG Heavy Chain Chimeric Protein as a Bivalent Antagonist of TNF Activity," J. Exp. Med 174:1483-1489, Rockefeller University Press, United States (1991).
PERJETA® (Pertuzumab) Highlights of Prescribing Information, United States Food and Drug Administration, 2012, 14 pages.
Perry, D., et al., "The UK National External Quality Assessment Scheme for Heritable Bleeding Disorders," Semin Thromb Hemost 40(2): 261-268, United Kingdom, (2014).
Petkova, S.B., et al., "Enhanced Half-Life of Genetically Engineered Human 1gG1 antibodies in a humanized FcRn mouse model: potential application in humorally mediated autoimmune disease," International Immunology 18(12): 1-11, Oxford University Press, United Kingdom (2006).
"Guideline on the clinical investigation of recombinant factor VIII and IX products" European Medicines Agency, Jul. 21, 2011, 20 pages.
Non-Final Office Action dated Feb. 16, 2017 in U.S. Appl. No. 14/982,934, filed Dec. 29, 2015.
Petrini, P., "Identifying and Overcoming Barriers to Prophylaxis in the Management of Haemophilia," Haemophilia 13(Suppl. 2):16-22, Blackwell Publishing Ltd., United States (2007).
Petrini, P., "What Factors Should Influence the Dosage and Interval of Prophylactic Treatment in Patients with Severe Haemophilia A and B?," Haemophilia 7:99-102, Blackwell Science Ltd., United States (2001).
Peyrafitte, M., et al., "New Standardized Chromogenic Assays for Automated Measurements of FIX or FIXa in Plasma and Therapeutic Concentrates," GTH Vienna (Austria) Feb. 4-7, 2009, Poster and Abstract, 2 pages.
Pierce, G.F., et al., "Gene therapy, bioengineered clotting factors and novel technologies for hemophilia treatment," Journal of Thrombosis and Haemostasis 5:901-906, Wiley Online Library, United States (2007).
Pipe, S.W., et al., "Progress in the molecular biology of inherited bleeding disorders," Haemophilia 14(Suppl. 3):130-137, Blackwell Publishing Ltd., United States (2008).
Piskin, B., et al., "Use of an Individual Mandibular Advancement Device for an Obstructive Sleep Apnea Patient with Facial Paralysis: A Short-Term Follow-up Case Report" Journal of Oral Rehabilitation 39:472-478, Blackwell Publishing Ltd, United States (2012).

(56) References Cited

OTHER PUBLICATIONS

Plug, I., et al., "Thirty Years of Hemophilia Treatment in the Netherlands, 1972-2001," Blood 104(12):3494-3500, American Society of Haemotology, United States (2004).
Poon, M.C., et al., "Comparison of Pharmacokinetics of Factor IX Concentrate and Factor IX Complex Preparations," Abstract, Presented at the XVth Congress of the International Society on Thrombosis and Hemostasis, Israel, Jun. 11-15, 1995.
Poon, M.C., et al., "Comparison of the recovery and half-life of a high-purity factor IX concentrate with those of a factor IX complex concentrate," Transfusion 35(4): 319-323, Wiley Online Library, United States (1995).
Poon, M.C., "Pharmacokinetics of factors IX, recombinant human activated factor VII and factor XIII," Haemophilia 12 (Suppl. 4):61-69, Blackwell Publishing Ltd., United States (2006).
Zhang, Y., et al., "Population pharmacokinetics (PK) of recombinant fusion protein linking coagulation factor IX with recombinant albumin (rIX-FP) in adult and pediatric patients with severe hemophilia B," poster, CSL Behring, 2016, 1 page.
Pouplard, C., et al.,"Influence of Source of Phospholipids for APTT-Based Factor IX Assays and Potential Consequences for the Diagnosis of Mild Haemophilia B," Haemophilia 15:365-368, Blackwell Publishing Ltd., United States (2009).
Powell, J.S., et al., "Long-Acting Recombinant Factor IX Fc Fusion Protein (rFIXFc) for Perioperative Management of Subjects with Haemophilia B in the Phase 3 B-Long Study," British Journal of Haematology, 168:124-134, John Wiley & Sons Ltd., Britain (2015).
Powell, J.S., et al., "Phase 3 Study of Recombinant Factor IX Fc Fusion Protein in Hemophilia B," New England Journal of Medicine 369(24):2313-2323, Massachusetts Medical Society, United States (2013).
PRALUENT® (Alirocumab), Highlights of Prescribing Information, United States Food and Drug Administration, 2015, 47 pages.
Factor IX Complex, PROFILNINE® Solvent Detergent Product Label, Aug. 2010, 6 pages.
PROLIA® (Denosumab), Highlights of Prescribing Information, United States Food and Drug Administration, 2010, 18 pages.
Pruthi, R.K., "Global and Standard Assays for Monitoring Factor Replacement Therapies," Prseented at THSNA Chicago 2016, 43 pages.
Pruthi, R.K., "Laboratory monitoring of new hemostatic agents for hemophilia," Seminars in Hematology 53:28-34, Elsevier, Netherlands (2016).
European Medicines Agency, "Public summary of opinion on orphan designation: Recombinant fusion protein consisting of human coagulation factor IX attached to the Fc domain of human IGG1 for the treatment of haemophilia B (congenital factor IX deficiency)," Mar. 3, 2011, Connnittee for Orphan Medicinal Products, 5 pages.
Pyzik, M., "FcRn: The Architect Behind the Immune and Nonimmune Functions of IgG and Albumin," The Journal of Immunology 194:4595-4603, American Association of Immunologist, United States (2015).
"Q2 2010 Biogen Idec Inc Earnings Conference Call—Final," Fair Disclosure Wire., Jul. 20, 2010, 15 pages.
Zheng et al., "Administration of Noncytolytic IL-10/Fc in Murine Models of Lipopolysacchatide-Induced Septic Shock and Allogeneic Islet Transplantation," J Immunol 154(10): 5590-5600, Ameiican Association of Immunologists (1995).
Qiao, S.W., et al., "Dependence of antibody-mediated presentation of antigen on FcRn," PNAS 105(27):9337-9342, The National Academy of Sciences, United States (2008).
Zhou et al., "Generation of mutated variants of the human form of the MHC class I-related receptor, FcRn, with increased affinity for mouse immunoglobulin G," J Mol Biol 332:901-913, Elsevier Ltd., (2003).
Quade-Lyssy, P., et al., "Oral Gene Therapy for Hemophilia B Using Chitosan-Formulated FIX Mutants," Journal of Thrombosis and Haemostasis 12:932-942, Wiley Blackwell, Britain (2014).
Liu, T., et al., "Recombinant FIX Fc fusion protein is effective for on demand treatment with significantly prolonged efficacy for prophylaxis in hemophilia B mice: O-TH-111," Journal of Thrombosis and Haemostasis 9(Suppl. 2):758, Jul. 2011.
Raghavan, M., et al., "Analysis of the pH dependence of the neonatal Fc receptor/immunoglobulin G interaction using antibody and receptor variants," Biochemistry 34:14649-14657, American Chemistry Society, United States (1995).
RAPTIVA® (Efalizumab) Highlights of Prescribing Information, United States Food and Drug Administration, 2009, 36 pages.
Rash, Supplementary Table 1: Characteristics of Fc Fusion Proteins, 2015, 10 pages.
Rath, T., et al., "Fc-Fusion Proteins and FcRn: Structural Insights for Longer-Lasting and More Effective Therapeutics," Crit Rev. Biotechnol. 35(2):235-254, 2015.
Reagan-Shaw, "Dose translation from animal to human studies revisited," FASEB J 22(3):659-661, Federation of American Societies for Experimental Biology, United States (2007).
REBINYN® (Coagulation Factor IX (Recombinant), GlycoPEGylated) lyphoilized powder for solution for intravenous injection, Product Label, 2017, 15 pages.
Santagostino, E., et al., "Recombinant fusion protein linking coagulation factor IX with albumin (rIX-FP) in previously treated adolescent and adult patients with hemophilia B: efficacy and safety from a Phase 3 pivotal clinical trial," poster, 1 page, 2016.
REPATHA® (Evolocumab) Highlights of Prescribing Information, United States Food and Drug Administration, 2015, 34 pages.
Ridgway et al., "Expression and Activity of IgF Receptor Alpha Chain-IgG Chimeric Molecules," Abstract 1448, The American Society for Cell Biology, Thirty-first Annual Meeting, Boston, Massachusetts, Dec. 8-12, 1991, J Cell Biology 115(3): 1a-570(a), 991, at p. 250a.
RITUXAN® (Rituximab) Highlights of Prescribing Information, United States Food and Drug Administration, 2016, 39 pages.
RIXUBIS® [Coagulation factor IX (Recombibnant)] for Intravenous Injection, Lyophilized powder for Solution, 2014, 27 pages.
Rodewald, R., et al., "Receptor Mediated transport of IgG," The Journal of Cell Biology 99(1 Pt 2):159s-164s, The Rockefeller University Press, United States (1984).
Rodewald, R., "Intestinal Transport of Antibodies in the Newborn Rat," The Journal of Cell Biology 58:189-211, The Rockefeller University Press, United States (1973).
Rodewald, R., "pH-Dependent Binding of Immunologbulins to Intestinal Cells of the Neonatal Rat," The Journal of Cell Biology 71:667-670, The Rockefeller University Press, United States (1976).
Rodewald, R., "Distribution of Immunologolbulin G Receptors in the Small Intestine of the Yong Rat," The Journal of Cell Biology 85:18-32 , The Rockefeller University Press, United States (1980).
GPG-290 and His A1 Binding (Biacore Results), Excel, Undated, 2 pages.
Roopenian, D.C., et al., "The MHC Class I-Like IgG Receptor Controls Perinatal IgG Transport, IgG Homeostasis, and Fate of IgG-Fc-Coupled Drugs," J. Immunol 170:3528-3533, The American Association of Immunologists, United States (2003).
Rosen et al., "Overestimation of N-glycoPEGylated Factor IX Activity in a One-Stage Factor IX Clotting Assay Owing to Silica-Mediated Premature Conversion to Activated Factor IX," Journal of Thrombosis and Haemostasis 14:1420-1427 , 2016.
Russell et al., "Intratracheal Administration of Recombinant Human Factor IX (BeneFiX™) Achieves Therapeutic Levels in Hemophilia B Dogs," Thromb Haemost 85:445-449, Schattauer GmbH, Germany (2001).
Russell, K.E., et al., "Reduced Bleeding Events with Subcutaneous Administration of Recombinant Human Factor IX in Immune-Tolerant Hemophilia B Dogs," Blood 102(13):4393-4398, American Society of Hematology, United States (2003).
Sanchez, L.M., et al., "Stoichiometry of the interaction between the major histocompatibility complex-related Fc receptor and its Fc ligand," Biochemistry 38:9471-9476, The American Society of Chemistry, United States (1999).
Santagostino, E., et al., "Safety and pharmacokinetics of a novel recombinant fusion protein linking coagulation factor IX with albumin (rIX-FP) in hemophilia B patients," Blood 120(12):2405-2411, American Society of Hematology, United States (2012).

(56) References Cited

OTHER PUBLICATIONS

Sanagostino, E., "Avoiding the Sub-Therapeutic Troughs: Long-acting rIX-FP," Presented at the 9th Annual Congress of the European Association for Haemophilia and Allied Disorders, Milan, Italy, 2016, 21 pages.
Coyle, T., et al., "An Open-Label phase I study to evaluate the pharmacokinetics and safety profile of Bay 94-9027, a PEGylated B-domain—deleted recombinant factor VIII, in a previously treated patients with severe hemophilia A," Abstract FP-MO-03.2-3, Haemophilia 18 (Suppl. 3):1-208, Blackwell Publishing, United States, 2012.
Santagostino, E., "Efficacy and Safety Results of two Phase 3 Pivotal Clinical Studies of Recombinant Fusion Protein Linking Factor IX with Albumin (rIX-FP) in Previously Treated Patients with Hemophilia B," IRCCS Ca' Granda Foundation, Maggiore Hospital, University of Milan, Italy, 2016, 38 pages.
Santagostino, E ., et al., "Long acting recombinant coagulation factor IX albumin fusion protein (rIX-FP) in hemophilia B: Results of a phase 3 trial," Blood 127(14):1761-1769, The American Society of Hematology, United States (2016).
Santagostino, E., et al., "Pharmacokinetic Results of Two Phase III Clinical Studies of Coagulation Factor IX (Recombinant) Albumin Fusion Protein (rIX-FP) in Previously Treated Patients with Hemophilia B (PROLONG-9FP)," Abstract, Blood 124: 1491, The American Society of Hematology, United States (2014).
Santagostino, E, " Prolong-9FP: Update on rIX-FP Clinical Studies," Feb. 2, 2015, 36 pages.
Zettlmeissl et al., "Expression and Characterization of Human CD4: Immunoglobulin Fusion Proteins," DNA and Cell Biology 9(5): 347-353 (1990).
Santagostino, E ., "Prolong-9FP Clinical Development Program—Phase I Results of Recombinant Fusion Protein Linking Coagulation Factor IX with Recombinant Albumin (rIX-FP)," Thrombosis Research 131S2:s7-S10, ElseVier, Netherlands (2013).
Santagostino, E, "Transforming the Treatment for Hemophilia B patients: Update on the Clinical Development of Recombinant Fusion Protein Linking Recombinant Coagulation Factor IX with Recombinant Albumin (rIX-FP)," Thrombosis Research 141S3:S5-S8, Elsevier, Netherlands (2016).
Sarav, M., et al., "Renal FcRn Reclaims Albumin but Facilitates Elimination of IgG," J Am Soc Nephrol 20:1941-1952, American Society of Nephrology, United States (2009).
Schmidt, S.R., "Fusion proteins as biopharmaceuticals—Applications and challenges," Current Opinion in Drug Discovery & Development 12(2):284-295, 2009.
Schoch, et al., "Charge-Mediated Influence of the Antibody Variable Domain on FcRn-Dependent Pharmacokinetics," PNAS 112(19):5997-6002, The Academy of National Sciences, United States (2015).
Schuck, P., et al., "Sedimentation equilibrium analysis of recombinant mouse FcRn with murine IgG1," Molecular Immunology 36:1117-1125, Elsevier Science Ltd., Netherlands (1999).
Schulte, S., "Pioneering Designs for Recombinant Coagulation Factors," Thrombosis Research 128(Suppl. 1):s9-S12, Elsevier Ltd., Netherlands (2011).
Schulte, S., "Challenges for new haemophilia products from a manufacturer's perspective," Thrombosis Research TR-05254:1-5, Elsevier Ltd., Netherlands (2013).
Schulte, S., "Innovative coagulation factors: albumin fusion technology and recombinant single-chain factor VIII," Thrombosis Research 131(Suppl. 2):S2-S6, Elsevier, Netherlands (2013).
Lee, M., et al., "Scientific and Standardization Connnittee Communication, The Design and Analysis of Pharmacokinetic Studies of Coagulation Factors," Posted on ISTH Website, Mar. 21, 2001, 9 pages.
Senter P.D., "Potent antibody drug conjugates for cancer therapy," Current Opinion in Chemical Biology 13:235-244, Elsevier Ltd., Netherlands (2009).
Shaprio, A., "Development of long-acting recombinant FVIII and FIX Fc fusion proteins for the management of hemophilia," Expert Opin Biol Ther 13(9):1287-1297, Informa, United Kingdom (2013).

GPG-290 and Thrombin Binding (Normalized Biacore Results), Undated, 1 page.
Simister et al., "An Fc receptor structurally related to MHC class I antigens," Nature 337(6203): 184-7 1989.
Simister et al., Isolation and characterization of an Fc receptor from neonatal rat small intestine, 1985.
Simister, N.E., "An IgG-Transporting Fc Receptor Expressed in the Syncytiotrophoblast of Human Placenta," Eur. J. Immunology 26: 1527-1531, Wiley Online Library, United Kingdom (1996).
Simponi® (Golimumab) Highlights of Prescribing Information, United States Food and Drug Administration, 2017, 59 pages.
Akilesh, S., et al., "The MHC Class I-like Fc Receptor Promotes Humorally Mediated Autoimmune Disease," The Journal of Clinical Investigation 113(9):1328-1333, Springer Science+Business Media, United States (2004).
Akilesh, S., "Podocytes use FcRn to Clear IgG from the Glomerular Basement Membrane," PNAS 105(3):967-972, National Academy of Sciences, United States (2008).
Sleep, D., "Albumin and its Application in Drug Delivery," Expert Opinion on Drug Delivery 12(5):793-812, Taylor & Francis, United States (2015).
Sockolosky, J .T., et al., "The Neonatal Fc Receptor, FcRn, as a target for Drug Delivery and Therapy," Adv. Drug Delivery. Rev. 91:109-124, HHS, United States (2015).
Sommer, J.M., "Comparative field study: impact of laboratory assay variability on the assessment of recombinant factor IX Fc protein (rFIXFc) activity," Blood Coagulation, Firbinolysis and Cellular Haemostasis, Thrombosis and Haemostasis , Wiley-Blackwell for the international Society on Thrombosis and Haemostasis, United States (2014).
Srivastava, Guidelines for the Management of Hemophilia, World Federation of Hemophilia, 2005, 56 pages.
Stamenkovic, I., "The B Lymphocyte Adhesion Molecule CD22 Interacts with Leukocyte Common Antigen CD45RO on T Cells and α2-6 Sialyltransferase, CD75, on B Cells," Cell 66:113-114, Cell Press, United States (1991).
Stelara® (Ustekinumab) Highlights of Prescribing Information, United States Food and Drug Administration, 2016, 37 pages.
Carlsson, K.S., et al., "On-Demand vs. Prophylactic Treatment for Severe Haemophilia in Norway and Sweden: Differences in Treatment Characteristics and Outcome," Haemophilia 9:556-566, Wiley Online Library, United States (2003).
Strensiq® (Asfotase-alpha) Highlights of Prescribing Information, United States Food and Drug Administration, 2015, 92 pages.
Strober, B.E., et al., "Alefacept for the treatment of psoriasis and other dermatologic diseases," Dermatologic Therapy 20:270-276, Blackwell Publishing, United States (2007).
Strohl, W.R., "Fusion Proteins for Half-Life Extension of Biologics as a Strategy to Make Biobetters," BioDrugs 29:215-239, Springer, United States (2015).
Stockschaleder, M., " From the program: Abstracts and Competitive Symposia," presented at the Pre-Convention Meeting, Kyoto, Jul. 24, 2011. 47 pages.
Subramanian, G.M., "Albinterferon α-2b: a genetic fusion protein for the treatment of chronic hepatitis C," Nature Biotechnology 25(12):1411-1419, Nature Publishing, United States (2007).
Summary of Product Characteristics—Alprolix, Annex I, II, III, p. 1-34, 2016.
Suzuki, T., et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR," J. Immunology 184:1968-1976, American Association of Immunologist, United States (2010).
Suzuki, N., "The features of clearance in recombinant factor IX (BeneFIX®)," Haemophilia 21:702-707, John Wiley & Sons, United States (2015).
Swedish Council on Health Technology Assessment, "Treatment of Hemophilia a and B and von Willebrand Disease," A Systematic review, Report No. 208E, May 2011, 268 pages.
Symphogen, Biovitrum Partner to Develop Sym001 in ITP HDN, Feb. 8, 2006, 3 pages.

(56) References Cited

OTHER PUBLICATIONS

WIR Staff, Syntonix, Biovitrum deal—BioCentury, Aug. 10, 2015, 1 page.
BioWORLD Today, Syntonix, Biovitrum in Deal on Long-Acting Clotting Product, vol. 17, No. 15. Jan. 24, 2006, 7 pages.
Taltz® (Ixekizumab) Highlights of Prescribing Information, United States Food and Drug Administration, 2016, 9 pages.
Tanzeum® (Albiglutide) Highlights of Prescribing Information, United States Food and Drug Administration, 2016, 56 pages.
Taylor, J.A., et al., "A New Era for Hemophilia B Treatment," Blood 127(14): 1733-1736, American Society of Hematology, United States (2017).
Telleman, P., et al., "The Role of the Brambell Receptor (FcRB) in Liver: Protection of Endocytosed Immunoglobin G (IgG) from Catabolism in Hepatocytes Rather than Transport of IgG to Bile," Immunology 100:245-251, Wiley Online Library, United States (2000).
Tremfya® (Guselkumab) Highlights of Prescribing Information, United States Food and Drug Administration, 2017, 24 pages.
Tesar, D.B., et al., "Ligand Valency Affects Transcytosis, Recycling and Intracellular Trafficking Mediated by the Neonatal Fc Receptor," Traffic 7:1127-1142, Blackwell Publishing Ltd.
The efficacy and safety of recombinant fusion protein linking coagulation factor IX with albumin (rIX-FP) in previously treated children with hemophilia B: results of a phase 3 pivotal clinical trial, 2016, 2 pages.
The Pink Sheet Daily, Swedish Orphan Biovitrum Returns Long-Acting Blood Clotting Factors to Biogen, retrieved from, https://pink.pharmaintellgience.informa.com/PS070244/SWEDISH-Orphan-Biovitruim-Returns-LongActing-Blood-Clotting-Factors-to-Biogen, Feb. 18, 2010, 2 pages.
Thompson, A.R., et al., "Hemophilia B: Factor IX Deficiency, Christmas Disease," retrieved from https://web.archive.org/web/20010428153913fw_/http:/www.geneclinics.org:80/profiles.hemob/, retrieved on Nov. 28, 2017.
Ticho, B., "Long-acting Clotting Factor Fc Fusion Proteins for Potential Use in Hemophilia," Biogen Idec, Mar. 25, 2009, 9 pages.
Zhang, Y., et al., "Population pharmacokinetics of a new long-acting recombinant coagulation factor IX albumin fusion protein for patients with severe hemophilia B," Journal of Thrombosis and Haemostasis 14:2132-2140, Wiley Online Library, United States (2016).
Tiefenbacher, S., et al., "Qualification of a Select One-Stage Activated Partial thromboplastin time-based clotting assay and two chromogenic assays for the post-administration monitoring of nonacog beta pegol," Journal of Thrombosis and Haemostasis 15:1901-1912, Wiley Online Library, United States (2017).
Complainant Bioverativ's Motion for Termination of the Investigation Based on Withdrawal of the Complaint, Motion for Suspension of Procedural Schedule Pending Ruling on Motion for Termination, and Motion for Waiver of the Two-Day Rule, Inv. No. 337-TA-1066, United States International Trade Commission, Washington D.C., Feb. 6, 2018.
Toby, G., et al., "Biochemical characterization of factor IX-Fc monomer, Abstract, OC-MO-083," Oral Presentations 7(2):1-1204, International Society on thrombosis and Haemostasis, 2009 2009.
Toby, G.G., "Recombinant Factor IX Fc Fusion Protein Maintains Full Procoagulant Properties and Exhibits Prolonged Efficacy in Hemophilia B Mice," PLOS One: 1-20, PLOS, United States (2016).
Traunecker, A., et al., "Highly Efficient Neutralization of HIV with Recombinant CD4-Immunoglobulin Molecules," Nature 339:68-70, Nature Publishing Inc., United States (1989).
Tripodi, A., "Thrombin Generation Assay and Its Application in the Clinical Laboratory," Clinical Chemistry 62(5):699-707, American Association for Clinical Chemistry, United States (2016).
TRULICITY® (Dulaglutide) Highlights of Prescribing Information, United States Food and Drug Administration, 2017, 51 pages.
Vaccaro, C., et al., "Divergent activities of an engineered antibody in murine and human systems have implications for therapeutic antibodies," PNAS 103(49):18709-18714, The National Academy of Sciences of the USA, United States (2006).
Vaishnaw, A.K., et al., "Pharmacokinetics, Biologic Activity, and Tolerability of Alefacept by Intravenous and Intramuscular Administration," Journal of Pharmacokinetics and Pharmacodynamics 29(5/6): 415-426, Springer, United States (2003).
Valentino, L.A., et al., "Multicenter, randomized, open-label study of on-demand treatment with two prophylaxis regimens of recombinant coagulation factor IX in haemophilia B subjects," Haemophilia 20:398-406, Wiley Online Library (2014).
Valentino, L.A., "Recombinant FIXFC: A Novel Therapy for the Royal Disease?," Expert Opin. Biol. Ther. 11(10):1361-1368, Taylor & Francis Online, United States (2011).
Van Den Berg, et al., "Long-Term Outcome of Individualized Prophylactic Treatment of Children with Severe Haemophilia," British Journal of Haematology 112:561-565, Wiley Online Library, United Kingdom (2001).
Van Dijk et al., "Can Long-Term Prophlaxis for Severe Haemophilia be Stopped in Adulthood? Results from Denmark and the Netherlands," British Journal of Haematology 130:107-112, Wiley Online Library, United Kingdom, Apr. 2005.
Vaughn, D.E., et al., "Identification of critical IgG binding epitopes on the neonatal Fc receptor," J. Mol. Biol 274:597-607, Academic Press Limited, United States (1997).
Vaughn, D.E., et al., "Structural basis of pH-dependent antibody binding by the neonatal Fc receptor," Structure 6(1):63-73, Cell Press, United States (1998).
View of NCT00716716, A Phase I/IIa Safety and Pharmacokinetic Study of Intravenous FIXFc in Previously Treated Hemophilia B, Jul. 15, 2008, 3 pages.
View of NCT01027364, B-LONG: An Open-Labe, Multicenter Evaluation of the Safety, Pharmacokinetics, and Efficacy of Recombinant, Long-acting Coagulation Factor IX Fc Fusion Protein (rFIXFc) in the Prevention and Treatment of Bleeding in Previously Treated Subjects with Hemophilia B, Jun. 30, 2011,3 pages.
View of NCT01425723, Long-Term Safety and Efficacy of Recombinant Human Coagulation Factor IX Fusion Protein (rFIXFc) in the Prevention and Treatment of Bleeding Episodes in Previously Treated Subjects with Hemophilia B, Aug. 29, 2011, 2 pages.
Walsh, G., et al., "Post-Translational Modifications in the Context of Therapeutic Proteins," Nature Biotechnology 24(10): 1241-1252, Nature Publishing Inc., United States (2006).
Walsh, G., "Post-Translational Modifications of Protein Biopharmaceuticals," Drug Discovery Today 15(17):773-780, Elsevier, Netherlands (2010).
Wang, W., et al., "Monoclonal antibodies with identical Fc sequences can bind to FcRn differentially with pharmacokinetic consequences," Drugs Metabolism and Disposition 39(9): 1469-1477, The American Society for Pharmacology and Experimental Therapeutics, United States (2011).
Waters, E.K., et al., "Thrombin Generation Assay Using Factor Xla to Measure Factors VIII and IX and Their GlycoPEGylated Derivatives is Robust and Sensitive" Journal of Thrombosis and Haemostasis 13:2041-2052, Wiley Online Library (2015).
Watson, S.R., et al., "A homing Receptor-IgG Chimera as a Probe for Adhesive Ligands of Lymph Node High Endothelial Venules," J. Cell. Biol. 110: 2221-2229, The Rockefeller University Press, United States (1990).
Watson, S.R., et al., "Neutrophil Influx into an Inflammatory Site Inhibited by a Soluble Homing Receptor-IgG Chimaera," Nature 349(10):164-167, Nature Publishing Group (1991).
Weimer, T., et al., "Prolonged in-vivo Half-Life of Factor VIIA by Fusion to Albumin," Thromb. Haemost 99:659-667, Wiley Online Library, United States (2008).
West et al., "Crystal structure and immunoglobulin G binding properties of the human major histocompatibility complex related Fc receptor," Biochemistry 39:9698-9708, American Chemistry Society, United States (2000).
White, G.C., "Recommendation of the Scientific Subcommittee on Factor VIII and Factor IX of the Scientific and Standardization Committee of the International Society on Thrombosis and Haemostasis," Thromb Haemost 85:560, Wiley Online Library, United States (2001).

(56) References Cited

OTHER PUBLICATIONS

White, G., et al., "Clinical Evaluation of Recombinant Factor IX, Seminars in Hematology," Seminars in Hematology 35(2):33-38, Elsevier, Netherlands (1998).
WHO Drug Information, vol. 27, No. 2, (Alprolix Sequence), 2012, 75 pages.
Wilmot, H., "Collaborative Study to Investigate the Comparability of Recombinant and New Generation Factor IX products with WHO International Standard for FIX Concentrate," Dec. 2013, 95 pages.
Wilmot, H.V., et al., "Recombinant Factor IX: Discrepancies Between One-Stage Clotting and Chromogenic Assays," Haemophilia 20:891-897, Wiley Online Library, United States (2014).
Wiswall, et al., "Wyeth BioPharma, The Effect of GPIbα Glycosylation on Ligand Binding," Jul. 2004, 17 pages.
Wozniak, M., et al., "Prothrombin complex concentrate for the urgent reversal of warfarin. Assessment of a standard dosing protocol," Transfusion and Apheresis Science 46:309-314, Elsevier, Netherlands (2012).
Wu, A.M., et al., "Arming Antibodies: prospects and challenges for immunoconjugates," Nature Biotechnology 23(9):1137-1146, Nature Publishing Group, United Kingdom (2005).
XOLAIR® (Omalizumab) Highlights of Prescribing Information, United States Food and Drug Administration, 2017.
Yeung, Y.A., et al., "Engineering human IgG1 affinity to human neonatal Fc receptor: impact of affinity improvement on pharmacokinetics in primates," The Journal of Immunology: 7663-7673, American Association of Immunologists, United States (2009).
Yoshida, M., et al., "Human neonatal Fc receptor mediates transport of IgG into luminal secretions for delivery of antigens to mucosal dendritic cells," Immunity 20: 769-783, Cell Press, United States (2004).
Yoshida, M., et al., "Neonatal Fc receptor for IgG regulates mucosal immune responses to luminal bacteria," The Journal of Clinical Investigation 116(8):2142-2152, American Society for Clinical Investigation, United States (2006).
Young, G., et al., "Extended half-life clotting factor concentrates: results from published clinical trials," Haemophilia 22(5):25-30, Wiley Online Library, United States (2016).
Yu, Y., et al., "Measurement of Factor IX Activity in Plasma-Derived and Recombinant Concentrates: Insights from Thrombin Generation and Activation-Based Assays," Journal of Thrombosis and Haemostasis 12:62-70, International Society on Thrombosis and Haemostasis, United States (2014).
Zalevsky, J., et al., "Enhanced antibody half-life improves in vivo activity," Nat Biotechnol., 29(2):157-159 NIH, United States (2010).
ZALTRAP® (Ziv-aflibercept) Highlights of Prescribing Information, United States Food and Drug Administration, 2012.
Bioverativ's Response to Initial Responses to CSL Behring Recombinant Facility AG's Initial Invalidity Disclosures, ITC Inv. No. 337-TA-1066, dated December Apr. 20, 2018, 185 pages.
Exhibit A "Table of Exemplary Support" to Bioverativ's Response to Initial Invalidity Disclosures, ITC Inv. No. 337-TA-1066, dated Dec. 8, 2017, 40 pages.
Exhibit C, Initial responses to Exhibit A-1 of CSL Behring's Initial Responses to CSL Behring's Initial Invalidity Disclosures, ITC Inv. No. 337-TA-1066, dated Nov. 15, 2017, 60 pages.
Defendants CSL Behring's Answer, Defenses, and counterclaims to the Complaint of Bioverativ Inc., C.A. No-17-914-GMS, dated Apr. 19, 2018, 93 pages.
"8. How do you know how much you need to infuse? What is recovery, and what are trough levels?" (publication date unknown) www.hemob.org/faq.
Biogen Idec Announces Mar. 25 Webcast of Research & Development Day (Mar. 18, 2009), investors.biogen.com/news-releases/news-release-details/biogen-idec-announces-march-25-webcast-research-development-day.
BIIB—Biogen Idec Research & Development Day—Breakout Session. (Mar. 25, 2009).
Ticho, B., "Long-acting Clotting Factor Fc Fusion Proteins for Potential Use in Hemophilia," Biogen Idec, Dated Mar. 25, 2009, 9 pages.
Abstracts from the 10th Workshop on Novel Technologies and Gene Transfer for Hemophilia, Feb. 5-6, 2010.
Ahlberg, Haemophilia in Sweden VII. Incidence, Treatment and Prophylaxis of Arthropathy and Other Musculo-Skeletal Manifestations of Haemophilia A and B, 36 (Suppl. 77) Acta Orthopaedica Scandinavica 3, 10-11, 78-80 (1965).
Baggio, A Recombinant Human Glucagon-Like Peptide (GLP)-1-Albumin Protein (Albugon) Mimics Peptidergic Activation of GLP-1 Receptor-Dependent Pathways Coupled with Satiety, Gastrointestinal Motility, and Glucose Homeostasis, 53 Diabetes 2492 (2004).
Bensen-Kennedy, Population PK of rIX-FP in Adult and Pediatric Patients with Hemophilia B FIX ±2%, 2015.
Biogen Idec, Biovitrum deal, Nov. 12, 2007.
Boehncke and Brembilla, "Immunogenicity of biologic therapies: causes and consequences," Expert Rev Clin Immunol, 14(6):513-523 (2018).
Butler et al., The Choice of Mammalian Cell Host and Possibilities for Glycosylation Engineering, 30 Current Opinion in Biotechnology 107 (2014).
Carlsson, M., et al., "Multidose Pharmacokinetics of Factor IX: Implications for Dosing in Prophylaxis," Haemophilia 4(2):83-88, Blackwell Publishing Ltd., England (1998).
Cinqair® (Reslizumab) Highlights of Prescribing Information, United States Food and Drug Administration, 2016.
clinicaltrials.gov "Phase I/IIa Study of FIXFc in Hemophilia B Patients," NCT00716716; US National Institutes of Health. (published Jul. 14, 2008) (last accessed on Jun. 7, 2019 at clinicaltrials.gov/ct2/history/NCT00716716?V_1=View#StudyPageTop).
clinicaltrials.gov "Phase I/IIa Study of FIXFc in Hemophilia B Patients," NCT00716716; US National Institutes of Health. (published Jul. 23, 2008) (last accessed on Jun. 7, 2019 at clinicaltrials.gov/ct2/history/NCT00716716?V_2=View#StudyPageTop).
clinicaltrials.gov "Phase I/IIa Study of FIXFc in Hemophilia B Patients," NCT00716716; US National Institutes of Health. (published Jan. 24, 2009) (last accessed on Jun. 7, 2019 at clinicaltrials.gov/ct2/history/NCT00716716?V_3=View#StudyPageTop).
clinicaltrials.gov "Phase I/IIa Study of FIXFc in Hemophilia B Patients," NCT00716716; US National Institutes of Health. (published Jan. 27, 2009) (last accessed on Jun. 7, 2019 at clinicaltrials.gov/ct2/history/NCT00716716?V_4=View#StudyPageTop).
clinicaltrials.gov "Phase I/IIa Study of FIXFc in Hemophilia B Patients," NCT00716716; US National Institutes of Health. (published Jan. 30, 2009) (last accessed on Jun. 7, 2019 at clinicaltrials.gov/ct2/history/NCT00716716?V_5=View#StudyPageTop).
clinicaltrials.gov "Phase I/IIa Study of FIXFc in Hemophilia B Patients," NCT00716716; US National Institutes of Health. (published Feb. 4, 2009) (last accessed on Jun. 7, 2019 at clinicaltrials.gov/ct2/history/NCT00716716?V_6=View#StudyPageTop).
clinicaltrials.gov "Phase I/IIa Study of FIXFc in Hemophilia B Patients," NCT00716716; US National Institutes of Health. (published Mar. 26, 2009) (last accessed on Jun. 7, 2019 at clinicaltrials.gov/ct2/history/NCT00716716?V_7=View#StudyPageTop).
clinicaltrials.gov "Phase I/IIa Study of FIXFc in Hemophilia B Patients," NCT00716716; US National Institutes of Health. (published Jun. 29, 2009) (last accessed on Jun. 7, 2019 at clinicaltrials.gov/ct2/history/NCT00716716?V_8=View#StudyPageTop).
clinicaltrials.gov "Phase I/IIa Study of FIXFc in Hemophilia B Patients," NCT00716716; US National Institutes of Health. (published Nov. 1, 2009) (last accessed on Jun. 7, 2019 at clinicaltrials.gov/ct2/history/NCT00716716?V_9=View#StudyPageTop).
Communication pursuant to Rule 114(2) EPC, dated Oct. 30, 2015, Third Party Observations (Article 115 EPC) for Application No. EP11804476.7, European Patent Office, Germany.
EP11804476.7—Summons to attend oral proceedings, dated Oct. 25, 2018.
EP11804476.7—Withdrawal of Application, dated Feb. 18, 2019.
Cooley et. al., Prophylactic efficacy of BeneFIX vs. Alprolix in hemophilia B mice, 128 Blood 286 (2016).

(56) References Cited

OTHER PUBLICATIONS

Dumont, J.A., et al., "Monomeric Fc fusions: impact on pharmacokinetic and biological activity of protein therapeutics," *BioDrugs* 20(3):151-160, Springer International, New Zealand (2006).

Dumont et al., "Evaluation of the Toxicology, Pharmacokinetics, and Local Tolerance of Recombinant Factor IX Fc Fusion Protein in Animals," Thomb Res 136:371-378, 2015.

ELM—OC-M0-084, Oral Presentation abstract—Dose Response and Prolonged Effect of 40K PEG-FIX on Bleeding in Hemophilia B Mice, Journal Compilation International Society on Thrombosis and Haemostasis 7 (Suppl. 22), 1-1204, at 134 (published online Jun. 15, 2009).

FDA News Release "FDA Approves First Coagulation Factor-albumin Fusion Protein to Treat Patients with Hemophilia B"—Mar. 4, 2016.

"Guideline on the clinical investigation of recombinant factor VIII and IX products" European Medicines Agency, Jul. 19, 2007, 20 pages.

Gray et al., Assay Discrepancies for New Generation FIX Products, National Institute for Biological Standards and Control, p. 70 (2016).

Hacker et al., Barriers to Compliance With Prophylaxis Therapy in Haemophilia, 7 Haemophilia 392 (2001).

Hansen, L., et al., "The pharmacokinetics of a long-acting factor ix (40K PEG-RFIX) in minipigs suggests at least a once-weekly dosing regime," *Journal of Thrombosis and Haemostasis* 7(Suppl. 2):134, International Society on Thrombosis and Haemostasis, England, Abstract OC-MO-085 (2009).

Hemophilia B: Treatment Guidelines (publication date unknown), www.clinlabnavigator.com/hemophilia-b.html.

Hoffman M. "Animal models of bleeding and tissue repair," Haemophilia 14(Suppl 3):62-67 (2008)).

Holm et al., The Activity of GlycoPEGylated Recombinant FIX (N9-GP) Can be Measured in Two-Stage Chromogenic and One-Stage Clotting Assays, International Society on Thrombosis and Haemostasis (2013).

Horn, et al., Performance of a Recombinant Fusion Protein Linking Coagulation Factor IX with Recombinant Albumin in One-Stage Clotting Assays, Journal of Thrombosis & Haemostasis (2018).

Hubbard et al., Recommendations on the Potency Labelling of Factor VIII and Factor IX Concentrates, 11 J. Thrombosis & Haemostasis, 988, 988 (2013).

IPR2018-01345—Expert Declaration of John Pasi, M.B. Ch.B., Ph.D., dated Oct. 23, 2018.

"Is it time to look beyond trough in hemophilia B?" www.beyondtrough.com/pharmacokineticprofile/ (Publication date unknown).

Key & Negrier, Coagulation Factor Concentrates: Past, Present, and Future, the Lancet, 370(9585), 439-448 (2007).

Lancé, A General Review of Major Global Coagulation Assays: Thrombelastography, Thrombin Generation Test and Clot Waveform Analysis, 13 Thrombosis J. 1, 2 (2015).

Ledger et al., Performance of a Recombinant Fusion Protein Linking Coagulation Factor IX with Albumin (rFIX-FP) in the One-Stage Assay, World Federation of Hemophilia (2016).

Lee et al., Textbook of Hemophilia, Blackwell Publishing, 2005.

Lee et al., "The Pharmacokinetics of Coagulation Factors," Haemophilia 12(Supp. 3):1-7, 2006.

Levin 2010—Levin et al., Lost in Translation, Bumps in the Road Between Bench and Bedside, JAMA 303(15) 1533-1534 at 1533 (2010).

Lochu et al., Influence of FIX and FVIII PEGYLATION on FIX and FVIII Activity Based on APTT Assays, 11 International Society on Thrombosis and Haemostasis 290 (2013).

Löfqvist 1997—Haemophilia prophylaxis in young patients—a long-term follow-up.

Lollar, Fill 'er up? Fill What up?, 128(2) Blood 156, (Jul. 14, 2016).

Lorenzo, A. "Syntonix, Biovitrum in Deal on Long-Acting Clotting Product," BioWorld Today vol. 17, No. 15. Jan. 24, 2006, 7 pages.

Metzner, H.J., et al., "Genetic Fusion to Albumin Improves the Pharmacokinetic Properties of Factor IX," Thrombosis and Haemostasis 102: 634-664, Schattauer GmbH, Germany (2009).

Metzner, Extending the Pharmacokinetic Half-Life of Coagulation Factors by Fusion to Recombinant Albumin, Thombosis and Haemostasis, 2013.

Monahan et al. "Safety and efficacy of investigator-prescribed BeneFIX® prophylaxis in children less than 6 years of age with severe haemophilia B." Haemophilia 16, 460-468 (Jan. 4, 2010).

Morfini et al., The design and analysis of half-life and recovery studies for factor VIII and factor IX. Factor VIII/Factor IX Scientific and Standardization Committee of the International Society for Thrombosis and Haemostasis, Thrombosis and Haemostasis 66:384-386, 1991.

National Hemophilia Foundation, MASAC Recommendation Concerning Prophylaxis (Regular Administration of Clotting Factor Concentrate to Prevent Bleeding), Nov. 3, 2007, 3 pages.

New Data Show ELOCTATE® and ALPROLIX® May Help Control Target Joint Bleeds in People with Hemophilia A and B (Dec. 15, 2015) media.biogen.com/news-releases/news-release-details/new-data-show-eloctater-and-alprolixr-may-help-control-target.

Nichols et al., "Protein replacement therapy and gene transfer in canine models of hemophilia A, hemophilia B, von Willebrand disease, and factor VII deficiency," ILAR J. 50:144-167 (2009)).

Nicklasson, Biovitrum Interim Report Jan. 1-Mar. 31, 2008 (Apr. 26, 2008).

Oganesyan et al., Structural Insights into Neonatal Fc Receptor-Based Recycling Mechanisms, 14 J. Biol. Chem. 7812, 7821 (2014).

Osborn et al. "Albutropin: a growth hormone-albumin fusion with improved pharmacokinetics and pharmacodynamics in rats and monkeys," 456 Eur. J. Pharmacology 149 (2002).

Peters, R., Abstract entitled "Enhanced Pharmacokinetics of Factor IX as a Monomeric Fc Fusion," 2007 J. Throm. & Haemostasis S2(5):O-M-001-O-M-096 at O-M-016, 1 page.

Peters, R.T., et al., "Prolonged Activity of Factor IX as a Monomeric Fc Fusion Protein," Blood, Thrombosis and Hemostasis, 115 (10):2057-2064, The American Society of Hematology, United States (Mar. 11, 2010).

Peters, R., Slides entitled "Enhanced Pharmacokinetics of Factor IX as a Monomeric Fc Fusion Protein," presented to the International Society on Thrombosis and Haemostasis Jul. 9, 2007, 14 pages.

Peters, Prolonging the Half-Life of Hemostatic Factors via the Neonatal Fc Receptor, ASH 2013 Annual Meeting.

Pierce, Long Acting Coagulation Factors and Fc Fusion Technology: Factor IX-Fc Phase 1/2 Trial Preliminary Results (Oct. 28, 2009).

Powell, J., et al., "Switching to recombinant factor IX Fc fusion protein prophylaxis results in fewer infusions, decreased factor IX consumption and lower bleeding rates," British Journal of Haematology 168:113-123, John Wiley & Sons Ltd., Britain, (2015).

Properties of Human Serum Albumin and Albumin Atomic Coordinates, Albumin.org (Apr. 19, 2016), albumin.org/properties-of-human-serum-albumin-and-albumin-atomic-coordinates.

Sabatino, et al., "Animal Models of Hemophilia," Prog. Mol. Biol. Transl. Sci, 105:141-209 (2012).

Santagostino et al., Venous Access in Haemophilic Children: Choice and Management, 16 Haemophilia (Suppl.) 20, 20 (2010).

Santagostino, ED22-3—Results of a phase I international clinical trial of recombinant fusion protein linking coagulation factor IX with ablumin (rIX-FP) in patients with hemophilia B (PROLONG-9FP) St. Gallen, Schweiz, Feb. 4, 2012.

Schulte, S., "Half-life extension through albumin fusion technologies," Thrombosis Research 124(2):S6-S8, Elsevier, United States (2009).

Screenshot of "Special Issue: Abstracts of the XXIXth International Congress of the World Federation of Hemophilia, Buenos Aires, Argentina, Jun. 17, 2010," Haemophilia 16(Suppl. 4):1-170.

Shankar, et al., "Scientific and regulatory considerations on the immunogenicity of biologics," Trends Biotechnology, 24(6):274-280 (2006).

Shapiro, A.D., et al., "The safety and efficacy of recombinant human blood coagulation factor IX in previously untreated patients with

(56) References Cited

OTHER PUBLICATIONS severe or moderately severe hemophilia B," Blood 105(2):518-525, American Society of Hematology, United States (2005).
Shapiro, A.D., et al., "Safety and prolonged biological activity following a single administration of a recombinant molecular fusion of native human coagulation factor IX and the Fc region of immunoglobulin G (IgG) (rFIXFc) to subjects with hemophilia B," Haemophilia 16(Suppl. 4):30, Blackwell Publishing Ltd., United Kingdom, Abstract 07FP07 (Jun. 17, 2010).
Shapiro et al., "Extending recombinant factor IX Fc fusion protein dosing interval to 14 or more days in patients with hemophilia B," Res Pract Thromb Haemost., 3(1):109-113 (2018).
Sheffield 2004, Effects of Genetic Fusion of Factor IX to Albumin on in vivo clearance in mice and rabbits.
Sommer et al., Comparative Field Study Evaluating the Activity of Recombinant Factor VIII Fc Fusion Protein in Plasma Samples at Clinical Haemostasis Laboratories, Haemophilia, vol. 20:294-300 (2014).
Soupourmas et al., Differential Investigation of Post-Translational Modifications in Recombinant and Plasma-Derived Human Coagulation FIX, ISTH Jul. 2017.
Stafford, Extravascular FIX and Coagulation, Thrombosis J. 2016, 14 (Suppl 1): 35.
Stern 1987—In vivo evidence of intravascular binding sites for coagulation factor IX.
Sung et al., An IFNβ-Albumin Fusion Protein that Displays Improved Pharmacokinetic and Pharmacodynamic Properties in Nonhuman Primates, 23 J. Interferon & Cytokine Research 25 (2003).
Toby et al, Pre-Clinical Studies of Novel Factor IX Concentrates, 2009.
Traunecker et al., Soluble CD4 molecules neutralize human immunodeficiency virus type 1, Nature 331: 84-86 (1988).
U.S. Appl. No. 13/855,434 File History.
Van Der Flier 2017—The Pharmacokinetic Profiles of Intravenously and Subcutaneously Administered Recombinant Factor IX Fc-XTEN in Cynomolgus Monkeys.
Vie et al., Human fusion proteins between interleukin 2 and IgM heavy chain are cytotoxic for cells expressing the interleukin 2 receptor, Proc. Natl. Acad. Sci. USA 89:11337-11341 (1992).
WFH—World Federation of Hemophilia, the World Federation of Hemophilia's Sixth Global Forum on the Safety and Supply of Treatment Products for Bleeding Disorders: Proceedings, (2009).
White, G.C. II., et al., "Scientific and Standardization Committee Communication, Definitions in Hemophilia, Recommendation of the Scientific Subcommittee on Factor VIII and Factor IX of the Scientific and Standardization Committee of the International Society on Thrombosis and Haemostasis" Thromb Haemost 85:560, Schattauer GmbH, Germany (2001).
Wunder et al., Albumin-Based Drug Delivery as Novel Therapeutic Approach for Rheumatoid Arthritis, 170 J. Immunology 4793 (2003).
Syntonix Pharmaceuticals Letter to Food and Drug Administration dated Nov. 8, 2006, with Pre-IND Briefing Document entitled "FIXFc Recombinant Fusion Protein for the Treatment of Hemophilia B" (75 pages) (Redacted).
Executive Summary of Mar. 28, 2011 Scientific Advisory Board meeting (1 page) (Redacted).
U.S. Pat. No. 9,623,091, Case: IPR2018-01313. US Patent Trial and Appeal Board Decision, dated Jan. 9, 2018 (30 pages).
U.S. Pat. No. 9,623,091, Case: IPR2018-01313, Patent Owner Preliminary Response, dated Oct. 10, 2018 (63 pages).
U.S. Pat. No. 9,623,091, Case: IPR2018-01313, Petition for Inter Partes Review of All Claims of U.S. Pat. No. 9,623,091, dated Jul. 2, 2018 (76 pages).
U.S. Pat. No. 9,623,091, Case: IPR2018-01345, US Patent Trial and Appeal Board Decision, dated Jan. 16, 2019 (23 pages).
U.S. Pat. No. 9,623,091, Case: IPR2018-01345, Patent Owner Preliminary Response, dated Oct. 23, 2018 (50 pages).
U.S. Pat. No. 9,623,091, Case: IPR2018-01345, Petition for Inter Partes Review of Claims 1-17, 22, 24, 28 of U.S. Pat. No. 9,623,091, dated Jul. 6, 2018 (58 pages).
IPR2018-01345—Expert Declaration of Rachel J. Watters, dated Jun. 22, 2018.
Quinlan et al., "Albumin: Biochemical Properties and Therapeutic Potential", Hepatology: Official Journal of the American Association for the Study of Liver Diseases, vol. 41, No. 6, Jun. 2005.
Schmidt et al., "Structure-Function Relationships in Factor IX and Factor IXa", Trends in Cardiovascular Medicine, vol. 13, No. 1, pp. 39-45, 2003.
IPR2018-01345—Expert Declaration of Corey Crisafulli, dated Jun. 29, 2018.
Saenko et al., "Strategies towards a longer acting factor VIII", Haemophilia, vol. 12, Suppl. 3, pp. 42-51, Jul. 2006.
Kaufman et al., "Expression, Purification, and Characterization of Recombinant y-Carboxylated Factor IX Synthesized in Chines Hamster Ovary Cells," The Journal of Biological Chemistry, vol. 261, No. 21. Issue of Jul. 25, 1986, pp. 9622-9628.
Schroeder et al., "Structure and function of immunoglobulins", J Clin Immunol Feb. 2010, pp. S41-S52.
Muller et al., "Improved Pharmacokinetics of Recombinant Bispecific Antibody Molecules by Fusion to Human Serum Albumin", Journal of biological Chemistry, vol. 282, No. 17, Apr. 27, 2007 pp. 12650-12659.
Pechtner et al. "A New Approach to Drug Therapy: Fc-Fusion Technology," Journal of Primary Healthcare, vol. 7, Issue 1, Jan. 2017.
McGraw et al., "Evidence for a prevalent dimorphism in the activation peptide of human coagulation factor IX", Proceedings of the National Academy of Sciences, vol. 82, No. 9, May 1985, pp. 2555-3062.
Amevive (alefacept) Dosing Instructions, Biogen Idec Inc., Sep. 2005.
Santagostino et al., "Prophylaxis in haemophilia B patients: unresolved issues and pharmacoeconomic implication", Haemophilia, vol. 16, Suppl. 6, pp. 13-17, 2010.
United States Patent and Trademark Office, Notice of Final Determination and Requirement for Election regarding Patent Term Extension Application for U.S. Pat. No. 8,329,182, dated Aug. 30, 2017.
IPR2018-01345—Expert Declaration of Claude Negrier, M.D., Ph.D., dated Jul. 5, 2018.
Agreed-Upon Claim Constructions During the ITC Proceedings.
Schafer et al., "Failure is an option: learning from unsuccessful proof-of-concept trials", Drug Discovery Today, vol. 13, Nos. 21/22, pp. 913-915, Nov. 2008.
IPR2018-01345—Expert Declaration of Dax Rodulfa Blemberg, dated Jun. 6, 2018.
Yoshitake et al., "Nucleotide Sequence of the Gene for Human Factor IX (Antihemophilic Factor B)", Biochemistry, vol. 24, pp. 3736-3750, Mar. 12, 1985.
IPR2018-01345—Expert Declaration of Brendan T. Jones, dated Oct. 23, 2018.
IPR2018-01345—Expert Declaration of Allen R. Rines, dated Oct. 23, 2018.
IPR2018-01345—Expert Declaration of Sylvia D. Hall-Ellis, Ph.D., dated Jul. 5, 2018.
Berntorp et al., "Consensus perspectives on prophylactic therapy for haemophilia: summary statement", Haemophilia, vol. 9, Supp. 1, 2003, pp. 1-4.
Alprolix Prescribing Information, Bioverativ Therapeutics Inc., updated 2018.
Fischer et al., "Prophylaxis for severe haemophilia: clinical challenges in the absence as well as in the presence of inhibitors", Haemophilia, vol. 14. Suppl. 3, 2008, pp. 196-201.
Proetzel, et al., "Humanized FcRn mouse models for evaluating pharmacokinetics of human IgG antibodies," Methods, vol. 65, 2014, pp. 148-153.
Choo et al., "Molecular cloning of the gene for human anti-haemophilic factor IX", nature, vol. 299, Sep. 9, 1982, pp. 178-180.
IPR2018-01313—Expert Declaration of John Pasi, M.B. Ch.B., Ph.D., dated Oct. 10, 2018.

(56) References Cited

OTHER PUBLICATIONS

Gater et al., "Haemophilia B: impact on patients and economic burden of disease", Thrombosis and Haemostasis 106: 398-404, 2011.
C.A. No. 17-914-RGA—Court's Claim Construction filed on Mar. 26, 2019.
C.A. No. 17-914-RGA—Bioverativ's Expert Declaration of Rodney M. Camire, Ph.D., served on Aug. 12, 2018 (Redacted).
C.A. No. 17-914-RGA—Bioverativ's Expert Report of James T. Carmichael, served on Aug. 12, 2018 (Redacted).
C.A. No. 17-914-RGA—Bioverativ's Expert Report of James T. Carmichael, served on Aug. 12, 2018—Exhibit 1—Patent Family Table.
C.A. No. 17-914-RGA—Bioverativ's Expert Report of James T. Carmichael, served on Aug. 12, 2018—Exhibit 2—Patent Family Tree.
C.A. No. 17-914-RGA—Bioverativ's Expert Report of James T. Carmichael, served on Aug. 12, 2018—Exhibit C—37 C.F.R. § 1.56 (1989).
C.A. No. 17-914-RGA—Bioverativ's Expert Report of James T. Carmichael, served on Aug. 12, 2018—Exhibit D—37 C.F.R. § 1.56 (1992).
C.A. No. 17-914-RGA—Bioverativ's Expert Report of James T. Carmichael, served on Aug. 12, 2018—Exhibit E—Duty of Disclosure, 56 Fed. Reg. 2021, 2022 (Jan. 17, 1992).
C.A. No. 17-914-RGA—Bioverativ's Expert Report of James T. Carmichael, served on Aug. 12, 2018—Exhibit F—Revision of the Duty to Disclose Information in Patent Applications and Reexamination Proceedings, 81 Fed. Reg. 74,987, 74,996 (proposed Oct. 21, 2016) (proposed language § 1.56(b)).
C.A. No. 17-914-RGA—Bioverativ's Expert Report of James T. Carmichael, served on Aug. 12, 2018—Exhibit G—U.S. Appl. No. 13/809,276: Screenshot of "Special Issue: Abstracts of the XXIXth International Congress of the World Federation of Hemophilia, Buenos Aires, Argentina, Jul. 10-14, 2010," Haemophilia 16(Suppl. 4):1-170.
C.A. No. 17-914-RGA—Bioverativ's Expert Report of Dr. John Pasi, served on Aug. 12, 2019 (Redacted).
C.A. No. 17-914-RGA—Bioverativ's Expert Declaration of Dr. E. Sally Ward, served on Aug. 12, 2019 (Redacted).
C.A. No. 17-914-RGA—CSL's Declaration of Sylvia D. Hall-Ellis, Ph.D., served on Jun. 27, 2019.
C.A. No. 17-914-RGA—CSL's Declaration of Sylvia D. Hall-Ellis, Ph.D., served on Jun. 27, 2019—Exhibit A—Peters & Bitonti, Enhanced Pharmacokinetics of Factor IX as a Monomeric Fc Fusion, 5(S2) J. Thrombosis & Haemostasis O-M-016 (Jul. 9, 2007).
C.A. No. 17-914-RGA—CSL's Declaration of Sylvia D. Hall-Ellis, Ph.D., served on Jun. 27, 2019—Exhibit B—Shapiro et al., Safety and prolonged biological activity following a single administration of a recombinant molecular fusion of native human coagulation factor IX and the Fc region of immunoglobulin G (IgG) (rFIXFc) to subjects with hemophilia B, Haemophilia 16(Suppl. 4):30 (2010).
C.A. No. 17-914-RGA—CSL's Declaration of Sylvia D. Hall-Ellis, Ph.D., served on Jun. 27, 2019—Exhibit C—World Federation of Hemophilia, Guidelines for the Management of Hemophilia https://web.archive.org/web/20050424185918/http://www.wfh.org/ShowDoc.asp?Rubrique=31&Document=438, Apr. 24, 2005.
C.A. No. 17-914-RGA—CSL's Declaration of Sylvia D. Hall-Ellis, Ph.D., served on Jun. 27, 2019—Exhibit D—Lorenzo, Syntonix, Biovitrium in Deal on Long-Acting Clotting Product, BioWorld Today, vol. 17, No. 15 (Jan. 24, 2006).
C.A. No. 17-914-RGA—CSL's Declaration of Sylvia D. Hall-Ellis, Ph.D., served on Jun. 27, 2019—Exhibit E—MASAC Recommendation Concerning Prophylaxis Document #179, National Hemophilia Foundation 1-3 (2007).
C.A. No. 17-914-RGA—CSL's Declaration of Sylvia D. Hall-Ellis, Ph.D., served on Jun. 27, 2019—Attachment 3—MARC Record for the Journal of Thrombosis and Haemostasis, British Library.
C.A. No. 17-914-RGA—CSL's Declaration of Sylvia D. Hall-Ellis, Ph.D., served on Jun. 27, 2019—Attachment 4—CD-ROM entitled "Geneva—2007 Jul. 6-12 XXIst Congress of the International Society on Thrombosis and Haemostasis".
C.A. No. 17-914-RGA—CSL's Declaration of Sylvia D. Hall-Ellis, Ph.D., served on Jun. 27, 2019—Attachment 5—MARC record for the Journal of Thrombosis and Haemostasis, OCLC Bibliographic Database.
C.A. No. 17-914-RGA—CSL's Declaration of Sylvia D. Hall-Ellis, Ph.D., served on Jun. 27, 2019—Attachment 6—Thrombosis MeSH Descriptor Data 2019—Medical Subject Heading D013927.
C.A. No. 17-914-RGA—CSL's Declaration of Sylvia D. Hall-Ellis, Ph.D., served on Jun. 27, 2019—Attachment 7—Hemostasis MeSH Descriptor Data 2019—Medical Subject Heading D006487.
C.A. No. 17-914-RGA—CSL's Declaration of Sylvia D. Hall-Ellis, Ph.D., served on Jun. 27, 2019—Attachment 8—Blood Coagulation Disorders MeSH Descriptor Data 2019—Medical Subject Heading D001778.
C.A. No. 17-914-RGA—CSL's Declaration of Sylvia D. Hall-Ellis, Ph.D., served on Jun. 27, 2019—Attachment 9—Declaration of Daksha Rupawala, dated May 16, 2019.
C.A. No. 17-914-RGA—CSL's Declaration of Sylvia D. Hall-Ellis, Ph.D., served on Jun. 27, 2019—Attachment 10—MARC Record for the Journal Haemophilia, National Library of Medicine.
C.A. No. 17-914-RGA—CSL's Declaration of Sylvia D. Hall-Ellis, Ph.D., served on Jun. 27, 2019—Attachment 11—MARC Record for the Journal Haemophilia Oclc Bibliographic Database.
C.A. No. 17-914-RGA—CSL's Declaration of Sylvia D. Hall-Ellis, Ph.D., served on Jun. 27, 2019—Attachment 12—Hemophilia A MeSH Descriptor Data 2019—Medical Subject Heading D006467.
C.A. No. 17-914-RGA—CSL's Declaration of Sylvia D. Hall-Ellis, Ph.D., served on Jun. 27, 2019—Attachment 13—Library of Congress Subject Heading—Hemophilia, Control No. sh85060214.
C.A. No. 17-914-RGA—CSL's Declaration of Sylvia D. Hall-Ellis, Ph.D., served on Jun. 27, 2019—Attachment 14—Library of Congress Subject Heading—Periodicals, Control No. sh85099890.
C.A. No. 17-914-RGA—CSL's Declaration of Sylvia D. Hall-Ellis, Ph.D., served on Jun. 27, 2019—Attachment 15—MARC Record for the Journal BioWorld Today, University of Denver.
C.A. No. 17-914-RGA—CSL's Declaration of Sylvia D. Hall-Ellis, Ph.D., served on Jun. 27, 2019—Attachment 16—Library of Congress Subject Heading—Biotechnology Periodicals, Control No. sh2007101988.
C.A. No. 17-914-RGA—CSL's Declaration of Sylvia D. Hall-Ellis, Ph.D., served on Jun. 27, 2019—Attachment 17—MARC Record for the Journal BioWorld Today, OCLC Bibliographic Database.
C.A. No. 17-914-RGA—CSL's Declaration of Sylvia D. Hall-Ellis, Ph.D., served on Jun. 27, 2019—Attachment 18—Declaration of Corey Crisafulli (Jun. 29, 2018).
C.A. No. 17-914-RGA—CSL's Declaration of Sylvia D. Hall-Ellis, Ph.D., served on Jun. 27, 2019—Attachment 19—World Federation of Hemophilia—Guidelines for the Management of Hemophilia (https://web.archive.org/web/20050424185918/http://www.wfh.org/ShowDoc.asp?Rubrique=31&Document=438, Apr. 24, 2005) (Webpage only).
C.A. No. 17-914-RGA—CSL's Expert Report of Maureane Hoffman, M.D., Ph.D., served on Jun. 27, 2019 (Redacted).
C.A. No. 17-914-RGA—CSL's Expert Report of Maureane Hoffman, M.D., Ph.D., served on Sep. 13, 2019 (Redacted).
C.A. No. 17-914-RGA—CSL's Expert Report of Leslie A. Khawli, Ph.D., served on Jul. 2, 2019 (Redacted).
C.A. No. 17-914-RGA—CSL's Expert Report of Leslie A. Khawli, Ph.D., served on Sep. 13, 2019 (Redacted).
C.A. No. 17-914-RGA—CSL's Expert Report of Claude Negrier, M.D., Ph.D., served on Jun. 27, 2019 (Redacted).
C.A. No. 17-914-RGA—CSL's Expert Report of Claude Negrier, M.D., Ph.D., served on Jun. 27, 2019—Exhibit 3—Sequence Alignment of Amino Acids 1 to 415 of SEQ ID No. 2 in the Patents-in-Suit and Amino Acids 47 to 461 of SEQ ID No. 8 in the '956 Patent (which correspond to the FIX portion of SEQ ID No. 8).
C.A. No. 17-914-RGA—CSL's Expert Report of Claude Negrier, M.D., Ph.D., served on Jun. 27, 2019—Exhibit 4—Sequence Align-

(56) References Cited

OTHER PUBLICATIONS ment of Amino Acids 1 to 415 of SEQ ID No. 2 in the Patents-in-Suit and SEQ ID No. 2 in the '755 Publication.
C.A. No. 17-914-RGA—CSL's Expert Report of Claude Negrier, M.D., Ph.D., served on Sep. 13, 2019 (Redacted).
C.A. No. 17-914-RGA—CSL's Expert Report of Teresa Stanek Rea, served on Jun. 27, 2019 (Redacted).
C.A. No. 17-914-RGA—CSL's Expert Report of Teresa Stanek Rea, served on Sep. 13, 2019 (Redacted).
C.A. No. 17-914-RGA—Deposition Transcript of Rodney M. Camire, Ph.D. taken on Sep. 18, 2019.
C.A. No. 17-914-RGA—Deposition Transcript of Teresa Stanek Rea taken on Sep. 20, 2019.
C.A. No. 17-914-RGA—Deposition Transcript of Dr. E. Sally Ward taken on Oct. 1, 2019.
C.A. No. 17-914-RGA—Bioverativ's Response to Defendants' First Set of Interrogatories, served on Aug. 29, 2018 (Redacted).
C.A. No. 17-914-RGA—CSL's Supplemental Invalidity Contentions served on Jun. 3, 2019 (Redacted).
C.A. No. 17-914-RGA—Deposition Transcript of James T. Carmichael taken on Oct. 17, 2019 (Redacted).
C.A. No. 17-914-RGA—Deposition Transcript of Maureane Hoffman taken on Oct. 16, 2019 (Redacted).
C.A. No. 17-914-RGA—Deposition Transcript of Leslie Khawli, Ph.D. taken on Oct. 11, 2019 (Redacted).
C.A. No. 17-914-RGA—Deposition Transcript of Claude Negrier, M.D., Ph.D. taken on Oct. 4, 2019 (Redacted).
C.A. No. 17-914-RGA—Deposition Transcript of John Pasi, MD, ChB. taken on Oct. 9, 2019 (Redacted).
C.A. No. 17-914—Opening Brief in Support of Defendants' Motion for Summary Judgment and Motions to Exclude Expert Opinions, dated Nov. 1, 2019 (Redacted Public Version).
C.A. No. 17-914—Declaration of Harry Hanson in Support of Defendants' Motion for Summary Judgment and Motions to Exclude Expert Opinions and Exhibits, dated Nov. 1, 2019 (Redacted Public Version).
Kitchen S, Gray E, Mertens K. Monitoring of modified factor VIII and IX products. Haemophilia. 2014;20:36-42.
Young G, Perry D, The International Prophylaxis Study Group. Laboratory assay measurement of modified clotting factor concentrates: a review of the literature and recommendations for practice. J Thromb Haemost. 2019;0(ja).
Wilmot HV, Gray E. Potency estimates for recombinant factor IX in the one-stage clotting assay are influenced by more than just the choice of activated partial thromboplastin time reagent. Haemophilia. 2018;24(5):e363-e368.

* cited by examiner

A

B

SEQUENCE LISTING

<160> NUMBER OF SEQ ID NOS: 4

<210> SEQ ID NO 1
<211> LENGTH: 7583
<212> TYPE: DNA
<213> ORGANISM: Artificial
<220> FEATURE:
<223> OTHER INFORMATION: FIX-Fc Chain DNA (pSYN-FIX-030)

<400> SEQUENCE: 1

```
gcgcgcgttg acattgatta ttgactagtt attaatagta atcaattacg gggtcattag     60
ttcatagccc atatatggag ttccgcgtta cataacttac ggtaaatggc ccgcctggct    120
gaccgcccaa cgacccccgc ccattgacgt caataatgac gtatgttccc atagtaacgc    180
caatagggac tttccattga cgtcaatggg tggagtattt acggtaaact gcccacttgg    240
cagtacatca agtgtatcat atgccaagta cgccccctat tgacgtcaat gacggtaaat    300
ggcccgcctg gcattatgcc cagtacatga ccttatggga ctttcctact tggcagtaca    360
tctacgtatt agtcatcgct attaccatgg tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta tataagcaga gctctctggc    600
taactagaga acccactgct tactggctta tcgaaattaa tacgactcac tatagggaga    660
cccaagcttc gcgacgtacg gccgccacca tgcagcgcgt gaacatgatc atggcagaat    720
caccaggcct catcaccatc tgccttttag gatatctact cagtgctgaa tgtacaggtt    780
tgtttccttt tttaaaatac attgagtatg cttgccttt agatatagaa atatctgatg    840
ctgtcttctt cactaaattt tgattacatg atttgacagc aatattgaag agtctaacag    900
ccagcacgca ggttggtaag tactgtggga acatcacaga ttttggctcc atgccctaaa    960
gagaaattgg ctttcagatt atttggatta aaaacaaaga ctttcttaag agatgtaaaa   1020
ttttcatgat gttttctttt ttgctaaaac taaagaatta ttctttttaca tttcagtttt   1080 tcttgatcat gaaaacgcca acaaaattct gaatcggcca agagtata atcaggtaa     1140 attggaagag tttgttcaag ggatctaga gagagaatgt atggaagaaa gtgtagtttt    1200
tgaagaagca cgagaagttt ttgaaaacac tgaaagaaca actgaatttt ggaagcagta    1260
```

```
tgttgatgga gatcagtgtg agtccaatcc atgtttaaat ggcggcagtt gcaaggatga    1320
cattaattcc tatgaatgtt ggtgtccctt tggatttgaa ggaaagaact gtgaattaga    1380
tgtaacatgt aacattaaga atggcagatg cgagcagttt tgtaaaaata gtgctgataa    1440
caaggtggtt tgctcctgta ctgagggata tcgacttgca gaaaaccaga agtcctgtga    1500
accagcagtg ccatttccat gtggaagagt ttctgtttca caacttcta agctcacccg     1560
tgctgagact gtttttcctg atgtggacta tgtaaattct actgaagctg aaaccatttt    1620
ggataacatc actcaaagca cccaatcatt taatgacttc actcgggttg ttggtggaga    1680
agatgccaaa ccaggtcaat tcccttggca ggttgttttg aatggtaaag ttgatgcatt    1740
ctgtggaggc tctatcgtta atgaaaaatg gattgtaact gctgcccact gtgttgaaac    1800
tggtgttaaa attacagttg tcgcaggtga acataatatt gaggagacag aacatacaga    1860
gcaaaagcga aatgtgattc gaattattcc tcaccacaac tacaatgcag ctattaataa    1920
gtacaaccat gacattgccc ttctggaact ggacgaaccc ttagtgctaa acagctacgt    1980
tacacctatt tgcattgctg acaaggaata cacgaacatc ttcctcaaat ttggatctgg    2040
ctatgtaagt ggctggggaa gagtcttcca caaagggaga tcagctttag ttcttcagta    2100
ccttagagtt ccacttgttg accgagccac atgtcttcga tctacaaagt tcaccatcta    2160
taacaacatg ttctgtgctg gcttccatga aggaggtaga gattcatgtc aaggagatag    2220
tgggggaccc catgttactg aagtggaagg gaccagtttc ttaactggaa ttattagctg    2280
gggtgaagag tgtgcaatga aggcaaata tggaatatat accaaggtgt cccggtatgt    2340
caactggatt aaggaaaaaa caaagctcac tgacaaaact cacacatgcc caccgtgccc    2400
agctccggaa ctcctgggcg gaccgtcagt cttcctcttc cccccaaaac ccaaggacac    2460
cctcatgatc tcccggaccc ctgaggtcac atgcgtggtg gtggacgtga gccacgaaga    2520
ccctgaggtc aagttcaact ggtacgtgga cggcgtggag gtgcataatg ccaagacaaa    2580
gccgcgggag gagcagtaca acagcacgta ccgtgtggtc agcgtcctca ccgtcctgca    2640
ccaggactgg ctgaatggca aggagtacaa gtgcaaggtc tccaacaaag ccctcccagc    2700
ccccatcgag aaaaccatct ccaaagccaa agggcagccc cgagaaccac aggtgtacac    2760
cctgccccca tcccgggatg agctgaccaa gaaccaggtc agcctgacct gcctggtcaa    2820
aggcttctat cccagcgaca tcgccgtgga gtgggagagc aatgggcagc cggagaacaa    2880
ctacaagacc acgcctcccg tgttggactc cgacggctcc ttcttcctct acagcaagct    2940
caccgtggac aagagcaggt ggcagcaggg gaacgtcttc tcatgctccg tgatgcatga    3000
ggctctgcac aaccactaca cgcagaagag cctctccctg tctccgggta aatgagaatt    3060
cagacatgat aagatacatt gatgagtttg gacaaaccac aactagaatg cagtgaaaaa    3120
aatgctttat ttgtgaaatt tgtgatgcta ttgctttatt tgtaaccatt ataagctgca    3180
ataaacaagt tggggtgggc gaagaactcc agcatgagat cccgcgctg gaggatcatc     3240
cagccggcgt cccggaaaac gattccgaag cccaaccttt catagaaggc ggcggtggaa    3300
tcgaaatctc gtagcacgtg tcagtcctgc tcctcggcca cgaagtgcac gcagttgccg    3360
gccgggtcgc gcaggcgaa ctcccgcccc cacggctgct cgccgatctc ggtcatggcc     3420
ggcccggagg cgtcccggaa gttcgtggac acgacctccg accactcggc gtacagctcg    3480
tccaggccgc gcacccacac ccaggccagg gtgttgtccg gcaccacctg gtcctggacc    3540
gcgctgatga caggtcac gtcgtcccgg accacaccgg cgaagtcgtc ctccacgaag     3600
tcccgggaga cccgagccg gtcggtccag aactcgaccg ctccggcgac gtcgcgcgcg    3660
```

```
gtgagcaccg gaacggcact ggtcaacttg gccatggttt agttcctcac cttgtcgtat    3720
tatactatgc cgatatacta tgccgatgat taattgtcaa cacgtgctga tcagatccga    3780
aaatggatat acaagctccc gggagctttt tgcaaaagcc taggcctcca aaaaagcctc    3840
ctcactactt ctggaatagc tcagaggcag aggcggcctc ggcctctgca taaataaaaa    3900
aaattagtca gccatggggc ggagaatggg cggaactggg cggagttagg ggcgggatgg    3960
gcggagttag gggcgggact atggttgctg actaattgag atgcatgctt tgcatacttc    4020
tgcctgctgg ggagcctggg actttccac acctggttgc tgactaattg agatgcatgc    4080
tttgcatact tctgcctgct ggggagcctg ggactttcc acccctcgt cgagctagct    4140 tcgtgaggct ccggtgcccg tcagtgggca gagcgcacat cgcccacagt ccccgagaag    4200 ttgggggggag gggtcggcaa ttgaaccggt gcctagagaa ggtggcgcgg ggtaaactgg    4260
gaaagtgatg tcgtgtactg gctccgcctt tttcccgagg gtgggggaga accgtatata    4320
agtgcagtag tcgccgtgaa cgttcttttt cgcaacgggg ttgccgccag aacacaggta    4380
agtgccgtgt gtggttcccg cgggcctggc ctctttacgg gttatggccc ttgcgtgcct    4440
tgaattactt ccacctggct ccagtacgtg attcttgatc ccgagctgga gccaggggcg    4500
ggccttgcgc tttaggagcc ccttcgcctc gtgcttgagt tgaggcctgg cctgggcgct    4560
ggggccgccg cgtgcgaatc tggtggcacc ttcgcgcctg tctcgctgct ttcgataagt    4620
ctctagccat ttaaaatttt tgatgacctg ctgcgacgct ttttttctgg caagatagtc    4680
ttgtaaatgc gggccaggat ctgcacactg gtatttcggt ttttggggcc gcgggcggcg    4740
acggggcccg tgcgtcccag cgcacatgtt cggcgaggcg gggcctgcga gcgcggccac    4800
cgagaatcgg acggggtag tctcaagctg gccggcctgc tctggtgcct ggcctcgcgc    4860
cgccgtgtat cgccccgccc tgggcggcaa ggctggcccg gtcggcacca gttgcgtgag    4920
cggaaagatg gccgcttccc ggccctgctc caggggctc aaaatggagg acgcggcgct    4980
cgggagagcg ggcgggtgag tcacccacac aaaggaaagg ggcctttccg tcctcagccg    5040
tcgcttcatg tgactccacg gagtaccggg cgccgtccag gcacctcgat tagttctgga    5100
gcttttggag tacgtcgtct ttaggttggg gggagggggtt ttatgcgatg gagtttcccc    5160
acactgagtg ggtggagact gaagttaggc cagcttggca cttgatgtaa ttctccttgg    5220
aatttgccct ttttgagttt ggatcttggt tcattctcaa gcctcagaca gtggttcaaa    5280 gttttttttct tccatttcag gtgtcgtgaa cacgtggtcg cggccgcgcc gccaccatgg    5340
agacagacac actcctgcta tgggtactgc tgctctgggt tccaggttcc actggtgaca    5400
aaactcacac atgcccaccg tgcccagcac ctgaactcct gggaggaccg tcagtcttcc    5460
tcttcccccc aaaacccaag gacaccctca tgatctcccg gacccctgag gtcacatgcg    5520
tggtggtgga cgtgagccac gaagaccctg aggtcaagtt caactggtac gtggacggcg    5580
tggaggtgca taatgccaag acaaagccgc gggaggagca gtacaacagc acgtaccgtg    5640
tggtcagcgt cctcaccgtc ctgcaccagg actggctgaa tggcaaggag tacaagtgca    5700
aggtctccaa caaagccctc ccagccccca tcgagaaaac catctccaaa gccaagggc    5760 agccccgaga accacaggtg tacaccctgc ccccatcccg cgatgagctg accaagaacc    5820
aggtcagcct gacctgcctg gtcaaaggct tctatcccag cgacatcgcc gtggagtggg    5880
agagcaatgg gcagccggag aacaactaca agaccacgcc tcccgtgttg gactccgacg    5940
gctccttctt cctctacagc aagctcaccg tggacaagag caggtggcag caggggaacg    6000
```

-continued

```
tcttctcatg ctccgtgatg catgaggctc tgcacaacca ctacacgcag aagagcctct    6060
ccctgtctcc gggtaaatga ctcgagagat ctggccggct gggcccgttt cgaaggtaag    6120
cctatcccta accctctcct cggtctcgat tctacgcgta ccggtcatca tcaccatcac    6180
cattgagttt aaacccgctg atcagcctcg actgtgcctt ctagttgcca gccatctgtt    6240
gtttgcccct cccccgtgcc ttccttgacc ctggaaggtg ccactcccac tgtcctttcc    6300
taataaaatg aggaaattgc atcgcattgt ctgagtaggt gtcattctat tctgggggt     6360 ggggtggggc aggacagcaa gggggaggat tgggaagaca atagcaggca tgctggggat    6420
gcggtgggct ctatggcttc tgaggcggaa agaaccagtg gcggtaatac ggttatccac    6480
agaatcaggg gataacgcag gaaagaacat gtgagcaaaa ggccagcaaa aggccaggaa    6540
ccgtaaaaag gccgcgttgc tggcgttttt ccataggctc cgcccccctg acgagcatca    6600
caaaaatcga cgctcaagtc agaggtggcg aaacccgaca ggactataaa gataccaggc    6660
gtttccccct agaagctccc tcgtgcgctc tcctgttccg accctgccgc ttaccggata    6720
cctgtccgcc tttctccctt cgggaagcgt ggcgctttct catagctcac gctgtaggta    6780
tctcagttcg gtgtaggtcg ttcgctccaa gctgggctgt gtgcacgaac cccccgttca    6840
gcccgaccgc tgcgccttat ccggtaacta tcgtcttgag tccaacccgg taagacacga    6900
cttatcgcca ctggcagcag ccactggtaa caggattagc agagcgaggt atgtaggcgg    6960
tgctacagag ttcttgaagt ggtggcctaa ctacggctac actagaagaa cagtatttgg    7020
tatctgcgct ctgctgaagc cagttacctt cggaaaaaga gttggtagct cttgatccgg    7080
caaacaaacc accgctggta gcggtggttt ttttgtttgc aagcagcaga ttacgcgcag    7140
aaaaaaagga tctcaagaag atcctttgat cttttctacg gggtctgacg ctcagtggaa    7200
cgaaaactca cgttaaggga ttttggtcat gacattaacc tataaaaata ggcgtatcac    7260
gaggcccttt cgtctcgcgc gtttcggtga tgacggtgaa aacctctgac acatgcagct    7320
cccggagacg gtcacagctt gtctgtaagc ggatgccggg agcagacaag cccgtcaggg    7380
cgcgtcagcg ggtgttggcg ggtgtcgggg ctggcttaac tatgcggcat cagagcagat    7440
tgtactgaga gtgcaccata tatgcggtgt gaaataccgc acagatgcgt aaggagaaaa    7500
taccgcatca ggcgccattc gccattcagg ctgcgcaact gttgggaagg gcgatcggtg    7560
cgggcctctt cgctattacg cca                                           7583
```

```
<210> SEQ ID NO 2
<211> LENGTH: 688
<212> TYPE: PRT
<213> ORGANISM: Artificial
<220> FEATURE:
<223> OTHER INFORMATION: FIX-Fc chain
<220> FEATURE:
<221> NAME/KEY: SIGNAL
<222> LOCATION: (-46)..(-19)
<220> FEATURE:
<221> NAME/KEY: PROPEP
<222> LOCATION: (-18)..(-1)
<220> FEATURE:
<221> NAME/KEY: mat_peptide
<222> LOCATION: (1)..(642)
<220> FEATURE:
<221> NAME/KEY: MISC_FEATURE
<222> LOCATION: (1)..(415)
<223> OTHER INFORMATION: FIX portion
<220> FEATURE:
<221> NAME/KEY: MISC_FEATURE
<222> LOCATION: (416)..(642)
<223> OTHER INFORMATION: Fc portion
```

```
<400> SEQUENCE: 2

Met Gln Arg Val Asn Met Ile Met Ala Glu Ser Pro Gly Leu Ile Thr
    -45                 -40                 -35
Ile Cys Leu Leu Gly Tyr Leu Leu Ser Ala Glu Cys Thr Val Phe Leu
-30             -25                 -20                     -15
Asp His Glu Asn Ala Asn Lys Ile Leu Asn Arg Pro Lys Arg Tyr Asn
                -10                  -5              -1   1
Ser Gly Lys Leu Glu Glu Phe Val Gln Gly Asn Leu Glu Arg Glu Cys
             5                  10                  15
Met Glu Glu Lys Cys Ser Phe Glu Glu Ala Arg Glu Val Phe Glu Asn
         20                  25                  30
Thr Glu Arg Thr Thr Glu Phe Trp Lys Gln Tyr Val Asp Gly Asp Gln
 35              40                  45                      50
Cys Glu Ser Asn Pro Cys Leu Asn Gly Gly Ser Cys Lys Asp Asp Ile
                 55                  60                  65
Asn Ser Tyr Glu Cys Trp Cys Pro Phe Gly Phe Glu Gly Lys Asn Cys
             70                  75                  80
Glu Leu Asp Val Thr Cys Asn Ile Lys Asn Gly Arg Cys Glu Gln Phe
             85                  90                  95
Cys Lys Asn Ser Ala Asp Asn Lys Val Val Cys Ser Cys Thr Glu Gly
     100                 105                 110
Tyr Arg Leu Ala Glu Asn Gln Lys Ser Cys Glu Pro Ala Val Pro Phe
 115                 120                 125                 130
Pro Cys Gly Arg Val Ser Val Ser Gln Thr Ser Lys Leu Thr Arg Ala
             135                 140                 145
Glu Thr Val Phe Pro Asp Val Asp Tyr Val Asn Ser Thr Glu Ala Glu
             150                 155                 160
Thr Ile Leu Asp Asn Ile Thr Gln Ser Thr Gln Ser Phe Asn Asp Phe
             165                 170                 175
Thr Arg Val Val Gly Gly Glu Asp Ala Lys Pro Gly Gln Phe Pro Trp
     180                 185                 190
Gln Val Val Leu Asn Gly Lys Val Asp Ala Phe Cys Gly Gly Ser Ile
 195                 200                 205                 210
Val Asn Glu Lys Trp Ile Val Thr Ala Ala His Cys Val Glu Thr Gly
             215                 220                 225
Val Lys Ile Thr Val Val Ala Gly Glu His Asn Ile Glu Glu Thr Glu
             230                 235                 240
His Thr Glu Gln Lys Arg Asn Val Ile Arg Ile Ile Pro His His Asn
     245                 250                 255
Tyr Asn Ala Ala Ile Asn Lys Tyr Asn His Asp Ile Ala Leu Leu Glu
     260                 265                 270
Leu Asp Glu Pro Leu Val Leu Asn Ser Tyr Val Thr Pro Ile Cys Ile
275                 280                 285                 290
Ala Asp Lys Glu Tyr Thr Asn Ile Phe Leu Lys Phe Gly Ser Gly Tyr
                 295                 300                 305
Val Ser Gly Trp Gly Arg Val Phe His Lys Gly Arg Ser Ala Leu Val
             310                 315                 320
Leu Gln Tyr Leu Arg Val Pro Leu Val Asp Arg Ala Thr Cys Leu Arg
     325                 330                 335
Ser Thr Lys Phe Thr Ile Tyr Asn Asn Met Phe Cys Ala Gly Phe His
     340                 345                 350
Glu Gly Gly Arg Asp Ser Cys Gln Gly Asp Ser Gly Gly Pro His Val
355                 360                 365                 370
```

Thr Glu Val Glu Gly Thr Ser Phe Leu Thr Gly Ile Ile Ser Trp Gly
                375                 380                 385

Glu Glu Cys Ala Met Lys Gly Lys Tyr Gly Ile Tyr Thr Lys Val Ser
            390                 395                 400

Arg Tyr Val Asn Trp Ile Lys Glu Lys Thr Lys Leu Thr Asp Lys Thr
        405                 410                 415

His Thr Cys Pro Pro Cys Pro Ala Pro Glu Leu Leu Gly Gly Pro Ser
    420                 425                 430

Val Phe Leu Phe Pro Pro Lys Pro Lys Asp Thr Leu Met Ile Ser Arg
435                 440                 445                 450

Thr Pro Glu Val Thr Cys Val Val Val Asp Val Ser His Glu Asp Pro
                455                 460                 465

Glu Val Lys Phe Asn Trp Tyr Val Asp Gly Val Glu Val His Asn Ala
            470                 475                 480

Lys Thr Lys Pro Arg Glu Glu Gln Tyr Asn Ser Thr Tyr Arg Val Val
        485                 490                 495

Ser Val Leu Thr Val Leu His Gln Asp Trp Leu Asn Gly Lys Glu Tyr
    500                 505                 510

Lys Cys Lys Val Ser Asn Lys Ala Leu Pro Ala Pro Ile Glu Lys Thr
515                 520                 525                 530

Ile Ser Lys Ala Lys Gly Gln Pro Arg Glu Pro Gln Val Tyr Thr Leu
                535                 540                 545

Pro Pro Ser Arg Asp Glu Leu Thr Lys Asn Gln Val Ser Leu Thr Cys
            550                 555                 560

Leu Val Lys Gly Phe Tyr Pro Ser Asp Ile Ala Val Glu Trp Glu Ser
        565                 570                 575

Asn Gly Gln Pro Glu Asn Asn Tyr Lys Thr Thr Pro Pro Val Leu Asp
    580                 585                 590

Ser Asp Gly Ser Phe Phe Leu Tyr Ser Lys Leu Thr Val Asp Lys Ser
595                 600                 605                 610

Arg Trp Gln Gln Gly Asn Val Phe Ser Cys Ser Val Met His Glu Ala
                615                 620                 625

Leu His Asn His Tyr Thr Gln Lys Ser Leu Ser Leu Ser Pro Gly Lys
            630                 635                 640

<210> SEQ ID NO 3
<211> LENGTH: 741
<212> TYPE: DNA
<213> ORGANISM: Artificial
<220> FEATURE:
<223> OTHER INFORMATION: Fc DNA sequence

<400> SEQUENCE: 3
atggagacag acacactcct gctatgggta ctgctgctct gggttccagg ttccactggt      60
gacaaaactc acatgtgccc accgtgccca gcacctgaac tcctgggagg accgtcagtc     120
ttcctcttcc ccccaaaacc caaggacacc ctcatgatct cccggacccc tgaggtcaca     180
tgcgtggtgg tggacgtgag ccacgaagac cctgaggtca agttcaactg gtacgtggac     240
ggcgtggagg tgcataatgc caagacaaag ccgcgggagg agcagtacaa cagcacgtac     300
cgtgtggtca gcgtcctcac cgtcctgcac caggactggc tgaatggcaa ggagtacaag     360
tgcaaggtct ccaacaaagc cctcccagcc ccatcgaga aaccatctc caaagccaaa       420 gggcagcccc gagaaccaca ggtgtacacc ctgcccccat cccgcgatga gctgaccaag     480
aaccaggtca gcctgacctg cctggtcaaa ggcttctatc ccagcgacat cgccgtggag     540

-continued

```
tgggagagca atgggcagcc ggagaacaac tacaagacca cgcctcccgt gttggactcc      600
gacggctcct tcttcctcta cagcaagctc accgtggaca gagcaggtg gcagcagggg       660 aacgtcttct catgctccgt gatgcatgag gctctgcaca accactacac gcagaagagc     720
ctctcccgtg tccgggtaa a                                                 741
```

```
<210> SEQ ID NO 4
<211> LENGTH: 247
<212> TYPE: PRT
<213> ORGANISM: Artificial
<220> FEATURE:
<223> OTHER INFORMATION: Fc chain
<220> FEATURE:
<221> NAME/KEY: SIGNAL
<222> LOCATION: (-20)..(-1)
<223> OTHER INFORMATION: Heterologous mouse Igk light chain signal
      peptide
<220> FEATURE:
<221> NAME/KEY: mat_peptide
<222> LOCATION: (1)..(227)
<223> OTHER INFORMATION: Mature Fc sequence

<400> SEQUENCE: 4

Met Glu Thr Asp Thr Leu Leu Leu Trp Val Leu Leu Leu Trp Val Pro
-20              -15                 -10                 -5

Gly Ser Thr Gly Asp Lys Thr His Thr Cys Pro Pro Cys Pro Ala Pro
        -1   1               5                  10

Glu Leu Leu Gly Gly Pro Ser Val Phe Leu Phe Pro Pro Lys Pro Lys
            15                  20                  25

Asp Thr Leu Met Ile Ser Arg Thr Pro Glu Val Thr Cys Val Val Val
        30                  35                  40

Asp Val Ser His Glu Asp Pro Glu Val Lys Phe Asn Trp Tyr Val Asp
45                  50                  55                  60

Gly Val Glu Val His Asn Ala Lys Thr Lys Pro Arg Glu Glu Gln Tyr
                65                  70                  75

Asn Ser Thr Tyr Arg Val Val Ser Val Leu Thr Val Leu His Gln Asp
            80                  85                  90

Trp Leu Asn Gly Lys Glu Tyr Lys Cys Lys Val Ser Asn Lys Ala Leu
        95                 100                 105

Pro Ala Pro Ile Glu Lys Thr Ile Ser Lys Ala Lys Gly Gln Pro Arg
    110                 115                 120

Glu Pro Gln Val Tyr Thr Leu Pro Pro Ser Arg Asp Glu Leu Thr Lys
125                 130                 135                 140

Asn Gln Val Ser Leu Thr Cys Leu Val Lys Gly Phe Tyr Pro Ser Asp
                145                 150                 155

Ile Ala Val Glu Trp Glu Ser Asn Gly Gln Pro Glu Asn Asn Tyr Lys
            160                 165                 170

Thr Thr Pro Pro Val Leu Asp Ser Asp Gly Ser Phe Phe Leu Tyr Ser
        175                 180                 185

Lys Leu Thr Val Asp Lys Ser Arg Trp Gln Gln Gly Asn Val Phe Ser
    190                 195                 200

Cys Ser Val Met His Glu Ala Leu His Asn His Tyr Thr Gln Lys Ser
205                 210                 215                 220

Leu Ser Leu Ser Pro Gly Lys
                225
```

FACTOR IX POLYPEPTIDES AND METHODS OF USE THEREOF

CROSS REFERENCE TO RELATED APPLICATIONS

This application is a continuation application of U.S. application Ser. No. 15/820,080, filed Nov. 21, 2017, which is a continuation of U.S. application Ser. No. 14/982,934, filed Dec. 29, 2015, which is a divisional application of U.S. application Ser. No. 13/793,796, filed Mar. 11, 2013, now U.S. Pat. No. 9,233,145, which is a continuation application of U.S. application Ser. No. 13/809,276, filed Apr. 24, 2013 under 35 U.S.C. § 371, now U.S. Pat. No. 9,670,475, and which is based on International Application No. PCT/US2011/043569, filed Jul. 11, 2011, which claims the benefit of U.S. Provisional Application No. 61/363,064, filed Jul. 9, 2010, U.S. Provisional Application No. 61/424,555, filed Dec. 17, 2010, U.S. Provisional Application No. 61/430,819, filed Jan. 7, 2011, U.S. Provisional Application No. 61/438,572, filed Feb. 1, 2011, U.S. Provisional Application No. 61/442,079, filed Feb. 11, 2011, and U.S. Provisional Application No. 61/470,951, filed Apr. 1, 2011, all of which are incorporated herein by reference in their entireties.

REFERENCE TO SEQUENCE LISTING SUBMITTED ELECTRONICALLY VIA EFS-WEB

The content of the electronically submitted sequence listing (Name: 4159.2730000D_SequenceListing_ST25.txt, Size: 20,446 bytes; and Date of Creation: Feb. 6, 2018) submitted in this application is incorporated herein by reference in its entirety.

BACKGROUND OF THE INVENTION

Field of the Invention

The present invention relates generally to the field of therapeutics for hemostatic disorders.

Background Art

Hemophilia B (also known as Christmas disease) is one of the most common inherited bleeding disorders in the world. It results in decreased in vivo and in vitro blood clotting activity and requires extensive medical monitoring throughout the life of the affected individual. In the absence of intervention, the afflicted individual will suffer from spontaneous bleeding in the joints, which produces severe pain and debilitating immobility; bleeding into muscles results in the accumulation of blood in those tissues; spontaneous bleeding in the throat and neck may cause asphyxiation if not immediately treated; renal bleeding; and severe bleeding following surgery, minor accidental injuries, or dental extractions also are prevalent.

Normal in vivo blood coagulation at minimum requires the serine proteases Factors II (prothrombin), VII, IX, X and XI (soluble plasma proteins); cofactors including the transmembrane protein tissue factor and the plasma proteins Factors V and VIII; fibrinogen, the transglutaminase Factor XIII, phospholipid (including activated platelets), and calcium. Additional proteins including kallikrein, high molecular weight kininogen, and Factor XII are required for some in vitro clotting tests, and may play a role in vivo under pathologic conditions.

In hemophilia, blood clotting is disturbed by a lack of certain plasma blood clotting factors. Hemophilia B is caused by a deficiency in Factor IX that may result from either the decreased synthesis of the Factor IX protein or a defective molecule with reduced activity. The treatment of hemophilia occurs by replacement of the missing clotting factor by exogenous factor concentrates highly enriched in Factor IX. However, generating such a concentrate from blood is fraught with technical difficulties, as is described below.

Purification of Factor IX from plasma (plasma derived Factor IX; pdFIX) almost exclusively yields active Factor IX. However, such purification of factor IX from plasma is very difficult because Factor IX is only present in low concentration in plasma (5 ug/mL. Andersson, Thrombosis Research 7: 451 459 (1975). Further, purification from blood requires the removal or inactivation of infectious agents such as HIV and HCV. In addition, pdFIX has a short half-life and therefore requires frequent dosing. Recombinant factor IX (rFIX) is also available, but suffers from the same short half-life and need for frequent dosing (e.g., 2-3 times per week for prophylaxis) as pdFIX. rFIX also has a lower incremental recovery (K value) compared to pdFIX, which necessitates the use of higher doses of rFIX than those for pdFIX.

Reduced mortality, prevention of joint damage and improved quality of life have been important achievements due to the development of plasma-derived and recombinant Factor IX. Prolonged protection from bleeding would represent another key advancement in the treatment of hemophilia B patients. However, to date, no products that allow for prolonged protection have been developed. Therefore, there remains a need for improved methods of treating hemophilia due to Factor IX deficiency that are more tolerable and more effective than current therapies.

BRIEF SUMMARY OF THE INVENTION

The present invention provides methods of administering Factor IX using chimeric polypeptides comprising Factor IX and hybrids of such chimeric polypeptides; chimeric polypeptides comprising Factor IX and hybrids of such chimeric polypeptides; polynucleotides encoding such chimeric and hybrid polypeptides; cells comprising such polynucleotides; and methods of producing such chimeric and hybrid polypeptides using such cells. In some embodiments, the Factor IX chimeric polypeptide is a Factor IX FcRn binding partner (BP) chimeric polypeptide such as a Factor IX Fc chimeric polypeptide. In other embodiments, the Factor IX chimeric polypeptide is a Factor IX-XTEN polypeptide.

The present invention provides a method of administering Factor IX to a subject in need thereof, comprising administering to the subject a dose of at least about 10, at least about 20, or at least about 25 IU/kg of a Factor IX FcRn BP chimeric polypeptide, e.g., a Factor IX-Fc chimeric polypeptide or a Factor IX-XTEN chimeric polypeptide, at about a once weekly or longer dosing interval.

In some embodiments, the plasma level of the chimeric polypeptide reaches an average trough of at least about 1 IU/dl after at least about 6 days in at least about 70%, at least about 80%, at least about 90%, or about 100% of a patient population or reaches a trough of at least about 1, 2, 3, 4, or 5 IU/dl after at least about 6 days in a subject. In some embodiments, the plasma level of said chimeric polypeptide reaches an average trough of about 1-5 or 1-3 IU/dl. Such trough or average trough may be reached after about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 days.

In some embodiments, the chimeric polypeptide has greatly reduced phosphorylation and sulfation in comparison to plasma derived Factor IX. In some embodiments the chimeric polypeptide is less than 25% phosphorylated and less than 25% sulfated, e.g., less than 25% fully phosphorylated and sulfated. In some embodiments, the chimeric polypeptide is less than about 10% phosphorylated and less than about 9% sulfated. In some embodiments, the chimeric polypeptide has a gamma carboxylation pattern/distribution, a gamma carboxylation content, a sialylation pattern/distribution, and/or a sialylation content similar to (i.e., within 10% of) or the same as those of the Factor IX Fc chimeric polypeptide in Examples 5-6.

In some embodiments, the chimeric polypeptide has an incremental recovery greater that 0.7 or greater than 0.75 ug/ml (antigen). In some embodiments, the chimeric polypeptide has a mean incremental recovery (K-Value) (activity; observed) of at least about 0.8, at least about 0.9, or at least about 1 IU/dL per IU/kg.

In some embodiments, the chimeric polypeptide exhibits one or more pharmacokinetic parameters, in said patient population or in said subject, selected from the group consisting of:

(a) a mean clearance (CL) (activity) in said patient population of about 3.36±0.93 mL/hour/kg; a mean clearance (CL) (activity) in said patient population of about 3.0-3.72, 3.0, 3.1, 3.2, 3.3, 3.4, 3.5, 3.6, 3.7, or 3.72 mL/hour/kg; a mean clearance (CL) (activity) in said patient population that is about 2.5 fold lower than the clearance of a polypeptide comprising said Factor IX without said FcRn BP; a clearance (CL) (activity) in said subject of about 1.84-4.58 mL/hour/kg (b) a mean residence time (MRT) (activity) in said patient population of at least about 68.05±11.16 hours; a mean MRT (activity) in said patient population of about 60-78, 60, 62, 64, 66, 68, 70, 72, 74, 76, or 78 hours; a mean MRT (activity) in said patent population that is about 3 fold longer than the mean MRT of a polypeptide comprising said Factor IX without said FcRn BP; a mean residence time (MRT) (activity) in said subject of about 53.1-85.8 hours; a mean residence time (MRT) (activity) in said subject of at least about 45, about 50, about 55, about 60, about 65, about 70, about 75, about 80, about 85, or about 90 hours;

(c) a mean $t_{1/2beta}$ (activity) in said patient population of about 52.5±9.2 hours; a mean $t_{1/2beta}$ (activity) in said patient population that is about 47-60 hours, about 47, about 48, about 49, about 50, about 51, about 52, about 53, about 54, about 55, about 56, about 57, about 58, about 59, about 60 hours; a mean $t_{1/2beta}$ (activity) in said patient population that is about 3 fold longer than the mean $t_{1/2beta}$ of a polypeptide comprising said Factor IX without said FcRn BP; a $t_{1/2beta}$ (activity) in said subject of about 40-67.4, about 40, about 45, about 50, about 55, about 60, about 65, about 70, or about 75 hours;

(d) a mean incremental recovery (K value) (activity; observed) in said patient population of about 0.93±0.18 IU/dL per IU/kg; a mean incremental recovery (K value) (activity; observed) in said patient population of about 0.85-1.0, about 0.85, about 0.86, about 0.87, about 0.88, about 0.89, about 0.90, about 0.91, about 0.92, about 0.93, about 0.94, about 0.95, about 0.96, about 0.97, about 0.98, about 0.99, about 1.0, about 1.05, about 1.10, or about 1.15 IU/dL per IU/kg; a mean incremental recovery (K value) (activity; observed) in said patient population that is about 24% better than the mean incremental recovery of a polypeptide comprising said Factor IX without said FcRn BP; an incremental recovery (K value) (activity; observed) in said subject of about 0.62-1.17 IU/dL per IU/kg;

(e) a mean Vss (activity) in said patient population of about 226±67.76 (corrected to 69.8) mL/kg; a mean Vss (activity) in said patient population of about 200-300, about 200, about 210, about 220, about 230, about 240, about 250, about 260, about 270, about 280, about 290, or about 300 mL/kg; a Vss (activity) in said subject of about 145-365 mL/kg;

(f) a mean AUC/dose (activity) in said patient population of about 32.44±10.75 IU*h/dL per IU/kg; a mean AUC/dose (activity) in said patient population of about 26-40, about 26, about 27, about 28, about 29, about 30, about 31, about 32, about 33, about 34, about 35, about 36, about 37, about 38, about 39, or about 40 IU*h/dL per IU/kg; an AUC/dose in said subject of about 21.80-54.30 IU*h/dL per IU/kg.

In some embodiments, the dose of chimeric polypeptide contains a significantly lower (10-100 fold) level (0.01-0.001%) of activated FIX (FIXa), than currently marketed Factor IX products such as MONONINE™ (pdFIX; CSL Behring)) or BENEFIX™ (Wyeth; rFIX) (0.1%). Such level may be 10, 20, 30, 40, 50, 60, 70, 80, 90, or 100 fold lower than currently marketed products, or 0.01, 0.05, 0.0033, 0.0025, 0.002, 0.00167, 0.00142, 0.00125, 0.00111, or 0.001%.

In some embodiments, the dosing interval is 6-18, 6-10, 9-18, at least 6, at least 7, at least 8, at least 9, at least 10, at least 11, at least 12, at least 13, at least 14, at least 15, at least 16, at least 17, or at least 18 days, weekly, two times monthly, or one time monthly. The dosing interval may be a prophylactic dosing interval, a fixed prophylactic dosing interval, or an individualized prophylactic dosing interval.

The methods of the invention are practiced on a subject in need of control or prevention of bleeding or bleeding episodes, in need of intermittent treatment, in need of prophylactic treatment, or in need of on-demand treatment.

The therapeutic doses that may be used in the methods of the invention are about 25-180, about 20-180, about 20-50, about 20-100, about 10-180, about 10-50, about 10-30, or about 50-100 IU/kg. The dose may be a fixed dose or an individualized dose.

In some embodiments, the chimeric polypeptide is administered intravenously or subcutaneously.

The subject in the methods of the invention may be a human subject or may be a non-human mammal. Non-human mammals include mice, dogs, primates, monkeys, cats, horses, cows, pigs, and other domestic animals and small animals.

The chimeric polypeptide may be in the form of a hybrid comprising a second polypeptide in association with said chimeric polypeptide, wherein said second polypeptide comprises or consists essentially of an FcRn BP, e.g., an Fc. The chimeric polypeptide may be at least 90%, at least 95%, or 100% identical to the Factor IX sequence, the Fc sequence, or both the Factor IX and Fc sequence in Tables 2A (SEQ ID NO:2) and/or 2B (SEQ ID NO:4), with or without the signal sequence(s) and propeptide.

The chimeric polypeptide or hybrid may be administered as part of a pharmaceutical composition comprising at least one excipient.

The invention also provides the above-described chimeric and hybrid polypeptides themselves, polynucleotides encoding them, a cultured human embryonic cells comprising the polynucleotides, and methods of producing such chimeric and hybrid polypeptides, and the polypeptides produced by such methods.

BRIEF DESCRIPTION OF THE DRAWINGS/FIGURES

FIG. 1. Schematic of one type of Factor IX chimeric polypeptide, a Factor IX-Fc hybrid.

Figure 2:
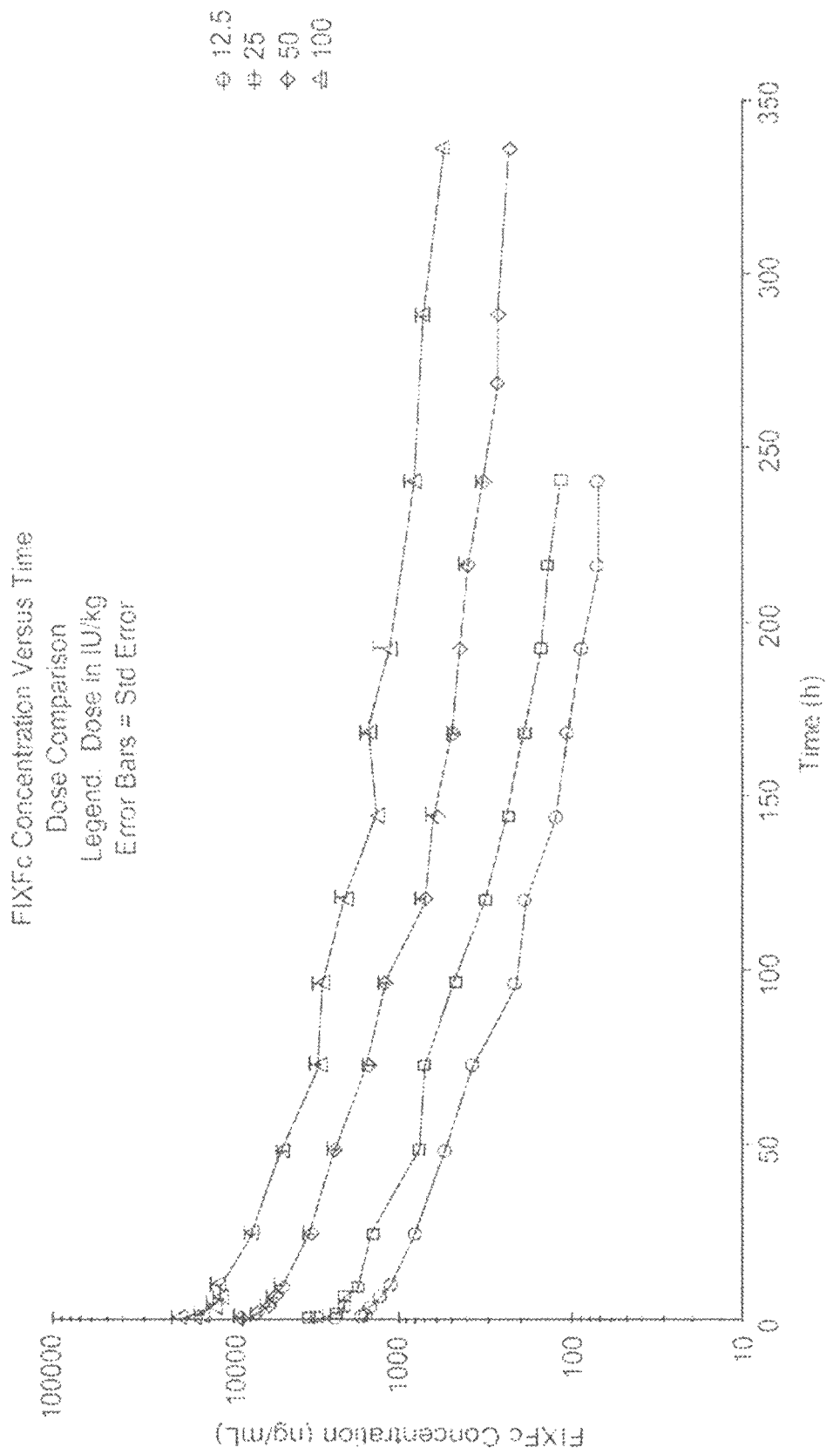

FIG. 2. Group mean FIXFc concentration versus time profiles; nominal dose comparison.

Figure 3:
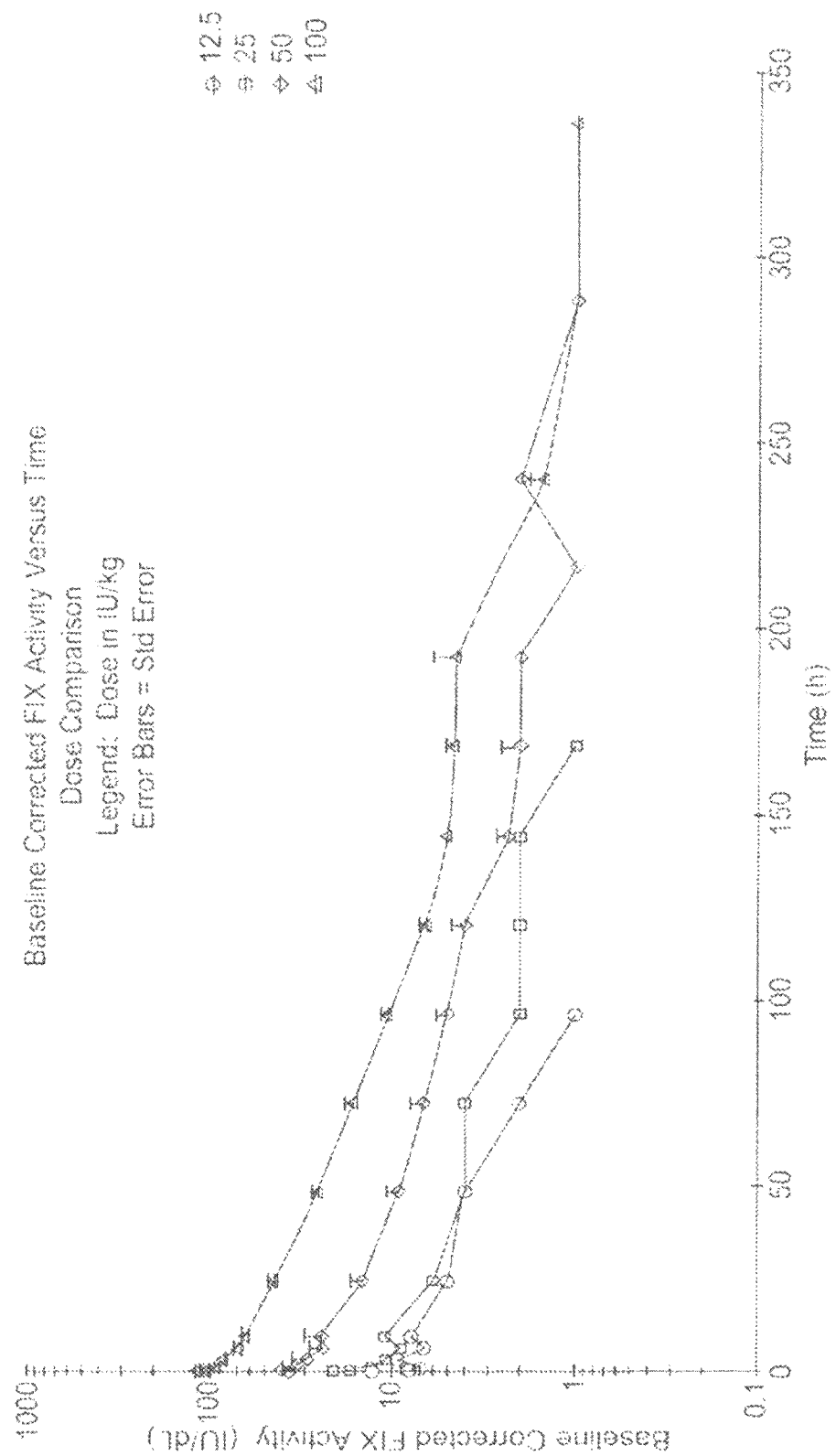

FIG. 3. Group mean FIXFc activity versus time profiles; nominal dose comparison.

Figure 4:
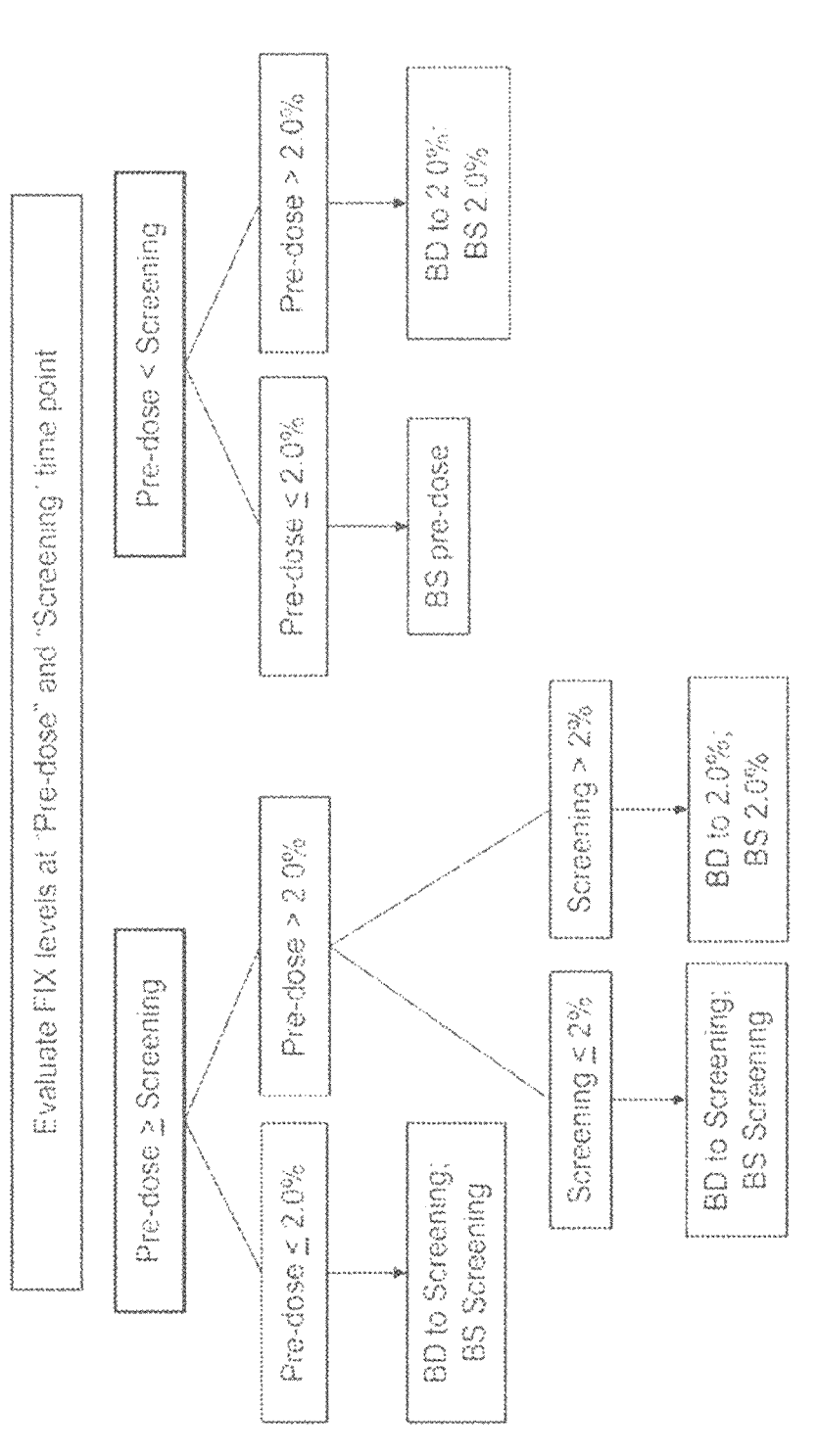

FIG. 4. The baseline subtraction decision tree.

Figure 5:
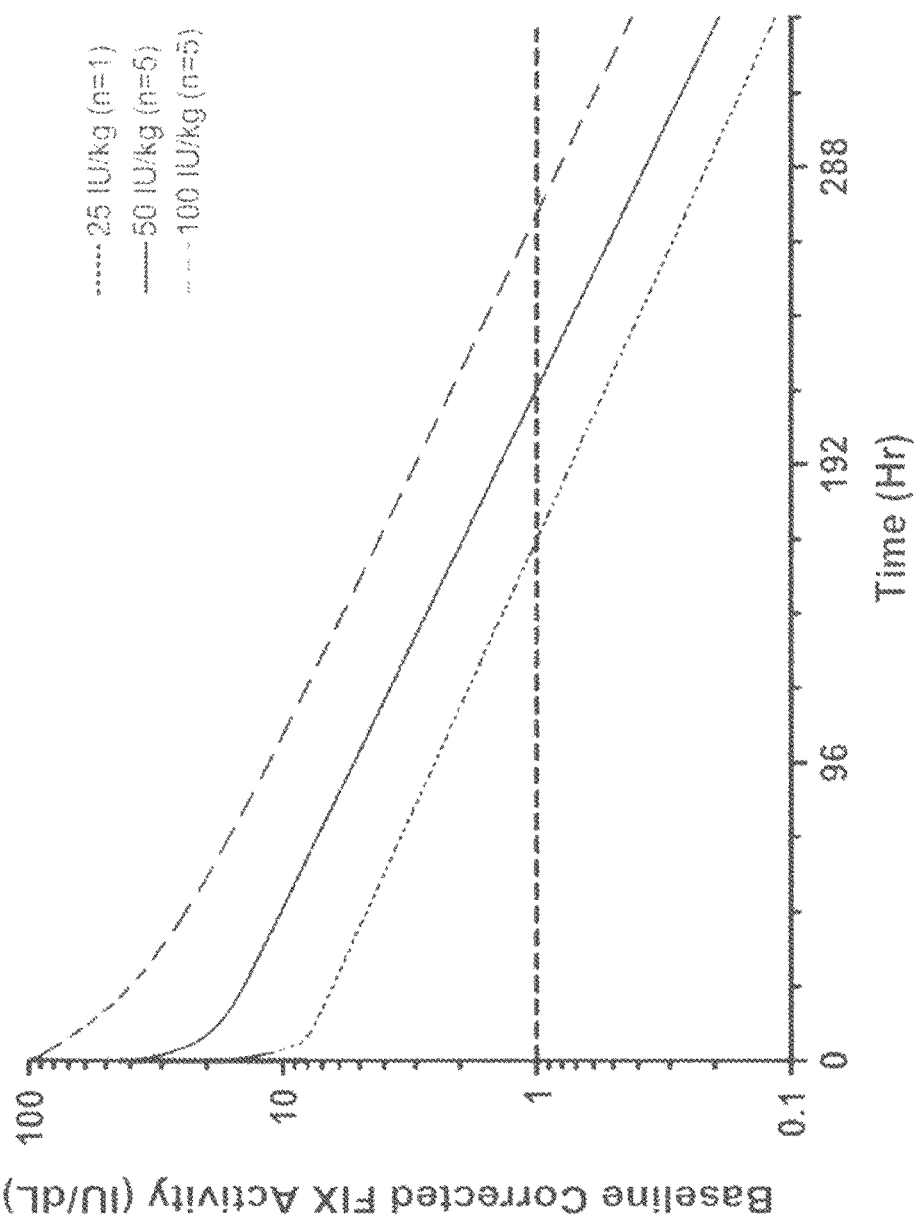

FIG. 5. Dose proportional increase in Cmax and AUC for FIX activity.

Figure 6:
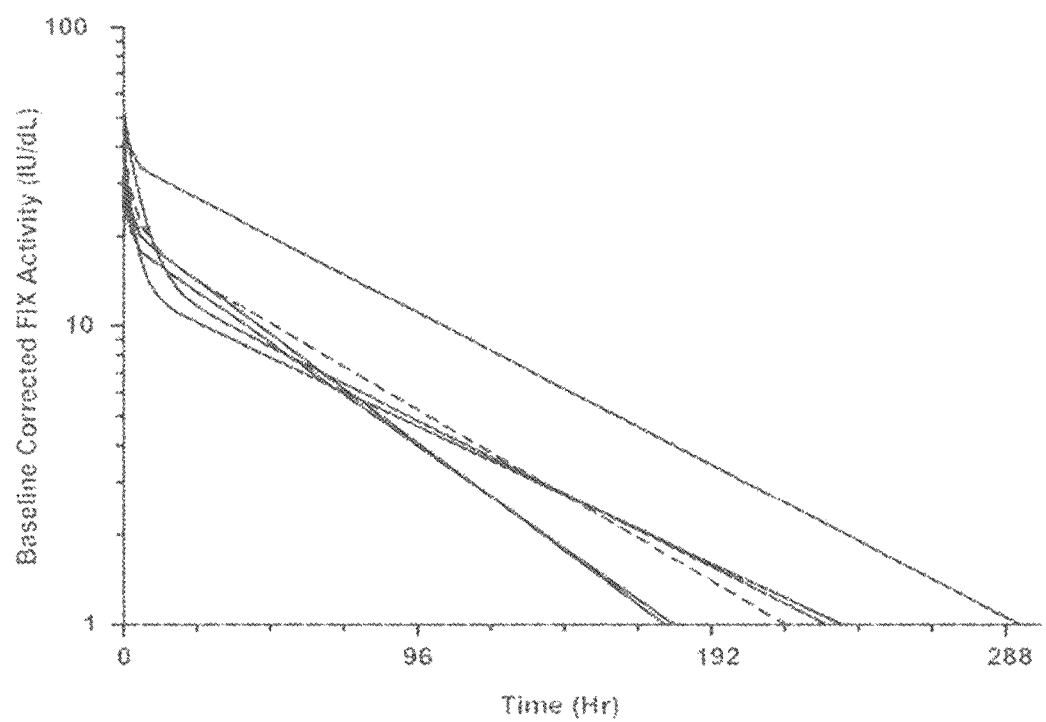
Figure 6:
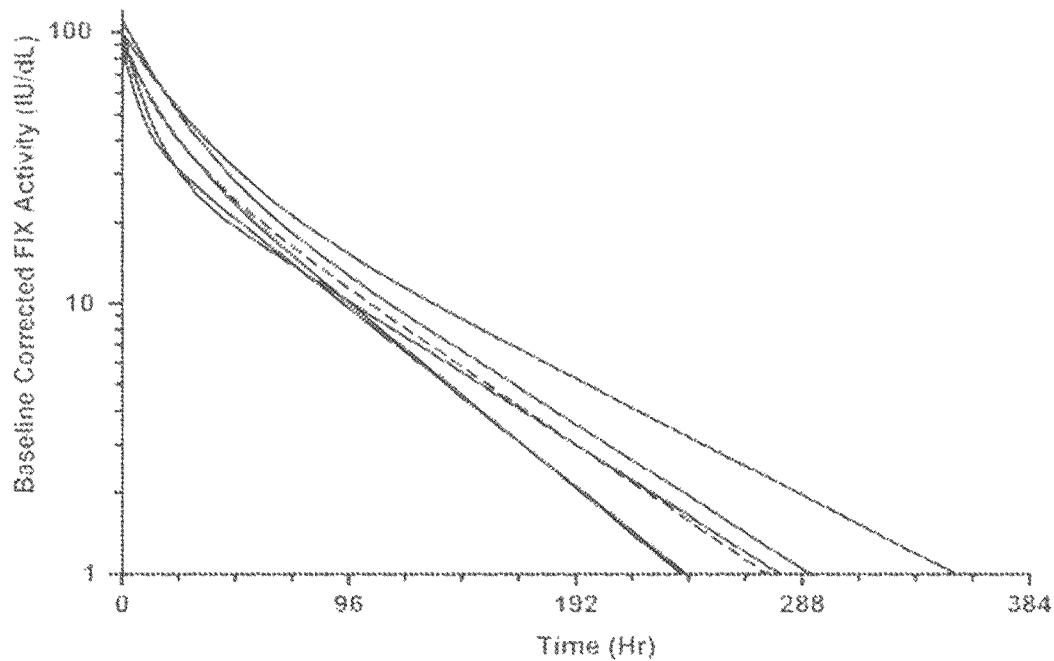

FIG. 6. Estimated Therapeutic Duration of rFIXFc at 50 (A) and 100 (B) IU/kg.

Figure 7:
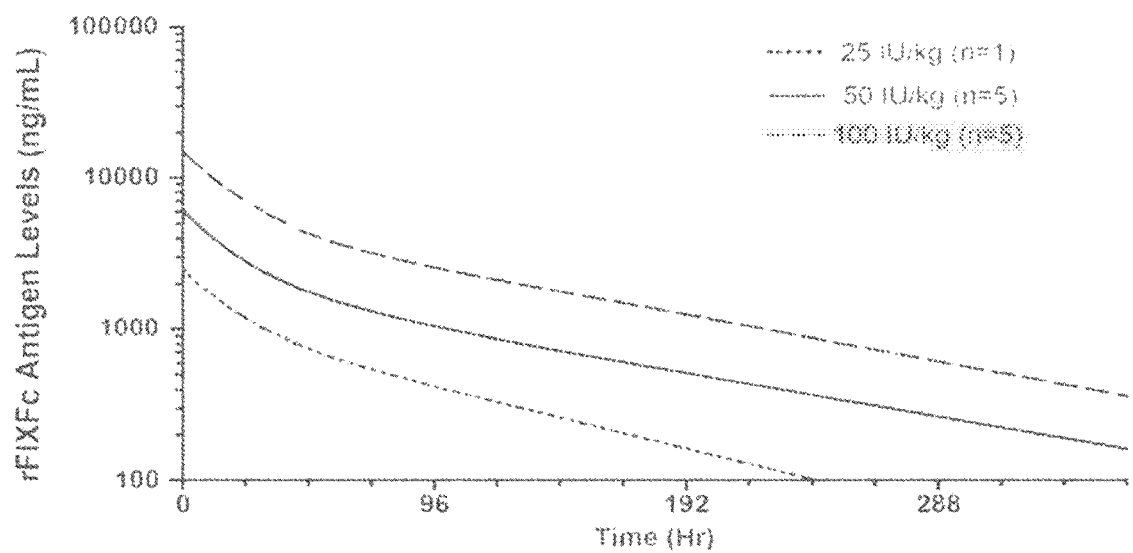

FIG. 7. Dose proportional increase in Cmax and AUC for FIX antigen.

Figure 8:
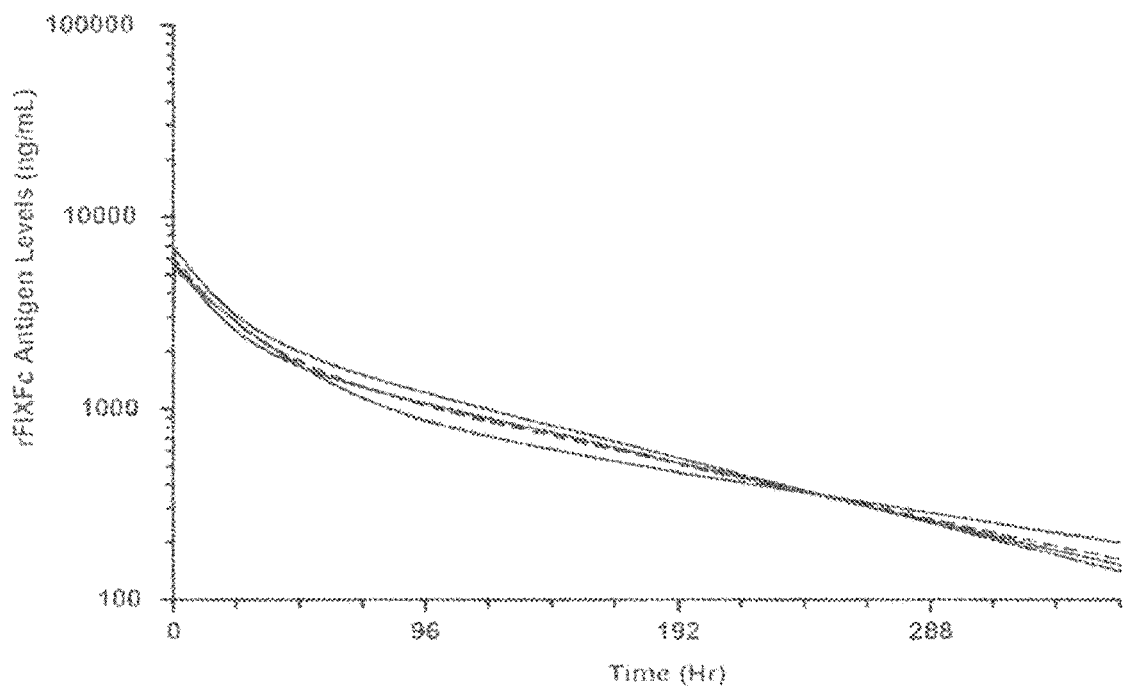
Figure 8:
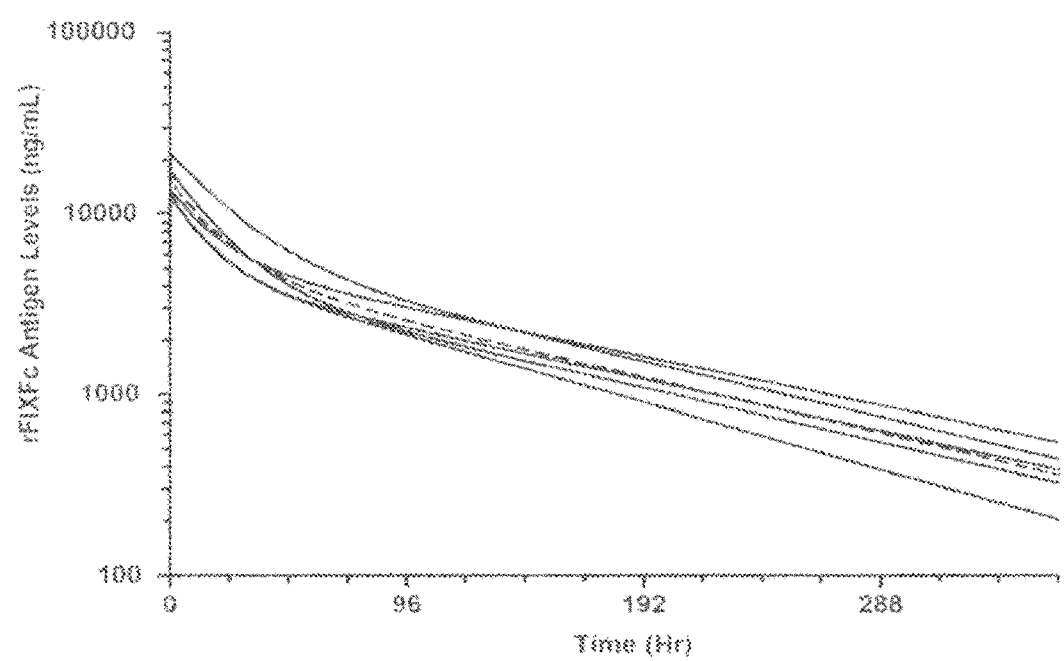

FIG. 8. Pharmacokinetic estimates for rFIXFc antigen at 50 (A) and 100 (B) IU/kg nominal doses.

Figure 9:
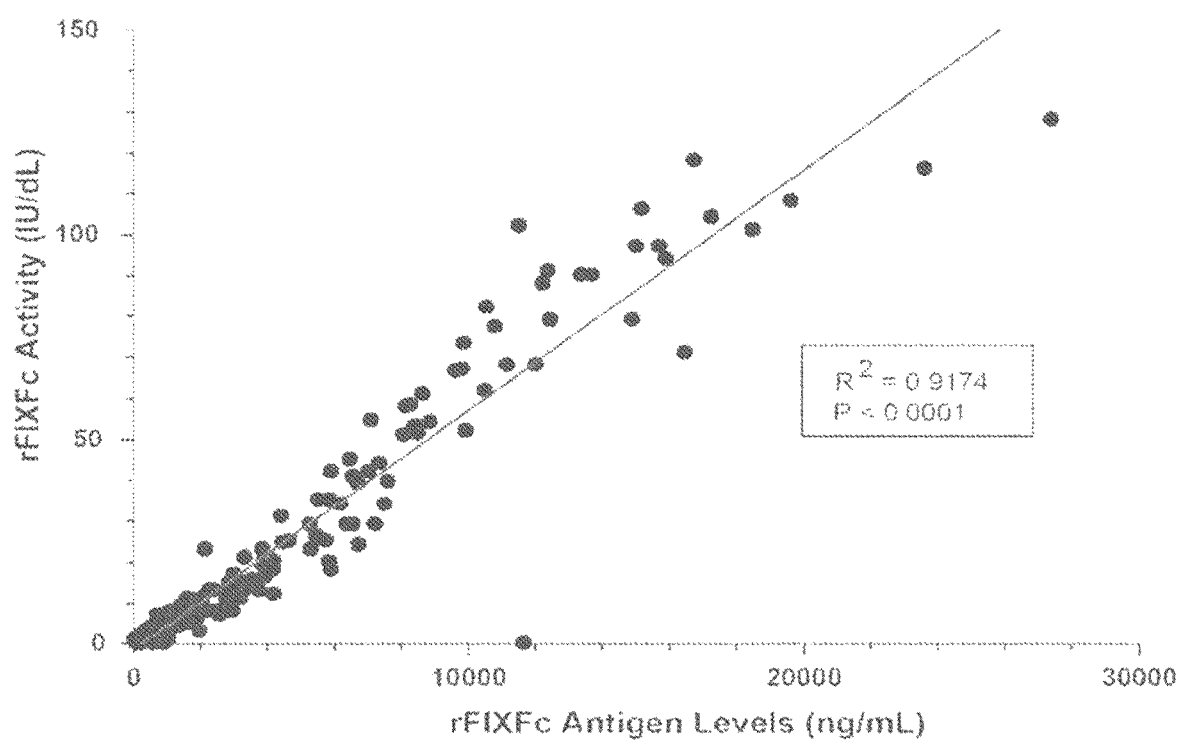

FIG. 9. Excellent correlation between rFIXFc activity and antigen levels. Note that due to recalculation of activity PK, as discussed in Example 11, $R^2$=0.946.

Figure 10:
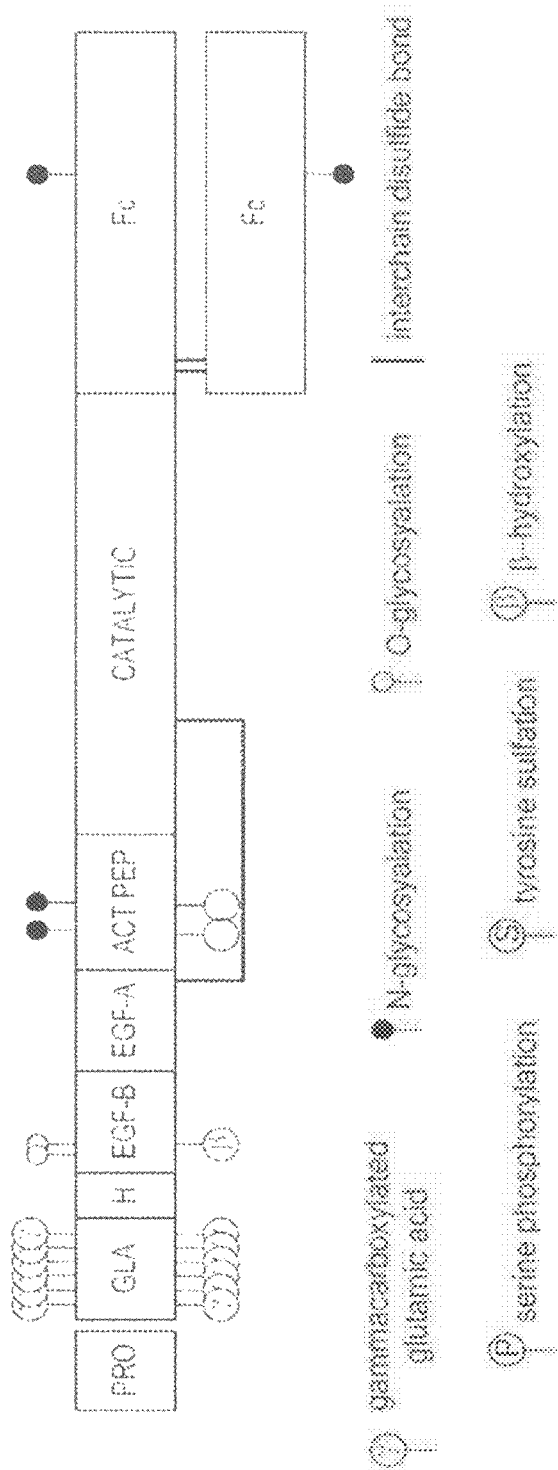

FIG. 10. rFIX-Fc domain structure and posttranslational modifications. PRO: Propeptide cleaved by processing enzyme. GLA: contains 12 γ-carboxylated glutamic acid (Gla) residues. ACT PEP: activation peptide cleaved to yield active protease. Other modifications: N- and O-glycosylation, Asp(64) β-hydroxylation, Tyr sulfation, Ser phosphorylation.

Figure 11:
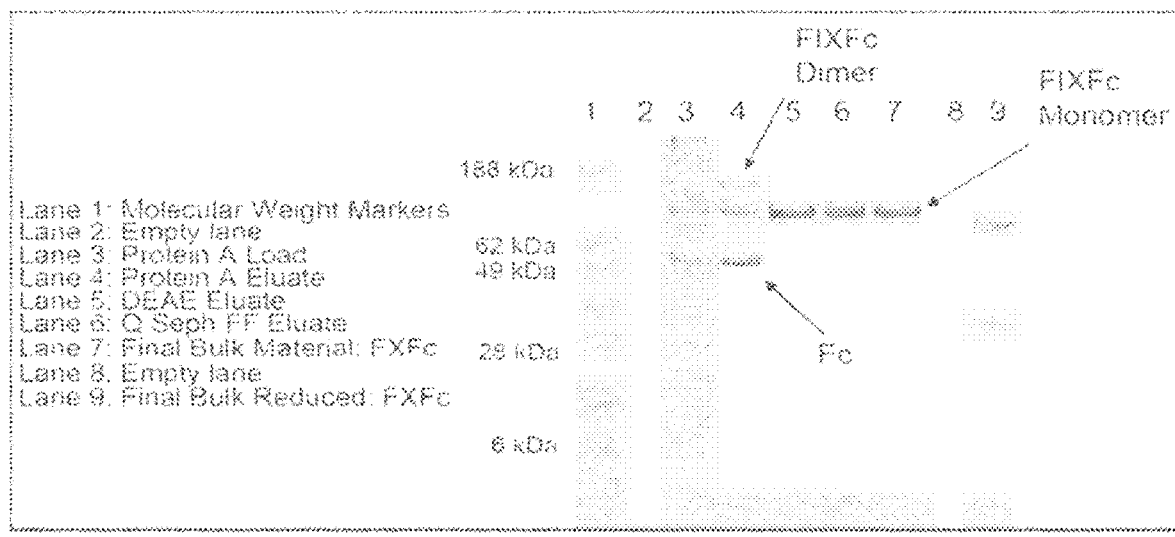

FIG. 11. SDS-PAGE gel of purification intermediates and purified FIXFc monomer. Samples from different steps in the purification of FIXFc were analyzed by non-reducing SDS-PAGE. Lane 1: SeeBlue Plus Molecular Weight Markers (Invitrogen). Lane 2: empty lane. Lane 3: Protein A load. Lane 4: Protein A eluate. Lane 5: Fractogel DEAE eluate. Lane 6: Q Seph FF eluate. Lane 7: final bulk FIXFc. Lane 8: empty lane. Lane 9: final bulk reduced FIXFc.

Figure 12:
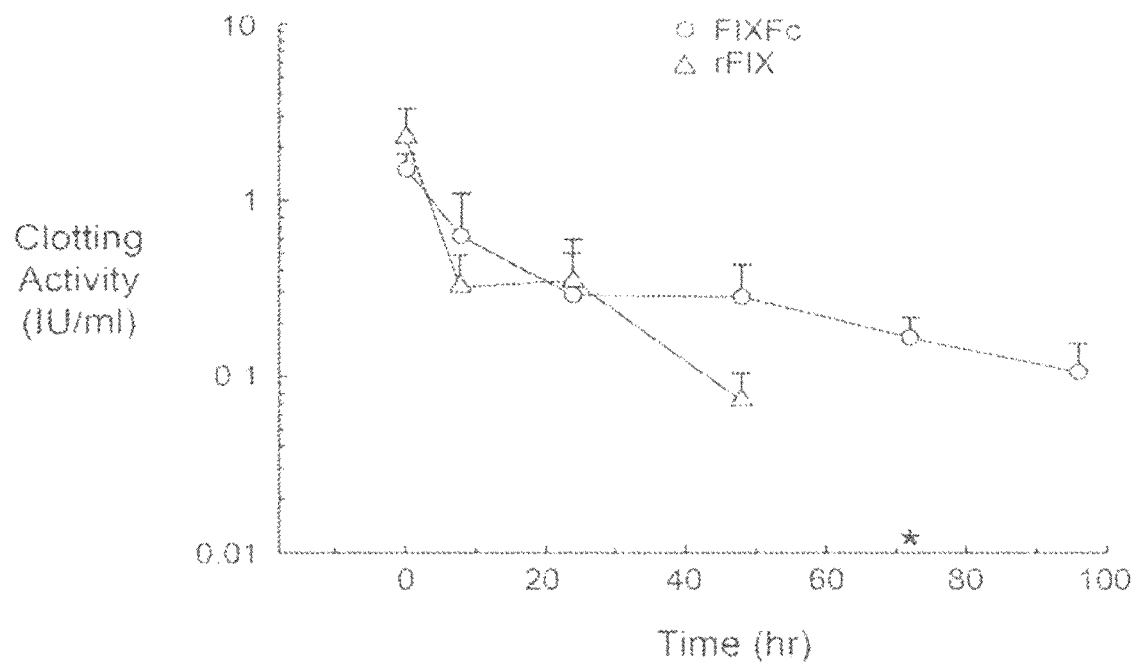

FIG. 12. Functional activity of FIXFc in FIX-deficient mice. FIX-deficient mice were dosed intravenously with 219 IU/kg FIXFc (3 or 4 per group, 6 groups, n=23) or 200 IU/kg rFIX (3 or 4 per group, 5 groups, n=23) at time=0. Blood samples were collected at various times after dosing (0.25 hr to 96 hr) and analyzed for clotting activity using FIX activity assay. * rFIX activity is undetectable in all of the mice at time points later than 48 hr after dosing.

Figure 13:
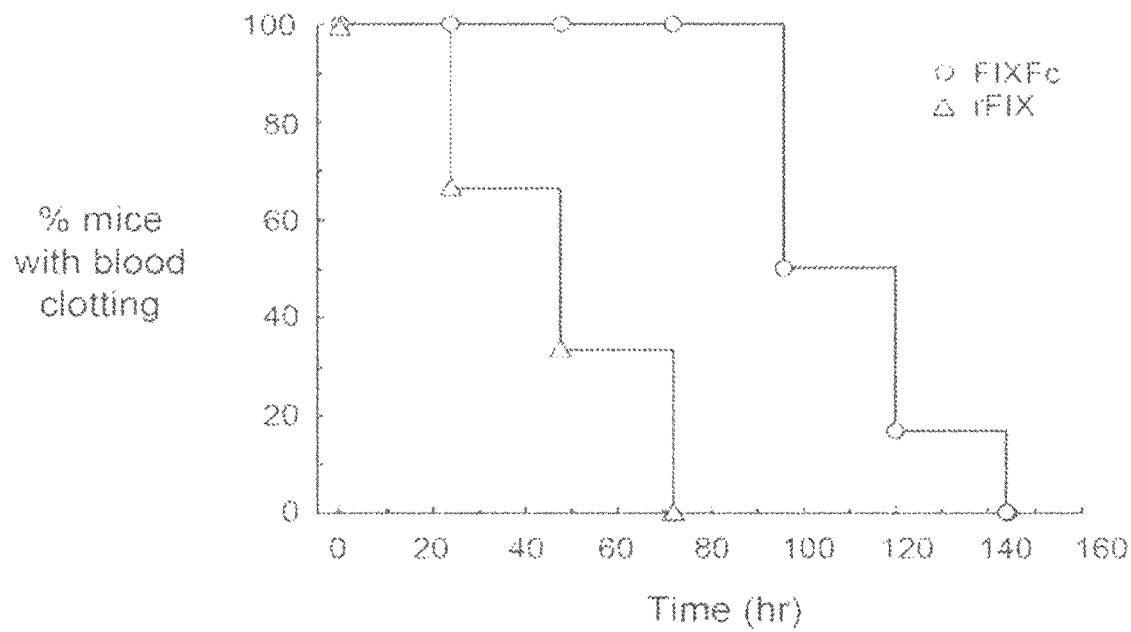

FIG. 13. Whole blood clotting time of FIXFc versus recombinant FIX in FIX-deficient mice. FIX-deficient mice (6 per group) were dosed intravenously with 50 IU/kg FIXFc or 50 IU/kg rFIX. Blood samples were collected before dosing and at various times after dosing. Blood samples were incubated at 37° C. and were visually inspected for the presence of a blood clot once per minute. The time needed for a clot to form was recorded and, once the clotting activity returned to baseline (i.e. no clot formation), no additional samples were obtained (samples collected 15 min to 144 hr for FIXFc or 15 min to 72 hr for rFIX).

Figure 14:
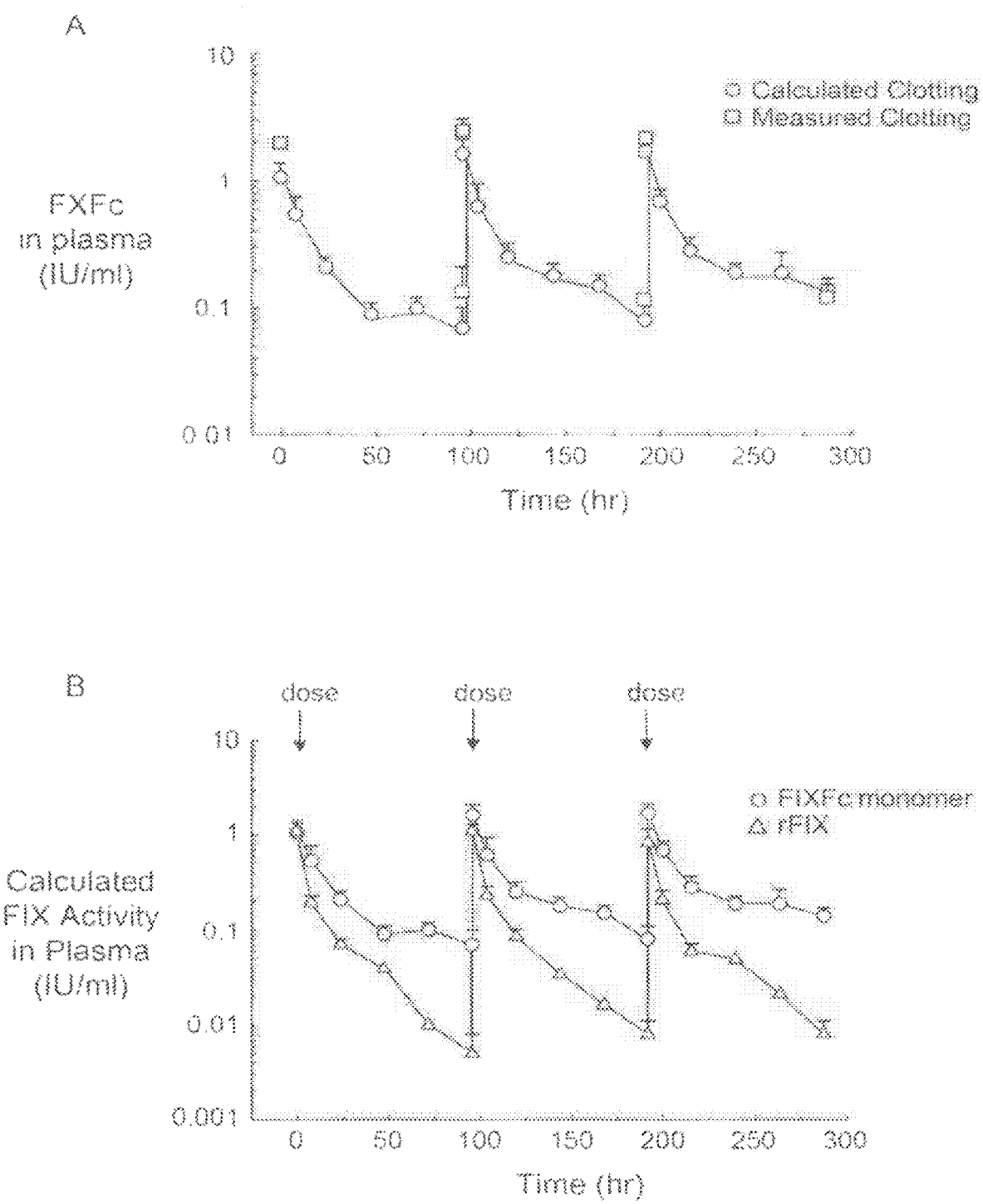

FIG. 14. Pharmacodynamics of FIXFc in FIX-deficient mice. FIX-deficient mice were dosed with 219 IU/kg FIXFc (5 per group, 6 groups, n=30) or 200 IU/kg rFIX (4 or 5 per group, 6 groups, n=28) on Day 0, 4 and 8. Plasma samples were collected by cardiac puncture at 15 min and 96 hr after each dose and clotting activity was measured using a FIX activity assay. Plasma was also collected by tail bleeds at 8, 24, 48, and 72 hr after each dose. FIXFc levels were measured in all of the samples using an ELISA specific for FIXFc. (A) Measured v. Calculated Activity. Clotting activity for FIXFc was measured using FIX activity assay 15 min and 96 h after three doses. The in vitro clotting activity for FIXFc was determined to be 43.8±5.4 IU/mg. Based on this activity (IU/mg) and the measured protein levels, a calculated plasma clotting activity level was determined for time points at 15 min, 8, 24, 48, 72 and 96 h after each dose. (B) In FIX-deficient mice treated with up to three doses of 200 IU/kg rFIX, FIX levels were measured using FIX-specific ELISA. Using the measured specific activities of FIXFc and rFIX, it was possible to compare calculated clotting activity for all samples analyzed by ELISA.

Figure 15:
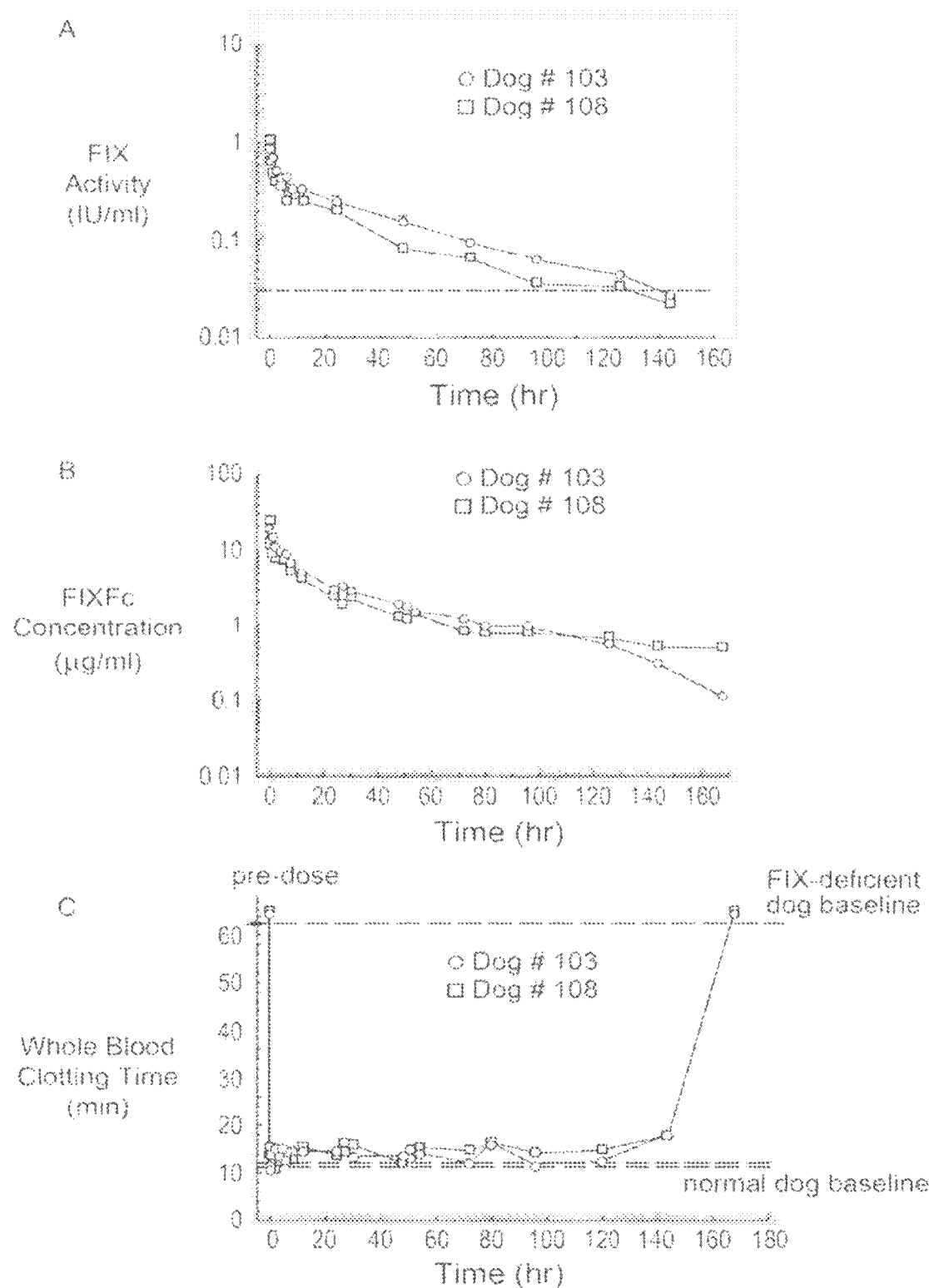

FIG. 15. Pharmacokinetics and pharmacodynamics of FIXFc in FIX-deficient dogs. Two dogs with hemophilia B were intravenously infused with 140 IU/kg FIXFc. Blood samples were collected at 5, 15, and 30 min, and at 1, 2, 4, 6, 8, 12, 24, 27, 30, 48, 51, 54, 72, 80, 96, 126, 144, and 168 hr. (A) A sandwich ELISA utilizing a FIX capture antibody and Fc-HRP detection antibody was used to measure the concentration of intact FIXFc in the Hemophilic B dog plasma samples. (B) FIX clotting activity was measured for all time points with respect to a standard curve generated with FIXFc. (C) Blood collected from animals was immediately analyzed for whole blood clotting time. Blood samples were incubated at 28° C. and were visually inspected for the presence of a clot once per minute, and the time in which a clot formed was recorded.

Figure 16:
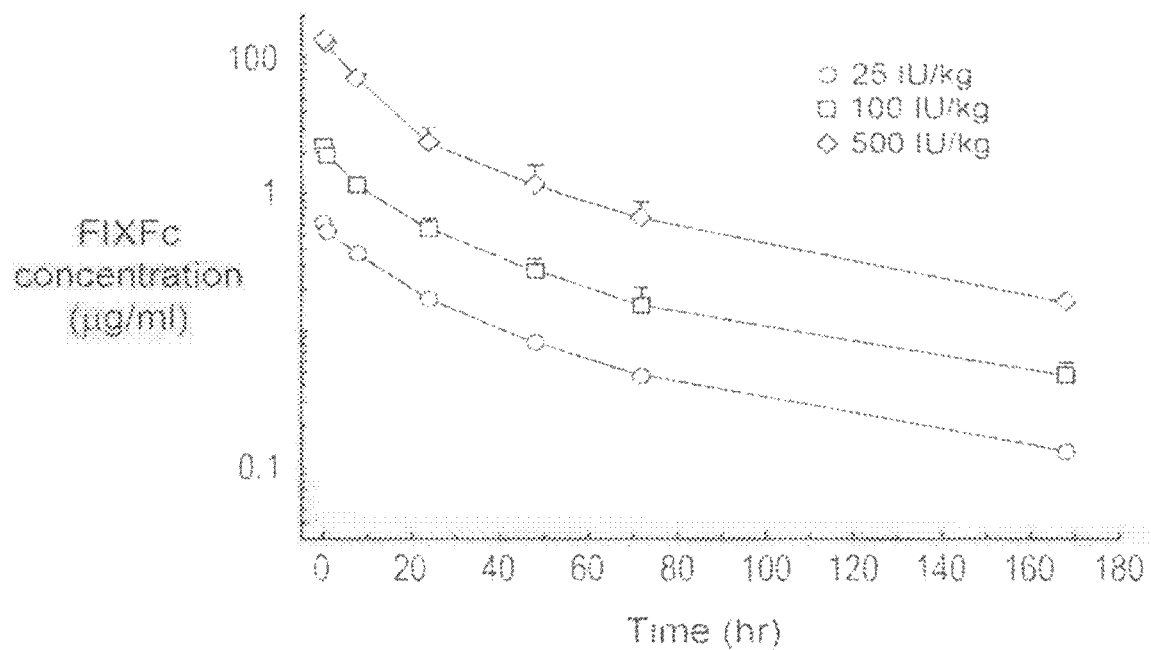

FIG. 16. Pharmacokinetics of FIXFc in Cynomolgus monkeys. Monkeys were administered a single dose (0.5, 2, and 10 mg/kg, corresponding to approximately 25, 100 or 500 IU/kg) of FIXFc (n=2, 3, and 3, respectively). Blood samples were collected at 0.25, 0.5, 1, 8, 24, 48, 72, 96, 120, 144 and 168 hr post-dose and plasma prepared for analysis of protein concentration by FIXFc-specific ELISA.

Figure 17:
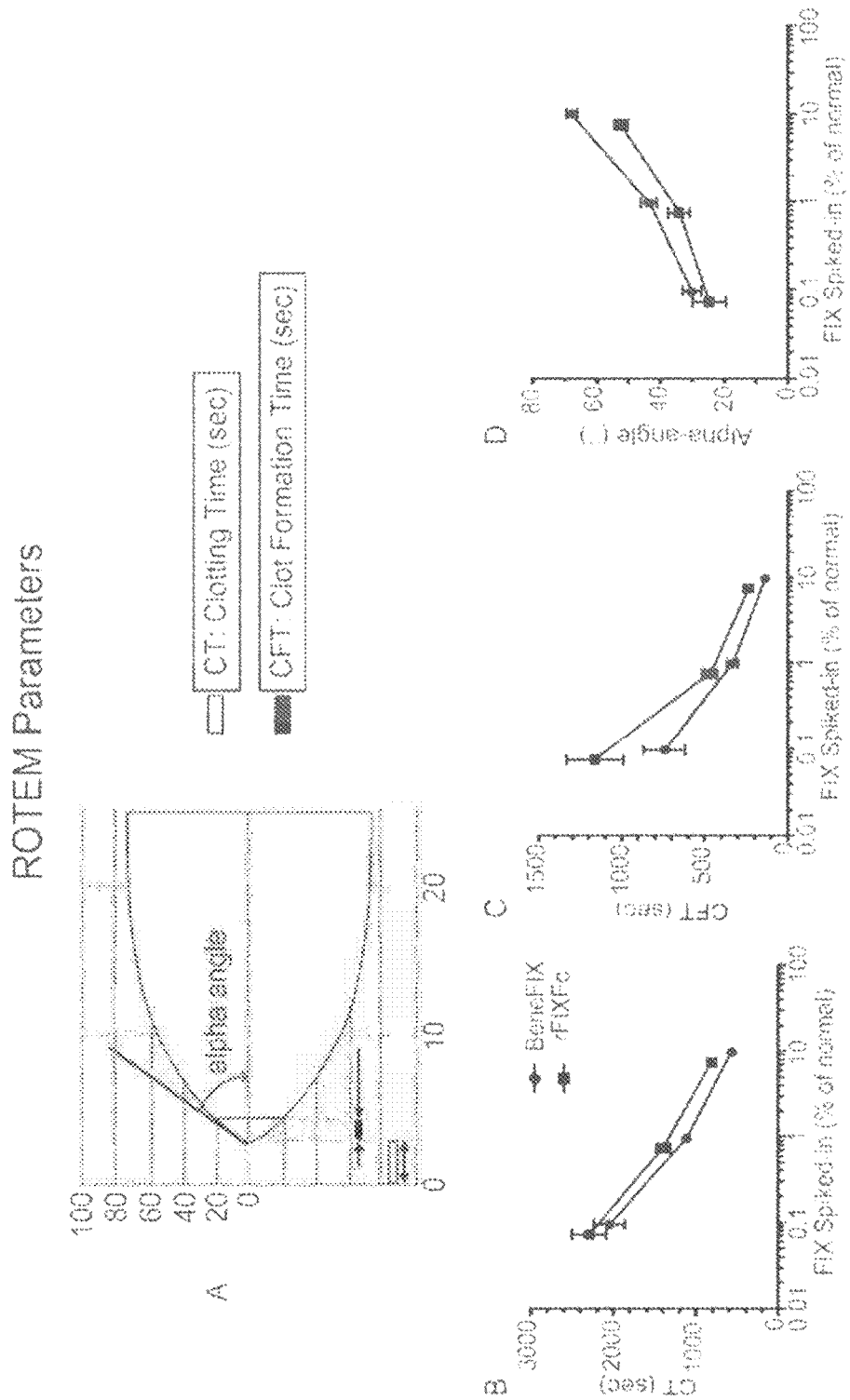

FIG. 17. rFIXFc and BENEFIX™ show comparable activity and dose response in whole blood from HemB mice. (A) ROTEM® Parameters. rFIX or BENEFIX™ were spiked into HemB mouse blood and clotting parameters were measured by ROTEM®. (B)-(D) Dose response, measuring (B) CT, (C) CFT, and (D) Alpha-angle.

Figure 18:
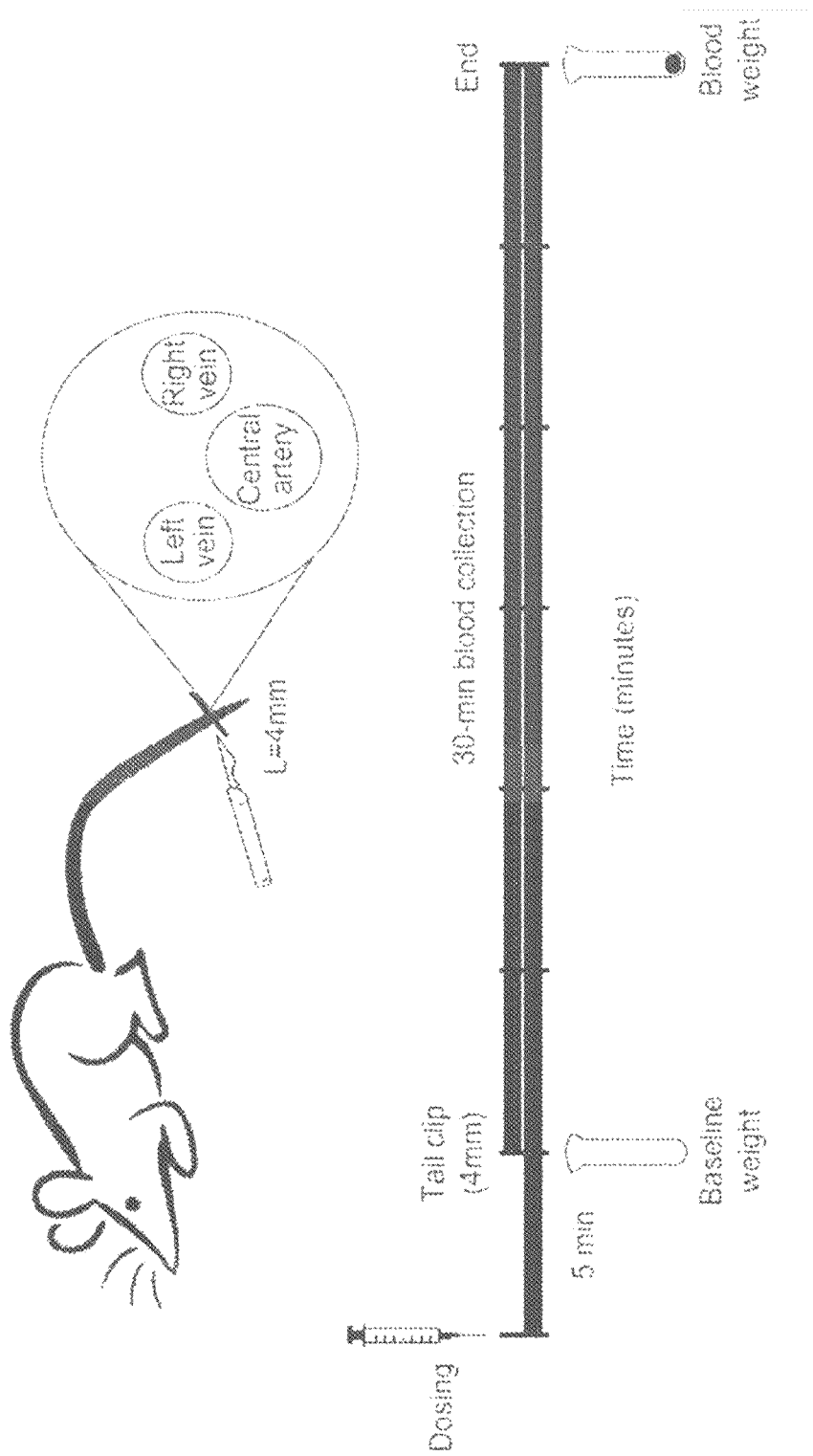

FIG. 18. Evaluation of acute efficacy in tail clip bleeding model of Hemophiliac mice.

Figure 19:
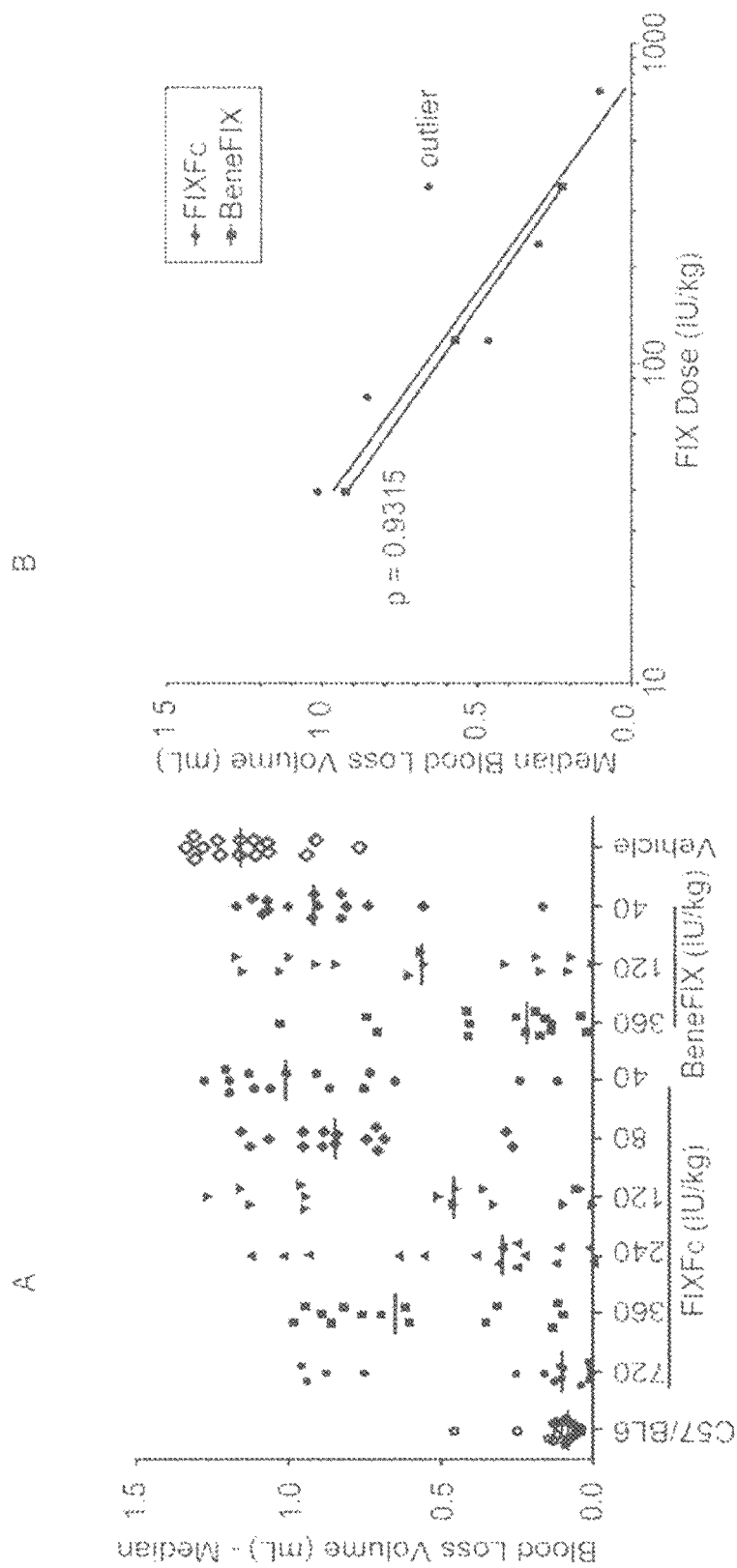

FIG. 19. (A) Blood loss following tail clip in individual HemB mice treated with rFIXFc or BENEFIX™. (B) Dose response of rFIXFc and BENEFIX™ in median blood loss following tail clip in HemB mice.

Figure 20:
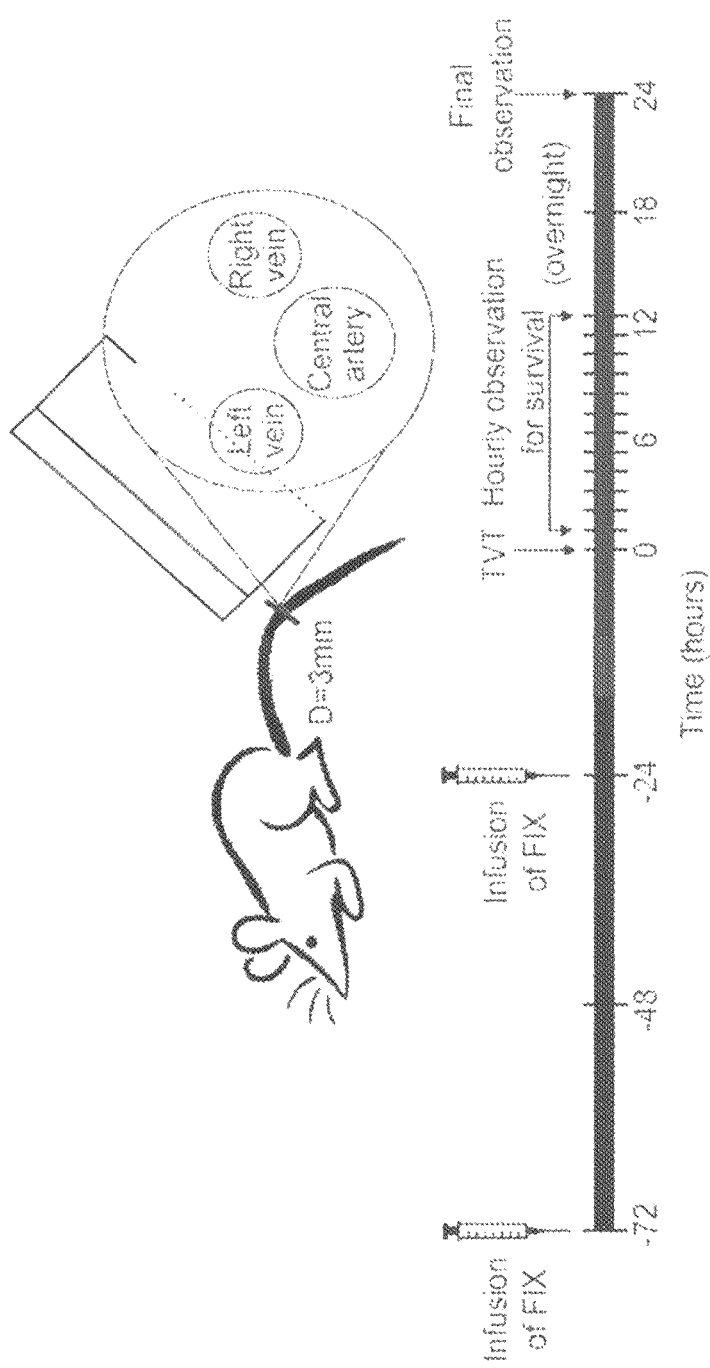

FIG. 20. Tail vein transection (TVT) bleeding model of HemB mice: a model for the venous bleeding characteristic of severe hemophilia patients.

Figure 21:
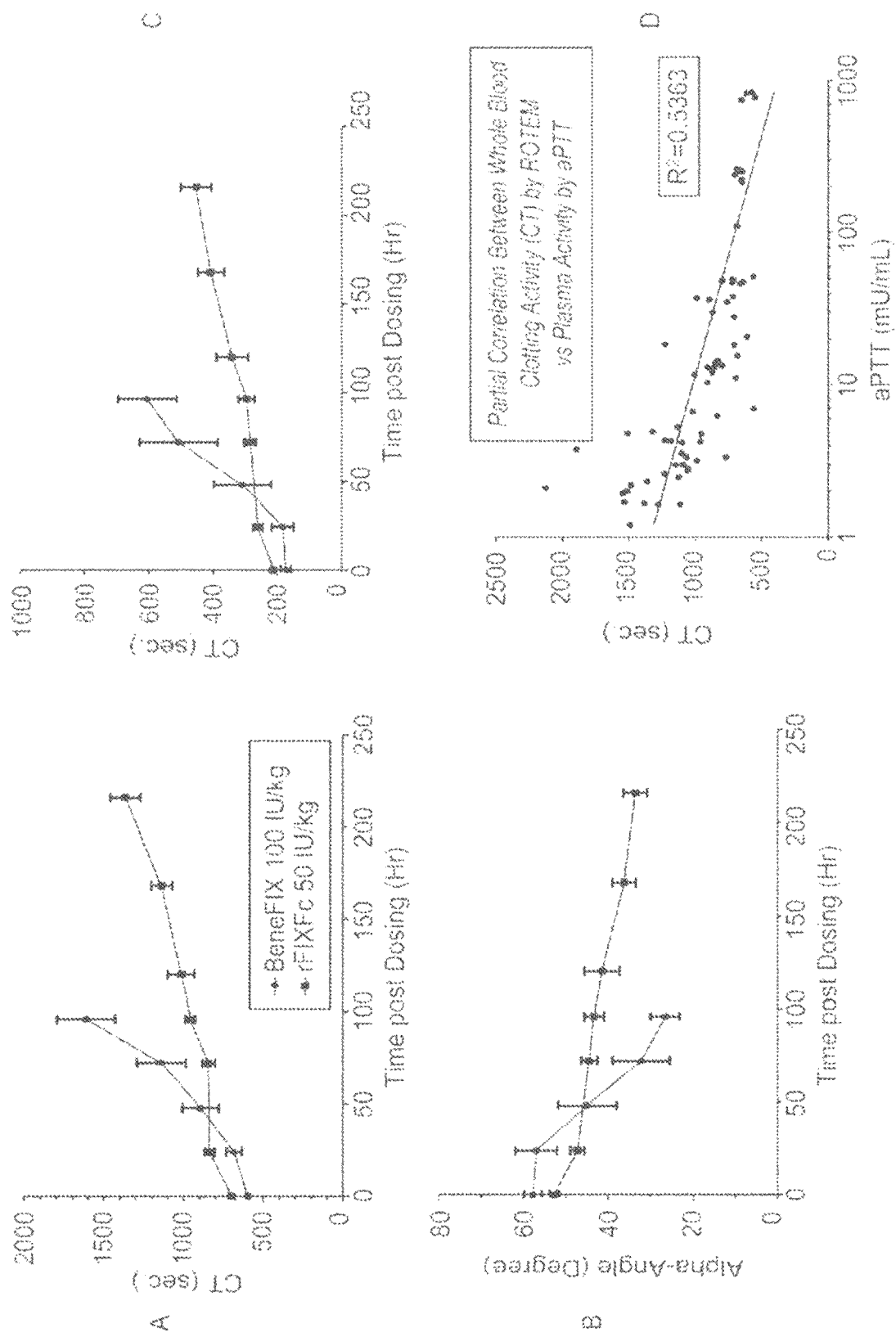

FIG. 21. Prolonged activity of rFIXFc relative to BENEFIX™ in treated HemB mice by whole blood ROTEM®. (A) CT, (B) CFT, (C) Alpha-angle, and (D) Partial correlation between whole blood clotting activity (CT) by ROTEM® versus plasma activity by aPTT.

Figure 22:
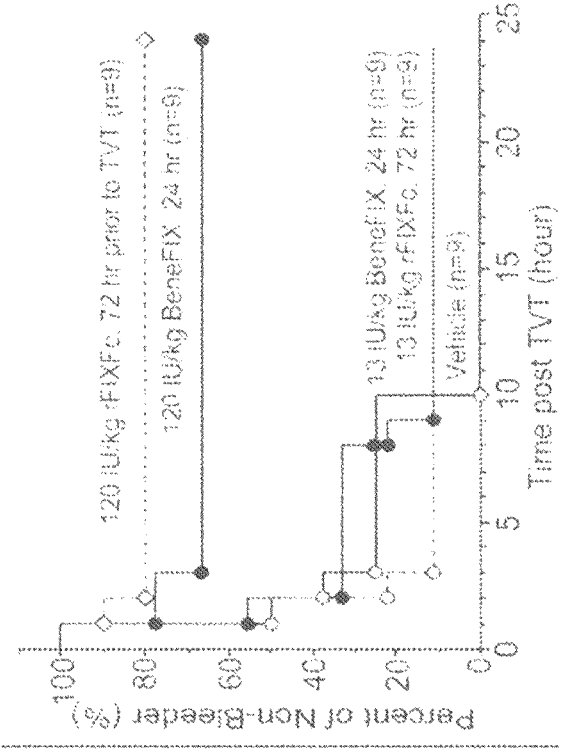
Figure 22:
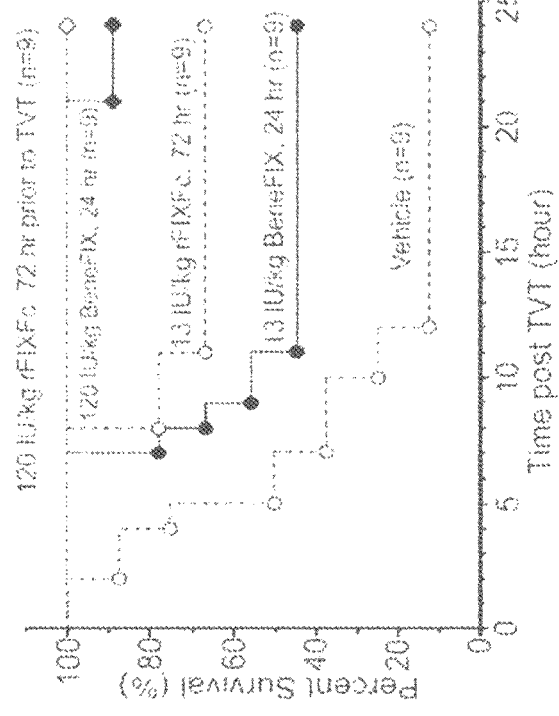

FIG. 22. Prolonged efficacy of FIXFc relative to BENEFIX™ in tail vein transection (TVT) bleeding model of HemB mice. (A) Survival: Survival rates were comparable in mice receiving BENEFIX™ 24 hours pre TVT as in mice receiving rFIXFc 72 hours pre TVT, and (B) Rebleed: Bleeding rates were comparable in mice receiving BENEFIX™ 24 hours pre TVT as in mice receiving rFIXFc 72 hours pre TVT.

Figure 23:
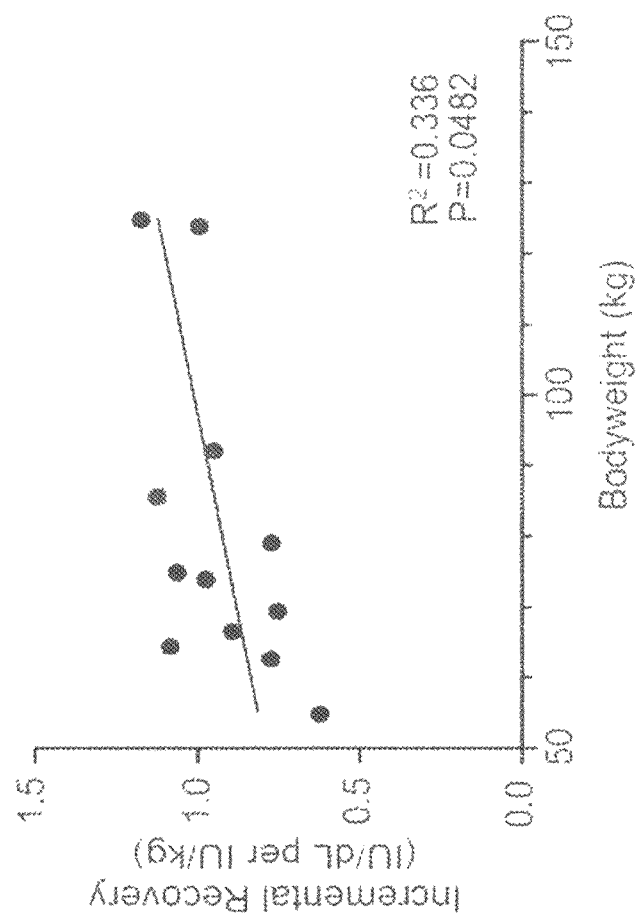

FIG. 23. Correlation between incremental recovery of rFIXFc activity versus body weight in 12 subjects who received a single dose of 12.5 to 100 IU/kg of rFIXFc.

Figure 24:
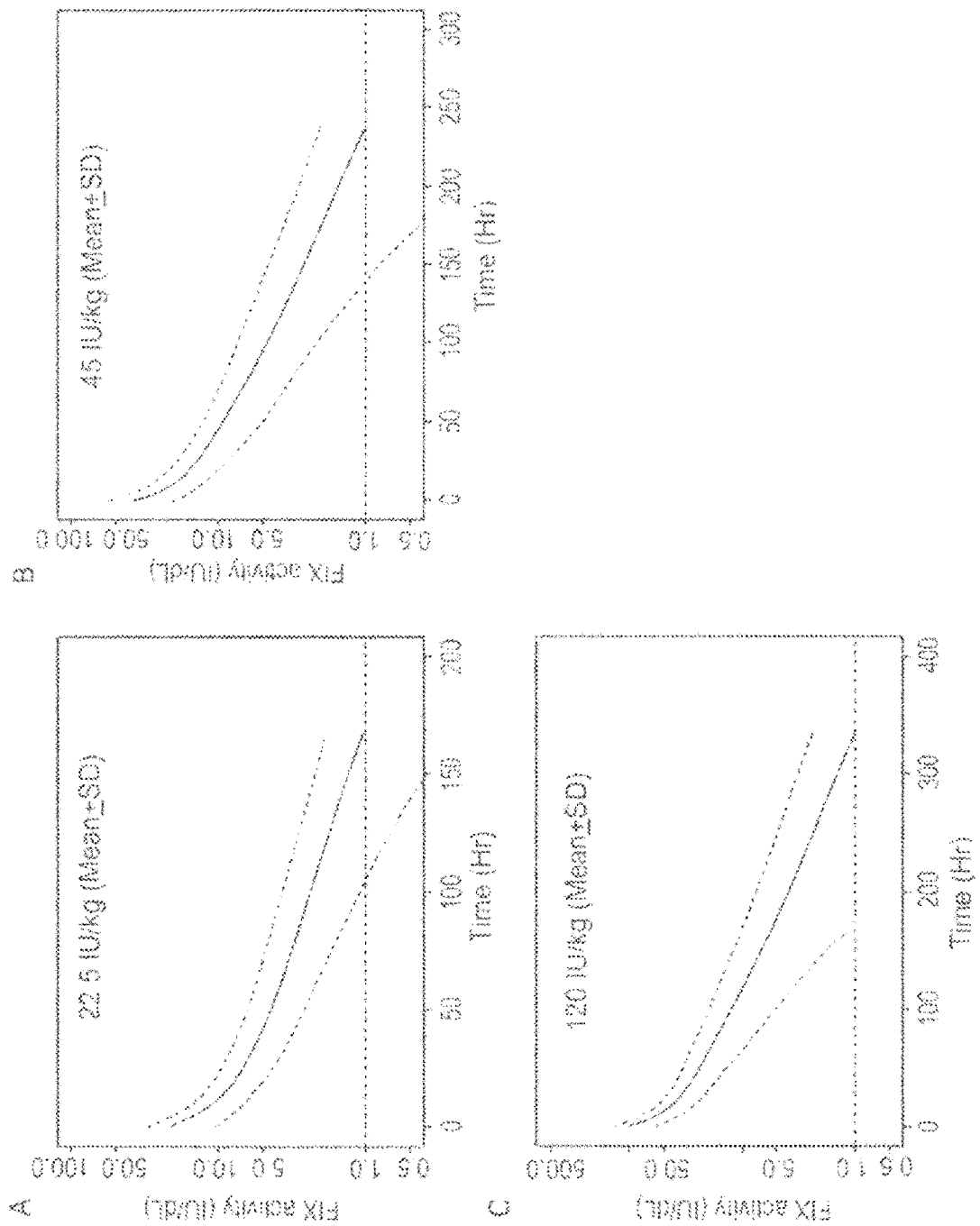

FIG. 24. Monte Carlo simulation using the structural PK model of rFIXFc activity to construct the activity-time profiles to achieve trough of 1 IU/dL above baseline following weekly (A), every 10 days (B), or every two week dosing regimens (C). The median population PK parameters and relevant inter- and intra-subject variabilities were adopted from the clinical Phase1/2a study. 1000 subjects were simulated per dosing regimen with 14 to 16 sampling points for each subject, and the mean±SD of the activity-time profiles of the 1000 subjects was constructed graphically for different dosing regimens.

Figure 25:
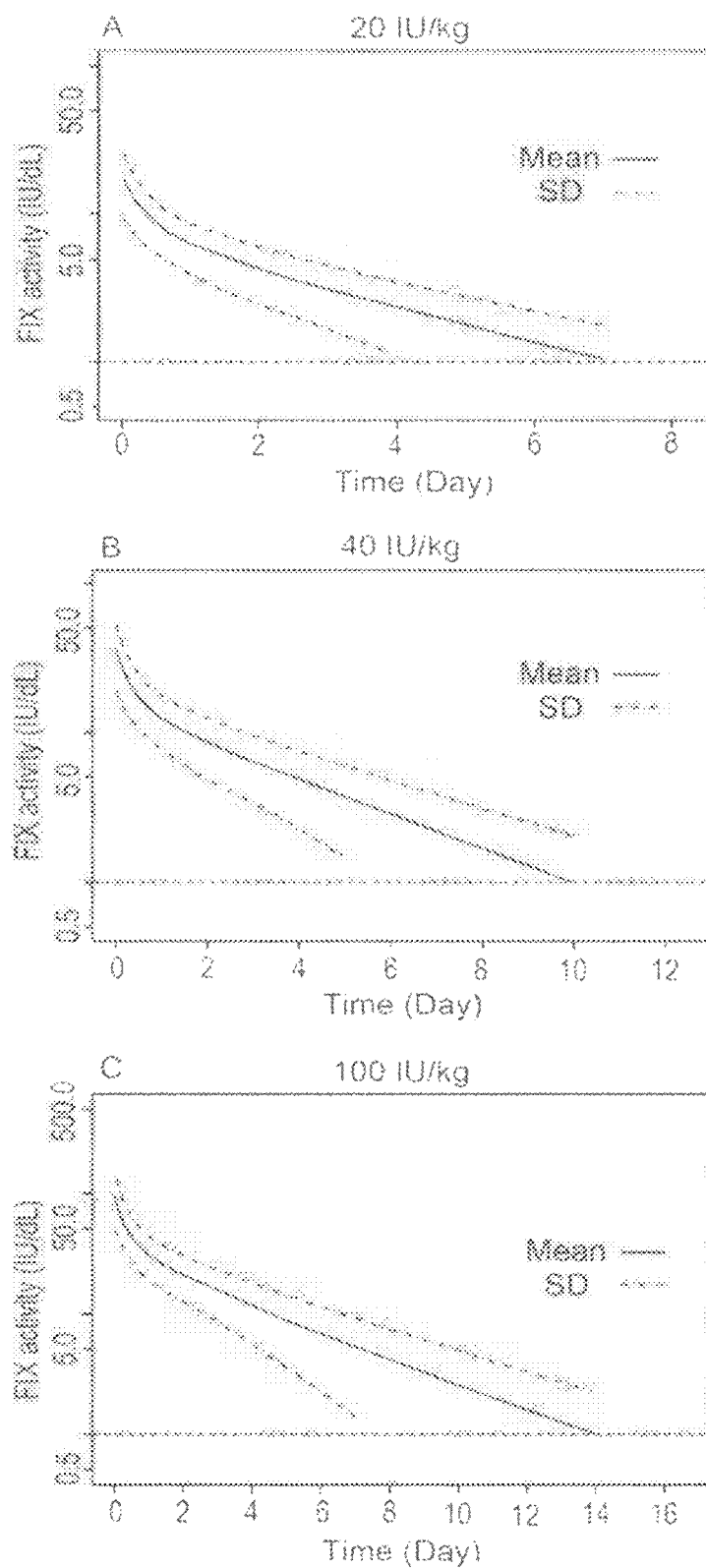

FIG. 25. Monte Carlo simulation for rFIXFc doses to achieve trough of 1 IU/dL (1%), based on recalculated pharmacokinetic data. (A) once weekly, (B) every 10 days, and (C) every two weeks.

DETAILED DESCRIPTION OF THE INVENTION

The present invention provides a method of treating Factor IX deficiency, e.g., Hemophilia B, with Factor IX using a longer dosing interval and/or improved pharmacokinetic parameters than is possible with currently known Factor IX products. The present invention also provides improved Factor IX chimeric polypeptides, Factor IX chimeric polynucleotides, and methods of production.

"Administering," as used herein, means to give a pharmaceutically acceptable Factor IX polypeptide of the invention to a subject via a pharmaceutically acceptable route. Preferred routes of administration are intravenous, e.g., intravenous injection and intravenous infusion, e.g., via central venous access. Additional routes of administration include subcutaneous, intramuscular, oral, nasal, and pulmonary administration, preferably subcutaneous. Factor IX chimeric polypeptides and hybrid proteins may be administered as part of a pharmaceutical composition comprising at least one excipient. Advantages of the present invention include: improved regimen compliance; reduced break through bleeds; increased protection of joints from bleeds; prevention of joint damage; reduced morbidity; reduced mortality; prolonged protection from bleeding; decreased thrombotic events; and improved quality of life.

"Chimeric polypeptide," as used herein, means a polypeptide that includes within it at least two polypeptides (or portions thereof such as subsequences or peptides) from different sources. Chimeric polypeptides may include two, three, four, five, six, seven, or more polypeptides or portions thereof from different sources, such as different genes, different cDNAs, or different animal or other species. Chimeric polypeptides may include one or more linkers joining the different polypeptides or portions thereof. Thus, the polypeptides or portions thereof may be joined directly or they may be joined indirectly, via linkers, or both, within a single chimeric polypeptide. Chimeric polypeptides may include additional peptides such as signal sequences and sequences such as 6His and FLAG that aid in protein purification or detection. In addition, chimeric polypeptides may have amino acid or peptide additions to the N- and/or C-termini. Exemplary chimeric polypeptides of the invention are Factor IX-FcRn BP chimeric polypeptides, e.g., Factor IX-Fc chimeric polypeptides such as the FIXFc in FIG. 1, SEQ ID NO:2 (Table 2) and Examples 1-4, with or without its signal sequence and propeptide. Another exemplary chimeric polypeptides of the invention include, but are not limited to, Factor IX-XTEN chimeric polypeptides. Factor IX can be fused to either N-terminus or C-terminus of XTEN.

The chimeric polypeptide may comprise a sequence at least 90% or at least 95% or 100% identical to the Factor IX and FcRn BP, e.g., the Fc amino acid sequence shown in Table 2A without a signal sequence and propeptide sequence (amino acids 1 to 642 of SEQ ID NO:2), or alternatively, with a propeptide sequence, or alternatively with a signal sequence and a propeptide sequence.

"Culture," "to culture" and "culturing," as used herein, means to incubate cells under in vitro conditions that allow for cell growth or division or to maintain cells in a living state. "Cultured cells," as used herein, means cells that are propagated in vitro.

"Factor IX" and "FIX," as used herein, means functional Factor IX polypeptide in its normal role in coagulation, unless otherwise specified. Thus, the term Factor IX includes variant polypeptides that are functional and the polynucleotides that encode such functional variant polypeptides. Preferred Factor IX polypeptides are the human, bovine, porcine, canine, feline, and murine Factor IX polypeptides. The full length polypeptide and polynucleotide sequences of Factor IX are known, as are many functional variants, e.g., fragments, mutants and modified versions. Factor IX polypeptides include full-length Factor IX, full-length Factor IX minus Met at the N-terminus, full-length Factor IX minus the signal sequence, mature Factor IX (minus the signal sequence and propeptide), and mature Factor IX with an additional Met at the N-terminus. Factor IX is preferably made by recombinant means ("recombinant Factor IX" or "rFIX"), i.e., it is not naturally occurring or derived from plasma.

A great many functional Factor IX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses Factor IX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant Factor IX molecules that exhibit increased protein stability, increased in vivo and in vitro half-life, and increased resistance to proteases at page 4, line 1 to page 19, line 11. WO 2007/149406 A2 also discloses chimeric and other variant Factor IX molecules at page 19, line 12 to page 20, line 9. International publication number WO 08/118507 A2, which is herein incorporated by reference in its entirety, discloses Factor IX mutants that exhibit increased clotting activity at page 5, line 14 to page 6, line 5. International publication number WO 09/051717 A2, which is herein incorporated by reference in its entirety, discloses Factor IX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant Factor IX molecules that have an increased number of glycosylation sites, which result in an increased half-life, at page 4, line 26 to page 12, line 6. International publication number WO 09/140015 A2, which is herein incorporated by reference in its entirety, discloses functional Factor IX mutants that an increased number of Cys residues, which may be used for polymer (e.g., PEG) conjugation, at page 11, paragraph [0043] to page 13, paragraph [0053].

In addition, hundreds of non-functional mutations in Factor IX have been identified in hemophilia patients, many of which are disclosed in Table 1, at pages 11-14 of International publication number WO 09/137254 A2, which is herein incorporated by reference in its entirety. Such non-functional mutations are not included in the invention, but provide additional guidance for which mutations are more or less likely to result in a functional Factor IX polypeptide.

The Factor IX (or Factor IX portion of a chimeric polypeptide) may be at least 90% or at least 95% or 100% identical to a Factor IX amino acid sequence shown in Table 2A without a signal sequence and propeptide sequence (amino acids 1 to 415 of SEQ ID NO:2), or alternatively, with a propeptide sequence, or with a propeptide and signal sequence (full length Factor IX).

Factor IX coagulant activity is expresses as International Unit(s) (IU). One IU of Factor IX activity corresponds approximately to the quantity of Factor IX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®). See, e.g., Example 3.

"FcRn binding partner," or "FcRn BP" as used herein, means functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term FcRn BP includes any variants of IgG Fc that are functional. For example, the region of the Fc portion of IgG that binds to the FcRn receptor has been described based on X-ray crystallography (Burmeister et al. 1994, Nature 372:379, incorporated herein by reference in its entirety). The major contact area of the Fc with the FcRn is near the junction of the CH2 and CH3 domains. Fc-FcRn contacts are all within a single Ig heavy chain. FcRn BPs include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al. 1994, J. Exp. Med. 180: 2377), incorporated herein by reference in its entirety.) An FcRn BP may comprise the CH2 and CH3 domains of an immunoglobulin with or without the hinge region of the immunoglobulin. Exemplary FcRn BP variants are provided in WO 2004/101740 and WO 2006/074199, incorporated herein by reference in its entirety.

FcRn BP also include albumin and fragments thereof that bind to the FcRn. Preferably the albumin is human albumin. Factor IX can be fused to either the N-terminal end of the albumin or to the C-terminal end of the albumin, provided the Factor IX component of the Factor IX-albumin fusion protein can be processed by an enzymatically-active pro-protein convertase to yield a processed Factor IX-containing polypeptide. Examples of albumin, e.g., fragments thereof, that may be used in the present invention are known. e.g., U.S. Pat. Nos. 7,592,010; 6,686,179; and Schulte, Thrombosis Res. 124 Suppl. 2:S6-S8 (2009), each of which is incorporated herein by reference in its entirety.

FcRn BP (or FcRn BP portion of a chimeric polypeptide) may contain one or more mutations, and combinations of mutations.

FcRn BP (or FcRn BP portion of a chimeric polypeptide) may contain mutations conferring increased half-life such as M252Y, S254T, T256E, and combinations thereof, as disclosed in Oganesyan et al., Mol. Immunol. 46:1750 (2009), which is incorporated herein by reference in its entirety; H433K, N434F, and combinations thereof, as disclosed in Vaccaro et al., Nat. Biotechnol. 23:1283 (2005), which is incorporated herein by reference in its entirety; the mutants disclosed at pages 1-2, paragraph [0012], and Examples 9 and 10 of U.S. 2009/0264627 A1, which is incorporated herein by reference in its entirety; and the mutants disclosed at page 2, paragraphs [0014] to [0021] of U.S. 20090163699 A1, which is incorporated herein by reference in its entirety.

FcRn BP (or FcRn BP portion of a chimeric polypeptide) may also include the following mutations: The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example the following single amino acid residues in human IgG1 Fc (Fcy 1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. In addition to alanine other amino acids may be substituted for the wild type amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Certain of these mutations may confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcyRI, FcyRIIA, FcyRIIB, and FcyRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie 1995, Therapeutic Immunology 2:77, which is incorporated herein by reference in its entirety; and Armour et al. 1999, Eur. J. Immunol. 29:2613, which is incorporated herein by reference in its entirety). As a further example of new functionality arising from mutations described above, affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, J. Biol. Chem. 276:6591, which is incorporated herein by reference in its entirety).

The FcRn BP (or FcRn BP portion of a chimeric polypeptide) may be at least 90% or at least 95% or 100% identical to the Fc amino acid sequence shown in Table 2A or B without a signal sequence (amino acids 1 to 227 of SEQ ID NO:2), or alternatively, with a signal sequence.

"Hybrid" polypeptides and proteins, as used herein, means a combination of a chimeric polypeptide with a second polypeptide. The chimeric polypeptide and the second polypeptide in a hybrid may be associated with each other via non-covalent protein-protein interactions, such as charge-charge or hydrophobic interactions. The chimeric polypeptide and the second polypeptide in a hybrid may be associated with each other via covalent bond(s) such as disulfide bonds. The chimeric peptide and the second peptide may be associated with each other via more than one type of bond, such as non-covalent and disulfide bonds. Hybrids are described in WO 2004/101740, WO2005/001025, U.S. Pat. Nos. 7,404,956, 7,348,004, and WO 2006/074199, each of which is incorporated herein by reference in its entirety. The second polypeptide may be a second copy of the same chimeric polypeptide or it may be a non-identical chimeric polypeptide. In preferred embodiments, the second polypeptide is a polypeptide comprising an FcRn BP, e.g., Fc. In preferred embodiments, the chimeric polypeptide is a Factor IX-FcRn BP, e.g., Factor IX-Fc chimeric polypeptide, and the second polypeptide consists essentially of Fc. See, e.g., FIG. 1, Examples 1-3, and Table 2 (SEQ ID NOs:2 and 4). See, e.g., U.S. Pat. No. 7,404,956, which is incorporated herein by reference. in its entirety.

The second polypeptide in a hybrid may comprise or consist essentially of a sequence at least 90% or at least 95% or 100% identical to the amino acid sequence shown in Table 2B without a signal sequence (amino acids 1 to 227 of SEQ ID NO:4), or alternatively, with a signal sequence.

The polypeptide of the present invention also includes Factor IX fused to one or more XTEN polypeptides. Schellenburger et al., Nat. Biotech. 27:1186-90 (2009), which is incorporated herein by reference in its entirety. Factor IX can be fused to either the N-terminal end of the XTEN polypeptide or to the C-terminal end of the XTEN polypeptide. XTEN polypeptides include, but are not limited to, those disclosed in WO 2009/023270, WO 2010/091122, WO 2007/103515, US 2010/0189682, and US 2009/0092582, each of which is incorporated herein by reference in its entirety.

"Dosing interval," as used herein, means the amount of time that elapses between multiple doses being administered to a subject. The dosing interval in the methods of the invention using a chimeric FIX-FcRn BP, e.g., a chimeric FIX-Fc, may be at least about one and one-half to eight times longer than the dosing interval required for an equivalent amount (in IU/kg) of said Factor IX without the FcRn BP, e.g., Fc portion (i.e., a polypeptide consisting of said FIX). The dosing interval when administering, e.g., a Factor IX-Fc chimeric polypeptide (or a hybrid) of the invention may be at least about one and one-half times longer than the dosing interval required for an equivalent amount of said Factor IX without the FcRn BP, e.g., Fc, portion (i.e., a polypeptide consisting of said Factor IX). The dosing interval may be at least about one and one-half to eight times longer than the dosing interval required for an equivalent amount of said Factor IX without, e.g., the Fc portion (or a polypeptide consisting of said Factor IX).

In some embodiments, the dosing interval is 6-18, 6-10, 9-18, at least 6, at least 7, at least 8, at least 9, at least 10, at least 11, at least 12, at least 13, at least 14, at least 15, at least 16, at least 17, or at least 18 days. The dosing interval may be at least about once weekly, and may be 6-10 days, e.g., about 7-10, about 7-9, about 7-8, about 8-10, about 9-10, about 6-7, about 8-9, about 6, about 7, about 8, about 9, or about 10 days.

The dosing interval may be 9-18 days, e.g., about 9-17, about 9-16, about 9-15, about 9-14, about 9-13, about 9-12, about 9-11, about 9-10 days, about 10-18, about 11-18, about 12-18, about 13-18, about 14-18, about 15-18, about 16-18, about 17-18 days, about 10-11, about 11-12, about 12-13, about 13-14, about 14-15, about 15-16, and about 16-17 days, about 9, about 10, about 11, about 12, about 13, about 14, about 15, about 16, about 17, or about 18 days. The dosing interval may be about 10-14 days. The dosing interval may be about every two weeks or twice monthly. The dosing interval may be longer than 18 days, e.g., about 19, about 20, about 21, about 22, about 23, about 24, about 25, about 26, about 27, about 28, about 29, about 30, about 31, about 32, about 33, about 34, about 35, about 36, about 37, about 38, about 39, or about 40 days. The dosing interval may be a fixed interval, e.g., 7 days for 25-50 IU/kg, 10-13 days for 50-100 IU/kg, or 14 days for 100-150 IU/kg. The fixed interval and dose are determined such that the combination of interval and dose will result in a trough of at least about 1-5 or at least about 1-3, or at least about 1, at least about 2, or at least about 3 IU/dl FIX activity in a population of subjects or in an individual subject. The fixed dosing interval may also be 7 days for 20-50 IU/kg, 10-14 days for 50-100 IU/kg, 14-16 days for 100-150 IU/kg, 7 days for 10-50 IU/kg, 10-13 days for 15-100 IU/kg, or 14-15 days for 50-150 IU/kg. The fixed dosing interval may also be 7 days for 10-30 IU/kg, 10 days 15-50 IU/kg, 11 days 20-70 IU/kg, 12 days 25-85 IU/kg, 13 days 30 to 100 IU/kg, 14 days 40 to 125 IU/kg, and 15 days for 50-150 IU/kg.

In preferred embodiments, the dosing interval is 20 IU/kg once weekly, 40 IU/kg every 10 days, or 100 IU/kg every two weeks (twice monthly).

The dosing interval may, alternatively, be an individualized interval that is determined for each subject based on pharmacokinetic data or other information about that subject. The individualized dose/dosing interval combination may be the same as those for fixed interval regimens in the preceding paragraphs, or may differ, as illustrated in the Examples. The regimen may initially be at a fixed dosing interval, and then it may change to an individualized dosing interval.

"On-demand treatment," as used herein, means treatment that is intended to take place over a short course of time and is in response to an existing condition, such as a bleeding episode, or a perceived short term need such as planned surgery. Conditions that may require on-demand treatment include a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. Bleeding episodes other than these are also included. The subject may be in need of surgical prophylaxis, peri-operative management, or treatment for surgery. Such surgeries include minor surgery, major surgery, tooth extraction, tonsillectomy, other dental/thoraco-facial surgeries, inguinal herniotomy, synovectomy, total knee replacement, other joint replacement, craniotomy, osteosynthesis, trauma surgery, intracranial surgery, intra-abdominal surgery, intrathoracic surgery. Surgeries other than these are also included. Additional conditions that may require on-demand treatment include those listed in Table 26.

Additional conditions that may require on-demand treatment include minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Additional reasons for on-demand treatment include the need for peri-operative management for surgery or dental extraction, major surgery, extensive oral surgery, urologic surgery, hernia surgery, orthopedic surgery such as replacement of knee, hip, or other major joint.

ABBREVIATIONS $AUC_{INF}$ Area under the concentration-time curve from zero to infinity
$AUC_\alpha$ Area under the concentration-time curve over the distribution phase
$AUC_\beta$ Area under the concentration-time curve over the elimination phase
Alpha HL Distribution phase half-life
Beta HL Elimination phase half-life; also referred to as $t_{1/2}$
C168 Estimated FIXFc activity above baseline at approximately 168 h after dose
$C_{max}$ Maximum concentration, occurring at $T_{max}$
CV % Percent coefficient of variation
Cl Clearance
IVR in vivo recovery (%)
K-Value Incremental recovery
MRT Mean residence time
N Number
NC Not Calculable
NR Not Reported
SD Standard Deviation
SE Standard Error
TBLP1 Model-predicted time after dose when FIXFc activity has declined to approximately 1 IU/dL above baseline
TBLP3 Model-predicted time after dose when FIXFc activity has declined to approximately 3 IU/dL above baseline
TBLP5 Model-predicted time after dose when FIXFc activity has declined to approximately 5 IU/dL above baseline
$V_{SS}$ Volume of distribution at steady state
$V_1$ Volume of distribution of the central compartment Pharmacokinetic (PK) parameters include the terms above and the following terms, which have their ordinary meaning in the art, unless otherwise indicated. Some of the terms are explained in more detail in the Examples. PK parameters may be based on FIX antigen level (often denoted parenthetically herein as "antigen") or FIX activity level (often denoted parenthetically herein as "activity"). In the literature, PK parameters are often based on FIX activity level due to the presence in the plasma of some patients of endogenous, inactive FIX, which interferes with the ability to measure administered (i.e., exogenous) FIX using antibody against FIX. However, when FIX is administered as part of a fusion protein containing a heterologous polypeptide such as a FcRn BP, administered (i.e., exogenous) FIX antigen may be accurately measured using antibody to the heterologous polypeptide. In addition, certain PK parameters may be based on model predicted data (often denoted parenthetically herein as "model predicted") or on observed data (often denoted parenthetically herein as "observed"), and preferably are based on observed data.

"Baseline," as used herein, is the lowest measured plasma Factor IX level in a subject prior to administering a dose. In the first-in-human study described in Example 1, the Factor IX plasma levels were measured at two time points prior to dosing: at a screening visit and immediately prior to dosing. Predose times were treated as zero (baseline) for the purpose of calculations, i.e., to generate "baseline subtracted" data. See, e.g., FIG. 4. Alternatively, (a) the baseline in patients whose pretreatment FIX activity is <1%, who have no detectable FIX antigen, and have nonsense genotypes is defined as 0%, (b) the baseline for patients with pretreatment FIX activity<1% and who have detectable FIX antigen is set at 0.5%, (c) the baseline for patients whose pretreatment FIX activity is between 1-2% is Cmin (the lowest activity throughout the PK study), and (d) the baseline for patients whose pretreatment FIX activity is ≥2% is 2%. Activity above the baseline pre-dosing is considered residue drug from prior treatment, and was decayed to baseline and subtracted from the PK data following rFIXFc dosing. See Example 11.

"Area under the plasma concentration versus time curve" ("AUC"), which, as used herein, is based upon the rate and extent of elimination of Factor IX following administration. AUC is determined over a specified time period, such as 12, 18, 24, 36, 48, or 72 hours, or for infinity using extrapolation based on the slope of the curve. Unless otherwise specified herein, AUC is determined for infinity ($AUC_{INF}$). AUC may also be calculated on a per dose basis. As with many of the other PK parameters, the determination of AUC may be carried out in a single subject, or in a population of subjects for which the average is calculated. In Example 1, the mean AUC/dose in the patient population was 32.44 IU*h/dL per IU/kg and the range for individual subjects was 21.80-54.30 IU*h/dL per IU/kg. (See Table 13 for mean AUC/dose based on activity.) Therefore, the mean AUC/dose in a patient population may be about 26-40, about 26, about 27, about 28, about 29, about 30, about 31, about 32, about 33, about 34, about 35, about 36, about 37, about 38, about 39, or about 40 IU*h/dL per IU/kg. See Table 14 for AUC/dose and other AUC parameters based on antigen.

"In vivo recovery" ("IVR") is represented by the incremental recovery (K-value), which is the observed peak activity minus predose level and then divided by the dose. IVR may also be calculated on a percentage basis, as is described in the Examples. For clarity, the units (K value or IU/dl per IU/kg versus %) are used herein. The mean IVR can be determined in a patient population, or the individual IVR can be determined in a single subject. The FIXFc used in the first-in-human study described in Example 1 exhibited a mean IVR of about 0.93 IU/dl per IU/kg in the patient population; and an IVR in each subject that ranged from 0.62 to 1.17 IU/dl per IU/kg (Table 13). Therefore, the chimeric polypeptide of the invention exhibits an mean IVR in a patient population of 0.85-1.15 (e.g., about 0.85, about 0.86, about 0.87, about 0.88, about 0.89, about 0.90, about 0.91, about 0.92, about 0.93, about 0.94, about 0.95, about 0.96, about 0.97, about 0.98, about 0.99, about 1.0, about 1.05, about 1.10, about 1.15) and an IVR in a subject of at least about 0.6, about 0.7, 0.8, about 0.9, about 1.0, about 1.1, or about 1.2 IU/dl per IU/kg.

"Clearance rate" ("CL"), as used herein, is a measure of the body's ability to eliminate a drug, and is expressed as the volume of plasma cleared of drug over time. The FIXFc used in the study described in Example 1 exhibited a mean CL of about 3.36 ml/hour/kg (see Table 13), which is about 2.5 fold lower than the CL (8.2 ml/hour/kg) of a polypeptide consisting of Factor IX (BENEFIX™); the range of CL values in individual subjects was 1.84-4.58 ml/h/kg. Therefore, a chimeric polypeptide of the invention exhibits a mean CL in a population of 3.0-3.72, 3.0, 3.1, 3.2, 3.3, 3.4, 3.5, 3.6, 3.7, or 3.72 mL/hour/kg For CL based on antigen, see Table 14.

"Mean residence time" ("MRT"), as used herein, is a measure of the average lifetime of drug molecules in the body. The FIXFc used in the study described in Example 1 exhibited a mean MRT of about 68.05 hours (see Table 13); the range of MRT values was 53.1-85.8 hours in individual subjects. Therefore, a chimeric polypeptide of the invention exhibits a mean MRT in a population of 60-78, about 60, about 62, about 64, about 66, about 68, about 70, about 72, about 74, about 76, or about 78 hours and a MRT in a subject of at least about 50, about 55, about 60, about 65, about 70, about 75, about 80, about 85, or about 90 hours. For MRT based on antigen, see Table 14.

"$t_{1/2\beta}$," or $t_{1/2\ beta}$" or "Beta HL," as used herein, is half-life associated with elimination phase, $t_{1/2\beta}$=(ln 2)/elimination rate constant associated with the terminal phase. In the study described in Example 1, the FIXFc used exhibited a mean $t_{1/2z}$ in a patient population that was about 52.5 hours (see Table 13) and the range of $t_{1/2\ \beta}$ values in individual subjects was 47-60 hours. Therefore, a chimeric polypeptide of the invention exhibits an average $t_{1/2\beta}$ greater than about 47, about 48, about 49, about 50, about 51, about 52, about 53, about 54, about 55, about 56, about 57, about 58, about 59, or about 60 hours. For $t_{1/2\beta}$ based on antigen, see Table 14.

"Trough," as used herein, is the lowest plasma Factor IX activity level reached after administering a dose of chimeric polypeptide of the invention or another Factor IX molecule and before the next dose is administered, if any. Trough is used interchangeably herein with "threshold." Baseline Factor IX levels are subtracted from measured Factor IX levels to calculate the trough level. In some embodiments, the trough is 1-5 or 1-3 IU/dl after about 6, about 7, about 8, about 9, about 10, about 11, about 12, about 13 or about 14 days. In some embodiments, the plasma level of the chimeric polypeptide reaches an average trough of at least about 1 IU/dl after at least about 6 days in at least about 70%, at least about 80%, at least about 90%, or about 100% of a patient population or reaches a trough of at least about 1, 2, 3, 4, or 5 IU/dl after at least about 6 days in a subject. In some embodiments, the plasma level of said chimeric polypeptide reaches an average trough of about 1-5 or 1-3 IU/dl. Such trough or average trough may be reached after about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 days.

"Volume of distribution at steady state (Vss)," as used herein, is the apparent space (volume) into which a drug distributes. Vss=the amount of drug in the body divided by the plasma concentration at steady state. In Example 1, the mean Vss found in the population was about 226 mL/kg and the range for subjects was about 145-365 mL/kg. (See Table 13.) Thus, the mean Vss in a patient population may be 200-300, about 200, about 210, about 220, about 230, about 240, about 250, about 260, about 270, about 280, about 290, or about 300 mL/kg. The Vss for individual subjects may be about 145, about 150, about 160, about 170, about 180, about 190, about 200, about 210, about 220, about 230, about 240, about 250, about 260, about 270, about 280, about 290, about 300, about 310, about 320, about 330, about 340, about 350, about 360, or about 370 ml/kg. For Vss based on antigen, see Table 14.

"Polypeptide," "peptide" and "protein" are used interchangeably and refer to a polymeric compound comprised of covalently linked amino acid residues.

"Polynucleotide" and "nucleic acid" are used interchangeably and refer to a polymeric compound comprised of covalently linked nucleotide residues. Polynucleotides may be DNA, cDNA, RNA, single stranded, or double stranded, vectors, plasmids, phage, or viruses. Polynucleotides include those in Table 1, which encode the polypeptides of Table 2 (see Table 1). Polynucleotides also include fragments of the polynucleotides of Table 1, e.g., those that encode fragments of the polypeptides of Table 2, such as the Factor IX, Fc, signal sequence, propeptide, 6His and other fragments of the polypeptides of Table 2.

"Prophylactic treatment," as used herein, means administering a Factor IX polypeptide in multiple doses to a subject over a course of time to increase the level of Factor IX activity in a subject's plasma. Preferably, the increased level is sufficient to decrease the incidence of spontaneous bleeding or to prevent bleeding in the event of an unforeseen injury. Prophylactic treatment decreases or prevents bleeding episodes, for example, those described under on-demand treatment. Prophylactic treatment may be fixed or may be individualized, as discussed under "dosing interval", e.g., to compensate for inter-patient variability.

"Subject," as used herein means a human or a non-human mammal. Non-human mammals include mice, dogs, primates, monkeys, cats, horses, cows, pigs, and other domestic animals and small animals. Subjects also include pediatric humans. Pediatric human subjects are birth to 20 years, preferably birth to 18 years, birth to 16 years, birth to 15 years, birth to 12 years, birth to 11 years, birth to 6 years, birth to 5 years, birth to 2 years, and 2 to 11 years of age.

The methods of the invention may be practiced on a subject in need of control or prevention of bleeding or bleeding episodes. Such subjects include those in need of control or prevention of bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Such subjects also include those need of pen-operative management, such as management of bleeding associated with surgery or dental extraction.

"Therapeutic dose," as used herein, means a dose that achieves a therapeutic goal, as described herein. The calculation of the required dosage of plasma derived Factor IX (pdFIX) is based upon the empirical finding that, on average, 1 IU of pdFIX per kg body weight raises the plasma Factor IX activity by approximately 1 IU/dL (1%). On that basis, the required dosage is determined using the following formula:

Required units=body weight (kg)×desired Factor IX rise (IU/dL or % of normal)×1 (IU/kg per IU/dL)

Because FIXFc, e.g., as described in the Examples and in FIG. 1, has an incremental recovery similar to pdFIX (different from that of BENEFIX™), the required dose is determined using the formula above, or adjusting it slightly. See also Table 26 for specific recommended doses for various on-demand treatment needs. For pediatric subjects using pdFIX, dosage guidance is the same as for adults. However, pediatric patients may have a lower incremental recovery, and the dosage may therefore need to be adjusted upwards.

The therapeutic doses that may be used in the methods of the invention are 10-180, 20-180, or 25-180 IU/kg, more specifically, preferred doses for a 6-10 day dosing interval are as follows: about 25-110, about 30-110, about 40-110, about 50-110, about 60-110, about 70-110, about 80-110, about 90-110, and about 100-110; about 30-100, about 30-90, about 30-80, about 30-70, about 30-60, about 30-50, about 30-40 IU/kg; about 40-110, about 50-100, about 60-90, and about 70-80 IU/kg; about 40-50, about 50-60, about 60-70, about 70-80, about 80-90, about 90-100, and about 100-110 IU/kg; about 25, about 30, about 35, about 40, about 45, about 50, about 55, about 60, about 65, about 70, about 75, about 80, about 85, about 90, about 95, about 100, about 105, and about 110 IU/kg. A 6-10 day dosing interval includes a weekly dosing interval. Additional therapeutic doses for a 6-10 day, e.g., weekly, dosing interval include 20-50, 20-100, and 20-180 IU/kg, more specifically, preferred doses for a 6-10 day, e.g., weekly, dosing interval are as follows: about 20-110, about 20-100, about 20-90, about 20-80, about 20-70, about 20-60, about 20-50, about 20-40, about 20-30, about 20-40, and about 20 IU/kg. See also Examples 10 and 11. Doses may be lower than 20 IU/kg if effective for a given patient, e.g., about 10, about 11, about 12, about 13, about 14, about 15, about 16, about 17, about 18, or about 19 IU/kg.

Preferred therapeutic doses for a 9-18 day, e.g., two times monthly, dosing interval are as follows: about 50-180, about 60-180, about 70-180, about 80-180, about 90-180, about 100-180, about 110-180, about 120-180, about 130-180, about 140-180, about 150-180, about 160-180, and about 170-180 IU/kg; about 90-170, about 90-160, about 90-150, about 90-140, about 90-130, about 90-120, about 90-110, and about 90-100 IU/kg; about 100-170, about 110-160, about 120-150, and about 130-140 IU/kg; about 90-100, about 100-110, about 110-120, about 120-130, about 130-140, about 140-150, about 150-160, and about 160-170 IU/kg; about 60, about 70, about 80, about 90, about 95, about 100, about 105, about 110, about 115, about 120, about 125, about 130, about 135, about 140, about 145, about 150, about 155, about 160, about 165, about 170, about 175, and about 180 IU/kg. See also Examples 10 and 11.

Preferred therapeutic doses are 10-50, 15-100, 20-100, 20-50, 50-100, 10, 20, 40, 50, and 100 IU/kg.

The therapeutic dose may be about 20-50, about 20-100, about 20-180, 25-110, about 30-110, about 40-110, about 50-110, about 60-110, about 70-110, about 80-110, about 90-110, about 100-110, about 30-100, about 30-90, about 30-80, about 30-70, about 30-60, about 30-50, about 30-40 IU/kg, about 40-110, about 50-100, about 60-90, about 70-80 IU/kg, about 40-50, about 50-60, about 60-70, about 70-80, about 80-90, about 90-100, about 100-110 IU/kg, about 20, about 25, about 30, about 35, about 40, about 45, about 50, about 55, about 60, about 65, about 70, about 75, about 80, about 85, about 90, about 95, about 100, about 105, and about 110 IU/kg. Such doses are preferred for dosing intervals of about 6-10, about 7-10, about 7-9, about 7-8, about 8-10, about 9-10, about 6-7, about 8-9, about 6, about 7, about 8, about 9, and about 10 days, and once weekly.

The therapeutic dose may about 90-180, about 100-180, about 110-180, about 120-180, about 130-180, about 140-180, about 150-180, about 160-180, and about 170-180 IU/kg. The dose may be about 90-170, about 90-160, about 90-150, about 90-140, about 90-130, about 90-120, about 90-110, and about 90-100 IU/kg. The dose may be about 100-170, about 110-160, about 120-150, and about 130-140 IU/kg. The dose may be about 90-100, about 100-110, about 110-120, about 120-130, about 130-140, about 140-150, about 150-160, and about 160-170 IU/kg. The dose may be about 90, about 95, about 100, about 105, about 110, about 115, about 120, about 125, about 130, about 135, about 140, about 145, about 150, about 155, about 160, about 165, about 170, about 175, and about 180 IU/kg. Such doses are preferred for dosing interval of about 9-18, about 9-17, about 9-16, about 9-15, about 9-14, about 9-13, about 9-12, about 9-11, about 9-10, about 10-18, about 11-18, about 12-18, about 13-18, about 14-18, about 15-18, about 16-18, about 17-18, about 10-11, about 11-12, about 12-13, about 13-14, about 14-15, about 15-16, and about 16-17 days, about 9, about 10, about 11, about 12, about 13, about 14, about 15, about 16, about 17, and about 18 days, one time monthly and two times monthly (every two weeks).

Preferred therapeutic dose and dosing intervals are as follows: 20 IU/kg once weekly, 40 IU/kg every 10 days, and 100 IU/kg every two weeks (twice monthly). Additional combinations of dose and dose interval include: a dose at least about 50 IU/kg and a dosing interval at least about 7 days, a dose at least about 100 IU/kg and a dosing interval at least about 9 days, a dose at least about 100 IU/kg and a dosing interval at least about 12 days, a dose at least about 150 IU/kg and a dosing interval at least about 14 days, 20-50 or 20-100 IU/kg and said dosing interval is one time weekly, a dose of 20-50 IU/kg and a dosing interval of 7 days, a dose of 50-100 IU/kg and a dosing interval of 10-14 days, or a dose of 100-150 IU/kg and a dosing interval of 14-16 days.

Preferred combinations of dosing interval and dose also include 10-50 IU/kg for 7 days, 15-100 IU/kg for 10-13 days, 50-150 IU/kg for 14-15 days, 10-30 IU/kg for 7 days, 15-50 IU/kg for 10 days, 20-70 IU/kg for 11 days, 25-85 IU/kg for 12 days, 30 to 100 IU/kg for 13 days, 40 to 125 IU/kg for 14 days, and 50-150 IU/kg for 15 days.

"Variant," as used herein, refers to a polynucleotide or polypeptide differing from the original polynucleotide or polypeptide, but retaining essential properties thereof, e.g., Factor IX coagulant activity or Fc (FcRn binding) activity. Generally, variants are overall closely similar, and, in many regions, identical to the original polynucleotide or polypeptide. Variants include polypeptide and polynucleotide fragments, deletions, insertions, and modified versions of original polypeptides.

Variant polynucleotides may comprise, or alternatively consist of, a nucleotide sequence which is at least 85%, 90%, 95%, 96%, 97%, 98% or 99% identical to, for example, the nucleotide coding sequence in SEQ ID NO:1 or 3 (the Factor IX portion, the Fc portion, individually or together) or the complementary strand thereto, the nucleotide coding sequence of known mutant and recombinant Factor IX or Fc such as those disclosed in the publications and patents cited herein or the complementary strand thereto, a nucleotide sequence encoding the polypeptide of SEQ ID NO:2 or 4 (the Factor IX portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

Variant polypeptides may comprise, or alternatively consist of, an amino acid sequence which is at least 85%, 90%, 95%, 96%, 97%, 98%, 99% identical to, for example, the polypeptide sequence shown in SEQ ID NO:2 or 4 (the Factor IX portion, the Fc portion, individually or together), and/or polypeptide fragments of any of these polypeptides (e.g., those fragments described herein).

By a nucleic acid having a nucleotide sequence at least, for example, 95% "identical" to a reference nucleotide sequence, it is intended that the nucleotide sequence of the nucleic acid is identical to the reference sequence except that the nucleotide sequence may include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be, for example, the entire sequence shown in SEQ ID NO:1 or 3, the ORF (open reading frame), or any fragment specified as described herein.

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. A preferred method for determining the best overall match between a query sequence (reference or original sequence) and a subject sequence, also referred to as a global sequence alignment, can be determined using the FASTDB computer program based on the algorithm of Brutlag et al. (Comp. App. Biosci. (1990) 6:237-245), which is herein incorporated by reference in its entirety In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 85%, 90%, 95%, 96%, 97%, 98% or 99% identical to, for instance, the amino acid sequences of SEQ ID NO:2 (the Factor IX portion, the Fc portion, individually or together) or 4, or a known Factor IX or Fc polypeptide sequence, can be determined conventionally using known computer programs. A preferred method for determining the best overall match between a query sequence (reference or original sequence) and a subject sequence, also referred to as a global sequence alignment, can be determined using the FASTDB computer program based on the algorithm of Brutlag et al., Comp. App. Biosci. 6:237-245(1990), incorporated herein by reference in its entirety. In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The polynucleotide variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides. For instance, one or more amino acids can be deleted from the N-terminus or C-terminus of the secreted protein without substantial loss of biological function. The authors of Ron et al., J. Biol. Chem. 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988), incorporated herein by reference in its entirety.)

Moreover, ample evidence demonstrates that variants often retain a biological activity similar to that of the naturally occurring protein. For example, Gayle and coworkers (J. Biol. Chem. 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild type.

As stated above, polypeptide variants include modified polypeptides. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

Having now described the present invention in detail, the same will be more clearly understood by reference to the following examples, which are included herewith for purposes of illustration only and are not intended to be limiting of the invention. All patents and publications referred to herein are expressly incorporated by reference.

Example 1. First-in-Human (FiH) Trial

The first-in-human study was an open label, dose-escalation, Phase 1/2 study to determine the safety, tolerability and pharmacokinetic (PK) parameters of FIXFc (recombinant human coagulation factor IX fusion protein). FIXFc is a recombinant fusion protein comprising human clotting factor IX coupled to the Fc domain from human IgG1. The fusion protein is expressed in human embryonic kidney cells (HEK 293). See Example 3.

FIXFc is being developed for the control and prevention of hemorrhagic episodes in patients with hemophilia B (congenital factor IX deficiency or Christmas disease), including the control and prevention of bleeding in surgical settings.

FIXFc is a recombinant fusion protein comprised of coagulation Factor IX (FIX) and an Fc domain of a human antibody (IgG1 isotype). The FIXFc molecule is heterodimeric with a FIXFc single chain (FIXFc-sc) and an Fc single chain (Fc-sc) bound together through two disulfide bonds in the hinge region of Fc. See FIG. 1 and Table 2.

rFIXFc drug product is a clear colorless solution intended for intravenous (IV) administration. rFIXFc is supplied as 1000 IU per a 5 mL volume in a 10 mL single use only vial. The Drug Product is packaged in USP Type I glass vials with bromobutyl stoppers and tear-off plain aluminum overseals. rFIXFc drug product contains 200 IU/mL in 10 mM sodium phosphate buffer pH 7.0 with addition of 145 mM NaCl and 0.1% polysorbate 20. The rFIXFc solution should not be diluted.

Study Design. A total of 14 previously treated patients with severe hemophilia B were enrolled and treated with FIXFc as an intravenous (IV) infusion over approximately 10 minutes. Six dose levels, 1, 5, 12.5, 25, 50, and 100 IU/kg were evaluated in the study. One patient per dose level was enrolled at dose levels 1, 5, 12.5, and 25 IU/kg, and at least three evaluable patients per dose level were enrolled at 50 and 100 IU/kg.

After the screening (scheduled within 14 days of the FIXFc dose), the treatment period for the patients began. The treatment period for each dose level included a single dose of FIXFc (Day 1) up until the completion of the 72-hour safety observation period (3 days) for dose levels 1 and 5 IU/kg or until the last PK sample was taken for patients in dose levels 12.5 to 100 IU/kg (approximately 10 days). Patients treated with 1, 5, 12.5, or 25 IU/kg were enrolled and treated in a sequential manner starting at 1 IU/kg. Patients receiving 50 IU/kg were not treated on the same day and at least one day separated dosing. After treatment of the 50 IU/kg patients, treatment of the 100 IU/kg patients began.

The post-treatment period was a 30-day safety observation period starting from the day the patient received the dose of FIXFc and overlapped with the treatment period since patients were undergoing the required study evaluations, such as PK sampling, during this time.

Patients assigned to dose levels 12.5 to 100 IU/kg had blood samples drawn to assess FIX activity and FIXFc concentration. Blood samples were to be drawn just prior to administration of FIXFc; 15 minutes following the end of the infusion; and at 1, 3, 6, 9, 24, 48, 72, 96, 120, 168, and 240 hours following the end of the infusion or until baseline FIX levels were reached. If a patient continued to have FIX levels above baseline at the 240-hour time point (Study Day 11), samples were taken at 288 hours (Study Day 13) and again at 336 hours (Study Day 15) if the FIX level was above baseline at Study Day 13.

Patient 10 received BENEFIX™ treatment for a bleed prior to scheduled FIXFc sampling at 216 hours post dosing. Consequently, FIXFc activity and antigen data for the 216 h and following time points were excluded from analysis. No additional deviations occurred that are felt to have affected the interim analysis results of this study.

For Factor IX antigen, pharmacokinetic analyses were performed on the individual patient observed FIXFc concentration versus time data following IV infusion of FIXFc. Primary analysis was performed using model-dependent methodology. FIXFc concentration data were computer-fitted to a two-compartment open model with elimination from the central compartment using user-defined initial parameter estimates for the calculation of initial parameter values. WinNonlin estimated microscopic rate constants were generated and FIXFc concentration data were weighted with the function of $1/(Y^{-hat}*Y^{-hat})$. Observed data for two subjects (e.g., Patients 5 and 6) were inadequately described by the two-compartment model. Consequently, model-independent analysis was performed on these two patients using WinNonlin noncompartmental analysis IV-Infusion input model (linear trapezoidal rule for AUC calculation). For noncompartmental analysis, the half-life was calculated from the beta phase using the data points that describe the terminal log-linear decline in the regression. A minimum of three points were used to describe elimination phase. This occurred approximately between 4 and 14 days. For PK analysis of antigen, the "mg/kg" dose equivalents were utilized. These values were determined based on a specific activity for FIXFc of 60.2 IU/mg. Actual sampling times, doses, and infusion durations were used for calculations. Nominal sampling times and doses were used for the creation of tables and concentration-time figures. Individual and mean PK parameters and descriptive statistics are presented. Formal statistical analysis was not performed because the dose range and the number of subjects in each cohort were too small for meaningful analysis.

For Factor IX activity, a baseline subtraction method was applied to the activity versus time profile according the baseline subtraction decision tree (FIG. 4). Activity values of <1% were defined at 1 IU/dL for baseline decay. Predose times were treated as zero for the purpose of calculations. In addition, baseline corrected activity data were truncated at time points that represented a return to baseline levels. Pharmacokinetic analyses were performed on the baseline subtracted FIX activity versus time data obtained following IV infusion administration of FIXFc. A model-dependent assessment was utilized for analysis of the IV-infusion dose groups. The baseline subtracted data were computer-fitted to a two-compartment open model with elimination from the central compartment using WinNonlin-defined parameter boundaries for the calculation of the initial parameter values. WinNonlin estimated microscopic rate constants were generated and FIXFc activity data were weighted with the function of $1/(Y^{-hat}*Y^{-hat})$. Actual sampling times, doses, and infusion durations were used for calculations. Nominal sampling times and doses were used for the creation of tables and concentration-time figures.

When unavailable from the actual data, the activity at 168 h post dosing (C168) and time to 1 IU/dL above baseline (TBLP1) of rFIXFc were obtained using the WinNonlin generated microscopic rate constants to simulate the FIXFc activity level versus time data. Individual and mean PK parameters and descriptive statistics are presented in this Example. Formal statistical analysis was not performed, because the dose range and the number of subjects in each cohort were too small for meaningful analysis.

Results for FIXFc antigen pharmacokinetics showed that FIXFc plasma concentrations increased sharply after the short IV infusion of FIXFc, with mean (±SD) $C_{max}$ values of 1670 (n=1), 2730 (n=1), 7510±2480 and 15400±3960 ng/mL for the 12.5, 25, 50, and 100 IU/kg nominal dose levels, respectively, and was reached within the first half-hour for all patients All FIXFc-treated patients had dose-related increases in systemic FIXFc plasma exposure (as assessed by $C_{max}$ and $AUC_{INF}$). Although limited to a single evaluable patient at the 12.5 and 25 IU/kg nominal dose, the observed increase in both C. and $AUC_{INF}$ was reasonably proportional to dose over the dose range evaluated. (Table 3 shows individual patient and group mean FIXFc antigen concentration versus time data; sorted by nominal dose, actual dose, infusion duration, and patient number. Table 4 shows individual patient and group mean FIXFc antigen PK summary data; sorted by nominal dose, actual dose, "mg/kg" equivalent dose, and patient number, shows individual patient and group mean FIXFc antigen PK summary data; sorted by nominal dose, actual dose, "mg/kg" equivalent dose, and patient number, and see Table 11.)

FIXFc plasma concentrations declined in a biexponential fashion following the short IV infusion. Both distribution (alpha) and elimination (beta) half-life values appeared to be dose-independent over the dose range evaluated with individual patient alpha and beta half-life values ranging from 9.79 to 21.2 hours and 71.0 to 140 hours, respectively. Mean alpha half-life values (±SD) for the 50 and 100 IU/kg nominal dose levels were 13.1±4.77 and 12.1±2.33 hours, respectively. Mean beta half-life values (±SD) for the 50 and 100 IU/kg nominal dose levels were 110±26.5 and 95.8±11.1 hours, respectively. In addition, primary PK parameter values for Cl, $V_{SS}$, and MRT were determined and, in general, all appeared to be dose-independent over the dose range evaluated. As indicated, this assessment is limited by single patient data at the 12.5 and 25 IU/kg nominal dose levels. (Table 12 and FIGS. 2, 7, and 8.)

Further, mean Cl values were 2.28±0.374 and 2.11±0.464 mL/h/kg for the 50 and 100 IU/kg nominal dose levels, respectively. Mean $V_{SS}$ values were 259±78.5 and 238±52.2 mL/kg for the 50 and 100 IU/kg nominal dose levels, respectively. In addition, mean MRT values were 112±21.5 and 114±17.1 h for the 50 and 100 IU/kg nominal dose levels.

Results for baseline corrected FIXFc activity pharmacokinetics showed that FIXFc activity increased sharply after the short IV infusion of FIXFc, with mean (±SD) model-predicted $C_{max}$ values of 11.9 (n=1), 19.9 (n=1), 41.6±8.97 and 98.2±8.21 IU/dL for the 12.5, 25, 50, and 100 IU/kg nominal dose levels, respectively, and was reached within the first half-hour for all patients. (Table 5 shows individual patient and group mean baseline corrected FIXFc activity versus time data; sorted by nominal dose, actual dose, infusion duration, and patient number and. Table 6 shows individual patient and group mean FIXFc activity PK summary data; sorted by nominal dose, actual dose, "mg/kg" equivalent dose, and patient number.)

All FIXFc-treated patients had dose-related increases in FIX activity (relative to predose baseline response). Although limited to a single evaluable patient at both the 12.5 and 25 IU/kg nominal dose levels, the observed increase in both $C_{max}$ and $AUC_{INF}$ was reasonably proportional to dose over the dose range evaluated. (Tables 6, 9, and 13 and FIGS. 3 and 5.)

After the end of the infusion, the decline in baseline corrected FIX activity exhibited biexponential decay; characterized by a rapid distribution (alpha) phase followed by a log-linear elimination (beta) phase. During the alpha phase, the rate of decline in FIXFc activity was variable with individual patient alpha half-life values ranging from 0.140 to 16.6 hours. The seemingly dose-dependent increase in mean alpha half-life values was confounded by a single patient at the 12.5 and 25 IU/kg nominal dose levels. In contrast, elimination (beta) half-life values appeared to be dose-independent over the dose range with individual patient beta half-life values ranging from 42.1 to 67.4 hours over the 25 to 100 IU/kg dose range. Although estimated and reported, the elimination half-life for patient 1 treated with 12.5 IU/kg of rFIXFc are not included in summary evaluation due to this patient's FIX levels being detectable for only up to 96 hours resulting in a truncated terminal phase and contributing to an underestimation of the terminal elimination half-life. Mean beta half-life values (±SD) for the 50 and 100 IU/kg nominal dose levels were 52.1±10.4 and 52.5±10.1 hours, respectively, and 52.5±9.2 (range 40-67.4) hours for combined 25, 50 and 100 IU/kg nominal doses. (Tables 6, 8 and 13).

In addition, primary PK parameter values for Cl, $V_1$, $V_{SS}$, and MRT were determined and, in general, all appeared to be dose-independent over the dose range evaluated.

Further, mean Cl values were 3.77±1.12 and 2.89±0.615 mL/h/kg for the 50 and 100 IU/kg nominal dose levels, respectively, and 3.36±0.928 mL/h/kg for the combined 25, 50, and 100 IU/kg nominal doses. (Tables 6, 8 and 13.)

Mean $V_{SS}$ values were 264±77.6 and 179±31.1 mL/kg for the 50 and 100 IU/kg nominal dose levels, respectively, and 226±69.8 mL/kg for the combined 25, 50, and 100 IU/kg nominal doses. (Tables 6, 8 and 13.) In addition, mean MRT values were 71.7±13.0 and 62.8±8.82 h for the 50 and 100 IU/kg nominal dose levels, respectively, and 68.05±11.16 h for the combined 25, 50, and 100 IU/kg nominal doses. (Tables 6, 8 and 13.)

In addition to the primary PK parameters, secondary PK parameters (e.g., C168, K-values, IVR, etc.) were determined to evaluate FIXFc duration of effect. As anticipated, dose-dependent increases in C168, TBLP1, TBLP3, and TBLP5 values were observed. In contrast, K-values and IVR values appeared to be dose-independent over the dose range evaluated. Over the full dose range, individual patient model-predicted and observed K-values ranged from 0.61 to 1.02 and 0.62 to 1.17 IU/dL per IU/kg, respectively. Mean model-predicted K-values for the 50 and 100 IU/kg nominal dose levels were 0.76 and 0.90 IU/dL per IU/kg, respectively, and 0.821±0.1387 (range 0.61-1.02) IU/dL per 1 IU/kg for combined 25, 50, and 100 IU/kg nominal doses. Mean model-predicted IVR values for the 50 and 100 IU/kg nominal dose levels were 34.5 and 35.1%, respectively. Mean observed K-values for the 50 and 100 IU/kg nominal dose levels were 0.86 and 1.02 IU/dL per IU/kg, respectively, and 0.926±0.1787 (range 0.97-1.17) IU/dL per 1 IU/kg for combined 25, 50, and 100 IU/kg nominal doses. Mean observed IVR values for the 50 and 100 IU/kg nominal dose levels were 39.2 and 39.8%, respectively. (Tables 6, 7, 8 and 13.) Table 7A-7B show7 shows individual patient and group mean FIXFc activity secondary PK summary data; sorted by nominal dose, actual dose, and patient number.

Each 1 IU/kg of infused rFIXFc raised plasma FIX activity by 0.93±0.18 IU/dl on average, and this incremental recovery (K value) showed weak positive correlation with body weight ($R^2$=0.336, p=0.048) (FIG. 23).

Pharmacokinetic estimates for FIXFc activity were consistent with those for rFIXFc antigen (e.g., compare Tables 13 and 14). Further, there was excellent correlation between rFIXFc activity and antigen levels, indicating the preservation of rFIXFc in vivo activity. (FIG. 9.) In addition, relative to historical data for BENEFIX™ (Wyeth), rFIXFc demonstrated (Table 8) the following:

Dose linearity from 25-100 IU/kg
3 fold increase in $t_{1/2beta}$
3 fold increase in mean residence time
24% improved incremental recovery
2.5 fold reduced clearance FIXFc is a recombinant fusion protein comprised of FIX attached to the Fc domain of human IgG1. FIXFc has been designed to be a long-acting version of FIX. Preclinical studies with FIXFc have shown a prolongation of the half-life of FIX activity compared to BENEFIX™, the commercially available recombinant FIX product. The rationale for this study was to evaluate the safety and PK of FIXFc in severe hemophilia B patients. For this study, 12 evaluable subjects aged 18 to 76 years were available for PK evaluation. Each subject received a single administration of FIXFc at a nominal dose of 12.5, 25, 50, or 100 IU/kg of body weight infused intravenously over approximately 10 minutes. Plasma samples for PK assessments of both FIXFc activity and antigen concentrations were obtained before infusion as well as up to 14 days after dosing. The PK of both FIXFc antigen and activity were independently characterized in this study using model-dependent and model-independent methods.

FIXFc was well tolerated following administration of single IV doses of 12.5, 25, 50, and 100 IU/kg of body weight. There was no evidence of drug-related serious adverse events in this study. No neutralizing or binding antibodies to rFIXFc were detected in any subject.

Approximate dose-proportional increases in $C_{max}$ and $AUC_{INF}$ were observed for both FIXFc antigen and activity following the administration of doses of 12.5 through 100 IU/kg, but the V and Cl were similar across all doses. These results indicate that FIXFc antigen and activity exhibited linear PK over the dose range evaluated. The relatively small V parameter values may indicate that FIXFc enters the interstitial fluid but does not cross the cell membrane into the intracellular fluids.

Peak plasma levels of FIXFc antigen and activity were observed within 0.5 h after the end of the infusion and remained detectable for several days after dosing. Evidence of reduced clearance and prolonged half-life was observed for both FIXFc antigen and activity.

Mean clearance and terminal elimination half-life values associated with FIXFc antigen concentrations for the 50 and 100 IU/kg dose levels were 2.28 and 2.11 mL/h/kg and 110 and 95.8 hours, respectively. Similarly, mean clearance and terminal elimination half-life values associated with FIXFc activity levels over the same dose range were 3.77 and 2.89 mL/h/kg and 52.1 and 52.5 hours, respectively. Comparison of FIXFc activity PK results observed in the current study to reported PK for BENEFIX™ activity (Summary of Product Characteristics of BENEFIX™; Nov. 18, 2009) revealed an approximate 3-fold reduction in FIXFc clearance and an approximate 3-fold increase in both FIXFc terminal elimination half-life and mean residence time relative to BENEFIX™.

With the observed improvements in PK, FIXFc will provide a prolonged protection from bleeding, allowing less frequent injections for individuals with Hemophilia B. Based on the results of this trial, rFIXFc may be dosed every two weeks or twice monthly using doses of 100 IU/kg and at least weekly using lower doses. Such a regimen requires fewer injections. In addition, the use of rFIXFc will have other potential clinical impacts such as: central venous access; improved regimen compliance; reduced break through bleeds; and increased protection of joints from bleeds.

Example 2. B-LONG Phase 1/2/3 Trial

This will be an open-label, multicenter evaluation of the safety, pharmacokinetics, and efficacy of recombinant, long-acting coagulant Factor IX Fc fusion (rFIXFc) in the prevention and treatment of bleeding in previously treated subjects with severe hemophilia B. Treatment with FIX products currently on the market necessitates dosing 2-3 times per week. A product with a prolonged half-life that extends the required dosing interval to once weekly or longer would be considered by the medical community as a significant improvement for the treatment of severe hemophilia patients.

Dose levels vary widely for rFIX products in clinical prophylaxis studies: the reported doses range from 10 to 171 IU/kg (Roth et al., Blood 98:3600 (2001)) or 40 to 100 IU/kg (MASAC Recommendation 177, National Hemophilia Foundation (October 2006)). Moreover, trough levels of FIX activity during prophylaxis treatment in subjects with no clinical signs of bleeding are predicted to range between 0.2 and 3.8 IU/dL (Carlsson et al., Hemophilia 4:83 (1998)). Considering the inter-individual patient variability, individualized dosage regimens based on the clinical status of a patient are common practice.

The results of a Phase 1/2a study (Example 1) evaluating the safety and pharmacokinetics of a single dose of a frozen liquid formulation of rFIXFc have demonstrated the drug is well tolerated at doses ranging from 1 to 100 IU/kg and the PK characterization suggests several advantages over currently available treatments, namely a half-life and MRT that are 3-fold longer than that previously reported for BENEFIX™ (61 hours vs. 19 hours). The purpose of this study is to determine the PK parameter estimates of the lyophilized rFIXFc in humans prospectively, to compare these with BENEFIX™ PK parameter estimates in humans, and to demonstrate the efficacy of lyophilized rFIXFc in the prevention and treatment of bleeding and the safety of its repeat dosing for previously treated subjects with severe hemophilia B.

The study will entail four arms: a low dose prophylaxis regimen (n=25), a high dose prophylaxis regimen (n=25), an on-demand regimen (n=20) and a major surgery regimen (n=5). The low dose regimen arm will include a PK subgroup (n=16) dosed with BENEFIX™, followed by crossover to rFIXFc.

The primary objectives of the study are: to evaluate the safety and tolerability of rFIXFc in all treatment arms; to evaluate the efficacy of rFIXFc in all treatment arms; and to evaluate the effectiveness of prophylaxis over on-demand therapy (comparison of the annualized number of bleeding episodes between Arms 1 and 2 versus on-demand regimen Arm 3).

The secondary objectives of the study are: to compare the PK parameter estimates of rFIXFc and BENEFIX™; to evaluate the efficacy of rFIXFc in the on-demand and surgical arms; to evaluate and compare the PK parameter estimates of rFIXFc at baseline and Week 26 (±1 week) in the PK subgroup; to evaluate subjects' response to treatment in all arms; and to evaluate rFIXFc consumption in all arms.

Main Inclusion Criteria:
Male and 12 years of age and older and weigh at least 40 kg
Diagnosed with hemophilia B (baseline Factor IX level less than or equal to 2%)
History of at least 100 exposure days to any Factor IX product
Platelet count≥100,000 cells/µL
INR (international normalized ratio)≤1.40 as defined by the testing laboratory's normal range
CD4 count≥200 cells/µL
Main Exclusion Criteria:
History of Factor IX inhibitors
Kidney or liver dysfunction
Diagnosed with another coagulation defect other than hemophilia B
Prior history of anaphylaxis associated with any FIX or IV immunoglobulin administration
Taking systemic immunosuppressive drugs (e.g., systemic corticosteriods; however, HAART (highly active antiretroviral therapy) is permitted)

Example 3. FIXFc Production in HEK293 Cells

FIXFc was produced in stably transfected HEK293 cells containing an expression cassette for FIXFc (native FIX fused directly to the Fc region) and an expression cassette for Fc alone. The cells also were transfected with an expression cassette for PCS, which is a processing enzyme that allows for full processing of the FIX propeptide. The transfected cells were grown in serum-free suspension media containing vitamin K, and they secreted three proteins: FIXFc dimer, FIXFc monomer (one FIXFc chain and one Fc chain), and Fc dimer. FIXFc monomer ("FIXFc") was purified by column chromatography (Protein A, Fractogel DEAE, and Q Sepharose pseudo-affinity elution with low ionic strength $CaCl_2$), and viral inactivated and filtered for administration to human subjects. Also see Peters et al., Blood. 2010 Mar. 11; 115(10):2057-64 (Epub 2010 Jan. 7); and U.S. Pat. No. 7,566,565; each of which is incorporated by reference herein in its entirety.

Coagulant activity of FIXFc was measured by quantitating its ability to restore the clotting activity of FIX-deficient plasma using an MLA Electra 1600C (Medical Laboratory Automation/Instrument Labs, Pleasantville, N.Y.). Results were compared to a calibration curve generated using serial dilutions of a World Health Organization FIX standard.

Serine phosphorylation and tyrosine sulfation of Factor IX are thought to be important for in vivo recovery. It has been reported that MONONINE™ (plasma purified Factor IX (pdFIX) marketed by CSL Berhing) has better in vivo recovery than BENEFIX™ (recombinant FIX (rFIX) marketed by Wyeth) because of the higher phosphorylation/sulfation level of MONONINE™ (>90%/>90% versus<10%/5%). However, FIXFc produced in HEK293 cells has almost no phosphorylation/sulfation (<10%/4%, which is very similar to BENEFIX™), and shows better IVR (1.0 IU/dl per IU/kg) than BENEFIX™ (0.7).

In addition, FIXFc produced as described above had a significantly lower (10-100 fold) level (0.01-0.001%) of activated FIX (FIXa), a product related impurity, than either MONONINE™ (pdFIX) or BENEFIX™ (rFIX) (0.1%). The resulting FIXFc will have fewer unwanted thrombotic events upon administration than MONONINE™ or BENEFIX™.

Example 4. Pediatric Studies: Extrapolation and Interrelation Between the Development in Adult and Pediatric Populations Patient characteristics that show relationships with FIX pharmacokinetics include age-dependent physiological changes (Björkman and Berntorp, Clin. Pharmacokinetics 40:815-32 (2001); and Bjorkman, Hemophilia 9(suppl 1):101-10 (2003)) and body size and composition (Shapiro, Hemophilia 11:571-82 (2005)). Thus, weight-adjusted clearance (CL) of FIX has generally been found to decrease with age and/or body weight during growth from infancy to adulthood, with a corresponding increase in terminal half-life ($t_{1/2}$). For rFIX product (BENEFIX™), CL and volume distribution at steady state (Vss) are increased in children and then remain constant during adulthood; thus, these parameters will be closely monitored in the pediatric studies.

Peak levels of FIX procoagulant activity (FIX:C) depend on the initial volume of distribution of FIX:C after single and/or repeated doses of FIX. The initial distribution of FIX is rapid. However, it has been shown that in vivo recovery (mean incremental recovery) for BENEFIX™ was typically 30% lower than that of a monoclonal antibody purified plasma derived coagulation factor (pdFIX) (Roth et al., Blood 98:3600-3606 (2001)). Furthermore, studies with pdFIX have shown that subjects 15 years of age and younger have a significantly lower recovery than those who are older (White et al., Thromb. Haemost. 73:779-84 (1995)). Therefore, monitoring of trough and peak levels will also be performed in the pediatric studies.

Since studies have shown that children may respond differently compared to adults, pharmacokinetic assessments at baseline with 50 IU/kg of rFIXFc will be performed in children with abbreviated pharmacokinetic sampling.

The Phase 1/2a study (SYN-FIXFc-07-001) evaluating the safety and pharmacokinetics profile of a single intravenous administration of rFIXFc in PTPs aged 18 years and above with severe hemophilia B was recently completed. Preliminary results from this initial exploration in humans demonstrates an approximately 3-fold increase in pharmacokinetic parameters (mean terminal half-life, MRT, and AUC) of rFIXFc compared with what has been reported in the literature for BENEFIX™ (see above). Additionally, rFIXFc was well tolerated and there were no sign of injection site reactions as well as no development of inhibitors. Together, these safety and pharmacokinetic results support the initiation of a Phase 1/2/3 registrational study (998HB102 Study (B-LONG), see above) evaluating the safety, pharmacokinetics, and efficacy of rFIXFc in prevention and treatment of bleeding in 104 PTPs (with at least 100 treatment EDs to previous products) 12 years and older with severe hemophilia B (<2%). Once sufficient safety data are available from the registrational study, a pediatrics program will be initiated to further investigate the safety and efficacy of rFIXFc in children. The demonstration of prolonged half-life of rFIX in humans will mean that less frequent injections will be needed for the prevention and treatment of bleeding to individuals with hemophilia B.

Phase 2/3 Pediatric PTPs Study in Previously Treated Children (<12 Years Old)

Once the data are available on 10 PTPs (≥12 years) for 26 EDs from the registrational study (998HB 102 Study), a Pediatric Study, phase 3 will be initiated. This Phase 2/3 pediatric study, in PTPs who had at least 50 EDs to FIX products prior to enrollment, will be conducted globally at approximately 25 clinical sites. Approximately 25 PTPs (to ensure 20 evaluable subjects), age 2-11 years with severe hemophilia B (<2 IU/dL [<2%] endogenous FIX), will be screened and selected according to the pre-defined criteria. All evaluable subjects will complete the pharmacokinetic portion of the study (PK with pre-study FIX product and then PK with rFIXFc) and will receive weekly dosing of rFIXFc for 52 weeks. This study will record incremental recovery, in vivo half-life, AUC, and clearance of rFIXFc. All subjects will undergo pharmacokinetic assessment at baseline with pre-study FIX and rFIXFc and the duration of the study for each subject will be approximately 69 weeks, including screening and follow-up.

Each subject will receive 50 IU/kg of rFIXFc at baseline for pharmacokinetic assessment followed by repeated weekly dosing with 50-60 IU/kg of rFIXFc. With regard to patient compliance, abbreviated pharmacokinetic sampling will be employed for pre-study product and for rFIXFc as follows: pre dose, end of injection, 30+10 minutes, 3±1 hours, 24±3 (Day 1), 72±3 (Day 3), 120±3 (Day 5), and 168±3 hours (Day 7) after the end of injection. In order to address immunogenicity, all subjects will be treated with rFIXFc weekly for a minimum of 50 EDs. Safety parameters will be included for immediate safety and tolerability assessment, such as: (a) vital signs (pulse, blood pressure, respiratory rate, temperature) at pre rFIXFc injection and 30 minutes post injection; (b) hematology and coagulation parameters; (c) clinical chemistry; (d) frequent FIX inhibitor determinations using the Nijmegen-modified Bethesda assay (immediately before first exposure, ED4 [Week 4], ED12, ED24, ED36, and ED50); and (e) adverse events.

Efficacy will be assessed by evaluation of number of bleeding episodes, bleeding intervals and number of treatments and consumption of FIX per annualized year and per event.

Phase 2/3 Pediatric PUPs Study In Previously Untreated Children (0-11 Years Old)

Once the data from 10 previously-treated children (2-11 years) with complete pharmacokinetics and 50 EDs are available in the preceding study, a Phase 2/3 pediatric PUPs study will be initiated. This study will be conducted globally at approximately 60 clinical sites. Up to 30 PUPs (to ensure 20 evaluable subjects) for 0 and above years with severe hemophilia B (<2 IU/dL [<2%] endogenous FIX) will be screened and selected according to the pre-defined criteria. Participation in the study will vary since the initiation treatment may begin using rFIXFc as modified prophylaxis regimen. Per patient study participation is expected to be approximately four years including screening and follow-up. During this time most patients are expected to achieve 50 EDs to rFIXFc. In order to address immunogenicity, all subjects will be treated with approximately 50 EDs of rFIXFc or for up to 4 years. Safety parameters will be included for immediate safety and tolerability assessment: (a) frequent FIX inhibitor determinations using the Nijmegen-modified Bethesda assay; and (b) adverse events.

Efficacy will be assessed by evaluation of number of bleeding episodes, bleeding intervals and number of treatments and consumption of FIX per annualized year and per event.

Example 5. Biochemical Characterization, Activity, and PK Analysis in Non-Human Animals The rFIXFc produced in Example 3 was characterized for its posttranslational modification, and the following results were obtained (see Table 15 and FIG. 11). The propeptide of rFIXFc was properly processed during production. rFIXFc's gamma-carboxylation pattern was similar to that of rFIX. Further, total Gla/molecule (11.2±0.7) of rFIXFc was comparable to rFIX. Because gamma-carboxylation at certain residues is essential for FIX activity, these are important results. In addition, Ser 158 phosphorylation and Tyr 155 sulfation of rFIXFc were comparable to rFIX. N-linked glycans in FIX are not fully sialylated, similar to rFIX. rFIXFc O-linked glycosylation in the first EGF domain was the same as FIX, albeit in different relative ratios. Asp 64 of rFIXFc had a higher degree of beta-hydroxylation than rFIX or plasma derived FIX (pdFIX). Activated FIX was present at a much lower level in the rFIXFc preparation than in the rFIX or pdFIX preparations, as is discussed in detail in Example 3.

In addition, rFIXFc was administered to various animal species to determine its activity and PK parameters. The results are shown in Table 16 and FIGS. 12-16.

Example 6. Gamma-Carboxylation

The goals of this study were to analyze and characterize γ-carboxylation of the glutamic acids (Gla) in a preclinical lot of FIXFc material and commercially available FIX products, to characterize the Gla content of an enriched "peak" fraction and a high salt elution "strip" fraction originating from a pseudo-affinity chromatography ion-exchange step, and to further separate an enriched "peak" and a high salt elution "strip" fraction by anion-exchange HPLC and further characterize the separated species.

To achieve these goals, a number of complementary analytical methods were developed. These include amino acid analysis (AAA) using basic hydrolysis to determine (total) Gla content, peptide map (LC/MS) using Lys-C peptides to determine Gla distribution, analytical anion-exchange HPLC of intact molecules to separate isoforms, and activated partial thromboplastin time (aPTT) to determine biological activity.

The two Gla (E) containing peptides are:
K1K2: YNSGKL$^7$E$^8$EFVQGNL$^{15}$ER$^{17}$ECM$^{20}$E$^{21}$EK
  [M+H]+6 Gla=2953.9
  [M+H]+5 Gla=2909.9
K3: CSF$^{26}$E$^{27}$EAR$^{30}$EVF$^{33}$ENT$^{36}$ERTT$^{40}$EFWK
  [M+H]+6 Gla=2959.9
  [M+H]+5 Gla=2915.9
  [M+H]+4 Gla=2871.9

Thirty micrograms of sample (originating from the enriched peak fraction, high salt strip fraction and each species from the analytical anion-exchange HPLC) was denatured, reduced, alkylated and digested with Lys-C (1:20, E:S). The digest was quenched with 2% TFA and injected onto a Jupiter C18 (2.0×250 mm) Phenomenex column. Separation was performed on an Agilent 1100 system. The column was maintained at 25° C. and peptides were eluted with a multi-step acetonitrile gradient. Mass spectrometry (Thermo-Fisher LCQ) was performed in "Triple Play" mode.

Complementary methods were developed to analyze and characterize the Gla content and distribution of preclinical rFIXFc material. The γ-carboxylation of glutamic acids (Gla) content and distribution in a preclinical lot of rFIXFc (enriched peak fraction) was performed and compared to commercially available products. Analysis demonstrated similar Gla content and distribution with respect to commercially available products. A high salt elution "strip" fraction was analyzed and compared to the enriched peak fraction. Analysis indicated a reduced level of γ-carboxylation.

The FIXFc (Enriched Peak Fraction) was isolated from pseudo-affinity chromatography ion-exchange step and further separated into 3 iso-forms by analytical anion exchange HPLC. AEX column load and separated species were highly γ-carboxylated. (The AEX column load is the strip fraction collected during a high salt elution step from the pseudo-affinity chromatography ion-exchange step.) AEX column load and separated species were biologically active. The Gla content and distribution was similar to rFIX. The peptide map indicates distribution of 4/5/6 Gla's on the K3 peptide. The peptide map indicates a high population of 6 Gla's on the K1K2 peptide and a trace level of 5 Gla's.

The FIXFc (Strip Peak Fraction) was isolated from pseudo-affinity chromatography ion-exchange step and further separated into 2 iso-forms by analytical anion exchange HPLC. AEX column load and separated species were reduced in γ-carboxylation level. There was reduced Gla content relative to FIXFc enriched peak fraction. A decreased level of biological activity was observed. The peptide map indicates an increased population of 5 Gla's in K1K2 relative to the enriched peak fraction and may suggest an impact on biological activity.

References (each of which is incorporated by reference herein in its entirety): Dumont J A, et al., Monomeric Fc Fusion Molecules in Therapeutic Abs-From Bench to Clinic, Ch. 33 p 779-795; Gillis S, et al., Protein Science (1997) 6:185; White G C, et al., J. Thrombosis and Haemostasis (1997) 78:261; Hansson K, and Stenflo J, Journal Thrombosis and Haemostasis (2005) 3:2633; and Peters R T, et al., Blood (2010) 115:2057.

Example 7. Evaluation of rFIXFc Pro-coagulant Activity in HemB Mice Bleeding Models Comparable potency of rFIXFc and BENEFIX™ was demonstrated in HemB mouse whole blood ROTEM in vitro and in a HemB mouse Tail Clip bleeding model in vivo.

The ability of rFIXFc to form firm and stable clots was evaluated by Rotation Thromboelastometry (ROTEM®, Pentapharm GmbH, Munich, Germany) with Calcium Chloride as activator (NATEM). Pooled whole blood collected via the vena cava from HemB mice was divided into seven aliquots, which were spiked with rFIXFc to a final concentration of 7.4%, 0.74% and 0.074% of normal plasma FIX activity, or BENEFIX™ to 10%, 1%, 0.1% of normal. As a negative control, a blood sample was spiked with FIX formulation buffer. A total of 10 blood pools from 5 HemB mice were generated to complete the assessment. The NATEM reaction was initiated by the addition of $CaCl_2$. Coagulation parameters, including Clotting Time (CT), Clot Formation Time (CFT) and Alpha Angle were assessed. The mean and SD of CT, CFT and alpha angle are summarized in Table 17. The dose responses for the three parameters are plotted in FIG. 17. All three parameters are comparable between rFIXFc and BENEFIX™ in the dose range tested (p>0.05 by one-way ANOVA (Kruskal-Wallis) analysis).

Acute efficacy of rFIXFc was also evaluated in HemB mouse Tail Clip bleeding model. (FIG. 18.) Male HemB mice were stratified for equal presentation of body weight and age in different treatment groups. Prior to tail clip injury, mice were anesthetized with a cocktail of 50 mg/kg Ketamine and 0.5 mg/kg Dexmedetomidine and placed on a heating pad to help maintain the body temperature. The tails of the mice were then immersed in 37° C. water for 10 minutes to dilate the lateral vein. After the vein dilation, rFIXFc, BENEFIX™ or vehicle were injected via the tail vein and 5 min later, the distal 4 mm of the tail were then cut off using a #11 scalpel with straight edge. The shed blood was collected into 13 ml of warm saline for 30 minutes and the blood loss was quantified gravimetrically. Six rFIXFc treatment groups (720, 360, 240, 120, 80, 40 IU/kg, n=15) and three BENEFIX™ treatment groups (360, 120, 40 IU/kg, n=15) were tested. The individual animal's blood loss value and dose response curve of median blood loss are shown in FIG. 19(A), and the median blood loss volume of each treatment group is summarized in Table 18. The dose response in median blood loss volume for both rFIXFc and BENEFIX™ are comparable (p=0.9315 by unpaired t test with Welch's correction).

To determine if the three-fold extended half-life of rFIXFc relative to BENEFIX™ resulted in prolonged efficacy of rFIXFc, the present inventors evaluated the efficacy of rFIXFc and BENEFIX™ in both ex-vivo ROTEM® assay and Tail Vein Transection bleeding model (TVT) in HemB mice. FIG. 20.

For ex vivo ROTEM®, male HemB mice received 50 IU/kg of rFIXFc or 100 IU/kg of BENEFIX™ by intravenous injection. Whole blood was collected from the vena cava of treated animals at 5 min, 24, 72, 96, 120, 168, and 216 hour post rFIXFc dosing (n=8 mice at each time point) or at 5 min, 24, 48, 72, and 96 hour post BENEFIX™ dosing (n=4 mice/time point). Blood samples were analyzed immediately by NATEM. The mean and SD for CT, CFT, and alpha angle are shown in Table 19, and the CT, CFT and alpha-angle versus time curves are shown in FIG. 21. In comparison to BENEFIX™, rFIXFc showed comparable CT, CFT, and alpha angle at 5 min, but significantly improved CT, CFT and alpha angle after 72 hrs despite a 2-fold lower dose relative to BENEFIX™.

To evaluate the prophylactic efficacy of rFIXFc and BENEFIX™, male HemB mice were stratified for equal representation of body weight and age in 9 different treatment groups. rFIXFc was administered by iv injection at a dose of 4 IU/kg, 13 IU/kg, 40 IU/kg and 120 IU/kg at 72 hours prior to tail vein transection, whereas the same doses of BENEFIX™ was administered at 24 hour prior to the injury. Prior to tail vein transection, mice were anesthetized with a cocktail of 50 mg/kg Ketamine/0.125 mg/kg Dexmedetomidine/0.1 mg/kg Buprenex. In order to allow the mice to maintain normal activity following tail vein transection, 1 mg/kg Atipamezole solution was given to reverse the effect of Dexmedetomidine, which immediately followed by the lateral tail vein transection with a straight edged number 11 surgical blade at an area where the diameter of the tail is approximately 3 mm. The shedding blood was washed away with warm saline to ensure clear observation of the wound, and the mouse was then single-housed in a clean cage with white paper bedding for the next 24 hours. The re-bleed and the physical activity were observed and recorded hourly up to 12 hour post injury. Moribund mice were euthanized immediately after identification, and a 24 hour post injury checkup was performed to complete the study. The Kaplan-Meier curve for Time to Euthanasia and chart of survival rates 24 hour post TVT were shown in FIG. 22. The Log-rank test determined that all treatment groups with higher than 4 IU/kg dose are significantly better than vehicle group (p<0.001). Furthermore, survival is comparable between mice that received the same dose of rFIXFc at 72 hrs prior to injury as that of BENEFIX™ at 24 hrs prior to injury (p=0.4886, 0.9268, 0.7279 and 0.5209 for 4, 13, 40 and 120 IU/kg dose groups respectively). The survival rates at 24 hour post TVT were plotted and ED50 value for each molecule were extrapolated from the curve, the ED50 for the two treatments are similar at 17.8 IU/kg for rFIXFc and 15.4 IU/kg for rFIX. Therefore, rFIXFc provided 3-fold longer duration of protection in HemB mice relative to a comparable dose of BENEFIX™ as measured by survival and re-bleed following tail vein transection injury. Therefore, rFIXFc provided 3-fold longer duration of protection in HemB mice relative to a comparable dose of BENEFIX™ as measured by survival and rebleed following tail vein transection injury.

In conclusion, as the data show, whereas 15.4 IU/kg of BENEFIX™ resulted in 50% of HemB mice surviving the tail vein transection at 24 hrs post dosing, 17.8 IU/kg of rFIXFc achieved 50% survival in animals that were injured at 72 hrs post dosing. Therefore, rFIXFc demonstrates a 3-fold longer prophylactic efficacy in correlation with its half-life extension relative to BENEFIX™. The results from the bleeding models are further corroborated by ex vivo ROTEM® analysis of whole blood from HemB mice treated with either 100 IU/kg of BENEFIX™ or 50 IU/kg of rFIXFc. At 5 min post dosing, comparable improvement in clot formation were observed in both treatment groups. However, the major ROTEM® parameters such as the clotting time, clot formation time and alpha-angle were significantly improved in rFIXFc-treated mice at 72 to 216 hrs following dosing despite a 2-fold lower dose of rFIXFc relative to BENEFIX™.

In summary, the acute potency of rFIXFc is comparable to that of BENEFIX™ as shown in both whole blood ROTEM® in vitro and the tail clip bleeding model in HemB mice. The prolonged prophylactic efficacy of rFIXFc was shown in ex vivo whole blood ROTEM® from treated HemB mice and was determined to be approximately 3-fold longer in comparison to BENEFIX™ in the tail vein transection bleeding model in HemB mice. The prolonged efficacy of rFIXFc correlates well with the 3-fold longer $T_{1/2}$ of rFIXFc relative to BENEFIX™ previously demonstrated in pharmacokinetic study in HemB mice. Therefore, rFIXFc is fully active for on-demand treatment while achieving significantly prolonged prophylactic protection with the potential to reduce the dosing frequency, which are under investigation in the phase 3 study.

Example 8. Pharmacokinetic and Pharmacodynamic Analysis of rFIXFc and BENEFIX™ Following a Single Subcutaneous Dose in FIX-Deficient Mice The pharmacokinetic (PK) and pharmacodynamic (PD) profiles of recombinant Factor IX-Fc (rFIXFc) and BENEFIX™ (rFIX) were determined following a single intravenous or subcutaneous injection of 200 or 400 IU/kg in FIX-deficient mice. Whole blood was collected via vena cava (n=4 mice/timepoint/treatment). The concentrations of rFIXFc and BENEFIX™ in plasma were determined using a human FIX-specific ELISA. The activities of rFIXFc and BENEFIX™ were determined using an activated partial thromboplastin time (aPTT) assay. PK analyses were performed using model-dependent methodology using Win-NonLin. Results are shown in Tables 22 and 23.

For FIXFc, the bioavailability in FIX-deficient mice was 38% for the 200 IU/kg dose and 38-46% for the combined dose (antigen ELISA) and 29% for the 200 IU/kg dose and 29-39% for the combined dose (aPTT activity assay) compared to rFIX, 23% and 19%, respectively. The rFIXFc had 1.5-1.7 fold (200 IU/kg dose) and 1.5-2.5 fold (combined doses) improved bioavailability compared to BENEFIX™.

For rFIXFc, the terminal half-life (antigen ELISA) was 62 hr for the 200 IU/kg dose and 51-62 hr for the combined doses and the terminal half-life (aPTT activity assay) was 42 hr for the 200 IU/kg dose and 40-42 hr for the combined doses, whereas for BENEFIX™ the terminal half-life was 24 hr (antigen ELISA) for the 200 IU/kg dose and 17 hr (aPTT activity assay) for the 200 IU/kg dose. This indicates a 2.5-2.6 fold (200 IU/kg dose and combined dose) improvement in half-life with rFIXFc.

In addition, as Tables 22 and 23 show, rFIXFc had 4.5-5.6 fold increase in AUC/dose and a 1.9-3.7 fold increase in Cmax/dose versus BENEFIX™.

Recombinant factor IX Fc fusion (rFIXFc) protein is a long-acting form of recombinant FIX (rFIX) that will provide less frequent dosing of rFIX for treatment of hemophilia B. From mice to non-human primates and in hemophilia B patients, rFIXFc has an approximately 3-fold longer half-life versus rFIX (BENEFIX™). For prophylactic treatment, intravenous delivery of rFIX remains a burdensome delivery method, especially for children and in patients with poorly accessible veins. Subcutaneous administration of rFIX presents as a more attractive delivery route that is less invasive and with less frequent dosing. As such, subcutaneous delivery of rFIXFc will cause less pain and discomfort than intravenous delivery and result in improved compliance due to being easier to administer and administered in less time than an intravenous route. Prophylaxis regimens will also improve quality-of-life and clinical outcomes will include decreased bleeding incidences.

The concentration of rFIXFc in mouse plasma was measured using a human FIX-specific ELISA that measured the FIX portion of the molecule and the mg/kg nominal dose was used in the analysis. A summary of the PK parameters for rFIXFc and BENEFIX™ are shown in Table 20 (antigen ELISA) and Table 21 (aPTT activity assay) for n=4/group. Both analysis by antigen and activity showed that the Cmax and AUC were significantly improved for rFIXFc versus BENEFIX™. Using the antigen ELISA, the bioavailability (F %) was 38% for rFIXFc versus 23% for BENEFIX™. Similarly, using the aPTT activity assay, the bioavailability was 29% for rFIXFc versus 19% for BENEFIX™. Thus, rFIXFc demonstrated an increase in bioavailability over BENEFIX™ by 1.5 to 1.6 fold. Measurements of elimination half-life showed that rFIXFc markedly increased the half-life whether measured by antigen (rFIXFc 62 hr versus BENEFIX™ 24 hr) or activity (rFIXFc 42 hr versus BENEFIX™ 17 hr) assays. These data show that rFIXFc had an extended half-life compared to BENEFIX™ by 2.6 to 2.5 fold.

The rFIXFc given subcutaneously to FIX-deficient mice demonstrated a PK and PD profile with increases in Cmax and AUC for rFIXFc compared to BENEFIX™. Overall, the bioavailability for rFIXFc ranged from 29% (activity) to 38% (antigen) with a half-life of 42 hr (activity) to 62 hr (antigen) compared to BENEFIX™, which had bioavailability from 19-23% and half-life from 17-24%, respectively. Thus, the half-life for rFIXFc delivered subcutaneously in FIX-deficient mice demonstrated about a 2.2 (antigen) to 3.3 (activity) fold increase over currently marketed rFIX products given intravenously. Overall, these data support the notion that rFIXFc delivered subcutaneously will be of clinical benefit for prophylactic treatment in hemophilia B patients.

Example 9. Pharmacokinetic Analysis of rFIXFc Following a Single Subcutaneous Dose in Cynomolgus Monkeys The pharmacokinetic (PK) profile of recombinant Factor IX-Fc (rFIXFc) was studied after a single subcutaneous dose of 50 IU/kg, 100 IU/kg or 200 IU/kg in cynomolgus monkeys. The concentration of rFIXFc in plasma was measured using a FIX-specific ELISA. Primary analysis was performed using model-dependent methodology using WinNonLin. See Tables 22-25.

Pharmacokinetic analysis of the plasma concentration versus time data (measured by FIX-specific ELISA) demonstrated that the bioavailability and terminal half-life were similar among doses. The bioavailabilities for rFIXFc were 40% (50 IU/kg), 34% (100 IU/kg), 36% (200 IU/kg), and 36-45% (combined doses) The terminal half-lives for rFIXFc were 61 hr (50 IU/kg), 45 hr (100 IU/kg), 49 hr (200 IU/kg), and 44-58 hr (combined doses).

The concentration of rFIXFc in monkey plasma was measured using a FIX-specific ELISA that measured the FIX portion of the molecule and the mg/kg nominal dose was used in the analysis. Spike and recovery analysis demonstrated the accuracy of this FIX-specific ELISA assay for detecting rFIXFc over the range of plasma concentrations assessed. A summary of the PK parameters for rFIXFc are shown in Table 22 (50 IU/kg), Table 23 (100 IU/kg) and Table 24 (200 IU/kg) for n=3/group. For rFIXFc SC, the geometric means and CV % of the geometric mean for Cmax were 860+22 (50 IU/kg), 1630+97 (100 IU/kg) and 3,750+26 (200 IU/kg), respectively indicating a dose-dependent increase. Similar increases were seen for AUC. The geometric means for bioavailability (F %) were 40+16 (50 IU/kg), 30+75 (100 IU/kg) and 36+27 (200 IU/kg), demonstrating that bioavailability was similar among doses. Measurements of terminal half-life showed that the half-life was similar among doses at 58+39 hr (50 IU/kg), 45+13 hr (100 IU/kg) and 46+44 hr (200 IU/kg).

The rFIXFc given subcutaneously to cynomolgus monkeys demonstrated a PK profile with dose-dependent increases in Cmax and AUC. Overall, the bioavailability ranged from 30-40% with a half-life of 45-58 hr. Thus, the half-life for rFIXFc delivered subcutaneously in monkeys demonstrated about a 2.8-fold increase over currently marketed rFIX products given intravenously. Overall, these data support the notion that rFIXFc delivered subcutaneously will be of clinical benefit for prophylactic treatment in hemophilia B patients.

Example 10. Predicted Prophylactic Dosing Regimens

In comparison with the standard recommended dose regimen of 25 to 40 IU/kg of FIX twice or three times weekly, the median rFIXFc activity PK results from the Phase 1/2a study described above suggest that about once weekly dosing of rFIXFc at about 22.5 IU/kg, or about every 10 days at about 45 IU/kg, or about every 2 weeks at about 120 IU/kg is sufficient to maintain a trough of 1% above baseline (FIG. 24). These model simulated estimates are validated by the available data from the Phase 1/2a trial, which fall entirely within the 95% confidence interval of the simulated activity-over-time curve. These regimens will often serve at the beginning of therapy. Considering the heterogeneity of reported clinical breakthrough bleeding events relative to trough level of plasma FIX activity, maintenance doses will need to be adjusted individually.

After recalculation of the PK results from the Phase 1/2 study (see Example 11), the new predicted dosing regimen, e.g., for prophylaxis, is 20 IU/kg once weekly, 40 IU/kg every 10 days, or 100 IU/kg every two weeks (twice monthly). See also Table 27 and FIG. 25.

Example 11. Recalculation of Pharmacokinetic Data from First in Human (FiH) Study (Example 1)

Subjects with a variety of hemophilia B genotypes, such as stop codon/nonsense and missense mutations, were included in the FiH study discussed in Example 1. Several subjects had markedly reduced endogenous FIX antigen levels which correlated with markedly reduced FIX activity, while a few subjects with missense genotypes had more antigen than measured activity, indicating a dysfunctional circulating protein. The pretreatment FIX activity in 2 subjects exceeded 2 IU/dL, likely due to an incomplete washout from their last infusion of FIX concentrate based on historical testing and disease phenotype. Based on this information, the PK data from Example 1 was recalculated without baseline subtraction, as is described below in detail. See Table 27.

In contrast to the PK calculations (based on activity) in Example 1, if the rFIXFc activity PK is modeled without baseline subtraction, as was recently reported for the PK analysis of a glycoPEGylated rFIX (Negrier et al., *Blood* DOI 10.1182/blood 2011 02 335596 (2011), which is herein incorporated by reference in its entirety), the resulting estimates of elimination half-life and MRT are much longer than the estimates in Example 1, at 82.2±21.6 and 96.8±22.0 hours (mean±SD), respectively. However, with the knowledge that not all severe hemophilia B patients have 0% endogenous FIX activity, and taking into account patient's genotype and endogenous FIX antigen level, the present inventors adopted a baseline subtraction analysis method in their PK modeling. Specifically, (a) the baseline in two patients was defined as 0% because their pretreatment FIX activity was <1%, they had no detectable FIX antigen and had nonsense genotypes, (b) the baseline for three patients was set at 0.5% because their pretreatment FIX activity was <1% and they had detectable FIX antigen, (c) for patients whose pretreatment FIX activity was between 1-2%, Cmin (the lowest activity throughout the PK study) was defined as baseline, and (d) for patients whose pretreatment FIX activity was ≥2%, 2% (which was the upper limit for enrollment into the trial) was the baseline. Activity above the baseline pre-dosing was considered residue drug from prior treatment, and was decayed to baseline and subtracted from the PK data following rFIXFc dosing.

The resulting mean terminal half-life (56.7±10.9 hours, range 42.4-74.5 hours) and MRT (71.8±10 hours, range 53.2-85.9 hours) of rFIXFc are approximately 3-fold longer than that reported for rFIX. The reported terminal half-life of rFIX is 19.3±4.97 hours (range 11.1-36.4 hours) and MRT 26.0±6.07 hours (range 15.8-46.1 hours). Roth et al., *Blood* 98: 3600-3606 (2001); and Summary of Product Characteristics for BENEFIX™, Electronic Medicines Compendium (2010) (worldwideweb.medicines.org.uk/emc/medicine/20376/SPC/BENEFIX™/#PHARMACODY NAMIC_PROPS), each of which his incorporated herein by reference in its entirety. Thus, the ranges for rFIXFc do not overlap the ranges for rFIX. Similarly, the mean CL of rFIXFc activity (3.18±0.78 mL/hr/kg, range 2.05-4.18 mL/hr/kg) is approximately 2.6-fold less than that reported for rFIX (8.40±2.01 mL/hr/kg, range 4.66-13.64 mL/hr/kg), while the Vss of both proteins are comparable at 4-5 times the plasma volume.

Although the same trend toward improvement was observed in the rFIXFc antigen PK, both the $T_{1/2}\alpha$ and $T_{1/2}\beta$ of rFIXFc antigen were significantly longer than that derived from FIX activity measurements. The $T_{1/2}\alpha$ estimated for rFIXFc antigen clearly deviates from that normally associated with FIX (2-3 hours). Furthermore, the probable incomplete washout from the pre-study replacement therapy before infusion of rFIXFc sometimes resulted in a higher baseline value, which in turn could lead to an underestimation of the rFIXFc $T_{1/2}\beta$, as measured by FIX activity. A number of subjects had an aPTT activity up to 3 IU/dL, well above the limit of quantification (1 IU/dL) for the aPTT assay, at later time points up to 336 hrs (14 days) post-dose. However, these time points were excluded from the estimation of the terminal half-life because the values were at or only slightly above pretreatment baselines, thus deemed to have returned to baseline. In contrast, the low but detectable terminal levels of rFIXFc may be unmasked by the specific and highly sensitive rFIXFc antigen ELISA, which detects as low as 0.1 IU/dL as compared to aPTT lower limit of 1.0 IU/dl.

The remaining PK parameters (activity) changed a small amount relative to elimination half-life and MRT. See Table 27(B). A dose-proportional, linear increase in FIX activity was observed based on $C_{max}$ occurring immediately after infusion and $AUC_{INF}$ (Table 4). FIX activity exhibited biexponential decay following infusion of rFIXFc, and was characterized by a rapid distribution (alpha) phase followed by a log-linear elimination (beta) phase. The mean distribution half-life ($T_{1/2}\alpha$) was highly variable for individual subjects (mean of 3.4 and 10.3 hours for the two higher dose groups) (Table 27(B)). The mean elimination half-life ($T_{1/2}\beta$) was dose independent over the therapeutic dose range tested, i.e., 53.5 hours, 57.5±8.2 hours, and 56.5±14.1 hours at 25 IU/kg, 50 IU/kg, and 100 IU/kg, respectively. The time to 1% (1 IU/dL) above baseline, an assessment of rFIXFc activity, showed a dose-proportional increase. It was 7.3, 10.1±1.5, and 12.3±2.5 days for doses of 25, 50, and 100 IU/kg, respectively. At 168 hours (1 week) post dose, the plasma FIX activity was sustained at 1.1 IU/dL, 2.5±0.9 IU/dL, and 4.6±1.7 IU/dL above baseline for the 25, 50, and 100 IU/kg dose groups, respectively. Also dose-independent were MRT, CL, and Vss over the dose range of 25 to 100 IU/kg. Furthermore, each 1 IU/kg of infused rFIXFc raised plasma FIX activity by 0.93±0.18 IU/dL on average (Table 27(B)), and this incremental recovery (K) showed weak positive correlation with body weight ($R^2=0.336$, p=0.048)

Long-term empirical clinical experience has suggested that a sustained plasma factor activity as low as 1 to 2 IU/dL will be adequate to prevent spontaneous bleeding events in severe hemophilia A and B patients, (Nilsson et al., *J. Intern. Med.* 232:25-32 (1992), which is herein incorporated by reference in its entirety), and increased bleeding events are associated with the amount of time under 1% of normal FVIII activity. Collins et al., *Thromb Haemost* 7:413-420 (2009), which is herein incorporated by reference in its entirety. Thus, PK analyses provide a means to optimize prophylactic treatment with individualized dose modeling to achieve sustained trough levels above 1% (1 IU/dL) of baseline, reduce peak/trough variation, and improve the cost effectiveness of treatment. Carlsson et al., *Haemophilia* 4:83-88 (1998); Kisker et al., *Haemophilia* 9:279-284 (2003), each of which is herein incorporated by reference in its entirety.

To construct the concentration-time profiles following different dosing regimens, Monte Carlo simulation was conducted using the population PK model of rFIXFc. The mean estimates of model parameters (CL, volume of distribution, inter-compartmental clearance, and volume of the second compartment) in the tested population, the interindividual variance, and the residual variability were adopted for this Phase1/2a study. Wang et al., *J. Clin. Pharmacol.* 49:1012-1024 (2009), which is herein incorporated by reference in its entirely. One thousand subjects were simulated per dosing regimen with 14 to 16 sampling points for each subject. There were 14 sampling points for weekly dosing, 15 for every 10 day dosing, and 16 for every other week dosing. The body weight (BW) was generated according to the published method, Wang et al. (2009). i.e., based on a power equation of Z=BW-0.5. The median BW in 1000 subjects was assumed to be 75 kg. Based on the simulated concentration-time profiles, the mean±standard deviation (SD) of the drug concentration-time profiles of the 1000 subjects was constructed graphically for different dosing regimens. FIG. 25.

In comparison with the standard recommended dose regimen of 25 to 40 IU/kg of FIX twice weekly, the median rFIXFc activity PK modeling results from this study show that once weekly dosing of rFIXFc at 20 IU/kg, or every 10 days at 40 IU/kg, or every 2 weeks at 100 IU/kg is sufficient to maintain a trough of 1% above baseline. FIG. 25. These model-simulated estimates are validated by the available data from this Phase 1/2a study, which fall entirely within the 95% confidence interval of the simulated activity-over-time curve. However, considering the heterogeneity of reported clinical breakthrough bleeding events relative to trough level of plasma FIX activity (Bjorkman, *Haemophilia* 9:101-110 (2003); Ahnstrom et al., *Haemophilia* 10:689-697 (2004), each of which is herein incorporated by reference in its entirety), the maintenance dose would likely require individual adjustment.

Tables

TABLE 1

| Polynucleotide Sequences: FIX-Fc |
|---|
| A. FIX-Fc Chain DNA Sequence (SEQ ID NO: 1, which encodes SEQ ID NO: 2) |

```
pSYN-FIX-030 Nucleotide sequence (nt 1 to 7583):
FIX exon 1 (signal peptide, 1st amino acid propeptide): nt 690-777
FIX mini intron: nt 778-1076
```

TABLE 1-continued

Polynucleotide Sequences: FIX-Fc

FIX propeptide sequence: nt 1077-1126
Mature FIX sequence: nt 1127-2371
Fc: nt 2372-3052

```
gcgcgcgttgacattgattattgactagttattaatagtaatcaattacggggtcattagttcatagcccatata
tggagttccgcgttacataacttacggtaaatggcccgcctggctgaccgcccaacgaccccgcccattgacgt
caataatgacgtatgttcccatagtaacgccaatagggactttccattgacgtcaatgggtggagtatttacggt
aaactgcccacttggcagtacatcaagtgtatcatatgccaagtacgccccctattgacgtcaatgacggtaaat
ggcccgcctggcattatgcccagtacatgaccttatgggactttcctacttggcagtacatctacgtattagtca
tcgctattaccatggtgatgcggttttggcagtacatcaatgggcgtggatagcggtttgactcacggggatttc
caagtctccacccattgacgtcaatgggagtttgttttggcaccaaaatcaacgggactttccaaaatgtcgta
acaactccgcccattgacgcaaatgggcggtaggcgtgtacggtggaggtctatataagcagagctctctggc
taactagagaacccactgcttactggcttatcgaaattaatacgactcactatagggagacccaagcttcgcgac
gtacggccgccaccatgcagcgcgtgaacatgatcatggcagaatcaccaggcctcatcaccatctgccttttag
gatatctactcagtgctgaatgtacagggtttgtttcctttttaaaatacattgagtatgcttgccttttagata
tagaaatatctgatgctgtcttcttcactaaattttgattacatgatttgacagcaatattgaagagtctaacag
ccagcacgcaggttggtaagtactgtgggaacatcacagattttggctccatgccctaaagagaaattggctttc
agattatttggattaaaaacaaagactttcttaagagatgtaaaattttcatgatgttttctttttgctaaaac
taaagaattattcttttacatttcagttttttcttgatcatgaaaacgccaacaaaattctgaatcggccaaagag
gtataattcaggtaaattggaagagtttgttcaagggaatctagagagagaatgtatgaagaaaagtgtagttt
tgaagaagcacgagaagttttttgaaaacactgaaagaacaactgaattttggaagcagtatgttgatggagatca
gtgtgagtccaatccatgtttaaatggcggcagttgcaaggatgacattaattcctatgaatgttggtgtccctt
tggatttgaaggaaagaactgtgaattagatgtaacatgtaacattaagaatggcagatgcgagcagtttttgtaa
aaatagtgctgataacaagtggtttgctcctgtactgagggatatcgacttgcagaaaaccagaagtcctgctga
accagcagtgccatttccatgtggaagagtttctgtttcacaaacttctaagctcaccgtgctgagactgtttt
tcctgatgtggactatgtaaattctactgaagctgaaaccattttggataacatcactcaaagcacccaatcatt
taatgacttcactcgggttgttggtggagaagatgccaaaccaggtcaattcccttggcaggttgttttgaatgg
taaagttgatgcattctgtgggaggctctatcgttaatgaaaaatggattgtaactgctgcccactgtgttgaaac
tggtgttaaaattacagttgtcgcaggtgaacataatattgaggagacagaacatacagagcaaaagcgaaatgt
gattcgaattattcctcaccacaactacaatgcagctattaataagtacaaccatgacattgccttctggaact
ggacgaacccttagtgctaaacagctacgttacacctatttgcattgctgacaaggaatacacgaacatcttcct
caaatttggatctggctatgtaagtggctggggaagagtcttccacaaagggagatcagcttttagttcttcagta
ccttagagttcccacttgttgaccgagccacatgtcttcgatctacaaagttcaccatctataacaacatgttctg
tgctggcttccatgaaggaggtagagattcatgtcaaggagatagtgggggaccccatgttactgaagtggaagg
gaccagtttcttaactggaattattagctggggtgaagagtgtgcaatgaaaggcaaatatggaatatataccaa
ggtgtcccggtatgtcaactggattaaggaaaaaacaaagctcactgacaaaactcacacatgcccaccgtgccc
agctccggaactcctgggcggaccgtcagtcttcctcttccccccaaaacccaaggacaccctcatgatctcccg
gacccctgaggtcacatgcgtggtggtggacgtgagccacgaagaccctgaggtcaagttcaactggtacgtgga
cggcgtggaggtgcataatgccaagacaaagccgcgggaggagcagtacaacagcacgtaccgtgtggtcagcgt
cctcaccgtcctgcaccaggactggctgaatggcaaggagtacaagtgcaaggtctccaacaaagcccttccagc
ccccatcgagaaaaccatctccaaagccaaagggcagccccgagaaccacaggtgtacaccctgcccccatcccg
ggatgagctgaccaagaaccaggtcagcctgacctgcctggtcaaaggcttctatcccagcgacatcgccgtgga
gtgggagagcaatgggcagccggagaacaactacaagaccacgcctcccgtgttggactccgacggctccttctt
cctctacagcaagctcaccgtggacaagagcaggtggcagcaggggaacgtcttctcatgctccgtgatgcatga
ggctctgcacaaccactacacgcagaagagcctctccctgtctccgggtaaatgagaattcagacatgataagat
acattgatgagtttggacaaaccacaactagaatgcagtgaaaaaaatgctttatttgtgaaatttgtgatgcta
ttgctttatttgtaaccattataagctgcaataaacaagttggggtgggcgaagaactccagcatgagatccccg
cgctgggaggatcatccagccggcgtcccggaaaacgattccgaagcccaacctttcatagaaggcggcggtggaa
tcgaaatctcgtagcacgtgtcagtcctgctcctcggccacgaagtgcacgcagttgccggccgggtcgcgcagg
gcgaactcccgcccccacggctgctcgccgatctcggtcatggccggcccggaggcgtcccggaagttcgtggac
acgacctccgaccactcggcgtacagctcgtccaggccgcgcacccacaccaggccagggtgttgtccggcacc
acctggtcctggaccgcgctgatgaacagggtcacgtcgtcccggaccacaccggcgaagtcgtcctccacgaag
tcccgggagaacccgagccggtcggtccagaactcgaccgctccggcgacgtcgcgcgcggtgagcaccggaacg
gcactggtcaacttggccatgtttagttcctcacccttgtcgtattatactatgccgatatactatgccgatgat
taattgtcaacacgtgctgatcagatccgaaaatggatatacaagctcccgggagcttttgcaaaagcctaggc
ctccaaaaaagcctcctcactacttctggaatagctcagaggcagaggcggcctcggcctctgcataaataaaa
aaattagtcagccatggggcggagaatgggcggaactgggcggagttagggggcggatggggagttaggggcg
ggactatggttgctgactaattgagatgcatgctttgcatacttctgcctgctggggagcctgggactttccac
acctggttgctgactaattgagatgcatgctttgcatacttctgcctgctggggagcctggggactttccacacc
ctcgtcgagctagcttcgtgaggctccggtgcccgtcagtgggcagagcgcacatcgcccacagtccccgagaag
ttgggggggaggggtcggcaattgaaccggtgcctagagaaggtggcgcggggtaaactgggaaagtgatgtcgtg
tactggctccgcctttttcccgagggtgggggagaaccgtatataagtgcagtagtcgccgtgaacgttcttttt
cgcaacgggtttgccgccagaacacaggtaagtgccgtgtgtggttcccgcgggcctggcctctttacgggttat
ggcccttgcgtgccttgaattacttccacctggctccagtacgtgattcttgatcccgagctggagcagggggcg
ggcctttgcgctttaggagccccttcgcctcgtgcttgagttggagtggtgggtacgtcagccatgagggaccgc
gaatctggtggcaccttcgcgcctgtctcgctgctttcgataagtctctagccatttaaaatttttgatgacctg
ctgcgacgctttttttctggcaagatagtcttgtaaatgcgggccaggatctgcacactggtatttcggttttg
gggccgcgggcggcgacggggcccgtgcgtcccagcgcacatgttcggcgaggcggggcctgcgagcgcggccac
cgagaatcggacgggggtagtctcaagctggccgcctgctctgtggtgcctgcctccgcgccgcgtgcggccc
cgccctgggcggcaaggctggcccggtcggcaccagttgcgtgagcggaaagatgccgcttcccggccctgctc
cagggggctcaaatggaggacgcggcgctcgggagagcgggcgggtgagtcacccacacaaaggaaagggcct
ttccgtcctcagccgtcgcttcatgtgactccacggagtaccgggcgccgtccaggcacctcgattagttctgga
gcttttggagtacgtcgtctttaggttggggggaggggttttatgcgatggagtttccccacactgagtgggtgg
agactgaagttaggccagcttggcacttgatgtaattctcctttggaatttgcccttttgagtttggatcttggt
tcattctcaagcctcagacagtggttcaaagtttttttcttccatttcaggtgtcgtgaacacggtcgcggcc
gcgccgccaccatggagacagacacactcctgctatgggtactgctgctctgggttccaggttccactggtgaca
aaactcacacatgcccaccgtgcccagcacctgaactcctgggaggaccgtcagtcttcctcttccccccaaaac
ccaaggacaccctcatgatctcccggacccctgaggtcacatgcgtggtggtggacgtgagccacgaagaccctg
```

TABLE 1-continued

| Polynucleotide Sequences: FIX-Fc |
|---|
| aggtcaagttcaactggtacgtggacggcgtggaggtgcataatgccaagacaaagccgcgggaggagcagtaca
acagcacgtaccgtgtggtcagcgtcctcaccgtcctgcaccaggactggctgaatggcaaggagtacaagtgca
aggtctccaacaaagccctcccagccccatcgagaaaaccatctccaaagccaaagggcagccccgagaaccac
aggtgtacaccctgcccccatcccgcgatgagctgaccaagaaccaggtcagcctgacctgcctggtcaaaggct
tctatcccagcgacatcgccgtggagtgggagagcaatgggcagccggagaacaactacaagaccacgcctcccg
tgttggactccgacggctccttcttcctctacagcaagctcaccgtggacaagagcaggtggcagcaggggaacg
tcttctcatgctccgtgatgcatgaggctctgcacaaccactacacgcagaagagcctctccctgtctccgggta
aatgactcgagagatctggccggctgggcccgtttcgaaggtaagcctatccctaaccctctcctcggtctcgat
tctacgcgtaccggtcatcatcaccatcaccattgagtttaaacccgctgatcagcctcgactgtgccttctagt
tgccagccatctgttgtttgcccctcccccgtgccttccttgaccctggaaggtgccactcccactgtcctttcc
taataaaatgaggaaattgcatcgcattgtctgagtaggtgtcattctattctgggggtggggtggggcaggac
agcaaggggaggattggaagacaatagcaggcatgctgggatgcggtgggctctatggcttctgaggcggaa
agaaccagtggcggtaatacggttatccacagaatcaggggataacgcaggaaagaacatgtgagcaaaaggcca
gcaaaaggccaggaaccgtaaaaaggccgcgttgctggcgtttttccataggctccgccccctgacgagcatca
caaaaatcgacgctcaagtcagaggtggcgaaacccgacaggactataaagataccaggcgtttccccctagaag
ctccctcgtgcgctctcctgttccgaccctgccgcttaccggatacctgtccgcctttctcccttcgggaagcgt
ggcgctttctcatagctcacgctgtaggtatctcagttcggtgtaggtcgttcgctccaagctgggctgtgtgca
cgaaccccccgttcagcccgaccgctgcgccttatccggtaactatcgtcttgagtccaacccggtaagacacga
cttatcgccactggcagcagccactggtaacaggattagcagagcgaggtatgtaggcggtgctacagagttctt
gaagtggtggcctaactacggctacactagaagaacagtatttggtatctgcgctctgctgaagccagttacctt
cggaaaaagagttggtagctcttgatccggcaaacaaaccaccgctggtagcggtggtttttttgtttgcaagca
gcagattacgcgcagaaaaaaggatctcaagaagatcctttgatcttttctacggggtctgacgctcagtggaa
cgaaaactcacgttaagggattttggtcatgacattaacctataaaaataggcgtatcacgaggccctttcgtct
cgcgcgtttcggtgatgacggtgaaaacctctgacacatgcagctcccggagacggtcacagcttgtctgtaagc
ggatgccgggagcagacaagcccgtcagggcgcgtcagcgggtgttggcgggtgtcggggctggcttaactatgc
ggcatcagagcagattgtactgagagtgcaccatatgcggtgtgaaataccgcacagatgcgtaaggagaaaa
taccgcatcaggcgccattcgccattcaggctgcgcaactgttgggaagggcgatcggtgcgggcctcttcgcta
ttacgcca |

B. Fc DNA sequence (mouse Igκ signal peptide underlined) (SEQ ID NO: 3, which encodes SEQ ID NO: 4) This is the Fc cassette from pSYN-FIX-030. In addition, there is a separate Fc expression cassette that was transfected into the cell line in plasmid pSYN-Fc-015 that encodes the same amino acid sequence, but contains a few noncoding changes. The second copy of Fc encoding sequence enables a better monomer: dimer ratio.

**atggagacagacacactcctgctatgggtactgctgctctgggttccaggttccactggtgacaaaactcacaca
tgcccaccgtgcccagcacctgaactcctgggaggaccgtcagtcttcctcttccccccaaaacccaaggacacc
ctcatgatctcccggacccctgaggtcacatgcgtggtggtggacgtgagccacgaagacccctgaggtcaagttc
aactggtacgtggacggcgtggaggtgcataatgccaagacaaagccgcgggaggagcagtacaacagcacgtac
cgtgtggtcagcgtcctcaccgtcctgcaccaggactggctgaatggcaaggagtacaagtgcaaggtctccaac
aaagccctcccagccccatcgagaaaaccatctccaaagccaaagggcagccccgagaaccacaggtgtacacc
ctgcccccatcccgcgatgagctgaccaagaaccaggtcagcctgacctgcctggtcaaaggcttctatcccagc
gacatcgccgtggagtgggagagcaatgggcagccggagaacaactacaagaccacgcctcccgtgttggactcc
gacggctccttcttcctctacagcaagctcaccgtggacaagagcaggtggcagcaggggaacgtcttctcatgc
tccgtgatgcatgaggctctgcacaaccactacacgcagaagagcctctccctgtctccgggtaaa**

TABLE 2

| Polypeptide Sequences |
|---|
| FIX-Fc Monomer Hybrid: created by coexpressing FIX-Fc and Fc chains. |

A. FIX-Fc chain (SEQ ID NO: 2):

(28 amino acid signal sequence underlined, 18 amino acid propeptide double underlined, Fc portion in italics.) The C-terminal lysine is not present in either subunit; this processing is often observed in recombinant proteins produced in mammalian cell culture, as well as with plasma derived proteins.

FIXFC-SC SUBUNIT:

FIX Signal Peptide: -46 MQRVNMIMAE SPGLITICLL GYLLSAEC

FIX Propeptide: -18 TVFLDHENAN KILNRPKR

```
  1 YNSGKLEEFV QGNLERECME EKCSFEEARE VFENTERTTE FWKQYVDGDQ
 51 CESNPCLNGG SCKDDINSYE CWCPFGFEGK NCELDVTCNI KNGRCEQFCK
101 NSADNKVVCS CTEGYRLAEN QKSCEPAVPF PCGRVSVSQT SKLTRAETVF
151 PDVDYVNSTE AETILDNITQ STQSFNDFTR VVGGEDAKPG QFPWQVVLNG
201 KVDAFCGGSI VNEKWIVTAA HCVETGVKIT VVAGEHNIEE TEHTEQKRNV
251 IRIIPHHNYN AAINKYNHDI ALLELDEPLV LNSYVTPICI ADKEYTNIFL
```

TABLE 2-continued

Polypeptide Sequences

FIX-Fc Monomer Hybrid: created by coexpressing FIX-Fc and Fc chains.

```
301 KFGSGYVSGW GRVFHKGRSA LVLQYLRVPL VDRATCLRST KFTIYNNMFC
351 AGFHEGGRDS CQGDSGGPHV TEVEGTSFLT GIISWGEECA MKGKYGIYTK
401 VSRYVNWIKE KTKLTDKTHT CPPCPAPELL GGPSVFLFPP KPKDTLMISR
451 TPEVTCVVVD VSHEDPEVKF NWYVDGVEVH NAKTKPREEQ YNSTYRVVSV
501 LTVLHQDWLN GKEYKCKVSN KALPAPIEKT ISKAKGQPRE PQVYTLPPSR
551 DELTKNQVSL TCLVKGFYPS DIAVEWESNG QPENNYKTTP PVLDSDGSFF
601 LYSKLTVDKS RWQQGNVFSC SVMHEALHNH YTQKSLSLSP GK
```

B. Fc chain (SEQ ID NO: 4)

20 amino acid heterologous mouse Igκ light chain signal peptide (underlined):
-20 METDTLLLWV LLLWVPGSTG Mature Fc sequence (corresponding to human IgG1 amino acids 221 to 447, EU numbering)

```
  1 DKTHTCPPCP APELLGGPSV FLFPPKPKDT LMISRTPEVT CVVVDVSHED
 51 PEVKFNWYVD GVEVHNAKTK PREEQYNSTY RVVSVLTVLH QDWLNGKEYK
101 CKVSNKALPA PIEKTISKAK GQPREPQVYT LPPSRDELTK NQVSLTCLVK
151 GFYPSDIAVE WESNGQPENN YKTTPPVLDS DGSFFLYSKL TVDKSRWQQG
201 NVFSCSVMHE ALHNHYTQKS LSLSPGK
```

TABLE 3

Individual Patient FIXFc Antigen Concentration versus Time Data; Sorted by Nominal Dose, Actual Dose, Infusion Duration, and Patient Number

| Actual Time (h) | Concentration (ng/mL) | Actual Time (h) | Concentration (ng/mL) | Actual Time (h) | Concentration (ng/mL) | Actual Time (h) | Concentration (ng/mL) |
|---|---|---|---|---|---|---|---|
| Patient 1 | | Patient 2 | | Patient 3 | | Patient 4 | |
| −0.50 | 0.0 | −1.23 | 0.0 | −0.18 | 0.0 | −0.18 | 0.0 |
| 0.17 | 2325.3 | 0.17 | 3352.1 | 0.28 | 5915.3 | 0.17 | 8166.5 |
| 0.42 | 1632.4 | 0.40 | 3017.3 | 0.42 | 6574.3 | 0.42 | 7362.3 |
| 1.17 | 1497.7 | 1.15 | 2280.7 | 1.17 | 5764.7 | 1.17 | 6723.4 |
| 3.18 | 1466.4 | 3.15 | 2077.5 | 3.17 | 4204.8 | 3.17 | 5291.4 |
| 6.13 | 1268.2 | 6.15 | 2054.7 | 6.17 | 3956.2 | 6.18 | 4673.1 |
| 9.12 | 1100.7 | 9.15 | 1700.4 | 9.17 | 3567.7 | 9.17 | 3954.6 |
| 24.12 | 805.0 | 24.23 | 1417.3 | 24.17 | 2805.6 | 24.17 | 3327.6 |
| 48.03 | 544.5 | 48.40 | 766.0 | 48.98 | 1727.7 | 48.20 | 2148.7 |
| 72.23 | 377.7 | 70.73 | 719.0 | 72.40 | 1165.8 | 72.17 | 1632.2 |
| 96.75 | 215.3 | 92.57 | 480.2 | 96.98 | 917.1 | 96.17 | 1234.4 |
| 120.13 | 192.6 | 119.98 | 326.3 | 121.23 | 673.9 | 120.13 | 894.0 |
| 141.95 | 128.6 | 141.10 | 241.1 | 168.65 | 568.2 | 144.18 | 645.2 |
| 169.45 | 112.4 | 167.98 | 194.6 | 240.15 | 265.4 | 168.22 | 564.1 |
| 192.37 | 93.6 | 192.85 | 160.1 | 290.97 | 286.4 | 192.20 | 509.2 |
| 216.28 | 76.1 | 216.98 | 149.0 | 337.98 | 238.5 | 216.23 | 474.5 |
| 237.30 | 76.4 | 238.65 | 125.7 | | | 240.23 | 446.1 |

| Actual Time (h) | Concentration (ng/mL) | Actual Time (h) | Concentration (ng/mL) | Actual Time (h) | Concentration (ng/mL) | Actual Time (h) | Concentration (ng/mL) |
|---|---|---|---|---|---|---|---|
| Patient 5 | | Patient 6 | | Patient 7 | | Patient 8 | |
| −0.18 | 0.0 | −0.07 | 0.0 | −1.27 | 0.0 | −1.37 | 0.0 |
| 0.17 | 7520.2 | 0.17 | 11671.7 | 0.22 | 7055.9 | 0.25 | 27413.4 |
| 0.43 | 7233.9 | 0.42 | 8654.5 | 0.42 | 6215.7 | 0.47 | 23640.8 |
| 1.20 | 6752.1 | 1.17 | 8880.4 | 1.17 | 5498.6 | 1.35 | 18505.6 |
| 3.15 | 5873.1 | 3.17 | 8509.3 | 3.17 | 4477.7 | 3.22 | 15708.1 |
| 6.23 | 5919.2 | 6.17 | 7618.7 | 6.17 | 4084.8 | 6.17 | 14915.6 |
| 9.20 | 5332.9 | 9.17 | 6584.2 | 9.17 | 3888.9 | 9.17 | 16486.4 |
| 24.17 | 4215.9 | 48.17 | 3217.7 | 24.17 | 2849.4 | 24.72 | 9937.8 |
| 48.15 | 2986.6 | 72.17 | 1651.6 | 48.82 | 1630.6 | 48.90 | 6383.5 |
| 72.15 | 1933.2 | 96.17 | 1580.1 | 72.57 | 1295.7 | 72.38 | 4190.6 |
| 96.03 | 1249.0 | 120.17 | 722.7 | 96.57 | 1150.7 | 96.40 | 3774.7 |
| 120.13 | 401.4 | 240.17 | 329.5 | 121.15 | 954.9 | 120.30 | 2514.9 |
| 144.03 | 482.3 | 288.17 | 292.7 | 144.10 | 780.6 | 168.77 | 1626.0 |
| 168.17 | 478.0 | 336.17 | 252.7 | 168.82 | 447.6 | 240.27 | 924.7 |

TABLE 3-continued

Individual Patient FIXFc Antigen Concentration versus Time Data; Sorted by Nominal Dose, Actual Dose, Infusion Duration, and Patient Number

| 192.12 | 433.7 | | | 192.77 | 446.5 | 288.83 | 682.4 |
| 216.15 | 368.9 | | | 240.57 | 427.8 | 337.03 | 586.4 |
| 240.07 | 264.0 | | | | | | |

| Actual Time (h) | Concentration (ng/mL) | Actual Time (h) | Concentration (ng/mL) | Actual Time (h) | Concentration (ng/mL) | Actual Time (h) | Concentration (ng/mL) |
|---|---|---|---|---|---|---|---|
| Patient 9 | | Patient 10 | | Patient 11 | | Patient 12 | |
| −0.82 | 0.0 | −0.48 | 0.0 | −0.15 | 0.0 | −1.12 | 0.0 |
| 0.28 | 15027.1 | 0.25 | 16760.0 | 0.23 | 19641.7 | 0.17 | 15194.5 |
| 0.63 | 13374.1 | 0.50 | 11529.0 | 0.47 | 17267.2 | 0.42 | 12255.7 |
| 1.17 | 12395.6 | 1.22 | 10566.3 | 1.22 | 15902.2 | 1.17 | 11171.3 |
| 3.20 | 10808.4 | 3.22 | 9889.0 | 3.22 | 13708.9 | 3.17 | 9835.4 |
| 6.22 | 9640.2 | 6.22 | 8290.2 | 6.25 | 12469.4 | 6.17 | 8513.2 |
| 9.15 | 10505.5 | 9.22 | 7114.7 | 9.22 | 12029.8 | 9.17 | 8413.0 |
| 23.15 | 6487.3 | 24.22 | 5877.0 | 24.22 | 8083.3 | 24.17 | 5538.2 |
| 46.62 | 5324.8 | 48.22 | 3980.4 | 47.72 | 4431.0 | 48.20 | 3885.5 |
| 70.10 | 2895.5 | 72.22 | 2455.6 | 71.88 | 2162.6 | 72.13 | 2959.9 |
| 94.15 | 3208.3 | 96.12 | 2052.6 | 191.72 | 1468.7 | 95.17 | 2215.4 |
| 118.13 | 2610.6 | 120.22 | 1302.5 | 263.72 | 428.6 | 119.17 | 1799.7 |
| 166.10 | 2007.2 | 144.22 | 1349.3 | | | 167.38 | 1339.7 |
| 238.15 | 1086.2 | 168.22 | 1221.0 | | | 239.50 | 892.4 |
| 286.15 | 942.8 | 192.18 | 910.2 | | | 287.25 | 646.9 |
| 335.57 | 621.3 | 216.22 | 136.2 | | | | |

TABLE 4

Individual Patient and Group Mean FIXFc Antigen Pharmacokinetic Summary Data

| Nominal Dose (IU/kg) | Actual Dose (IU/kg) | Equivalent Dose (mg/kg) | Patient | $C_{max}$ (ng/mL) | $AUC_{INF}$ (h*ng/mL) | Cl* (mL/h/kg) | $V_{SS}$* (mL/kg) | MRT* (h) | Alpha HL* (h) | Beta HL* (h) |
|---|---|---|---|---|---|---|---|---|---|---|
| 12.5 | 13.714 | 0.228 | 1 | 1670 | 91300 | 2.50 | 245 | 98.2 | 21.2 | 107 |
| | | | N | 1 | 1 | 1 | 1 | 1 | 1 | 1 |
| 25 | 27.250 | 0.453 | 2 | 2730 | 144000 | 3.14 | 273 | 87.1 | 11.3 | 71.0 |
| | | | N | 1 | 1 | 1 | 1 | 1 | 1 | 1 |
| 50 | 54.5 | 0.905 | 3 | 5470 | 356000 | 2.54 | 366 | 144 | 18.6 | 138 |
| | 54.5 | 0.905 | 4 | 6910 | 389000 | 2.32 | 244 | 105 | 10.6 | 85.3 |
| | *54.5* | *0.905* | *5* | *7520* | *416000* | *2.17* | *184* | *84.5* | *NC* | *94.3* |
| | *54.513* | *0.906* | *6* | *11700* | *531000* | *1.71* | *190* | *112* | *NC* | *140* |
| | 55.878 | 0.928 | 7 | 5950 | 348000 | 2.67 | 310 | 116 | 10.1 | 93.9 |
| | | | N | 5 | 5 | 5 | 5 | 5 | 3 | 5 |
| | | | Mean | 7510 | 408000 | 2.28 | 259 | 112 | 13.1 | 110 |
| | | | SD | 2480 | 73900 | 0.374 | 78.5 | 21.5 | 4.77 | 26.5 |
| | | | SE | 1110 | 33100 | 0.167 | 35.1 | 9.60 | 2.75 | 11.8 |
| | | | Geometric Mean | 7230 | 403000 | 2.26 | 250 | 111 | 12.6 | 108 |
| | | | CV % Geometric Mean | 30.3 | 17.1 | 17.6 | 30.8 | 19.4 | 34.9 | 23.8 |
| 100 | 109 | 1.81 | 10 | 12500 | 667000 | 2.72 | 263 | 96.8 | 9.79 | 78.0 |
| | 109 | 1.81 | 8 | 21600 | 1200000 | 1.51 | 156 | 103 | 15.7 | 94.3 |
| | 109 | 1.81 | 9 | 13400 | 998000 | 1.81 | 248 | 137 | 11.5 | 107 |
| | 109.176 | 1.81 | 11 | 17200 | 844000 | 2.15 | 226 | 105 | 13.0 | 97.1 |
| | 109.441 | 1.82 | 12 | 12500 | 778000 | 2.34 | 295 | 126 | 10.6 | 102 |
| | | | N | 5 | 5 | 5 | 5 | 5 | 5 | 5 |
| | | | Mean | 15400 | 897000 | 2.11 | 238 | 114 | 12.1 | 95.8 |
| | | | SD | 3960 | 206000[a] | 0.464[b] | 52.2[c] | 17.1 | 2.33 | 11.1 |
| | | | SE | 1770 | 92000 | 0.208 | 23.3 | 7.64 | 1.04 | 4.96 |
| | | | Geometric Mean | 15100 | 878000 | 2.06 | 232 | 113 | 11.9 | 95.2 |
| | | | CV % Geometric Mean | 24.5 | 22.9 | 22.9 | 24.7 | 14.8 | 118.7 | 12.2 |

*CL, Vss, MRT, T½α and T½β for combined 12.5-100 IU/kg doses are 2.30 ± 0.46 (1.51-2.72); 250 ± 58.2 (156-366); 110 ± 18.5 (84.5-144); 12.0 ± 4.0 (10.1-18.6, not including two patients whose PK parameters were determined by non-compartmental analysis); and 101 ± 20.9 (78-140), respectively.

Due to correction of rounding or other errors,

[a] should be 207,000, and

[b] should be 0.468,

[c] should be 52.1.

TABLE 5

Individual Patient and Group Mean FIXFc Activity and Baseline
Corrected FIXFc Activity versus Time Data; Sorted by Nominal
Dose, Actual Dose, Infusion Duration, and Patient Number

| Actual Time (h) | Result (IU/dL) | Baseline Corrected Result (IU/dL) | Actual Time (h) | Result (IU/dL) | Baseline Corrected Result (IU/dL) | Actual Time (h) | Result (IU/dL) | Baseline Corrected Result (IU/dL) |
|---|---|---|---|---|---|---|---|---|
| Patient 1 | | | Patient 2 | | | Patient 3 | | |
| −309.80 | 2 | NC | −310.60 | 3 | NC | −524.08 | <1.0 | NC |
| −0.50 | 3 | 0.0 | −1.23 | 2 | 0.0 | −0.18 | 2 | 0.0 |
| 0.17 | 16 | 13.0 | 0.17 | 23 | 21.0 | 0.28 | 44 | 42.0 |
| 0.42 | 11 | 8.1 | 0.40 | 19 | 17.0 | 0.42 | 31 | 29.0 |
| 1.17 | 10 | 7.1 | 1.15 | 15 | 13.0 | 1.17 | 27 | 25.1 |
| 3.18 | 12 | 9.4 | 3.15 | 13 | 11.0 | 3.17 | 22 | 20.2 |
| 6.13 | 9 | 6.6 | 6.15 | 11 | 9.0 | 6.17 | 18 | 16.4 |
| 9.12 | 10 | 7.9 | 9.15 | 13 | 11.0 | 9.17 | 17 | 15.6 |
| 24.12 | 7 | 5.0 | 24.23 | 8 | 6.0 | 24.17 | 12 | 11.0 |
| 48.03 | 6 | 4.0 | 48.40 | 6 | 4.0 | 48.98 | 7 | 6.0 |
| 72.23 | 4 | 2.0 | 70.73 | 6 | 4.0 | 72.40 | 6 | 5.0 |
| 96.75 | 3 | 1.0 | 92.57 | 4 | 2.0 | 96.98 | 6 | 5.0 |
| 120.13 | 3 | 1.0 | 119.98 | 4 | 2.0 | 121.23 | 5 | 4.0 |
| 141.95 | 3 | 1.0 | 141.10 | 4 | 2.0 | 168.65 | 3 | 2.0 |
| 169.45 | 2 | 0.0 | 167.98 | 3 | 1.0 | 240.15 | 1 | 0.0 |
| 192.37 | 3 | 1.0 | 192.85 | 2 | 0.0 | 290.97 | 1 | 0.0 |
| 216.28 | 3 | 1.0 | 216.98 | 3 | 1.0 | 337.98 | 1 | 0.0 |
| 237.30 | 3 | 1.0 | 238.65 | 3 | 1.0 | 675.22 | 2 | 1.0 |
| 746.22 | 3 | 1.0 | 891.90 | 2 | 0.0 | | | |

| Actual Time (h) | Result (IU/dL) | Baseline Corrected Result (IU/dL) | Actual Time (h) | Result (IU/dL) | Baseline Corrected Result (IU/dL) | Actual Time (h) | Result (IU/dL) | Baseline Corrected Result (IU/dL) |
|---|---|---|---|---|---|---|---|---|
| Patient 4 | | | Patient 5 | | | Patient 6 | | |
| −285.52 | 1 | NC | −104.18 | <1.0 | NC | −503.20 | 3 | NC |
| −0.18 | <1.0 | 0.0 | −0.18 | <1.0 | 0.0 | −0.07 | 3 | 0.0 |
| 0.17 | 59 | 58.0 | 0.17 | 35 | 34.0 | 0.17 | 3 | 0.0 |
| 0.42 | 45 | 44.0 | 0.43 | 30 | 29.0 | 0.42 | 64 | 61.0 |
| 1.17 | 40 | 39.0 | 1.20 | 25 | 24.0 | 1.17 | 57 | 54.1 |
| 3.17 | 30 | 29.0 | 3.15 | 21 | 20.0 | 3.17 | 54 | 51.3 |
| 6.18 | 26 | 25.0 | 6.23 | 19 | 18.0 | 6.17 | 42 | 39.6 |
| 9.17 | 22 | 21.0 | 9.20 | NR | NR | 9.17 | 43 | 40.9 |
| 24.17 | 14 | 13.0 | 24.17 | 13 | 12.0 | 24.17 | 26 | 24.0 |
| 48.20 | 9 | 8.0 | 48.15 | 9 | 8.0 | 48.17 | 17 | 15.0 |
| 72.17 | 8 | 7.0 | 72.15 | 7 | 6.0 | 72.17 | 13 | 11.0 |
| 96.17 | 5 | 4.0 | 96.03 | 5 | 4.0 | 96.17 | 10 | 8.0 |
| 120.13 | 4 | 3.0 | 120.13 | 4 | 3.0 | 120.17 | 9 | 7.0 |
| 144.18 | 4 | 3.0 | 144.03 | 3 | 2.0 | 168.17 | 6 | 4.0 |
| 168.22 | 3 | 2.0 | 168.17 | 2 | 1.0 | 240.17 | 4 | 2.0 |
| 192.20 | 3 | 2.0 | 192.12 | 2 | 1.0 | 288.17 | 3 | 1.0 |
| 216.23 | 2 | 1.0 | 216.15 | 2 | 1.0 | 336.17 | 4 | 2.0 |
| 240.23 | 2 | 1.0 | 240.07 | 2 | 1.0 | 504.17 | 3 | 1.0 |
| 720.73 | <1.0 | 0.0 | 547.07 | <1.0 | 0.0 | | | |

| Actual Time (h) | Result (IU/dL) | Baseline Corrected Result (IU/dL) | Actual Time (h) | Result (IU/dL) | Baseline Corrected Result (IU/dL) | Actual Time (h) | Result (IU/dL) | Baseline Corrected Result (IU/dL) |
|---|---|---|---|---|---|---|---|---|
| Patient 7 | | | Patient 8 | | | Patient 9 | | |
| −438.43 | <1.0 | NC | −120.42 | <1.0 | NC | −193.05 | 8 | NC |
| −1.27 | 4 | 0.0 | −1.37 | <1.0 | 0.0 | −0.82 | 3 | 0.0 |
| 0.22 | 46 | 42.0 | 0.25 | 129 | 128.0 | 0.28 | 100 | 97.0 |
| 0.42 | 38 | 34.1 | 0.47 | 117 | 116.0 | 0.63 | 93 | 90.1 |
| 1.17 | 30 | 26.2 | 1.35 | 102 | 101.0 | 1.17 | 94 | 91.1 |
| 3.17 | 28 | 24.5 | 3.22 | 98 | 97.0 | 3.20 | 80 | 77.3 |
| 6.17 | 24 | 20.8 | 6.17 | 80 | 79.0 | 6.22 | 69 | 66.6 |
| 9.17 | 22 | 19.2 | 9.17 | 72 | 71.0 | 9.15 | 64 | 61.9 |
| 24.17 | 14 | 12.4 | 24.72 | 53 | 52.0 | 23.15 | 47 | 45.0 |
| 48.82 | 10 | 9.0 | 48.90 | 30 | 29.0 | 46.62 | 25 | 23.0 |
| 72.57 | 6 | 5.0 | 72.38 | 19 | 18.0 | 70.10 | 17 | 15.0 |
| 96.57 | 5 | 4.0 | 96.40 | 14 | 13.0 | 94.15 | 13 | 11.0 |
| 121.15 | 4 | 3.0 | 120.30 | 9 | 8.0 | 118.13 | 9 | 7.0 |
| 144.10 | 3 | 2.0 | 168.77 | 6 | 5.0 | 166.10 | 5 | 3.0 |
| 168.82 | 2 | 1.0 | 240.27 | 3 | 2.0 | 238.15 | 3 | 1.0 |
| 192.77 | 2 | 1.0 | 288.83 | 2 | 1.0 | 286.15 | 2 | 0.0 |

TABLE 5-continued

Individual Patient and Group Mean FIXFc Activity and Baseline Corrected FIXFc Activity versus Time Data; Sorted by Nominal Dose, Actual Dose, Infusion Duration, and Patient Number

| 240.57 | 2 | 1.0 | 337.03 | 2 | 1.0 | 335.57 | 2 | 0.0 |
| 744.57 | 3 | 2.0 | 840.28 | <1.0 | 0.0 | 741.77 | 3 | 1.0 |

| Actual Time (h) | Result (IU/dL) | Baseline Corrected Result (IU/dL) | Actual Time (h) | Result (IU/dL) | Baseline Corrected Result (IU/dL) | Actual Time (h) | Result (IU/dL) | Baseline Corrected Result (IU/dL) |
|---|---|---|---|---|---|---|---|---|
| Patient 10 | | | Patient 11 | | | Patient 12 | | |
| −334.63 | 1 | NC | −912.28 | 2 | NC | −342.58 | 2 | NC |
| −0.48 | 2 | 0.0 | −0.15 | 2 | 0.0 | −1.12 | 2 | 0.0 |
| 0.25 | 120 | 118.0 | 0.23 | 110 | 108.0 | 0.17 | 108 | 106.0 |
| 0.50 | 104 | 102.0 | 0.47 | 106 | 104.0 | 0.42 | 90 | 88.0 |
| 1.22 | 84 | 82.1 | 1.22 | 96 | 94.0 | 1.17 | 70 | 68.0 |
| 3.22 | 75 | 73.2 | 3.22 | 92 | 90.0 | 3.17 | 69 | 67.0 |
| 6.22 | 60 | 58.4 | 6.25 | 81 | 79.0 | 6.17 | 55 | 53.0 |
| 9.22 | 56 | 54.6 | 9.22 | 70 | 68.0 | 9.17 | 55 | 53.0 |
| 24.22 | 36 | 35.0 | 24.22 | 53 | 51.0 | 24.17 | 37 | 35.0 |
| 48.22 | 21 | 20.0 | 47.72 | 33 | 31.0 | 48.20 | 25 | 23.0 |
| 72.22 | 14 | 13.0 | 71.88 | 25 | 23.0 | 72.13 | 14 | 12.0 |
| 96.12 | 11 | 10.0 | 167.72 | 8 | 6.0 | 95.17 | 10 | 8.0 |
| 120.22 | 7 | 6.0 | 191.72 | 8 | 6.0 | 119.17 | 7 | 5.0 |
| 144.22 | 6 | 5.0 | 263.72 | 4 | 2.0 | 167.38 | 6 | 4.0 |
| 168.22 | 6 | 5.0 | 359.72 | 3 | 1.0 | 239.50 | 3 | 1.0 |
| 192.18 | 4 | 3.0 | 383.97 | 3 | 1.0 | 287.25 | 2 | 0.0 |
| 216.22 | 85 | 84.0 | 890.97 | 14 | 12.0 | 526.42 | 4 | 2.0 |
| 744.95 | 2 | 1.0 | | | | | | |

Note:
Data in bold represent a return to baseline and were excluded from analysis.

TABLE 6

Individual Patient and Group Mean FIXFc Activity Pharmacokinetic Summary Data; Sorted by Nominal Dose, Actual Dose, and Patient Number

| Nominal Dose (IU/kg) | Actual Dose (IU/kg) | Patient | $C_{max}$ (IU/dL) | $AUC_{INF}$ (h*IU/dL) | $AUC_\alpha$ (%) | $AUC_\beta$ (%) | AUC/Dose (IU*h/dL per IU/kg) | Cl (mL/h/kg) | $V_1$ (mL/kg) | $V_{SS}$ (mL/kg) | MRT (h) | Alpha HL (h) | Beta HL (h) |
|---|---|---|---|---|---|---|---|---|---|---|---|---|---|
| 12.5 | 13.714 | 1 | 11.9 | 418 | 0.231 | 99.8 | 30.5 | 3.28 | 102 | 157 | 48.0 | 0.140 | 33.3 |
| | N | | 1 | 1 | 1 | 1 | 1 | 1 | 1 | 1 | 1 | 1 | 1 |
| 25 | 27.25 | 2 | 19.9 | 753 | 2.50 | 97.8 | 27.6 | 3.62 | 134 | 275 | 76.0 | 1.20 | 54.0 |
| | N | | 1 | 1 | 1 | 1 | 1 | 1 | 1 | 1 | 1 | 1 | 1 |
| 50 | 54.5 | 3 | 34.5 | 1280 | 5.7 | 94.5 | 23.5 | 4.26 | 155 | 365 | 85.8 | 2.32 | 62.9 |
| | 54.5 | 4 | 48.5 | 1450 | 12.4 | 87.7 | 26.6 | 3.76 | 111 | 282 | 75.1 | 3.64 | 58.9 |
| | 54.5 | 5 | 33.0 | 1190 | 1.5 | 98.3 | 21.8 | 4.58 | 160 | 274 | 59.9 | 0.840 | 42.1 |
| | 54.513 | 6 | 53.5 | 2960 | 1.0 | 99.1 | 54.3 | 1.84 | 100 | 149 | 81.1 | 1.07 | 56.7 |
| | 55.878 | 7 | 38.6 | 1270 | 2.2 | 97.9 | 22.7 | 4.41 | 141 | 248 | 56.4 | 1.07 | 40.0 |
| | N | | 5 | 5 | 5 | 5 | 5 | 5 | 5 | 5 | 5 | 5 | 5 |
| | Mean | | 41.6 | 1630 | 4.56 | 95.5 | 29.8 | 3.77 | 133 | 264 | 71.7 | 1.79 | 52.1 |
| | SD | | 8.97[a] | 750 | 4.75 | 4.70 | 13.8 | 1.12 | 26.7 | 77.6 | 13.0 | 1.19 | 10.4 |
| | SE | | 4.01 | 335 | 2.13 | 2.10 | 6.18 | 0.501 | 11.9 | 34.7 | 5.79 | 0.531 | 4.65 |
| | Geometric Mean | | 40.9 | 1530 | 2.98 | 95.4 | 27.9 | 3.59 | 131 | 254 | 70.7 | 1.52 | 51.3 |
| | CV % Geometric Mean | | 21.4 | 39.1 | 136.5 | 5.0 | 39.4 | 39.4 | 21.1 | 33.8 | 18.8 | 68.6 | 21.0 |
| 100 | 109 | 10 | 98.9 | 3330 | 18.5 | 81.3 | 30.6 | 3.28 | 109 | 216 | 65.9 | 6.53 | 54.6 |
| | 109 | 8 | 111 | 4580 | 28.9 | 71.1 | 42.0 | 2.38 | 98.0 | 145 | 61.1 | 13.2 | 54.2 |
| | 109 | 9 | 92.1 | 3540 | 17.0 | 82.9 | 32.5 | 3.08 | 118 | 163 | 53.1 | 9.43 | 42.4[d] |
| | 109.176 | 11 | 99.1 | 5150 | 28.6 | 71.3 | 47.2 | 2.12 | 110 | 162 | 76.2 | 16.6 | 67.4 |
| | 109.441 | 12 | 89.9 | 3060 | 9.2 | 90.8 | 28.0 | 3.58 | 121 | 207 | 57.9 | 4.19 | 43.8 |
| | N | | 5 | 5 | 5 | 5 | 5 | 5 | 5 | 5 | 5 | 5 | 5 |
| | Mean | | 98.2 | 3930 | 20.4 | 79.5 | 36.1 | 2.89 | 111 | 179 | 62.8 | 9.99 | 52.5 |
| | SD | | 8.21[b] | 893[c] | 8.37 | 8.37 | 8.17 | 0.615 | 8.98 | 31.1 | 8.82 | 4.99 | 10.1 |
| | SE | | 3.67 | 399 | 3.74 | 3.74 | 3.65 | 0.275 | 4.02 | 13.9 | 3.95 | 2.23 | 4.51 |
| | Geometric Mean | | 97.9 | 3860 | 18.9 | 79.1 | 35.4 | 2.83 | 111 | 177 | 62.4 | 8.92 | 51.7 |
| | CV % Geometric Mean | | 8.2 | 22.4 | 49.7 | 10.5 | 22.4 | 22.5 | 8.2 | 17.4 | 13.8 | 59.4 | 19.0 |

Due to correction of rounding or other errors,
[a] should be 8.98,
[b] should be 8.23,
[c] should be 892, and
[d] should be 42.2.

TABLE 7A-7B

Individual Patient and Group Mean FIXFc Activity Secondary Pharmacokinetic Summary Data; Sorted by Nominal Dose, Actual Dose, and Patient Number

| Nominal Dose (IU/kg) | Actual Dose (IU/kg) | Patient | C168[a] (IU/dL) | TBLP1[b] (Day) | TBLP3[c] (Day) | TBLP5[d] (Day) | K Value[e] (IU/dL per IU/kg) | K Value[f] (IU/dL per IU/kg) | In Vivo Recovery[g] (%) | In Vivo Recovery[h] (%) |
|---|---|---|---|---|---|---|---|---|---|---|
| 12.5 | 13.714 | 1 | *0.264* | *4.34* | 2.13 | 1.11 | 0.87 | 0.95 | 30.8 | 33.6 |
|  |  | N | 1 | 1 | 1 | 1 | 1 | 1 | 1 | 1 |
| 25 | 27.25 | 2 | 1.09 | 7.28 | 3.72 | 2.06 | 0.73 | 0.77 | 31.8 | 33.5 |
|  |  | N | 1 | 1 | 1 | 1 | 1 | 1 | 1 | 1 |
| 50 | 54.5 | 3 | 2.09 | *9.79* | 5.64 | 3.70 | 0.63 | 0.77 | 33.0 | 40.2 |
|  | 54.5 | 4 | 2.08 | 9.58 | 5.69 | 3.89 | 0.89 | 1.06 | 37.8 | 45.2 |
|  | 54.5 | 5 | 1.22 | 7.50 | 4.72 | 3.42 | 0.61 | 0.62 | 33.6 | 34.6 |
|  | 54.513 | 6 | 4.61 | 12.2 | 8.47 | 6.72 | 0.98 | 1.12 | 38.2 | 43.6 |
|  | 55.878 | 7 | 1.17 | 7.37 | 4.74 | 3.51 | 0.69 | 0.75 | 29.9 | 32.6 |
|  |  | N | 5 | 5 | 5 | 5 | 5 | 5 | 5 | 5 |
|  | Mean |  | 2.23 | 9.29 | 5.85 | 4.25 | 0.76 | 0.86 | 34.5 | 39.2 |
|  | SD |  | 1.40 | 1.98 | 1.54 | 1.39 | 0.17 | 0.22 | 3.5 | 5.5 |
|  | SE |  | 0.627 | 0.886 | 0.687 | 0.623 | 0.074 | 0.0963 | 1.6 | 2.5 |
|  | Geometric Mean |  | 1.96 | 9.12 | 5.71 | 4.10 | 0.75 | 0.84 | 34.4 | 38.9 |
|  | CV % Geometric Mean |  | 60.0 | 21.2 | 24.1 | 28.6 | 21.5 | 25.4 | 10.2 | 14.4 |

| Nominal Dose (IU/kg) | Actual Dose (IU/kg) | Patient | C168[a] (IU/dL) | TBLP1[b] (Day) | TBLP3[c] (Day) | TBLP5[d] (Day) | K Value[e] (IU/dL per IU/kg) | K Value[f] (IU/dL per IU/kg) | In Vivo Recovery[g] (%) | In Vivo Recovery[h] (%) |
|---|---|---|---|---|---|---|---|---|---|---|
| 100 | 109 | 10 | 4.08 | *11.6* | 8.01 | 6.34 | 0.91 | 1.08 | 43.4 | 51.8 |
|  | 109 | 8 | 4.88 | 12.1 | 8.57 | 6.92 | 1.02 | 1.17 | 28.7 | 33.1 |
|  | 109 | 9 | 3.09 | 9.87 | 7.07 | 5.78 | 0.84 | 0.89 | 39.7 | 41.8 |
|  | 109.176 | 11 | 6.77 | 14.7 | 10.3 | 8.21 | 0.91 | 0.99 | 27.8 | 30.3 |
|  | 109.441 | 12 | 3.09 | 9.96 | 7.07 | 5.72 | 0.82 | 0.97 | 35.8 | 42.2 |
|  |  | N | 5 | 5 | 5 | 5 | 5 | 5 | 5 | 5 |
|  | Mean |  | 4.38 | 11.6 | 8.20 | 6.59 | 0.90 | 1.02 | 35.1 | 39.8 |
|  | SD |  | 1.53 | 1.97 | 1.34 | 1.03 | 0.0784 | 0.11 | 6.8 | 8.5 |
|  | SE |  | 0.685 | 0.881 | 0.597 | 0.459 | 0.0351 | 0.0482 | 3.0 | 3.8 |
|  | Geometric Mean |  | 4.19 | 11.5 | 8.12 | 6.53 | 0.90 | 1.02 | 34.5 | 39.1 |
|  | CV % Geometric Mean |  | 34.1 | 16.5 | 15.7 | 15.0 | 8.6 | 10.5 | 19.8 | 21.6 |

[a]C168 = Estimated FIX activity above baseline at approximately 168 h after dose. Value in italics was estimated from simulations performed using a one-compartment model and patient microscopic rate constants.
[b]TBLP1 = Model-predicted time after dose when FIX activity has declined to approximately 1 IU/dL above baseline. Values in italics were estimated from simulations performed using a one-compartment model and patient microscopic rate constants.
[c]TBLP3 = Model-predicted time after dose when FIX activity has declined to approximately 3 IU/dL above baseline.
[d]TBLP5 = Model-predicted time after dose when FIX activity has declined to approximately 5 IU/dL above baseline.
[e]K-Value was calculated using model predicted $C_{max}$ value generated from background subtracted results divided by dose.
[f]K-Value was calculated using the observed maximum post dose sample result; K-value = (Baseline Subtracted $C_{max}$ observed)/Dose).
[g]In-vivo Recovery = 100 × (Model Predicted $C_{max}$ from baseline subtracted data/Dose) × Plasma Volume (dL)/Dose in IU; where plasma volume in mL = (23.7 × Ht in cm) + (9.0 × Wt in kg) − 1709.
[h]In-vivo Recovery = 100 × (Baseline Subtracted Observed $C_{max}$) × Plasma Volume (dL)/Dose in IU; where plasma volume in mL = (23.7 × Ht in cm) + (9.0 × Wt in kg) − 1709.

TABLE 8

Phase 1/2a Study: Comparison of PK Parameters for rFIXFc and BENEFIX ™

| Parameters | *rFIXFc [Mean ± SD (min-max)] [N = 11] | [†]BENEFIX ™ [Mean ± SD (min-max)] [N = 11] |
|---|---|---|
| $t_{1/2}$ (hours) | 52.5 ± 9.2 (40-67.4) | 19.3 ± 4.97 (11.1-36.4) |
| MRT (hours) | 68.05 ± 11.16 (53.1-85.8) | 26.0 ± 6.07 (15.81-46.09) |
| CL (mL/hour/kg) | 3.36 ± 0.93 (1.84-4.58) | 8.4 ± 2.01 (4.66-13.64) |
| Incremental Recovery (IU/dL per IU/kg) | 0.93 ± 0.18 (0.62-1.17)[a] | 0.75 ± 0.23 (0.34-1.38) |
| $C_{max}$ (IU/dL per IU/kg) | 24 hrs post-injection |  |
| AUC | 48 hrs post-injection |  |

*Estimates from 2-compartmental analysis of FIX activity at the nominal doses 25, 50 and 100 IU/kg (n = 11)
[†]Summary of Product Characteristics of BENEFIX ™ (Nov. 18, 2009); Median and range (n = 56)
[a]Range corrected due to rounding or other errors as 0.63-1.18.

Relative to Historical Data for BENEFIX™, rFIX-Fc demonstrated:

3× increase in half-life and mean residence time

24% improved incremental recovery relative 2.5× reduced clearance

TABLE 9

Phase 1/2a Study: Dose Proportional Increase in Cmax and AUC of rFIXFc (activity)

| Dose (IU/kg) | # of Patients | Cmax (IU/dL) [Mean ± SD (min-max)] | AUC (h*IU/dL) [Mean ± SD (min-max)] |
|---|---|---|---|
| 25 | 1 | 19.9 | 753 |
| 50 | 5 | 41.6 ± 8.97 (33.0-53.5) | 1630 ± 750 (1190-2960) |
| 100 | 5 | 98.2 ± 8.21 (89.9-111.0) | 3930 ± 893 (3060-5150) |

Also see FIG. 5.

TABLE 10

Estimated Therapeutic Duration of rFIXFc at 50 and 100 IU/kg Doses.

| Parameter | Geo Median |
|---|---|
| FIX:C on Day 7 | 2.0 IU/dL (above baseline) |
| Time to 1 IU/dL above baseline | 9.1 days |
| Time to 3 IU/dL above baseline | 5.7 days |
| FIX:C on Day 7 | 4.2 IU/dL (above baseline) |
| Time to 1 IU/dL above baseline | 11.5 days |
| Time to 3 IU/dL above baseline | 8.1 days |

Also see FIG. 6A-6B.

TABLE 11

Dose Proportional Increase in Cmax and AUC for rFIXFc Antigen.

| Dose (IU/kg) | # of patients | Cmax (ng/mL) [Mean ± SD] | AUC (h*ng/mL) [Mean ± SD] |
|---|---|---|---|
| 25 | 1 | 2,730 | 144,000 |
| 50 | 5 | 7,510 ± 2,480 | 408,000 ± 73,900 |
| 100 | 5 | 15,400 ± 3,960 | 897,000 ± 206,000 |

Also see FIG. 7.

TABLE 12

Pharmacokinetic Estimates for rFIXFc Antigen

| Parameters | 50 IU/kg [Mean ± SD] (N = 5) | 100 IU/kg [Mean ± SD] (N = 5) |
|---|---|---|
| CL (mL/hour/kg) | 2.28 ± 0.37 | 2.11 ± 0.46 |
| Vss (mL/kg) | 259 ± 78.5 | 238 ± 52.2 |
| MRT (hours) | 112 ± 21.5 | 114 ± 17.1 |
| $t_{1/2}$ (hours) | 110 ± 26.5 | 95.8 ± 11.1 |

Also see FIG. 8A-8B.

TABLE 13

Mean PK Values Based on Activity

| | Cmax (IU/dL) | AUCINF (h*IU/dL) | AUCa (%) | AUCb (%) | AUC/Dose (IU*h/dL per IU/kg) | Cl (mL/kg) | V1 (mL/h/kg) | VSS (mL/kg) | MRT (h) | $t_{1/2}\alpha$ (h) | $t_{1/2}\beta$ (h) |
|---|---|---|---|---|---|---|---|---|---|---|---|
| n | 11 | 11 | 11 | 11 | 11 | 11 | 11 | 11 | 11 | 11 | 11 |
| Mean | 65.364 | 2596.636 | 11.591 | 88.427 | 32.436 | 3.555 | 123.364 | 226.000 | 68.045 | 5.463 | 52.455 |
| Std Dev | 32.9708 | 1497.1234 | 10.4490 | 10.5210 | 10.7506 | 0.9257 | 21.2804 | 69.7582 | 11.1637 | 5.4197 | 9.1674 |
| % CV | 50.4420 | 57.6563 | 90.1479 | 11.8980 | 33.1435 | 27.5890 | 17.2501 | 30.8664 | 16.4063 | 99.2128 | 17.4768 |
| Median | 53.500 | 2960.000 | 9.200 | 90.800 | 28.000 | 3.580 | 118.000 | 216.000 | 65.900 | 3.640 | 54.200 |
| Minimum | 19.90 | 753.00 | 1.00 | 71.10 | 21.80 | 1.84 | 98.00 | 145.00 | 53.10 | 0.84 | 40.00 |
| Maximum | 111.00 | 5150.00 | 28.90 | 99.10 | 54.30 | 4.58 | 160.00 | 365.00 | 85.80 | 16.60 | 67.40 |
| Geo. mean | 56.951 | 2181.294 | 6.781 | 87.826 | 31.020 | 3.226 | 121.767 | 216.533 | 67.218 | 3.326 | 51.715 |

| | C168 [1] (IU/dL) | TBLP1 [2] (Day) | TBLP3 [3] (Day) | TBLP5 [4] (Day) | Incremental Recovery [5] (IU/dL per IU/kg) | Incremental Recovery [6] (IU/dL per IU/kg) | In Vivo Recovery [7] (%) | In Vivo Recovery [8] (%) |
|---|---|---|---|---|---|---|---|---|
| n | 11 | 11 | 11 | 11 | 11 | 11 | 11 | 11 |
| Mean | 3.106 | 10.177 | 6.727 | 5.115 | 0.821 | 0.926 | 34.518 | 38.991 |
| Std Dev | 1.8231 | 2.3315 | 2.0089 | 1.8975 | 0.1387 | 0.1787 | 4.9250 | 6.6636 |
| % CV | 58.6897 | 22.9088 | 29.8623 | 37.0944 | 16.8921 | 19.2940 | 14.2678 | 17.0900 |
| Median | 3.090 | 9.870 | 7.070 | 5.720 | 0.840 | 0.970 | 33.600 | 40.200 |
| Minimum | 1.09 | 7.28 | 3.72 | 2.06 | 0.61 | 0.62 | 27.80 | 30.30 |
| Maximum | 6.77 | 14.70 | 10.30 | 8.21 | 1.02 | 1.17 | 43.40 | 51.80 |
| Geo. mean | 2.621 | 9.938 | 6.447 | 4.761 | 0.810 | 0.910 | 34.202 | 38.486 |

Footnotes:
Note:
PK parameter values were determined by 2-compartmental method.
Geo. Mean = Geometric Mean
[1] C168 = FIX activity above baseline at 168 hr after dose.
[2] TBLP1 = Estimated time after dose when FIX activity has declined to 1 IU/dL above baseline.
[3] TBLP3 = Estimated time after dose when FIX activity has declined to 3 IU/dL above baseline.
[4] TBLP5 = Estimated time after dose when FIX activity has declined to 5 IU/dL above baseline.
[5] Incremental Recovery was calculated using model predicted Cmax value generated from background subtracted results divided by dose.
[6] Incremental Recovery was calculated using the observed maximum post-dose sample result; Incremental Recovery = (Baseline Subtracted Cmax observed)/Dose.
[7] In-vivo Recovery = 100 × (Model Predicted Cmax from baseline subtracted data/Dose) × Plasma Volume (dL)/Dose in IU; where plasma volume in mL = (23.7 × Ht in cm) + (9.0 × Wt in kg) − 1709.
[8] In-vivo Recovery = 100 × (Baseline Subtracted Observed Cmax) × Plasma Volume (dL)/Dose in IU; where plasma volume in mL = (23.7 × Ht in cm) + (9.0 × Wt in kg) − 1709.

TABLE 14

Mean PK Values Based on Antigen Level.

| Nominal Dose (IU/kg) | Actual Dose (IU/kg) | Equivalent Dose (mg/kg) | Patient | $C_{max}$ (ng/mL) | $AUC_{INF}$ (h*ng/mL) | Cl (mL/h/kg) | $V_{SS}$ (mL/kg) | MRT (h) | Alpha HL (h) | Beta HL (h) |
|---|---|---|---|---|---|---|---|---|---|---|
| 12.5 | 13.714 | 0.228 | 1 | 1670 | 91300 | 2.5 | 245 | 98.2 | 21.2 | 107 |
| 25 | 27.25 | 0.453 | 2 | 2730 | 144000 | 3.14 | 273 | 87.1 | 11.3 | 71 |
| 50 | 54.5 | 0.905 | 3 | 5470 | 356000 | 2.54 | 366 | 144 | 18.6 | 138 |
|  | 54.5 | 0.905 | 4 | 6910 | 389000 | 2.32 | 244 | 105 | 10.6 | 85.3 |
|  | 54.5 | 0.905 | 5 | 7520 | 416000 | 2.17 | 184 | 84.5 | NC | 94.3 |
|  | 54.513 | 0.906 | 6 | 11700 | 531000 | 1.71 | 190 | 112 | NC | 140 |
|  | 55.878 | 0.928 | 7 | 5950 | 348000 | 2.67 | 310 | 116 | 10.1 | 93.9 |
| 100 | 109 | 1.81 | 10 | 12500 | 667000 | 2.72 | 263 | 96.8 | 9.79 | 78 |
|  | 109 | 1.81 | 8 | 21600 | 1200000 | 1.51 | 156 | 103 | 15.7 | 94.3 |
|  | 109 | 1.81 | 9 | 13400 | 998000 | 1.81 | 248 | 137 | 11.5 | 107 |
|  | 109.176 | 1.81 | 11 | 17200 | 844000 | 2.15 | 226 | 105 | 13 | 97.1 |
|  | 109.441 | 1.82 | 12 | 12500 | 778000 | 2.34 | 295 | 126 | 10.6 | 102 |
|  |  |  | N | 12 | 12 | 12 | 12 | 12 | 12 | 12 |
|  |  |  | Mean | 9929.0 | 563525.0 | 2.3 | 250.0 | 109.6[b] | 13.2[c] | 100.7[e] |
|  |  |  | SD | 5940.0 | 339925.0 | 0.5[a] | 58.2 | 18.5 | 4.0[d] | 20.9 |
|  |  |  | SE | 1715.0 | 98128.0 | 0.1 | 16.8 | 5.3 | 1.3 | 6.0 |
|  |  |  | Geometric Mean | 8014.0 | 452356.0 | 2.3 | 243.7 | 108.2 | 12.8 | 98.8 |

Due to correction of rounding or other errors,
[a]should be 0.46,
[b]should be 110,
[c]should be 12.0,
[d]should be 3.95, and
[e]should be 101.

TABLE 15

Biochemical characterization of Factor IX

| Gamma-carboxylation |  | FIXFc | rFIX | pdFIX |
|---|---|---|---|---|
| aa 1-23 | %6 Gla | 97.8 | 96.9 | 99.6 |
| (K1K2 peptide) | %5 Gla | 2.2 | 3.1 | 0.4 |
|  | %4 Gla | 0 | 0 | 0 |
| aa 24-43 | %6 Gla | 61.3 | 63.7 | 98.9 |
| (K3 peptide) | %5 Gla | 26.3 | 30.9 | 1.1 |
|  | %4 Gla | 12.5 | 5.4 | 0 |
| Total Gla/mol, peptide map |  | 11.5 | 11.6 | 12.0 |
| Total Gla/mol, AAA |  | 11.3 ± 0.3 | 11.5 ± 0.3 | (12) |
| Propeptide content |  | none detected | none detected | none detected |
| β-hydroxylation Asp 64 |  | 70% | 49% | 37% |
| Sulfation of Tyr 155 |  | 4% | 5% | (>90%) |
| Phosphorylation of Ser 158 |  | <10% | <10% | (>90%) |
| Ala 148/Thr 148 |  | 0/100% | 100/0% | 30/70% |
| Activated FIX |  | 0.0125% | 0.109 +/- 0.00185% | 0.21 +/- 0.010% |
| FXIa Activation |  | 94.8 +/- 2.4% | 96.6 +/- 1.8% | Not done |

TABLE 16

Summary of terminal half-lives of FIXFc and BENEFIX ™ after a single intravenous dose.

| Species | BENEFIX ™ | FIXFc |
|---|---|---|
| Normal mice | 12.3 hr | 47.2 ± 4.8 hr |
| FIX-deficient mice | 13.2 hr | 46.2 ± 10.1 hr |
| FcRN KO mice | 16.5 ± 3.0 hr | 16.9 ± 2.1 hr |
| FcRN Tg32b mice | 14.2 ± 2.9 hr | 53.0 ± 6.6. hr |
| Rats | 5.8 hr | 34.8 ± 5.3 hr |
| FIX-deficient dogs | 14-18 hr * | 47.5 hr |
| Monkey | 12.7 hr [†] | 47.3 ± 9.1 hr |

* Brinkhous et al, Blood, 1996; 88: 2603-2610
[†] McCarthy et al, 2002, Thromb Haemost, 2002; 87: 824-830

TABLE 17

Summary of in vitro ROTEM ® parameters for rFIXFc and BENEFIX ™ spiked in pooled HemB mouse whole blood

|  | % of Normal Activity | CT (sec) (Mean ± SD) | CFT (sec) (Mean ± SD) | Alpha Angle (°) (Mean ± SD) |
|---|---|---|---|---|
| rFIXFc | 0.074 | 2263 ± 209 | 1152 ± 170 | 24 ± 5 |
| (n = 10 pools) | 0.74 | 1371 ± 82 | 459 ± 45 | 34 ± 5 |
|  | 7.4 | 790.8 ± 30 | 226 ± 20 | 52 ± 2 |
| BENEFIX ™ | 0.1 | 2019 ± 178 | 732 ± 123 | 30 ± 3 |
| (n = 10 pools) | 1 | 1090 ± 38 | 324 ± 33 | 43 ± 3 |
|  | 10 | 551.1 ± 38 | 127 ± 10 | 67 ± 2 |

TABLE 18

Median blood loss following tail dip in HemB mice treated with rFIXFc or BENEFIX ™

| Dose (IU/kg) | Median Blood Loss (mL) | | |
|---|---|---|---|
| | rFIXFc (n = 15/dose) | BENEFIX ™ (n = 15/dose) | Vehicle (n = 18) |
| 720 | 0.101 | | |
| 360 | 0.651 | 0.218 | |
| 240 | 0.298 | | |
| 120 | 0.4567 | 0.564 | |
| 80 | 0.8474 | | |
| 40 | 1.0097 | 0.918 | |
| 0 | | | 1.1586 |

TABLE 19

Ex vivo ROTEM ® parameter in HemB mice treated with rFIXFc and BENEFIX ™

| | Time (hour) | CT (sec) (Mean ± SD) | CFT (sec) (Mean ± SD) | Alpha Angle (degree) (Mean ± SD) |
|---|---|---|---|---|
| 100 IU/kg BENEFIX ™ (n = 4 mice/ time point) | 0.083 | 599 ± 23 | 174 ± 16 | 58 ± 2 |
| | 24 | 682 ± 49 | 184 ± 34 | 57 ± 5 |
| | 48 | 897 ± 114 | 310 ± 89 | 45 ± 7 |
| | 72 | 1141 ± 155 | 508 ± 123 | 32 ± 7 |
| | 96 | 1613 ± 181 | 605 ± 92 | 27 ± 3 |
| 50 IU/kg rFIXFc (n = 8 mice/ time point) | 0.083 | 700 ± 18 | 213 ± 9 | 53 ± 1 |
| | 24 | 836 ± 31 | 261 ± 15 | 47 ± 2 |
| | 72 | 845 ± 38 | 285 ± 17 | 45 ± 2 |
| | 96 | 957 ± 30 | 296 ± 26 | 43 ± 2 |
| | 120 | 1014 ± 83 | 342 ± 50 | 42 ± 4 |
| | 168 | 1139 ± 65 | 408 ± 41 | 36 ± 3 |
| | 216 | 1366 ± 96 | 453 ± 48 | 34 ± 3 |

TABLE 20A

PK parameters of rFIXFc and BENEFIX ™ (200 IU/kg) following subcutaneous injection of a single dose in FIX-deficient mice (Antigen ELISA)

| Compound | Dose ng/kg | V/F mL/kg | Tlag Hr | $AUC_{INF}$ Hr*ng/mL | Absorption HL Hr | Elimination HL Hr | CL/F mL/Hr/kg | Tmax Hr | Cmax ng/mL | $AUC_{INF}$/Dose Hr · kg/mL | Cmax/Dose g/mL | F % |
|---|---|---|---|---|---|---|---|---|---|---|---|---|
| BeneFIX | 727273 | 3920 | 2.86 | 6397 | 1.96 | 23.9 | 114 | 10.6 | 148 | 0.00880 | 0.204 | 23.3 |
| rFIXFc | 3278689 | 2071 | 0.896 | 141370 | 7.67 | 61.9 | 23.2 | 27.3 | 1178 | 0.0431 | 0.359 | 38.1 |

TABLE 20B

PK parameters of rFIXFc and BENEFIX ™ (200 IU/kg) following subcutaneous injection of a single dose in FIX-deficient mice (aPTT activity assay)

| Compound | Dose IU/kg | V/F dL/kg | Tlag Hr | $AUC_{INF}$ Hr*IU/dL | Absorption HL Hr | Elimination HL Hr | CL/F dL/Hr/kg | Tmax Hr | Cmax IU/dL | $AUC_{INF}$/Dose Hr*kg/dL | Cmax/Dose g/dL | F % |
|---|---|---|---|---|---|---|---|---|---|---|---|---|
| BeneFIX | 207 | 54.8 | 0.631 | 93.9 | 7.01 | 17.2 | 2.20 | 16.0 | 2.04 | 0.454 | 9.86 | 18.9 |
| rFIXFc | 172 | 25.1 | 2.32 | 418 | 6.84 | 42.4 | 0.411 | 23.8 | 4.82 | 2.43 | 28.0 | 29.1 |

TABLE 21

PK and PD Analysis of rFIXFc and BENEFIX ™ After a Single Subcutaneous Dose in FIX-Deficient Mice.

| | Assay | AUC/Dose (Hr*kg/mL) | Elim. Half-Life (Hr) | CL/F (mL/Hr/kg)/ % | Tmax (Hr) | Cmax/Dose (kg/mL) | F (%) |
|---|---|---|---|---|---|---|---|
| rFIXFc 200 IU/kg | Antigen | 0.041 | 61.9 | 23.2 | 27.3 | 0.00035 | 38.1 |
| BENEFIX ™ 200 IU/kg | Antigen | 0.0073 | 23.9 | 114 | 10.6 | 0.00017 | 23.3 |
| Ratio (rFIXFc/BENEFIX ™) | Antigen | 5.62 | 2.59 | 0.20 | 2.58 | 2.05 | 1.63 |
| rFIXFc 400 IU/kg | Antigen | 0.042 | 50.9 | 23.7 | 18.3 | 0.00045 | 45.6 |
| BENEFIX ™ 400 IU/kg | Antigen | 0.0089 | 20.2 | 113 | 8.13 | 0.00024 | 20.2 |
| Ratio (rFIXFc/BENEFIX ™) | Antigen | 4.72 | 2.52 | 0.21 | 2.25 | 1.91 | 2.26 |
| rFIXFc 200 IU/kg | Activity | 0.021 | 42.4 | 41.1 | 23.8 | 0.00024 | 29.1 |
| BENEFIX ™ 200 IU/kg | Activity | 0.0047 | 17.2 | 220 | 16.0 | 0.00010 | 18.9 |
| Ratio (rFIXFc/BENEFIX ™) | Activity | 4.47 | 2.46 | 0.19 | 1.49 | 2.40 | 1.54 |
| rFIXFc 400 IU/kg | Activity | 0.028 | 40.3 | 35.6 | 15.9 | 0.00037 | 39.2 |
| BENEFIX ™ 400 IU/kg | Activity | 0.0052 | 15.6 | 193 | 18.1 | 0.00010 | 15.5 |
| Ratio (rFIXFc/BENEFIX ™) | Activity | 5.38 | 2.58 | 0.18 | 0.88 | 3.70 | 2.53 |

TABLE 22

PK parameters of rFIXFc (50 IU/kg) following subcutaneous injection of a single dose in cynomolgus monkeys.

| Group | Animal_ID | V/F (mL/kg) | AUC (Hr*ng/mL) | Absorption HL (Hr) | Terminal HL (Hr) | CL/F (mL/Hr/kg) | Tmax (Hr) | Cmax (ng/mL) | AUC/D (Hr*kg/mL) | F (%) |
|---|---|---|---|---|---|---|---|---|---|---|
| 50 | 5C4 | 545 | 109000 | 8.42 | 50.2 | 7.53 | 26.1 | 1050 | 0.133 | 43.7 |
| IU/kg | C37716 | 975 | 108000 | 6.4 | 89 | 7.6 | 26.2 | 685 | 0.132 | 43.3 |
| rFIXFc | C41440 | 622 | 82500 | 8.54 | 43.4 | 9.93 | 24.9 | 885 | 0.101 | 33.1 |
| | N | 3 | 3 | 3 | 3 | 3 | 3 | 3 | 3 | 3 |
| | Mean | 714 | 99800 | 7.79 | 60.9 | 8.35 | 25.7 | 873 | 0.122 | 40.1 |
| | SD | 229 | 14900 | 1.2 | 24.6 | 1.37 | 0.685 | 182 | 0.0183 | 6.03 |
| | SE | 132 | 8630 | 0.695 | 14.2 | 0.79 | 0.396 | 105 | 0.0106 | 3.48 |
| | Geometric Mean | 691 | 99000 | 7.72 | 57.9 | 8.28 | 25.7 | 860 | 0.121 | 39.7 |
| | CV % Geometric Mean | 31.2 | 15.8 | 16.4 | 39.4 | 15.8 | 2.68 | 21.7 | 15.9 | 15.9 |

TABLE 23

PK parameters of rFIXFc (100 IU/kg) following subcutaneous injection of a single dose in cynomolgus monkeys.

| Group | Animal_ID | V/F (mL/kg) | AUC (Hr*ng/mL) | Absorption HL (Hr) | Terminal HL (Hr) | CL/F (mL/Hr/kg) | Tmax (Hr) | Cmax (ng/mL) | AUC/D (Hr*kg/mL) | F (%) |
|---|---|---|---|---|---|---|---|---|---|---|
| 100 | 29109 | 1630 | 69800 | 11.4 | 48.1 | 23.5 | 31 | 644 | 0.0426 | 14.0 |
| IU/kg | 605097 | 561 | 207000 | 5.12 | 49.2 | 7.9 | 18.6 | 2250 | 0.126 | 41.5 |
| rFIXFc | C35785 | 387 | 238000 | 6.37 | 39 | 6.89 | 19.9 | 2970 | 0.145 | 47.8 |
| | N | 3 | 3 | 3 | 3 | 3 | 3 | 3 | 3 | 3 |
| | Mean | 858 | 172000 | 7.62 | 45.4 | 12.8 | 23.2 | 1950 | 0.105 | 34.4 |
| | SD | 671 | 89600 | 3.31 | 5.58 | 9.3 | 6.79 | 1190 | 0.0546 | 18.0 |
| | SE | 388 | 51700 | 1.91 | 3.22 | 5.37 | 3.92 | 687 | 0.0315 | 10.4 |
| | Geometric Mean | 707 | 151000 | 7.18 | 45.2 | 10.9 | 22.6 | 1630 | 0.0921 | 30.3 |
| | CV % Geometric Mean | 86.2 | 75.5 | 43.1 | 12.8 | 75.5 | 28.2 | 96.9 | 75.5 | 75.5 |

TABLE 24

PK parameters of rFIXFc (200 IU/kg) following subcutaneous injection of a single dose in cynomolgus monkeys.

| Group | Animal_ID | V/F (mL/kg) | AUC (Hr*ng/mL) | Absorption HL (Hr) | Terminal HL (Hr) | CL/F (mL/Hr/kg) | Tmax (Hr) | Cmax (ng/mL) | AUC/D (Hr*kg/mL) | F (%) |
|---|---|---|---|---|---|---|---|---|---|---|
| 200 | 50883 | 855 | 408000 | 3.36 | 73.7 | 8.03 | 15.7 | 3310 | 0.124 | 40.9 |
| IU/kg | C31129 | 461 | 415000 | 6.42 | 40.4 | 7.91 | 20.2 | 5030 | 0.127 | 41.6 |
| rFIXFc | C41410 | 147 | 262000 | 11.5 | 32.6 | 3.12 | 26.7 | 3160 | 0.0799 | 26.3 |
| | N | 3 | 3 | 3 | 3 | 3 | 3 | 3 | 3 | 3 |
| | Mean | 487 | 362000 | 7.08 | 48.9 | 6.36 | 20.9 | 3830 | 0.110 | 36.3 |
| | SD | 354 | 86100 | 4.08 | 21.8 | 2.8 | 5.51 | 1040 | 0.0263 | 8.67 |
| | SE | 205 | 49700 | 2.36 | 12.6 | 1.62 | 3.18 | 598 | 0.0152 | 5.00 |
| | Geometric Mean | 387 | 354000 | 6.27 | 46 | 5.83 | 20.4 | 3750 | 0.108 | 35.5 |
| | CV % Geometric Mean | 110 | 26.4 | 67.6 | 44.2 | 58.3 | 27 | 25.9 | 26.5 | 26.5 |

TABLE 25

PK Analysis of rFIXFc Following a Single Subcutaneous Dose in Cynomolgus Monkeys

| rFIXFc (IU/kg) | | AUC (Hr*ng/mL) | Abs Half-Life (Hr) | Elim. Half-Life (Hr) | CL/F (mL/Hr/kg)/% | Tmax (Hr) | Cmax (ng/mL) | F (%) |
|---|---|---|---|---|---|---|---|---|
| 50 | Geo. Mean | 99,000 | 7.72 | 57.9 | 8.28 | 25.7 | 860 | 39.7 |
| | CV % Geo. Mn | 15.8 | 16.4 | 39.4 | 15.8 | 2.68 | 21.7 | 15.9 |
| 100 | Geo. Mean | 221,959 | 5.71 | 43.8 | 7.38 | 19.2 | 2,585 | 44.5 |
| | CV % Geo. Mn | 9.89 | 15.5 | 16.5 | 9.70 | 4.78 | 19.8 | 10.0 |

TABLE 25-continued

PK Analysis of rFIXFc Following a Single Subcutaneous Dose in Cynomolgus Monkeys

| rFIXFc (IU/kg) | | AUC (Hr*ng/mL) | Abs Half-Life (Hr) | Elim. Half-Life (Hr) | CL/F (mL/Hr/kg)/% | Tmax (Hr) | Cmax (ng/mL) | F (%) |
|---|---|---|---|---|---|---|---|---|
| 200 | Geo. Mean | 354,000 | 6.27 | 46 | 5.83 | 20.4 | 3,750 | 35.5 |
| | CV % Geo. Mn | 26.4 | 67.6 | 44.2 | 58.3 | 27 | 25.9 | 26.5 |

Bioavailability ranged from 35.5 to 44.5% for rFIXFc
Elimination half-life ranged 43.8 to 57.9 hrs for rFIXFc

TABLE 26

Dosing Guidelines For rFIXFc Therapy In Hemophilia B

| Type of Hemorrhage | Factor IX Level Required (%) | Frequency of Doses (hrs) |
|---|---|---|
| Minor | | |
| Epistaxis | | |
| Hemarthroses, uncomplicated | 20-30 | 48 |
| Superficial muscular | 20-30 | 48 |
| Superficial soft tissue | 20-30 | 48 |
| Moderate | | |
| Epistaxis | | |
| Intramuscular with dissection | 25-50 | 48 |
| Soft tissue with dissection | 25-50 | 48 |
| Mucous membranes | 25-50 | 48 |
| Dental extractions | 25-50 | 48 |
| Hematuria | 25-50 | 48 |
| Hemarthroses, with limited motion | 40-80 | 48 |
| Major | | |
| Epistaxis | 50-100 | 24-48 |
| Pharynx | 50-100 | 24-48 |
| Retropharynx | 50-100 | 24-48 |
| Retroperitoneum | 50-100 | 24-48 |
| Surgery | 50-100 | 24-48 |
| CNS | 50-100 | 24-48 |

Patient should consult with the their physicians, but should take only 1 follow-up dose not less than 24-48 hours after the initial dose.

TABLE 27

Comparison of data using calculations in (A) Example 1 and (B) Example 11.

A

Parameter (mean ± SD)

| Dose (IU/kg) | n | $C_{max}$ (IU/dL) | $AUC_{INF}$ (h · IU/dL) | CL (mL/h/kg) | Vss (mL/kg) | MRT (h) | T½α (h) | T½β (h) | Incremental Recovery (IU/dL per IU/kg)* | $C_{168\,h}$ (IU/dL)† | Time to 1% above baseline (Day)‡ |
|---|---|---|---|---|---|---|---|---|---|---|---|
| 25 | 1 | 19.9 | 753 | 3.62 | 275 | 76.0 | 1.20 | 54.0 | 0.77 | 1.09 | 7.28 |
| 50 | 5 | 41.6 ± 8.97/8.98 | 1630 ± 750 | 3.77 ± 1.12 | 264 ± 77.6 | 71.7 ± 13.0 | 1.79 ± 1.19 | 52.1 ± 10.4 | 0.86 ± 0.22 | 2.23 ± 1.40 | 9.29 ± 1.98 |
| 100 | 5 | 98.2 ± 8.21/8.23 | 3930 ± 893 | 2.89 ± 0.615 | 179 ± 31.1 | 62.8 ± 8.82 | 9.99 ± 4.99 | 52.5 ± 10.1 | 1.02 ± 0.11 | 4.38 ± 1.53 | 11.6 ± 1.97 |
| 25-100 | 11 | NA§ | NA§ | ND | ND | ND | ND | ND | ND | NA§ | NA§ |

B

Parameter (mean ± SD) (Range)

| Dose (IU/kg) | n | $C_{max}$ (IU/dL) | $AUC_{INF}$ (h · IU/dL) | CL (mL/h/kg) | Vss (mL/kg) | MRT (h) | T½α (h) | T½β (h) | Incremental Recovery (IU/dL per IU/kg)* | $C_{168\,h}$ (IU/dL)† | Time to 1% above baseline (Day)‡ |
|---|---|---|---|---|---|---|---|---|---|---|---|
| 25 | 1 | 20.4 | 766 | 3.56 | 271 | 76.2 | 0.61 | 53.5 | 0.77 | 1.11 | 7.3 |
| 50 | 5 | 47.5 ± 12.8 (33.0-61.1) | 1700 ± 550 (1300-2660) | 3.44 ± 0.84 (2.05-4.18) | 262 ± 55.4 (163-296) | 76.8 ± 6.7 (67.9-85.9) | 3.4 ± 3.4 (0.13-8.72) | 57.5 ± 8.2 (47.9-67.2) | 0.87 ± 0.21 (0.63-1.12) | 2.46 ± 0.89 (1.63-3.92) | 10.1 ± 1.5 (8.4-12.3) |
| 100 | 5 | 98.5 ± 7.9 (90.8-110) | 4020 ± 986 (3090-5130) | 2.84 ± 0.66 (2.13-3.55) | 183 ± 27.9 (162-221) | 65.9 ± 10.3 (53.2-76.5) | 10.3 ± 5.6 (3.97-16.6) | 56.5 ± 14.1 (42.4-74.5) | 1.02 ± 0.11 (0.89-1.18) | 4.65 ± 1.73 (3.08-6.85) | 12.3 ± 2.5 (9.9-15.0) |

TABLE 27-continued

Comparison of data using calculations in (A) Example 1 and (B) Example 11.

| 25-100 | 11 | NA[§] | NA[§] | 3.18 ± 0.78 (2.05-4.18) | 227 ± 58.6 (162-296) | 71.8 ± 10.0 (53.2-85.9) | NA[§] | 56.7 ± 10.9 (42.4-74.5) | 0.93 ± 0.18 (0.63-1.18) | NA[§] | NA[§] |

Results presented are mean ± SD with range listed in the parentheses
$C_{max}$ indicates maximum concentration;
$AUC_{INF}$, area under the curve (time zero extrapolated to infinite time);
CL, clearance;
Vss, volume of distribution at steady state;
MRT, mean residence time;
T½α, distribution half-life;
T½β, elimination half-life;
NA, not applicable
*Incremental recovery was calculated using observed $C_{max}$ subtracted with pretreatment baseline value and divided by dose
[†]Plasma FIX activity above baseline at 168 hours (7 days) post dose
[‡]Model-predicted time after dose when FIX activity declined to 1 IU/dL above subject's baseline
[§]Data are not applicable because parameters are not dose - independent, thus the mean and SD values were not calculated across the different dose groups

What is claimed:

1. A method of treating hemophilia B, comprising intravenously administering to a human subject in need thereof multiple doses of about 50 IU/kg to about 100 IU/kg of a chimeric Factor IX (FIX) polypeptide comprising human FIX having an amino acid sequence identical to amino acids 1 to 415 of SEQ ID NO:2 and a FcRn binding partner (FcRn BP) at a dosing interval of 7 days between two doses, wherein the FcRn BP is human albumin, and wherein the administration treats the human subject by reducing the frequency of spontaneous bleeding.

2. The method of claim 1, wherein each of the multiple doses is 50 IU/kg to 75 IU/kg.

3. The method of claim 1, wherein each of the multiple doses is 50 IU/kg.

4. The method of claim 1, wherein each of the multiple doses is 55 IU/kg.

5. The method of claim 1, wherein each of the multiple doses is 60 IU/kg.

6. The method of claim 1, wherein each of the multiple doses is 65 IU/kg.

7. The method of claim 1, wherein each of the multiple doses is 70 IU/kg.

8. The method of claim 1, wherein each of the multiple doses is 75 IU/kg.

9. The method of claim 1, wherein the chimeric polypeptide further comprises a linker joining the FIX and the human albumin.

10. The method of claim 9, wherein the linker joins the FIX to the N-terminal end of the human albumin.

11. The method of claim 1, wherein the subject exhibits plasma FIX activity above 1 IU/dL during the dosing interval as measured by a one stage clotting assay that determines activated partial thromboplastin time.

12. The method of claim 11, wherein each of the multiple doses is 50 IU/kg to 75 IU/kg.

13. The method of claim 11, wherein each of the multiple doses is 50 IU/kg.

14. The method of claim 11, wherein each of the multiple doses is 55 IU/kg.

15. The method of claim 11, wherein each of the multiple doses is 60 IU/kg.

16. The method of claim 11, wherein each of the multiple doses is 65 IU/kg.

17. The method of claim 11, wherein each of the multiple doses is 70 IU/kg.

18. The method of claim 11, wherein each of the multiple doses is 75 IU/kg.

19. The method of claim 11, wherein the chimeric polypeptide further comprises a linker joining the FIX and the human albumin.

20. The method of claim 19, wherein the linker joins the FIX to the N-terminal end of the human albumin.

* * * * *